US012642523B2

(12) United States Patent
Shelton, IV et al.

(10) Patent No.: US 12,642,523 B2
(45) Date of Patent: Jun. 2, 2026

(54) POWERED SURGICAL INSTRUMENT

(71) Applicant: Cilag GmbH International, Zug (CH)

(72) Inventors: Frederick E. Shelton, IV, Hillsboro, OH (US); David C. Yates, Morrow, OH (US); Jason L. Harris, Lebanon, OH (US); Jerome R. Morgan, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 27 days.

(21) Appl. No.: 18/538,710

(22) Filed: Dec. 13, 2023

(65) Prior Publication Data

US 2024/0108330 A1 Apr. 4, 2024

Related U.S. Application Data

(60) Division of application No. 16/916,575, filed on Jun. 30, 2020, now abandoned, which is a continuation of (Continued)

(51) Int. Cl.
| | |
|---|---|
| *A61B 17/072* | (2006.01) |
| *A61B 17/068* | (2006.01) |
| A61B 17/00 | (2006.01) |

(52) U.S. Cl.
CPC .......... *A61B 17/068* (2013.01); *A61B 17/072* (2013.01); *A61B 17/07207* (2013.01);

(Continued)

(58) Field of Classification Search
CPC ........... A61B 2017/00017; A61B 2017/00367; A61B 2017/00022; A61B 2017/00137;

(Continued)

(56) References Cited

U.S. PATENT DOCUMENTS

| | | |
|---|---|---|
| 5,817,093 A | 10/1998 | Williamson, IV et al. |
| 6,775,575 B2 | 8/2004 | Bommannan et al. |

(Continued)

FOREIGN PATENT DOCUMENTS

| | | | | |
|---|---|---|---|---|
| EP | 2881046 A2 * | 6/2015 | ....... | A61B 17/07207 |
| GB | 2441306 A * | 3/2008 | ............. | A61B 18/18 |

(Continued)

*Primary Examiner* — Linda J. Hodge
(74) *Attorney, Agent, or Firm* — Lempia Summerfield Katz LLC

(57) ABSTRACT

A method of operating a surgical instrument is disclosed. The surgical instrument includes an electronic system comprising an electric motor coupled to the end effector; a motor controller coupled to the motor; a parameter threshold detection module configured to monitor multiple parameter thresholds; a sensing module configured to sense tissue compression; a processor coupled to the parameter threshold detection module and the motor controller; and a memory coupled to the processor. The memory stores executable instructions that when executed by the processor cause the processor to monitor multiple levels of action thresholds and monitor speed of the motor and increment a drive unit of the motor, sense tissue compression, and provide rate and control feedback to the user of the surgical instrument.

14 Claims, 127 Drawing Sheets

Related U.S. Application Data application No. 16/146,885, filed on Sep. 28, 2018, now Pat. No. 10,729,432, which is a continuation of application No. 15/459,546, filed on Mar. 15, 2017, now Pat. No. 10,524,787, which is a continuation of application No. 14/640,746, filed on Mar. 6, 2015, now Pat. No. 9,808,246.

(52) U.S. Cl.
CPC .............. *A61B 2017/00017* (2013.01); *A61B 2017/00022* (2013.01); *A61B 2017/00367* (2013.01); *A61B 2017/00398* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC ........... A61B 2017/00221; A61B 2017/00398; A61B 34/00; A61B 34/30; A61B 17/068–07292
See application file for complete search history.

(56) References Cited

U.S. PATENT DOCUMENTS

| | | | |
|---|---|---|---|
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,143,923 B2 | 12/2006 | Shelton, IV et al. |
| 7,959,050 B2 | 6/2011 | Smith et al. |
| 8,012,170 B2 | 9/2011 | Whitman et al. |
| 8,062,236 B2 | 11/2011 | Soltz |
| 8,453,906 B2 | 6/2013 | Huang et al. |
| 8,591,400 B2 | 11/2013 | Sugiyama |
| 8,608,045 B2 | 12/2013 | Smith et al. |
| 8,967,443 B2 | 3/2015 | McCuen |
| 8,968,308 B2 | 3/2015 | Horner et al. |
| 9,072,535 B2 | 7/2015 | Shelton, IV et al. |
| 9,149,325 B2 | 10/2015 | Worrell et al. |
| 9,161,803 B2 | 10/2015 | Yates et al. |
| 9,265,585 B2 | 2/2016 | Wingardner et al. |
| 9,307,986 B2 | 4/2016 | Hall et al. |
| 9,326,767 B2 | 5/2016 | Koch, Jr. et al. |
| 9,326,788 B2 | 5/2016 | Batross et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,393,017 B2 | 7/2016 | Flanagan et al. |
| 9,398,911 B2 | 7/2016 | Auld |
| 9,420,967 B2 | 8/2016 | Zand et al. |
| 9,468,438 B2 | 10/2016 | Baber et al. |
| 9,554,794 B2 | 1/2017 | Baber et al. |
| 9,629,623 B2 | 4/2017 | Lytle, IV et al. |
| 9,629,629 B2 | 4/2017 | Leimbach et al. |
| 9,649,110 B2 | 5/2017 | Parihar et al. |
| 9,675,354 B2 | 6/2017 | Weir et al. |
| 9,687,230 B2 | 6/2017 | Leimbach et al. |
| 9,690,362 B2 | 6/2017 | Leimbach et al. |
| 9,700,309 B2 | 7/2017 | Jaworek et al. |
| 9,724,094 B2 | 8/2017 | Baber et al. |
| 9,733,663 B2 | 8/2017 | Leimbach et al. |
| 9,737,301 B2 | 8/2017 | Baber et al. |
| 9,743,929 B2 | 8/2017 | Leimbach et al. |
| 9,750,499 B2 | 9/2017 | Leimbach et al. |
| 9,757,128 B2 | 9/2017 | Baber et al. |
| 9,782,169 B2 | 10/2017 | Kimsey et al. |
| 9,788,836 B2 | 10/2017 | Overmyer et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,814,460 B2 | 11/2017 | Kimsey et al. |

| | | | |
|---|---|---|---|
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,867,612 B2 | 1/2018 | Parihar et al. |
| 9,883,860 B2 | 2/2018 | Leimbach et al. |
| 9,888,919 B2 | 2/2018 | Leimbach et al. |
| 9,895,148 B2 | 2/2018 | Shelton, IV et al. |
| 9,901,342 B2 | 2/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,085,748 B2 | 10/2018 | Morgan et al. |
| 10,111,679 B2 | 10/2018 | Baber et al. |
| 10,117,649 B2 | 11/2018 | Baxter, III et al. |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,159,483 B2 | 12/2018 | Beckman et al. |
| 10,180,463 B2 | 1/2019 | Beckman et al. |
| 10,182,816 B2 | 1/2019 | Shelton, IV et al. |
| 10,188,385 B2 | 1/2019 | Kerr et al. |
| 10,201,364 B2 | 2/2019 | Leimbach et al. |
| 10,226,250 B2 | 3/2019 | Beckman et al. |
| 10,245,027 B2 | 4/2019 | Shelton, IV et al. |
| 10,245,028 B2 | 4/2019 | Shelton, IV et al. |
| 10,245,033 B2 | 4/2019 | Overmyer et al. |
| 10,321,907 B2 | 6/2019 | Shelton, IV et al. |
| 10,383,629 B2 | 8/2019 | Ross et al. |
| 10,405,857 B2 | 9/2019 | Shelton, IV et al. |
| 10,441,279 B2 | 10/2019 | Shelton, IV et al. |
| 10,470,762 B2 | 11/2019 | Leimbach et al. |
| 10,524,787 B2 | 1/2020 | Shelton, IV et al. |
| 10,548,504 B2 | 2/2020 | Shelton, IV et al. |
| 10,617,412 B2 | 4/2020 | Shelton, IV et al. |
| 10,687,806 B2 | 6/2020 | Shelton, IV et al. |
| 10,729,432 B2 | 8/2020 | Shelton, IV et al. |
| 2009/0090763 A1* | 4/2009 | Zemlok ........... A61B 17/07207 227/175.2 |
| 2010/0270355 A1* | 10/2010 | Whitman ............. A61B 17/068 227/176.1 |
| 2011/0155781 A1* | 6/2011 | Swensgard ...... A61B 17/07207 227/176.1 |
| 2012/0211542 A1 | 8/2012 | Racenet |
| 2012/0238796 A1* | 9/2012 | Conlon ................. A61B 90/13 318/639 |
| 2014/0246473 A1* | 9/2014 | Auld ................ A61B 17/07207 227/175.1 |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0277017 A1* | 9/2014 | Leimbach .............. A61B 17/32 227/175.3 |
| 2015/0122870 A1* | 5/2015 | Zemlok ........... A61B 17/07207 227/176.1 |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2016/0066913 A1 | 3/2016 | Swayze et al. |

(56)  References Cited

U.S. PATENT DOCUMENTS

| | | | | |
|---|---|---|---|---|
| 2016/0100839 A1* | 4/2016 | Marczyk | ......... | A61B 17/07207 |
| | | | | 227/176.1 |
| 2016/0249910 A1 | 9/2016 | Shelton, IV et al. | | |
| 2021/0015480 A1 | 1/2021 | Shelton, IV et al. | | |

FOREIGN PATENT DOCUMENTS

| | | | | | |
|---|---|---|---|---|---|
| KR | 201500083107 | * | 7/2015 | ... | A61B 2017/00022 |
| WO | WO-0149227 A1 | * | 7/2001 | ....... | A61B 17/00234 |

* cited by examiner

ANVIL OPEN

ANVIL OPEN

RIGHT SIDE

ANVIL OPEN
LEFT SIDE

CLOSED AND LOCKED

ANVIL CLOSED

RIGHT SIDE

ANVIL CLOSED
LEFT SIDE

FIRED
RIGHT SIDE

TIME (t)

6300

SLOPE = $\frac{\Delta S}{\Delta t}$ = RATE OF CHANGE OF ANVIL STRAIN

13058a

13102

13058a

13102

13102

13058a

POWERED SURGICAL INSTRUMENT

CROSS-REFERENCE TO RELATED APPLICATIONS

This application is a divisional application claiming priority under 35 U.S.C. § 121 to U.S. patent application Ser. No. 16/916,575, entitled POWERED SURGICAL INSTRUMENT, filed Jun. 30, 2020, now U.S. Patent Application Publication No. 2021/0015480, which is a continuation application claiming priority under 35 U.S.C. § 120 to U.S. patent application Ser. No. 16/146,885, entitled POWERED SURGICAL INSTRUMENT, filed Sep. 28, 2018, which issued on Aug. 4, 2020 as U.S. Pat. No. 10,729,432, which is a continuation application claiming priority under 35 U.S.C. § 120 to U.S. patent application Ser. No. 15/459,546, entitled POWERED SURGICAL INSTRUMENT, filed Mar. 15, 2017, which issued on Jan. 7, 2020 as U.S. Pat. No. 10,524,787, which is a continuation application claiming priority under 35 U.S.C. § 120 to U.S. patent application Ser. No. 14/640,746, entitled POWERED SURGICAL INSTRUMENT, filed Mar. 6, 2015, which issued on Nov. 7, 2017 as U.S. Pat. No. 9,808,246, the entire disclosures of which are hereby incorporated by reference herein.

BACKGROUND

The present disclosure relates to surgical instruments and, in various circumstances, to surgical stapling and cutting instruments and staple cartridges therefor that are designed to staple and cut tissue.

BRIEF DESCRIPTION OF THE DRAWINGS

The features and advantages of the present disclosure, and the manner of attaining them, will become more apparent and the present disclosure will be better understood by reference to the following description of the present disclosure taken in conjunction with the accompanying drawings, wherein:

FIG. 28, which is divided into

FIG. 108 illustrates a perspective cutaway view of the anvil and the magnet, FIG. 109 illustrates a side cutaway view of the anvil and the magnet, and FIG. 110 illustrates a top cutaway view of the anvil and the magnet;

FIG. 118 illustrates a cutaway view of the distal sensor plug and FIG. 119 further illustrates the magnetic field sensor and the processor operatively coupled to the flex board such that they are capable of communicating;

FIG. 120 illustrates an aspect of an end effector with a flex cable operable to provide power to sensors and electronics in the distal tip of the anvil portion;

Figures 121, 122, 123:
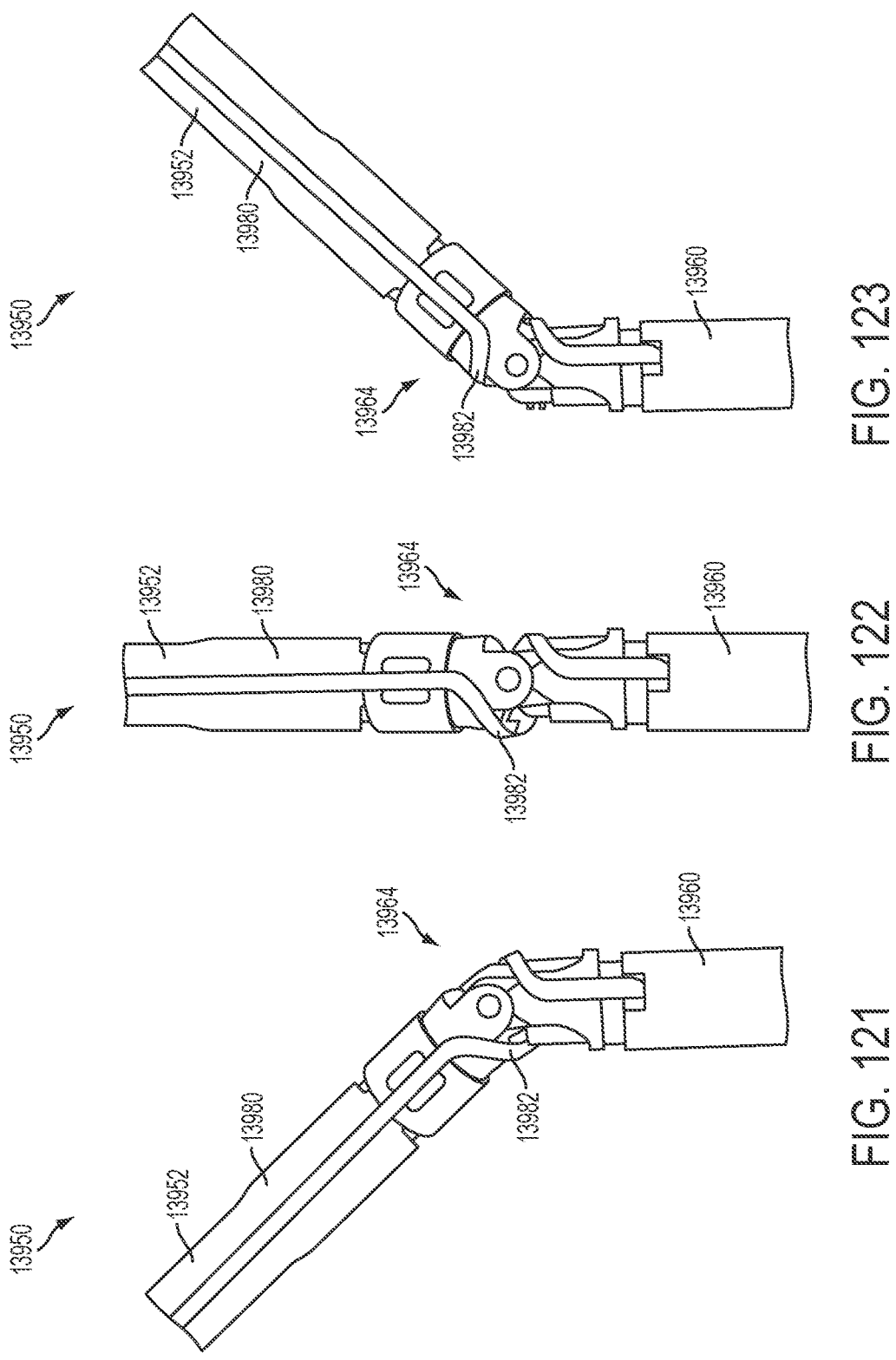
Figure 124:
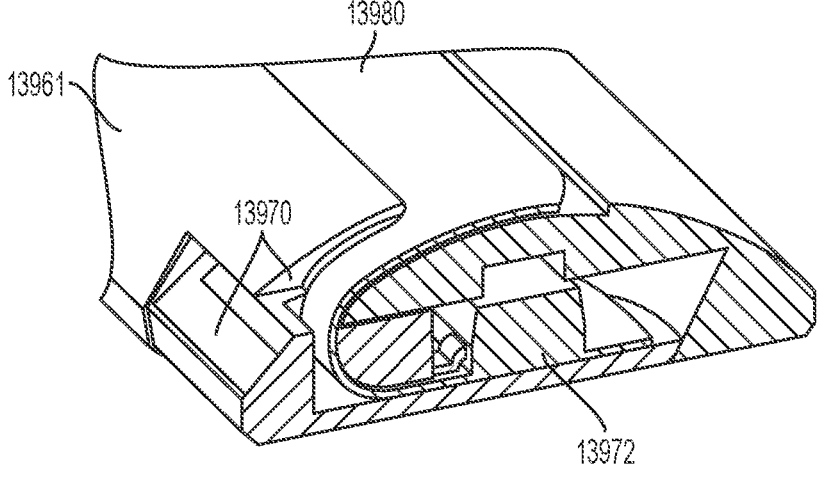
Figure 125:
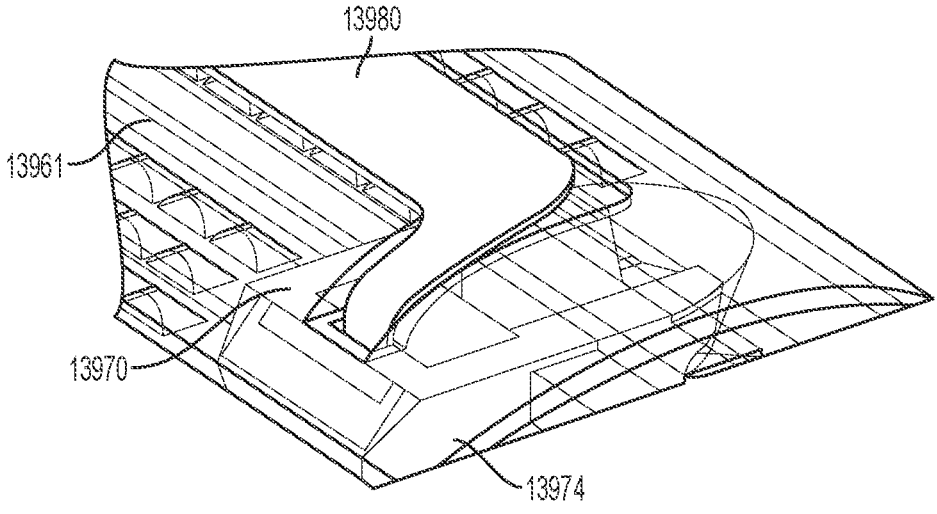

FIGS. 121-123 illustrate the operation of the articulation joint and flex cable of the end effector where FIG. 121 illustrates a top view of the end effector with the end effector pivoted −45 degrees with respect to the shaft assembly, FIG. 122 illustrates a top view of the end effector, and FIG. 123 illustrates a top view of the end effector with the end effector pivoted +45 degrees with respect to the shaft assembly;

FIG. 124 illustrates cross-sectional view of the distal tip of an aspect of an anvil with sensors and electronics; and FIG. 125 illustrates a cutaway view of the distal tip of the anvil.

Figure 126:
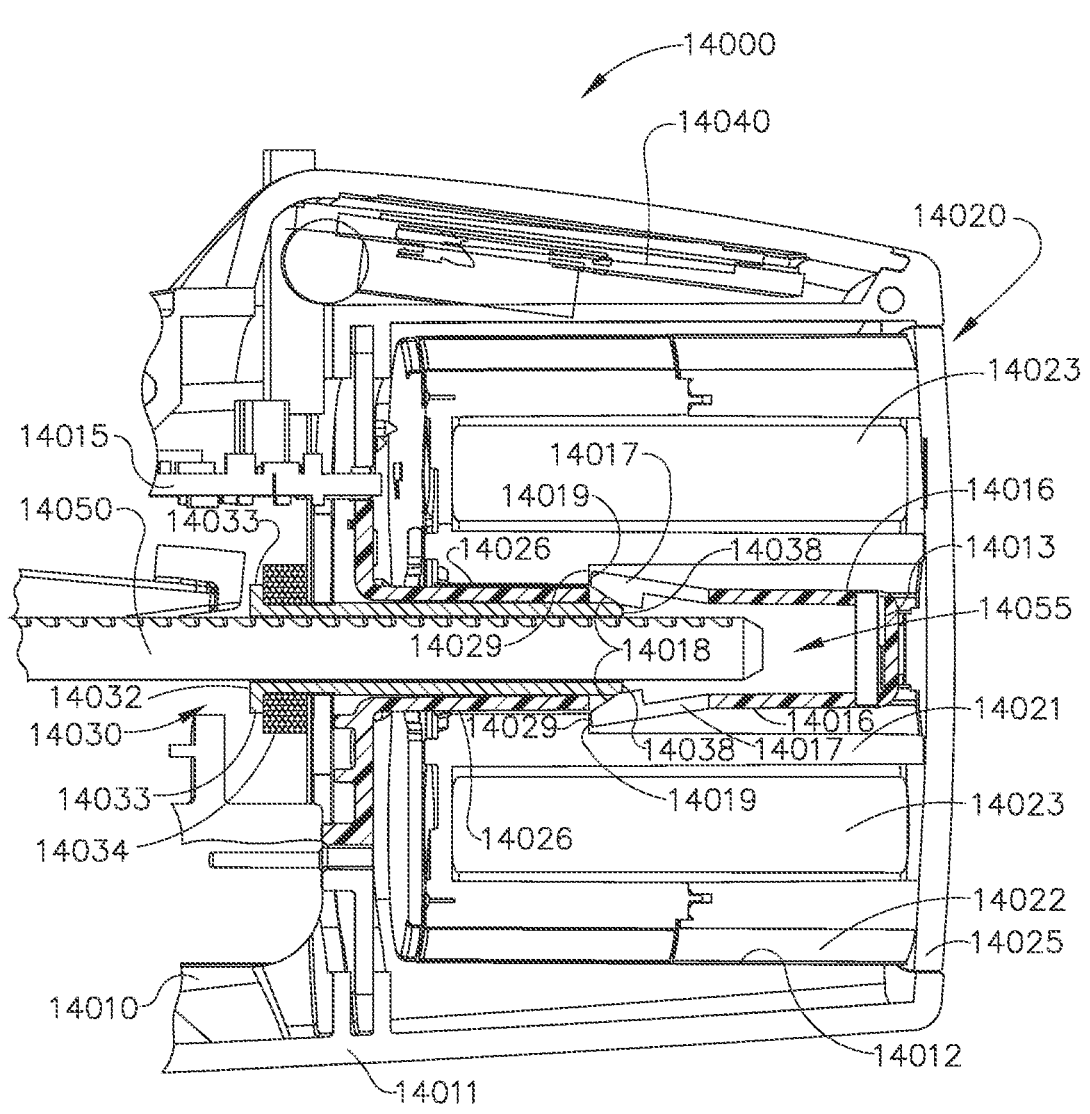
Figures 127, 128:
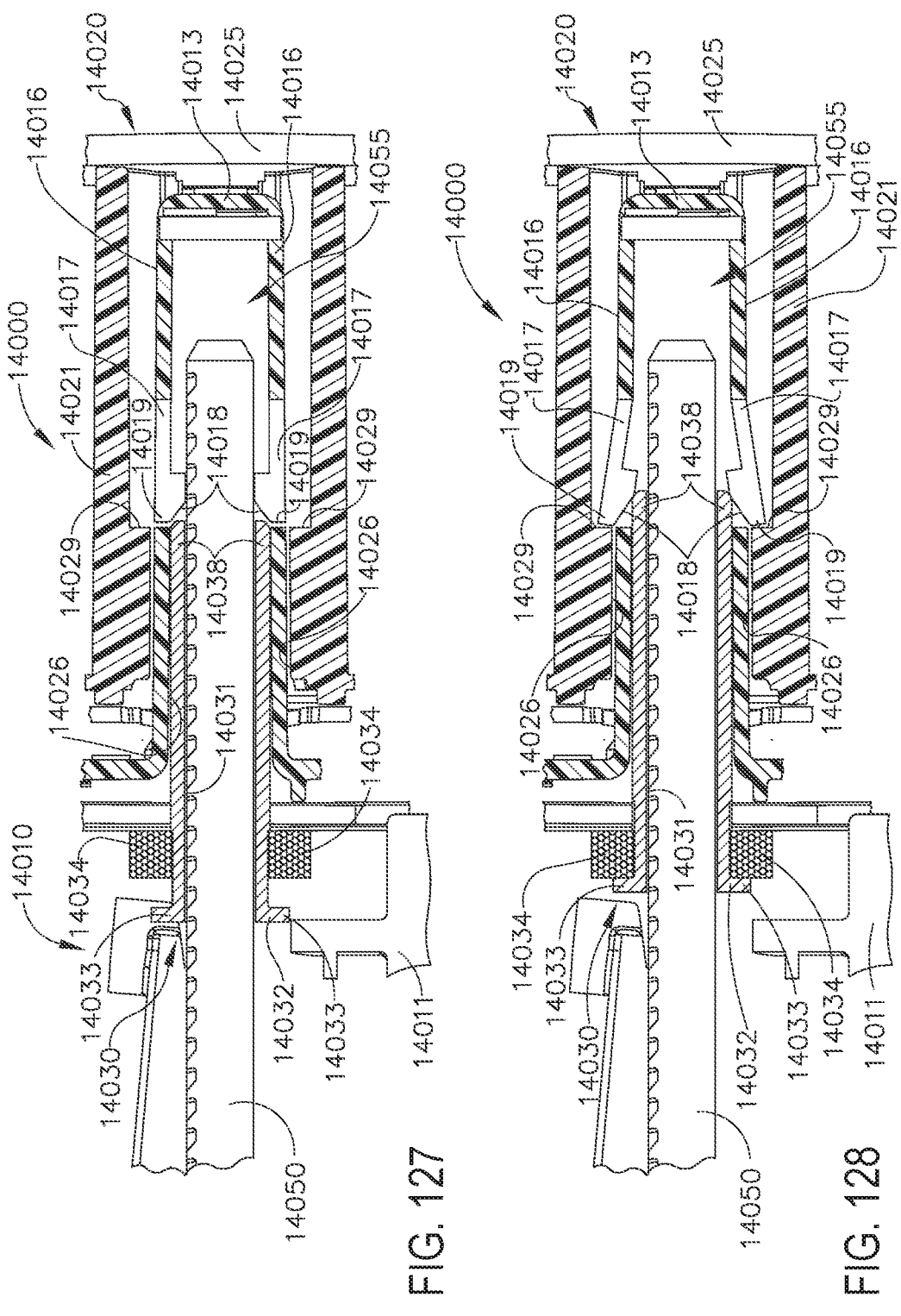
Figures 129, 130:
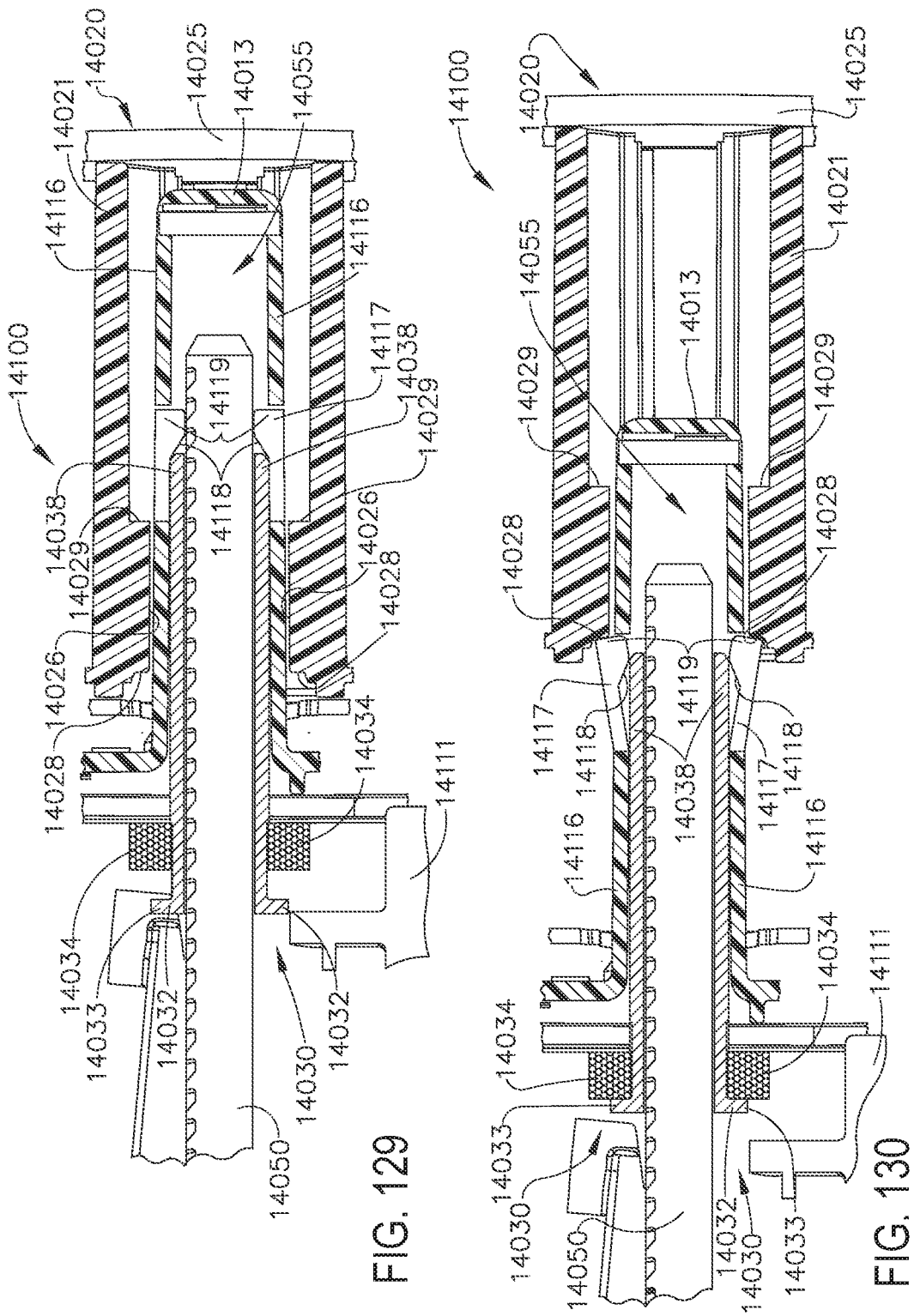
Figure 131:
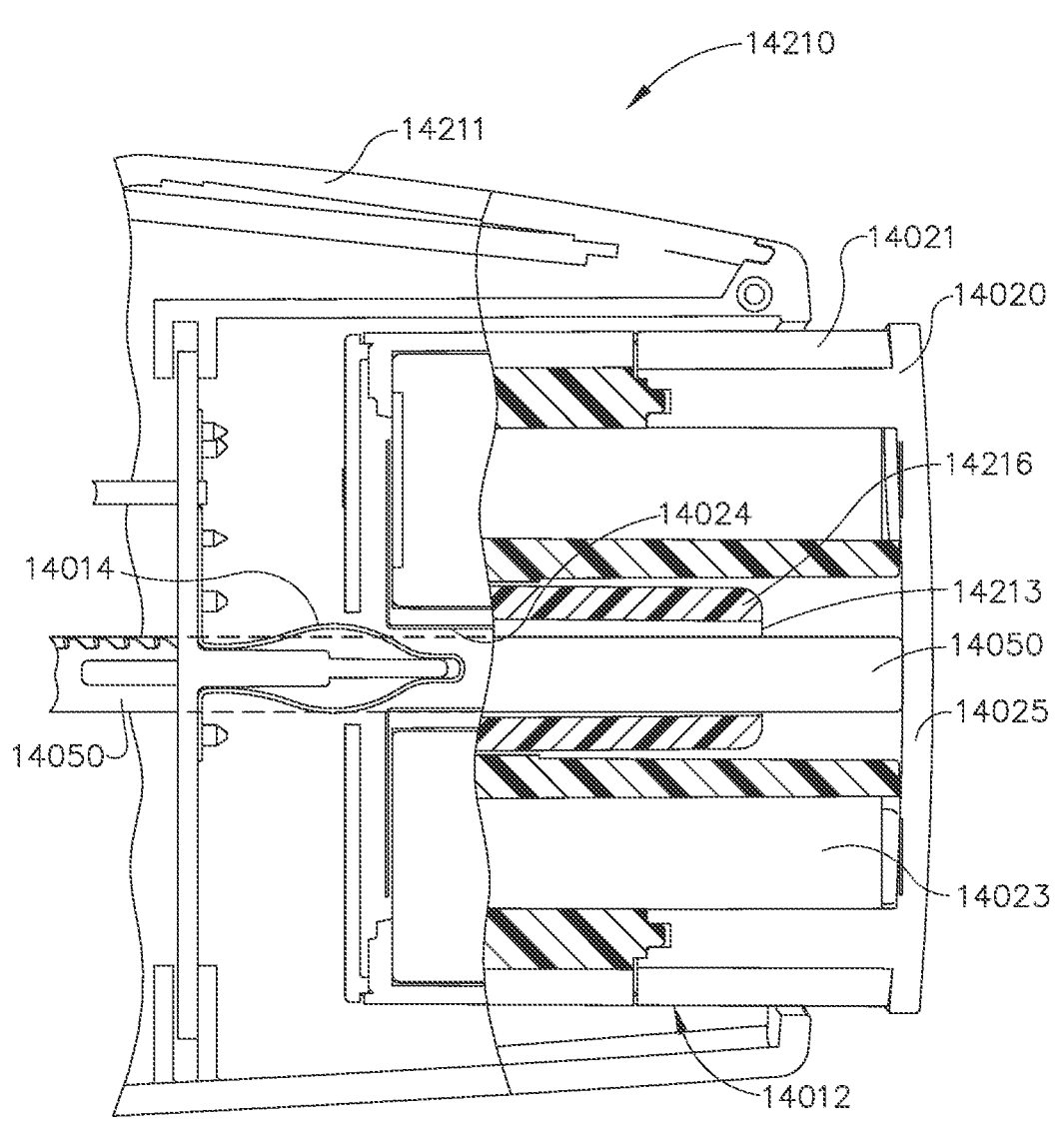
Figure 132:
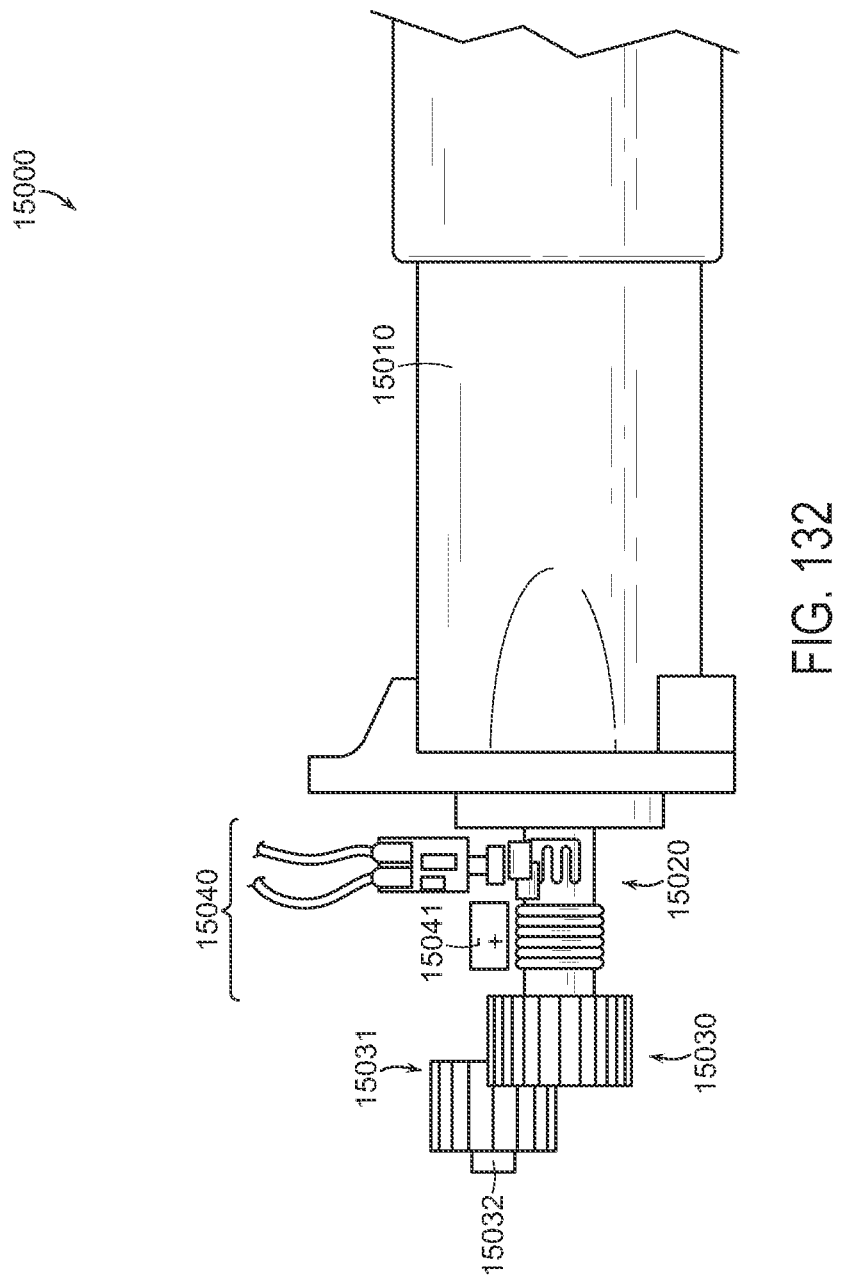

FIG. 126 is a partial cross-sectional view of a handle of a surgical instrument comprising a battery and a battery lock in accordance with at least one embodiment;

FIG. 127 is partial cross-sectional view of the handle of FIG. 126 illustrating the battery lock in an unlocked configuration;

FIG. 128 is a partial cross-sectional view of the handle of FIG. 126 illustrating the battery lock in a locked configuration;

FIG. 129 is a partial cross-sectional view of a handle of a surgical instrument comprising a battery lockout in accordance with at least one embodiment illustrated in an unlocked configuration;

FIG. 130 is a partial cross-sectional view of the handle of FIG. 129 illustrating the battery lockout in a locked-out configuration;

FIG. 131 is a partial cross-sectional view of a battery lockout in accordance with an alternative embodiment illustrated in a locked-out configuration;

FIG. 132 depicts a surgical instrument system comprising a motor including a shaft, a gear train, an output shaft

Figure 133:
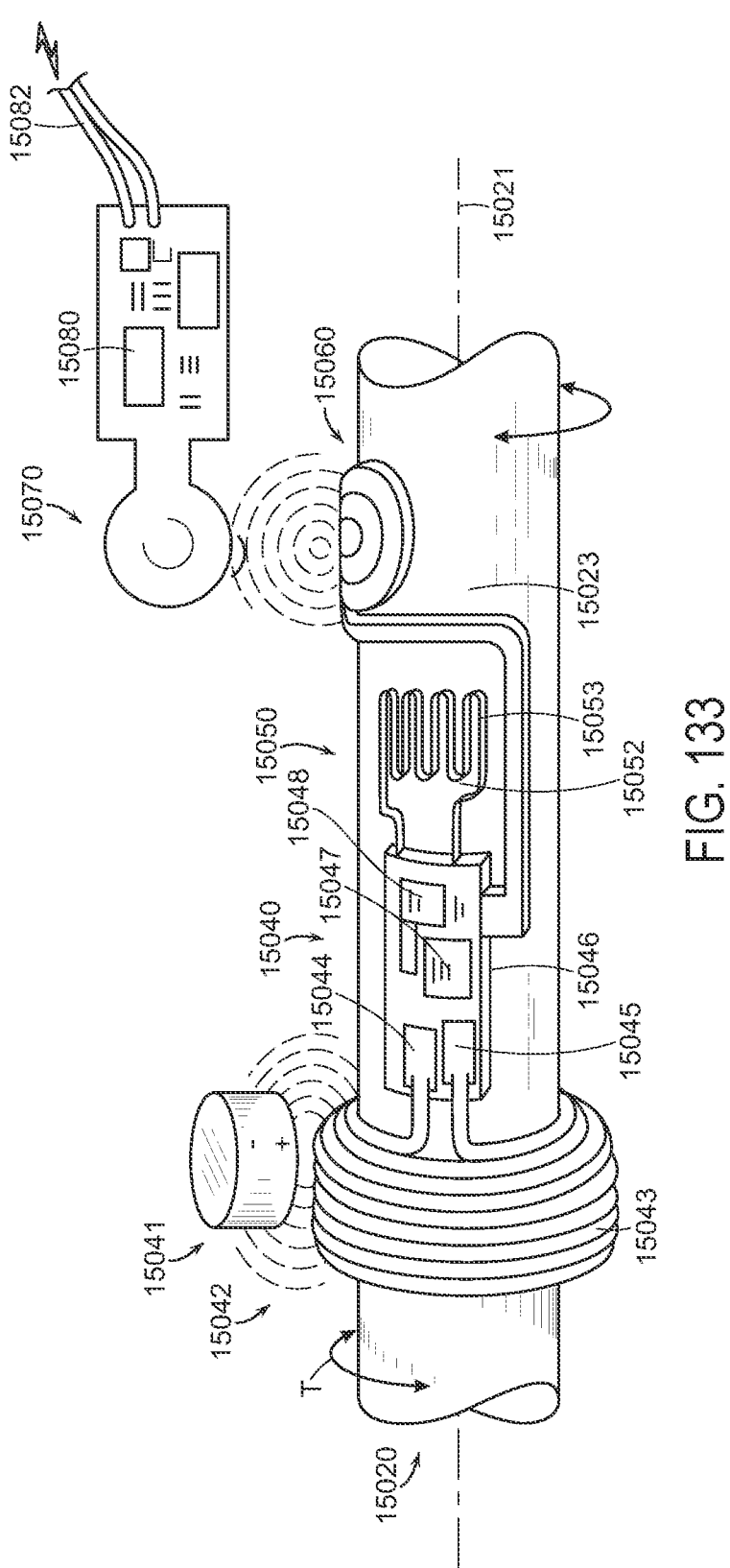
Figure 134:
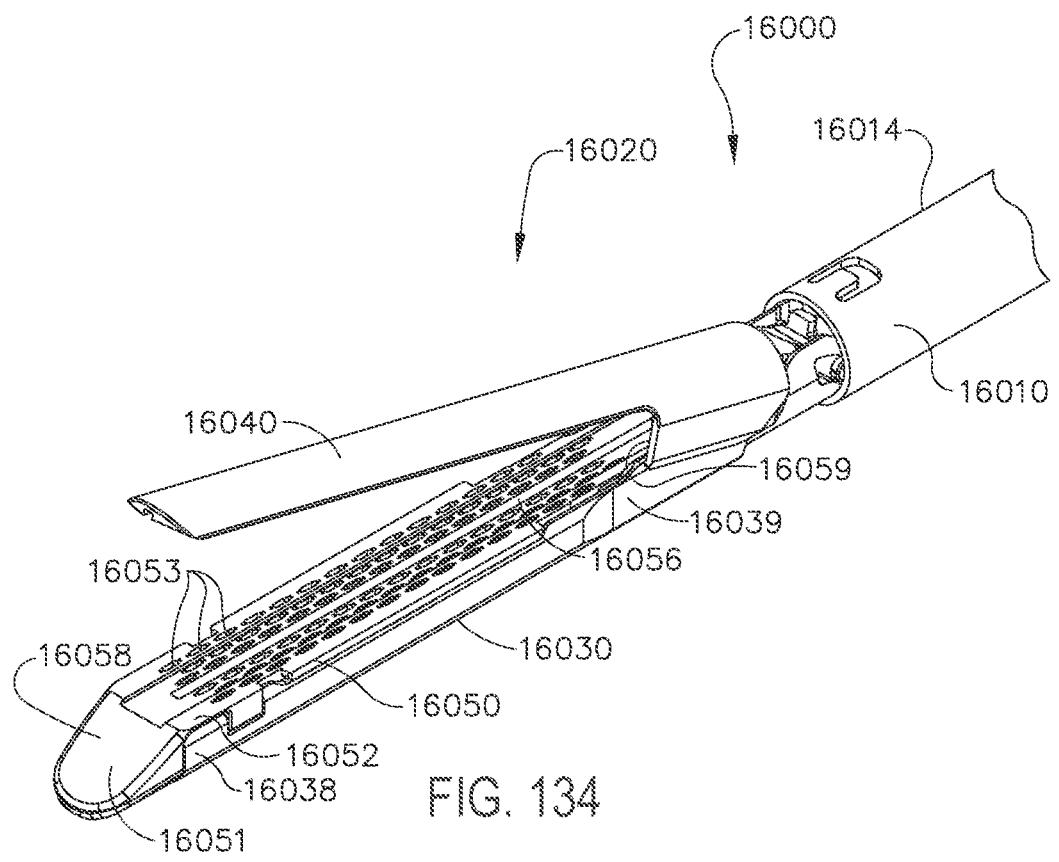
Figures 135, 136:
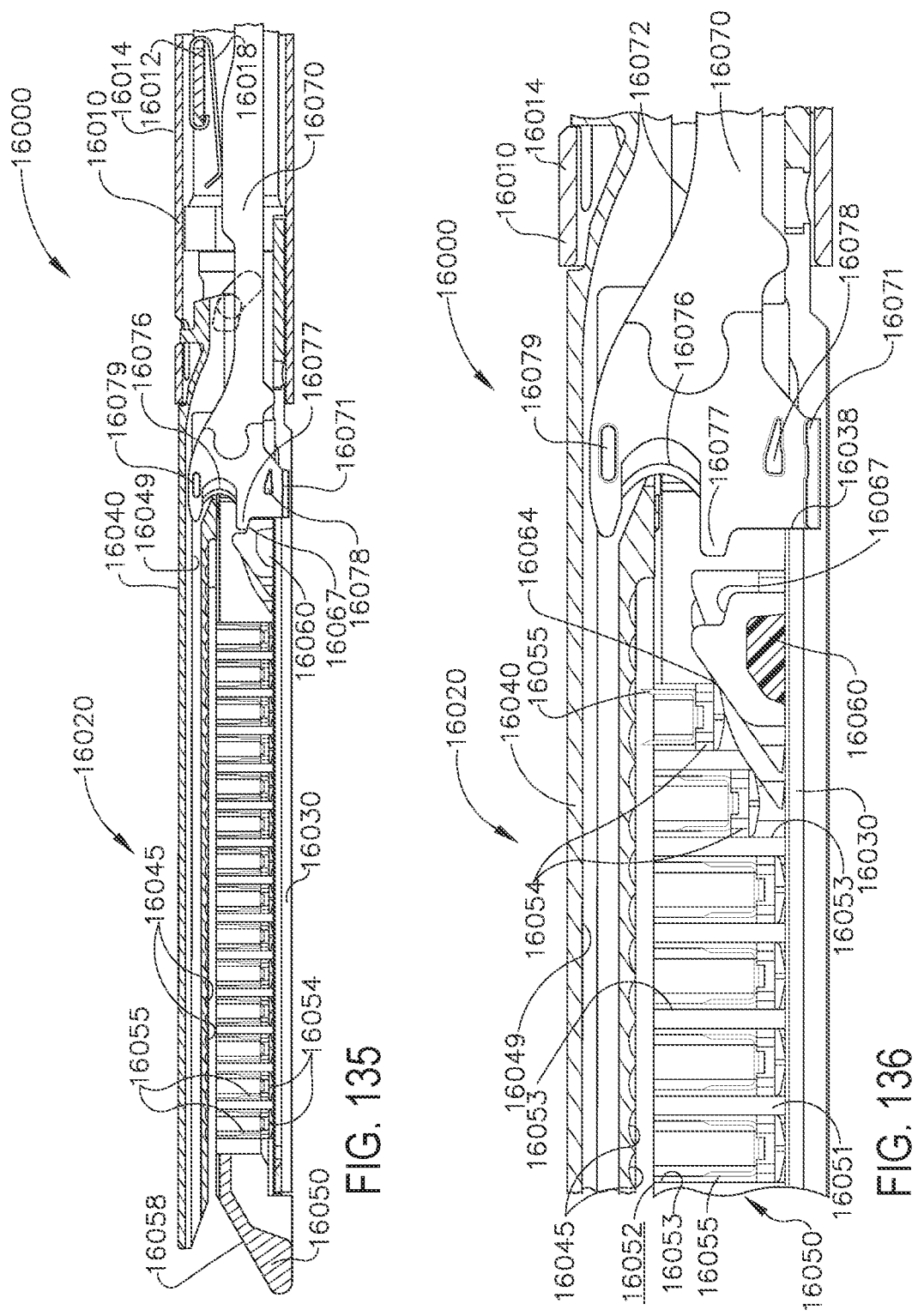
Figures 137, 138:
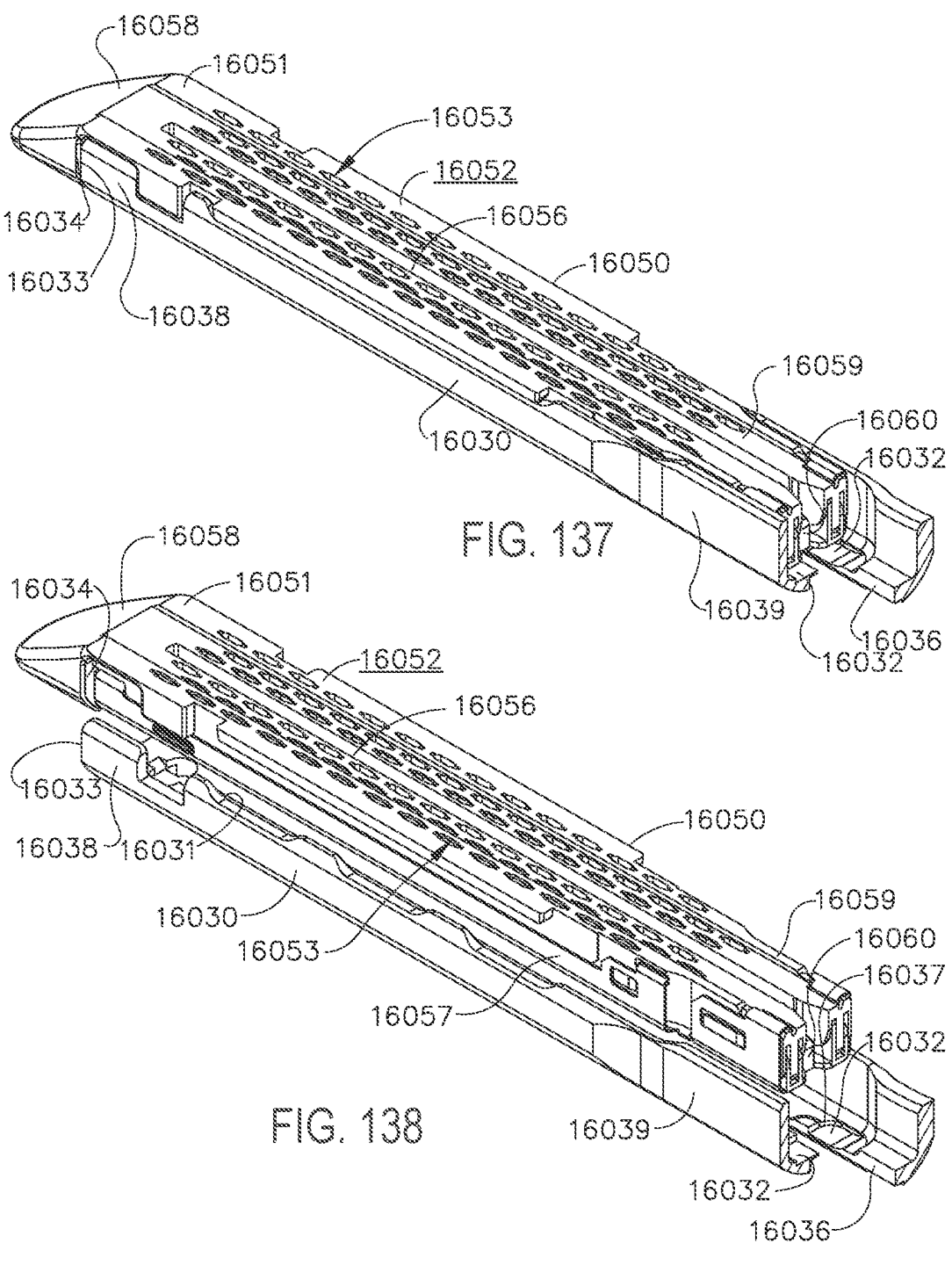
Figure 139:
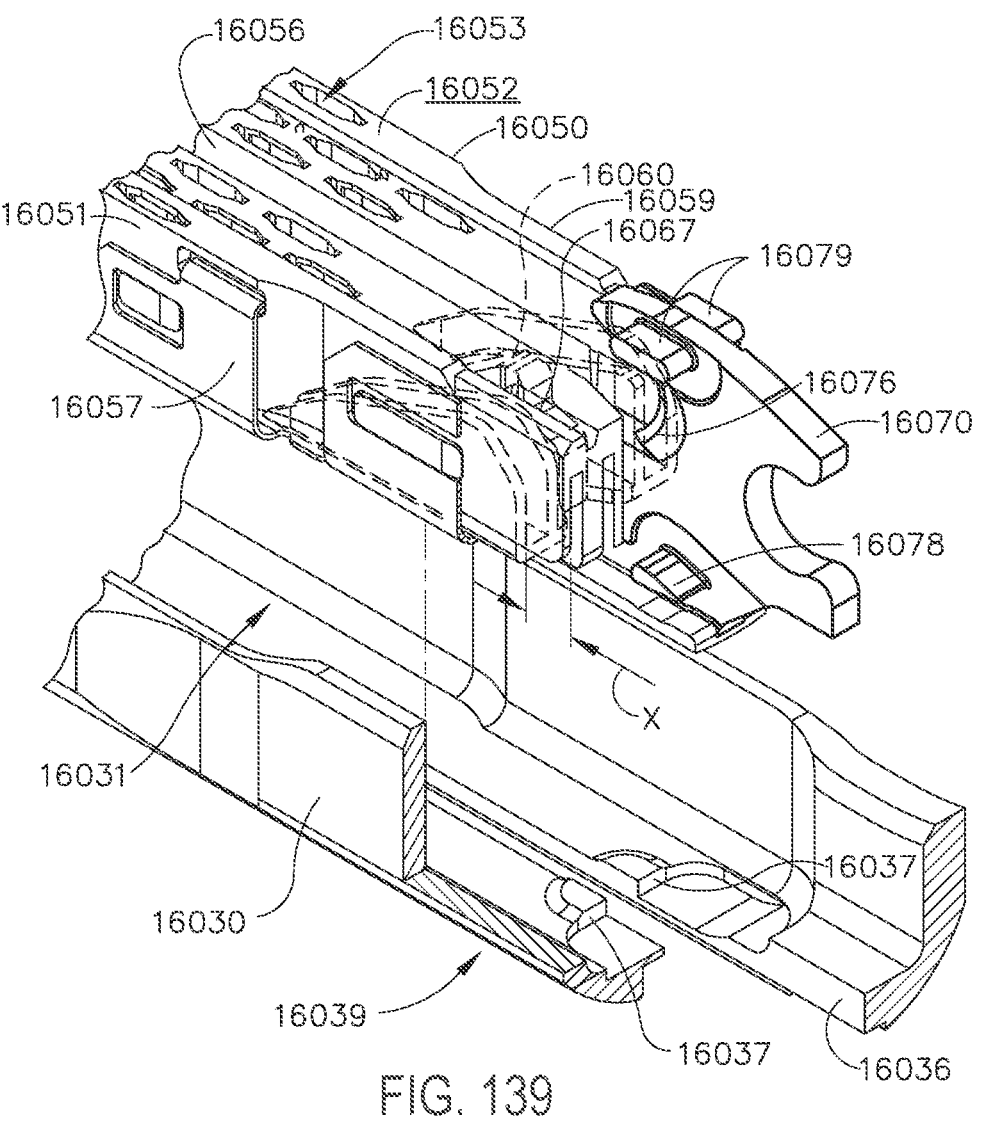
Figure 140:
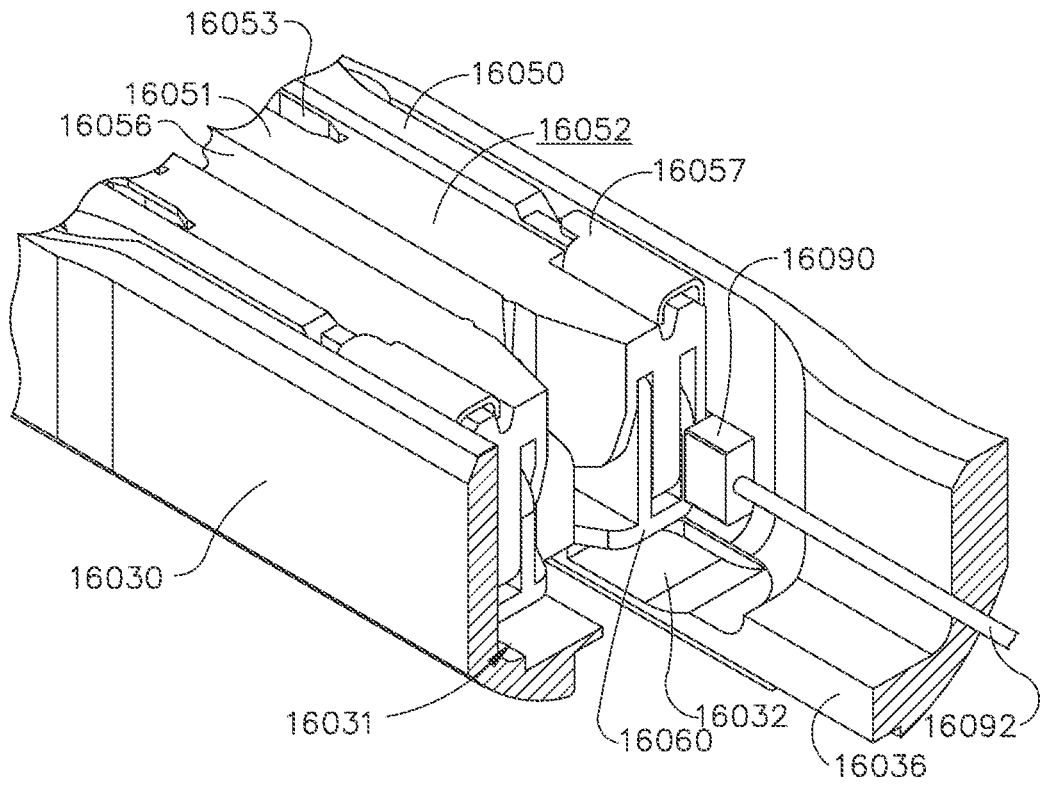
Figures 141, 142:
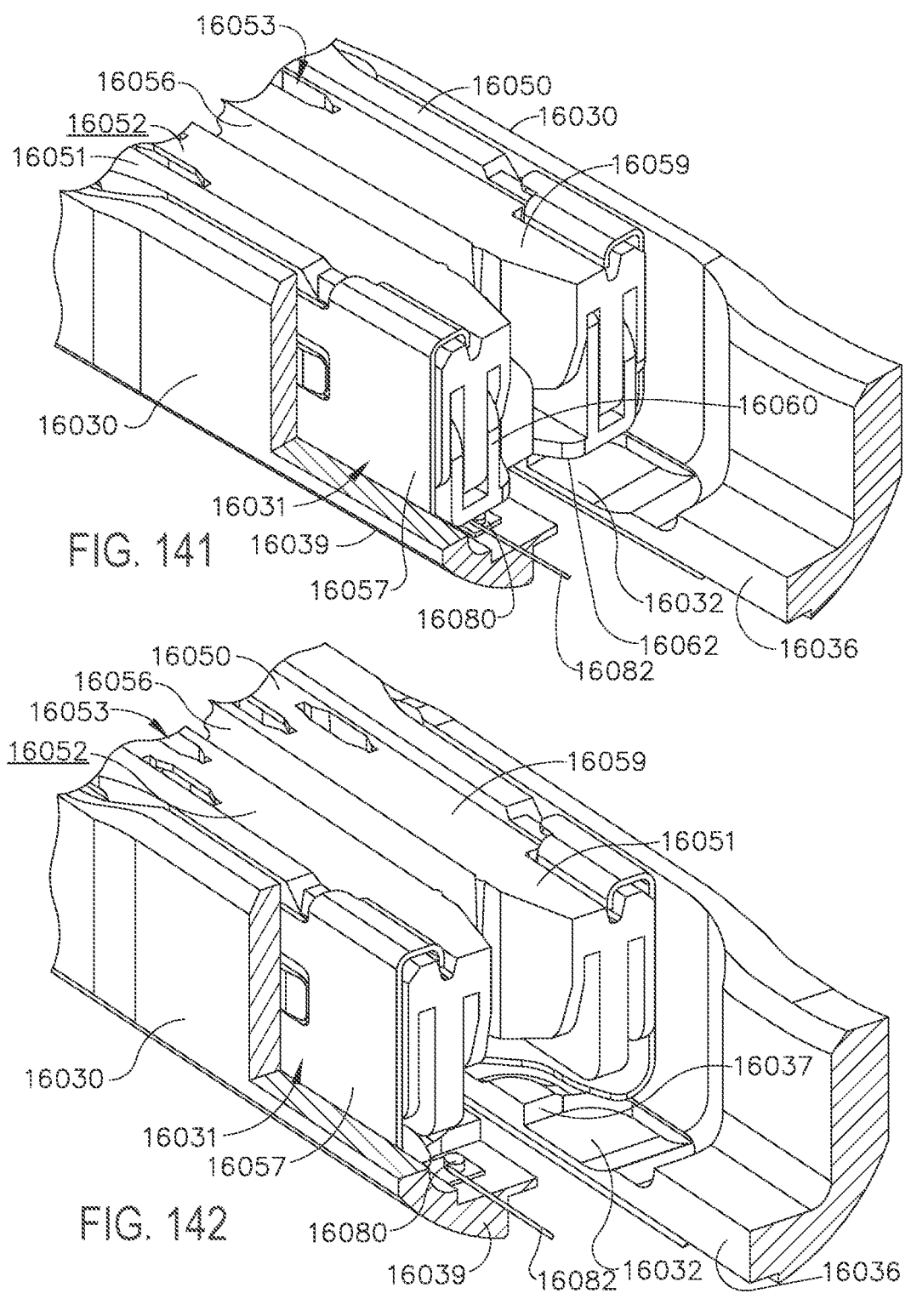
Figure 143:
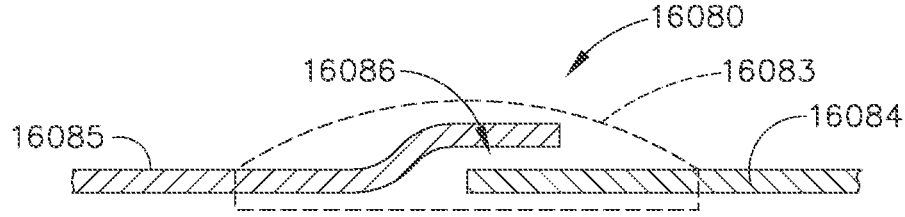
Figure 144:
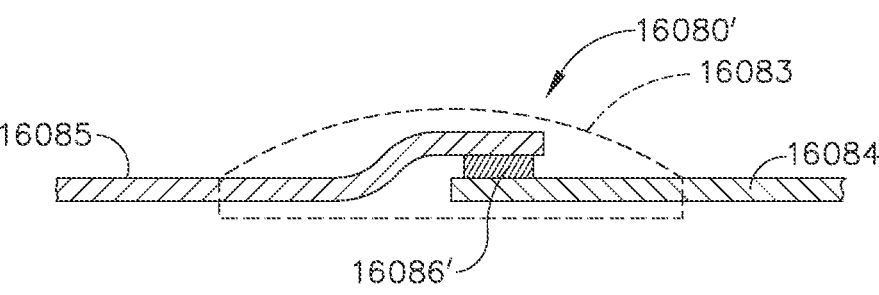

7 operably coupled to the motor shaft, and power generation means mounted to the motor shaft in accordance with at least one embodiment;

FIG. 133 depicts the motor shaft of FIG. 132 which includes a strain gauge and means for transmitting information from the motor shaft, i.e., a rotating plane, to a stationary plane mounted to the motor shaft and, in addition, means for interpreting the information being transmitted from the motor shaft;

FIG. 134 is a perspective view of an end effector of a surgical stapling instrument including a cartridge channel, a staple cartridge positioned in the cartridge channel, and an anvil;

FIG. 135 is a cross-sectional elevational view of the surgical stapling instrument of FIG. 134 illustrating a sled and a firing member in an unfired position;

FIG. 136 is a detail view depicting the sled of FIG. 135 in a partially advanced position and the firing member in its unfired position;

FIG. 137 is a perspective view of the staple cartridge of FIG. 134 prior to being inserted into the cartridge channel of FIG. 134;

FIG. 138 is a perspective view of the staple cartridge of FIG. 134 fully seated in the cartridge channel of FIG. 134;

FIG. 139 is a schematic of the staple cartridge and cartridge channel of FIG. 134 and the sled and the firing member of FIG. 135 depicting a m is-insertion of the staple cartridge into the cartridge channel and the effect on the sled that such a m is-insertion can cause;

FIG. 140 is a partial perspective view of an end effector of a surgical stapling instrument in accordance with at least one embodiment including a sensor configured to sense whether a staple cartridge has been m is-inserted in the manner depicted in FIG. 139;

FIG. 141 is a partial perspective view of an end effector of a surgical stapling instrument in accordance with at least one embodiment including a sensor configured to detect whether the sled has been unintentionally advanced;

FIG. 142 is a partial perspective view of the end effector of FIG. 141 illustrating the sled in an unintentionally advanced position;

FIG. 143 is a cross-sectional view of the sensor of FIG. 141 in accordance with at least one embodiment; and FIG. 144 is a cross-sectional view of the sensor of FIG. 141 in accordance with at least one alternative embodiment.

DESCRIPTION

Applicant of the present application owns the following patent applications that were filed on Mar. 6, 2015 and which are each herein incorporated by reference in their respective entireties:

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;

U.S. patent application Ser. No. 14/640,831, entitled MONITORING SPEED CONTROL AND PRECI-

8

SION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,780, entitled SURGICAL INSTRUMENT COMPRISING A LOCKABLE BATTERY HOUSING, now U.S. Pat. No. 10,245,033;

U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412; and U.S. patent application Ser. No. 14/640,799, entitled SIGNAL AND POWER COMMUNICATION SYSTEM POSITIONED ON A ROTATABLE SHAFT, now U.S. Pat. No. 9,901,342.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAIL-OUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTER-ACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEG-MENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled USE OF POLARITY OF HALL MAGNET DETECTION TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STA-BILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOS-ING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERA-TION OF THE SURGICAL INSTRUMENT, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

The present disclosure provides an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples. The features illustrated or described in connection with one example may be combined with the features of other examples. Such modifications and variations are intended to be included within the scope of the present disclosure.

Reference throughout the specification to "various aspects," "some aspects," "one aspect," or "an aspect", or the like, means that a particular feature, structure, or characteristic described in connection with the aspect is included in at least one aspect. Thus, appearances of the phrases "in various aspects," "in some aspects," "in one aspect", or "in an aspect", or the like, in places throughout the specification are not necessarily all referring to the same aspect. Furthermore, the particular features, structures, or characteristics may be combined in any suitable manner in one or more aspects. Thus, the particular features, structures, or characteristics illustrated or described in connection with one aspect may be combined, in whole or in part, with the features structures, or characteristics of one or more other aspects without limitation. Such modifications and variations are intended to be included within the scope of the present disclosure.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIGS. 1-6 depict a motor-driven surgical cutting and fastening instrument 10 that may or may not be reused. In the illustrated examples, the instrument 10 includes a housing 12 that comprises a handle assembly 14 that is configured to be grasped, manipulated and actuated by the clinician. The housing 12 is configured for operable attachment to an interchangeable shaft assembly 200 that has a surgical end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" also may represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

Figure 1:
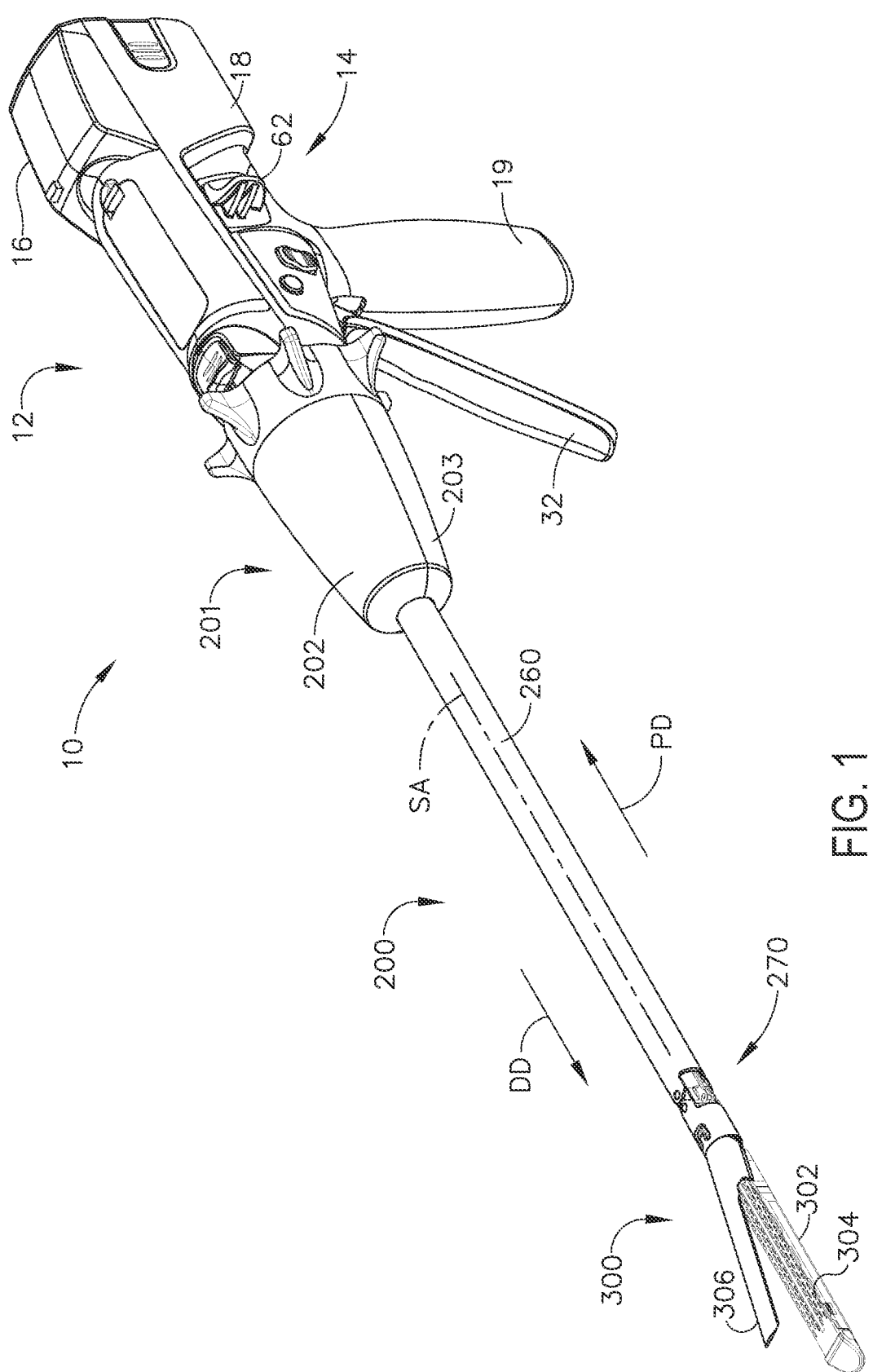
FIG. 1 is a perspective view of a surgical instrument that has an interchangeable shaft assembly operably coupled thereto.
Figure 2:
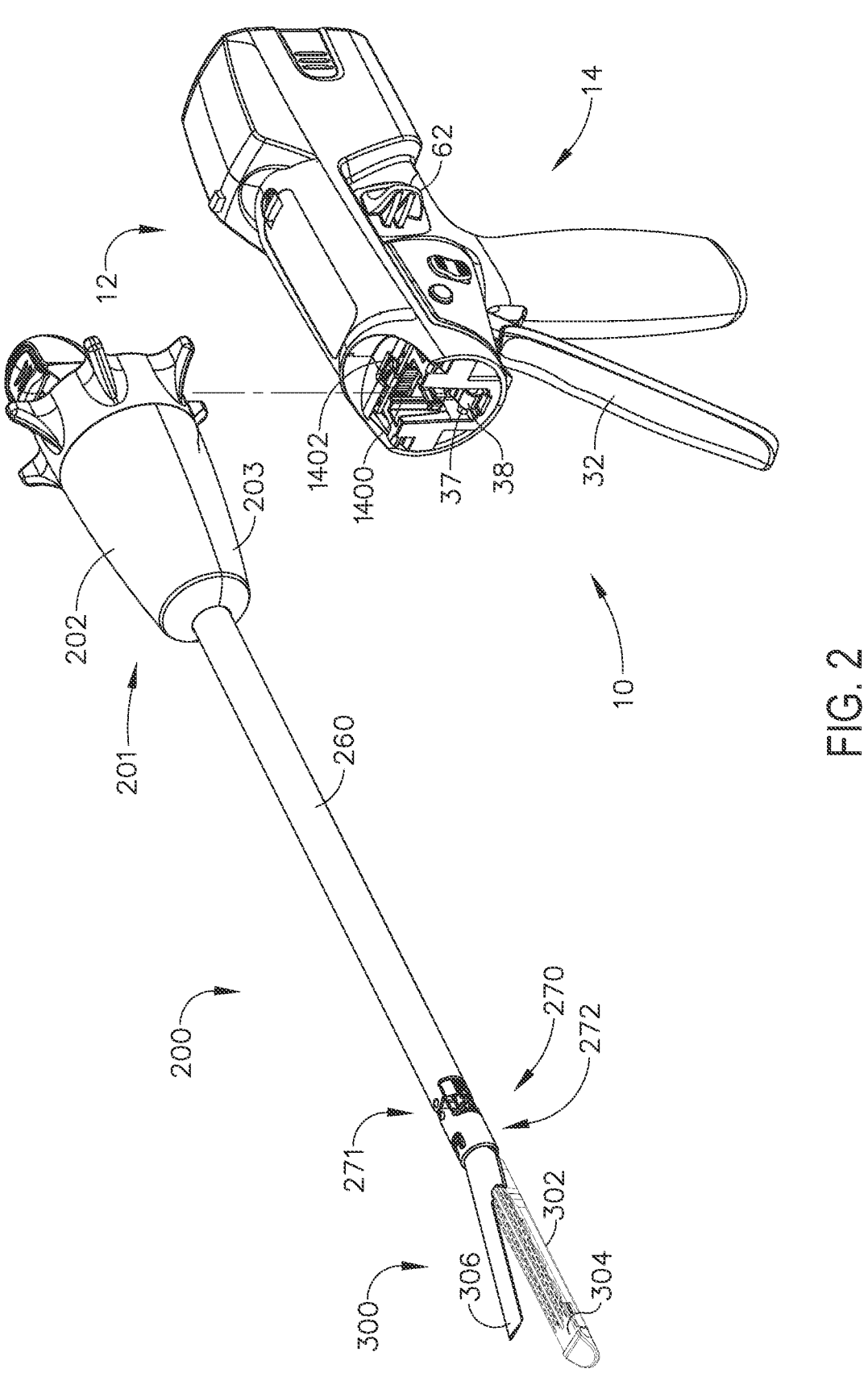
FIG. 2 is an exploded assembly view of the interchangeable shaft assembly and surgical instrument of FIG. 1.
Figure 3:
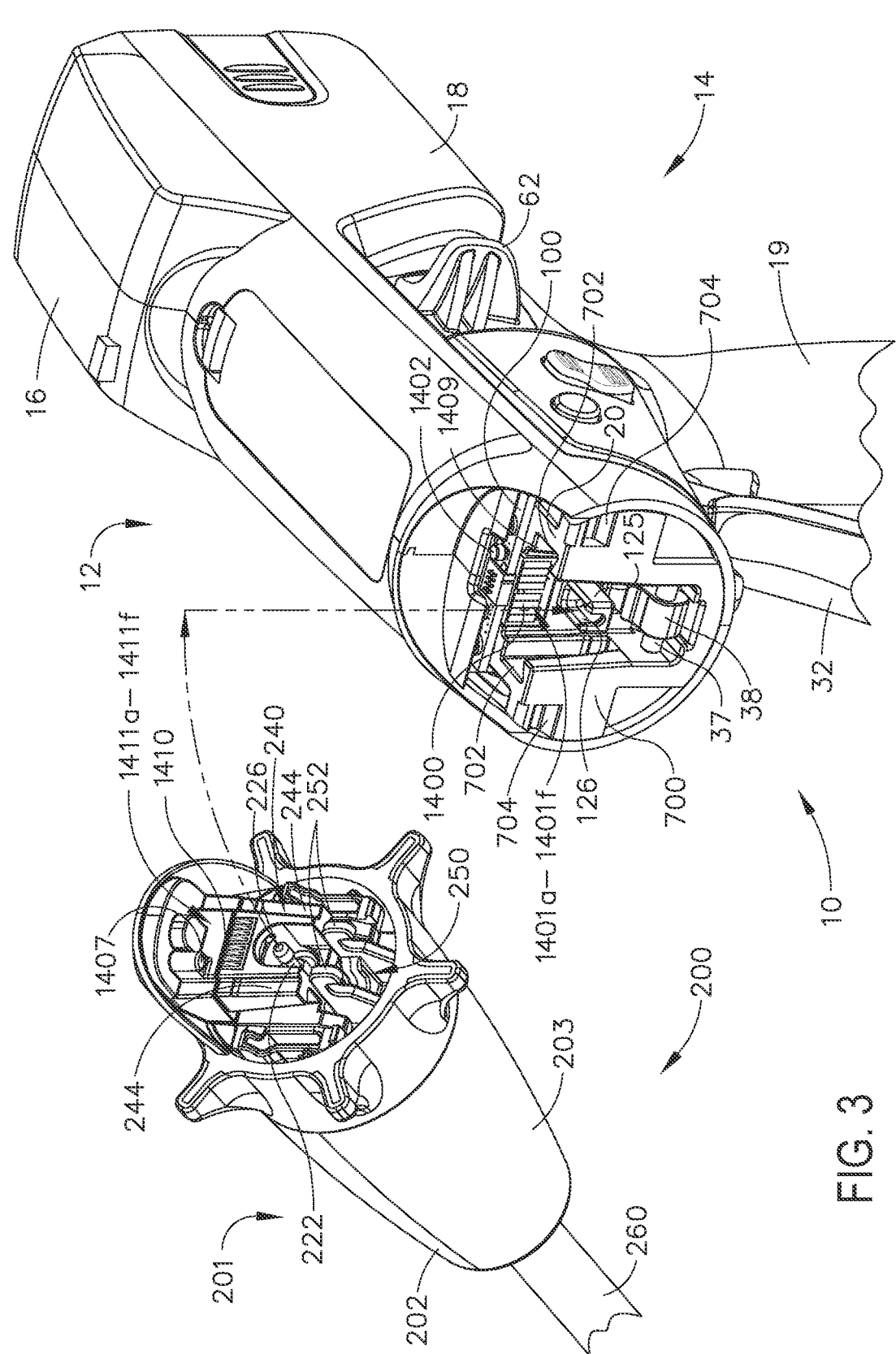
FIG. 3 is another exploded assembly view showing portions of the interchangeable shaft assembly and surgical instrument of FIGS. 1 and 2.

The housing 12 depicted in FIGS. 1-3 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
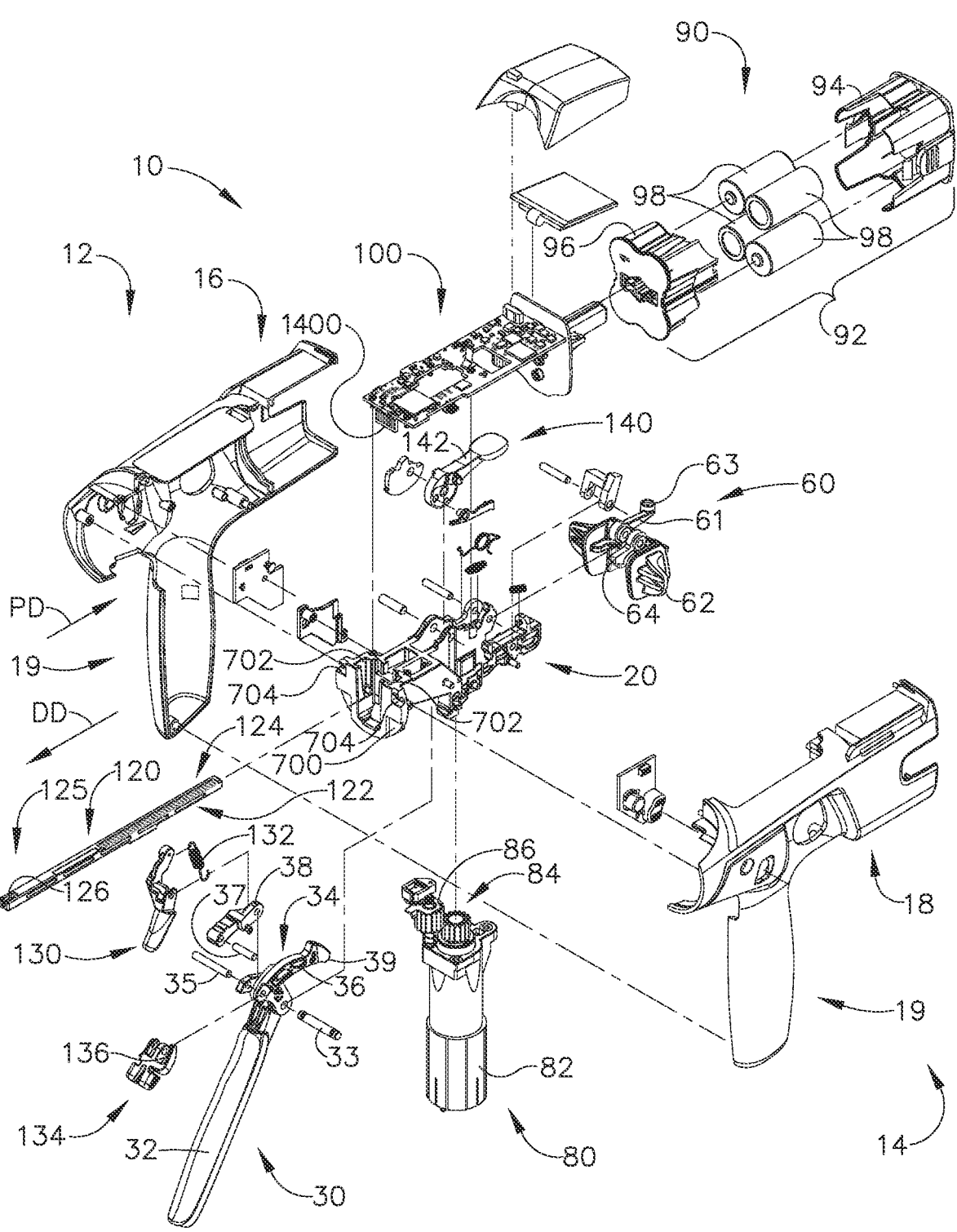
FIG. 4 is an exploded assembly view of a portion of the surgical instrument of FIGS. 1-3.

FIG. 1 illustrates the surgical instrument 10 with an interchangeable shaft assembly 200 operably coupled thereto. FIGS. 2 and 3 illustrate attachment of the interchangeable shaft assembly 200 to the housing 12 or handle assembly 14. As shown in FIG. 4, the handle assembly 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle assembly 14 operably supports a plurality of drive systems therein that are configured to generate and apply various control motions to corresponding portions of the interchangeable shaft assembly that is operably attached thereto.

Referring now to FIG. 4, the handle assembly 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the housing 14 by a pin 33. Such arrangement enables the closure trigger 32 to be manipulated by a clinician such that when the clinician grips the pistol grip portion 19 of the handle assembly 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As shown in FIG. 4, the closure linkage assembly 34 may include a first closure link 36 and a second closure link 38 that are pivotally coupled to the closure trigger 32 by a pin 35. The second closure link 38 also may be referred to herein as an "attachment member" and include a transverse attachment pin 37.

Still referring to FIG. 4, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle assembly 14, the first closure link 36 pivots upward to a point wherein the locking pawl 64 drops into retaining engagement with the locking wall 39 on the first closure link 36 thereby preventing the closure trigger 32 from returning to the unactuated position. See FIG. 18. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements also may be employed.

Figure 13:
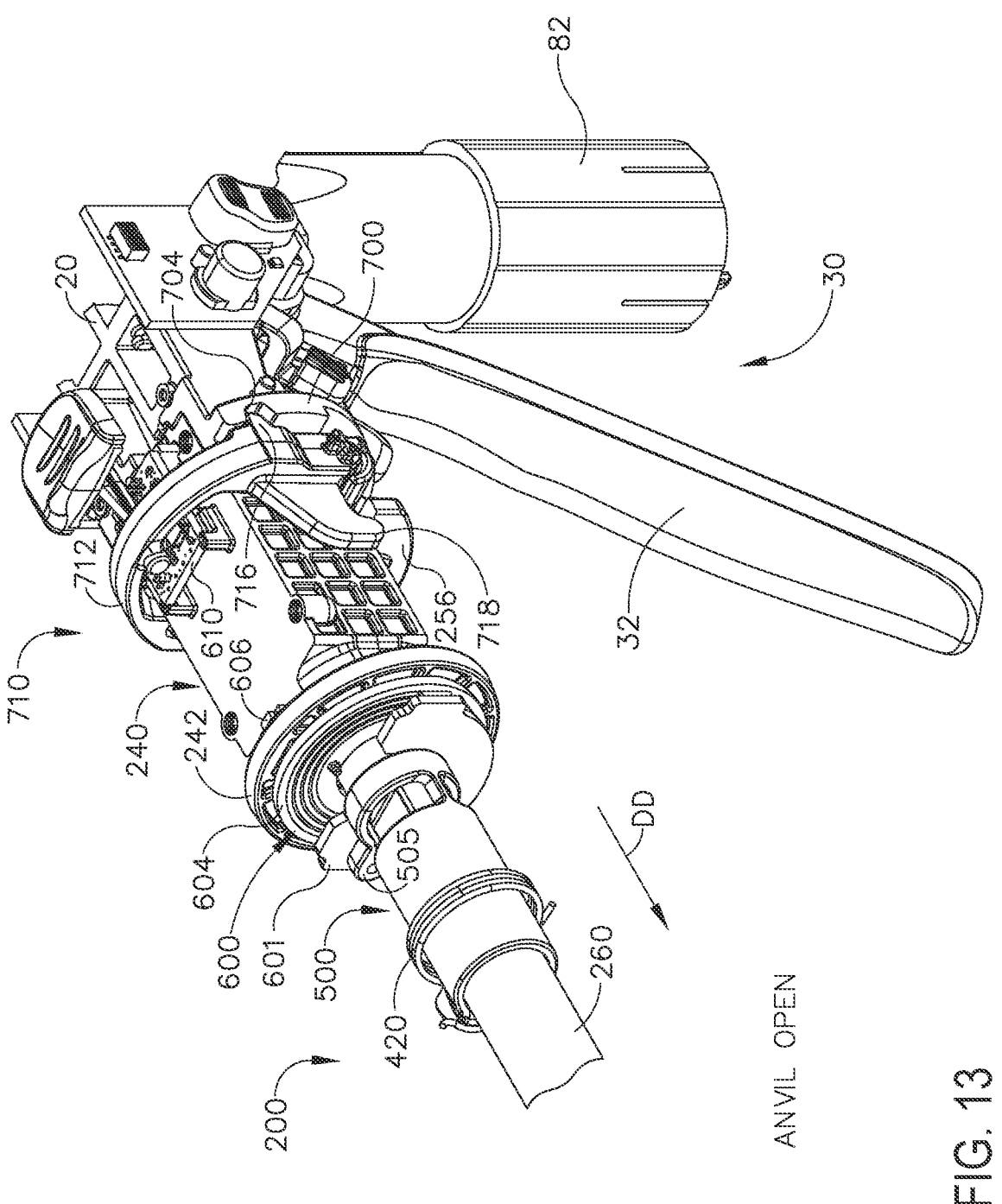
FIG. 13 is a perspective view of a portion of the interchangeable shaft assembly of FIG. 11 operably coupled to a portion of the surgical instrument of FIG. 1 illustrated with the closure trigger thereof in an unactuated position.
Figure 14:
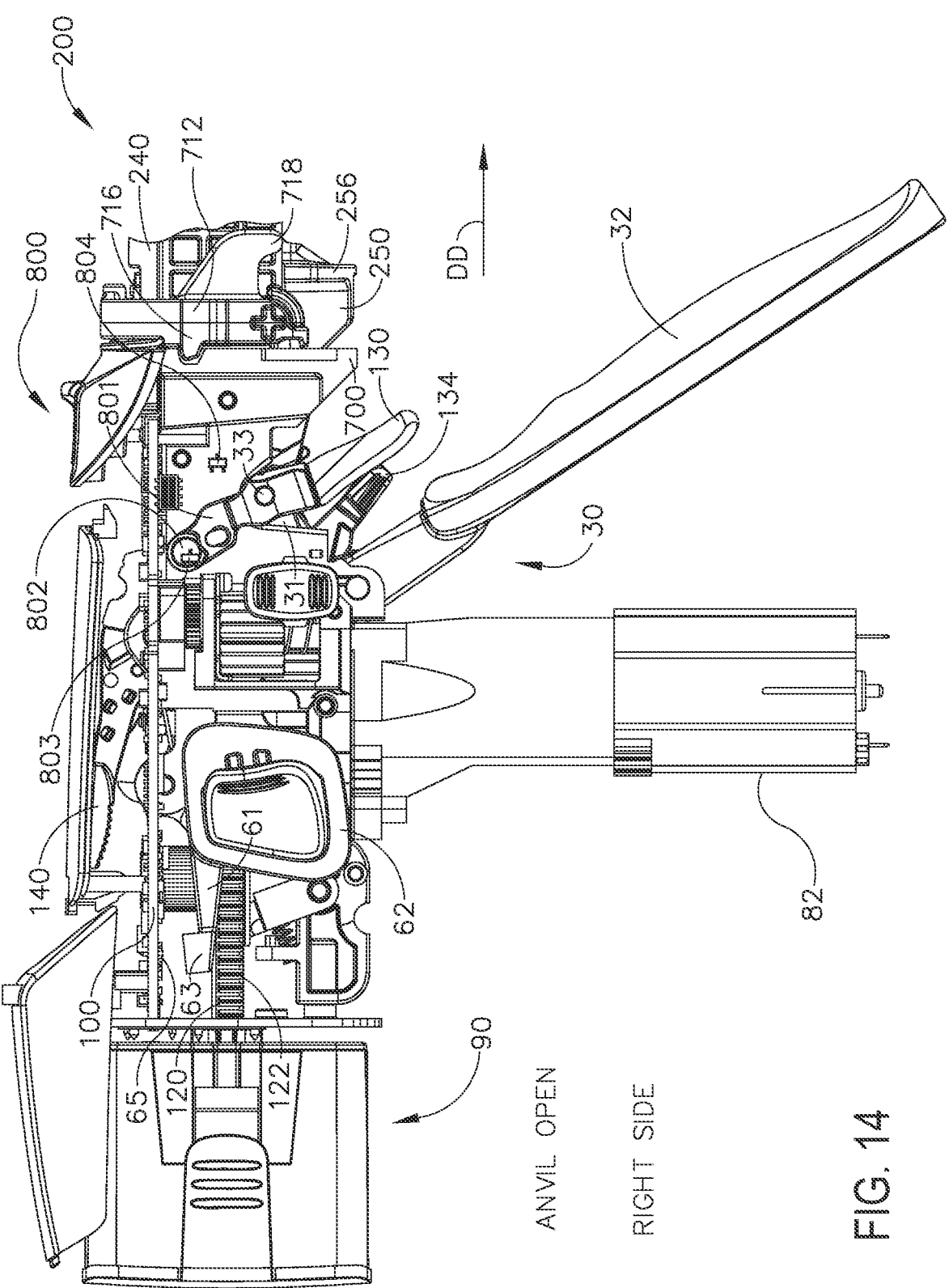
FIG. 14 is a right side elevational view of the interchangeable shaft assembly and surgical instrument of FIG. 13.
Figure 15:
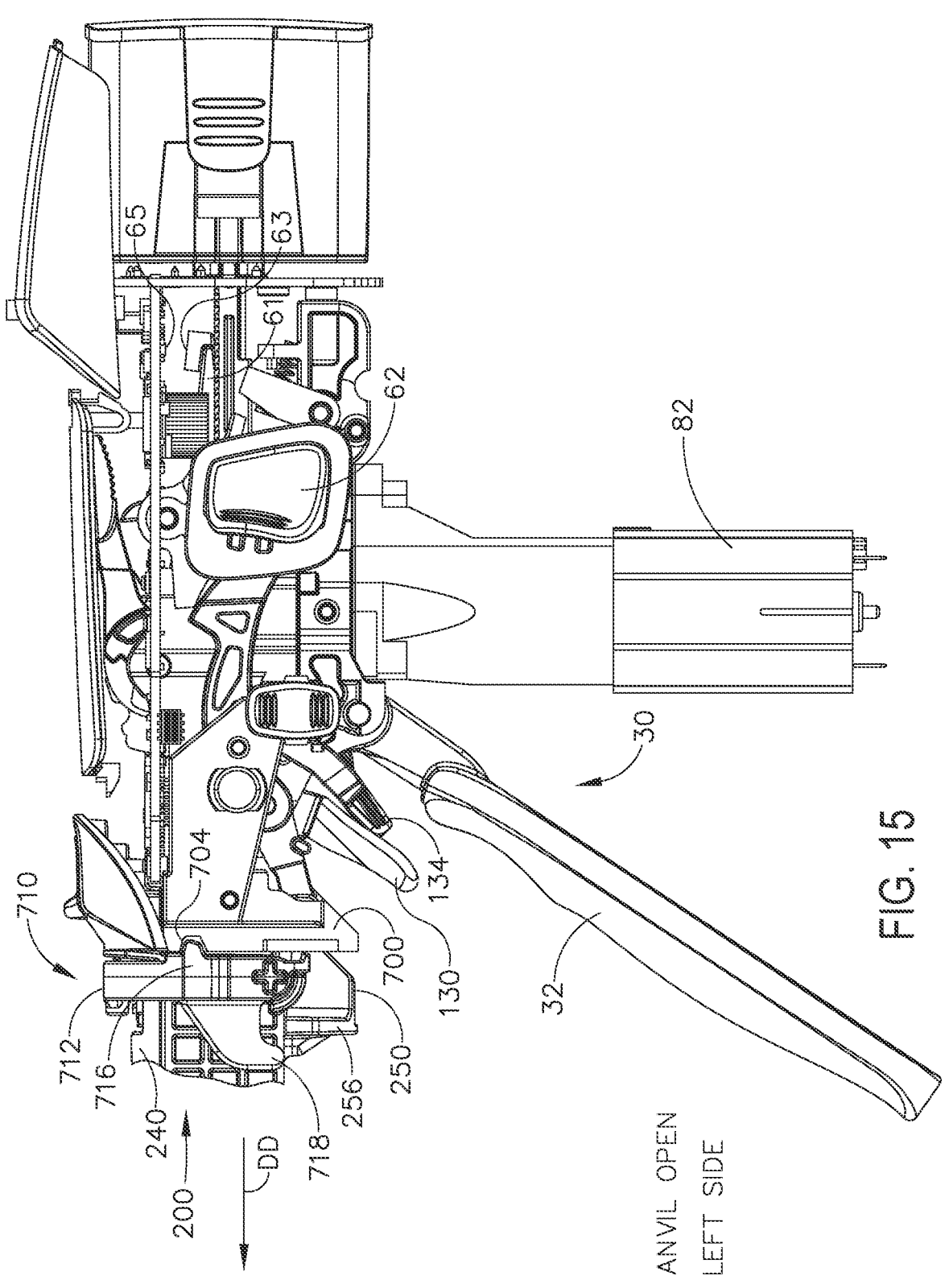
FIG. 15 is a left side elevational view of the interchangeable shaft assembly and surgical instrument of FIGS. 13 and 14.
Figure 16:
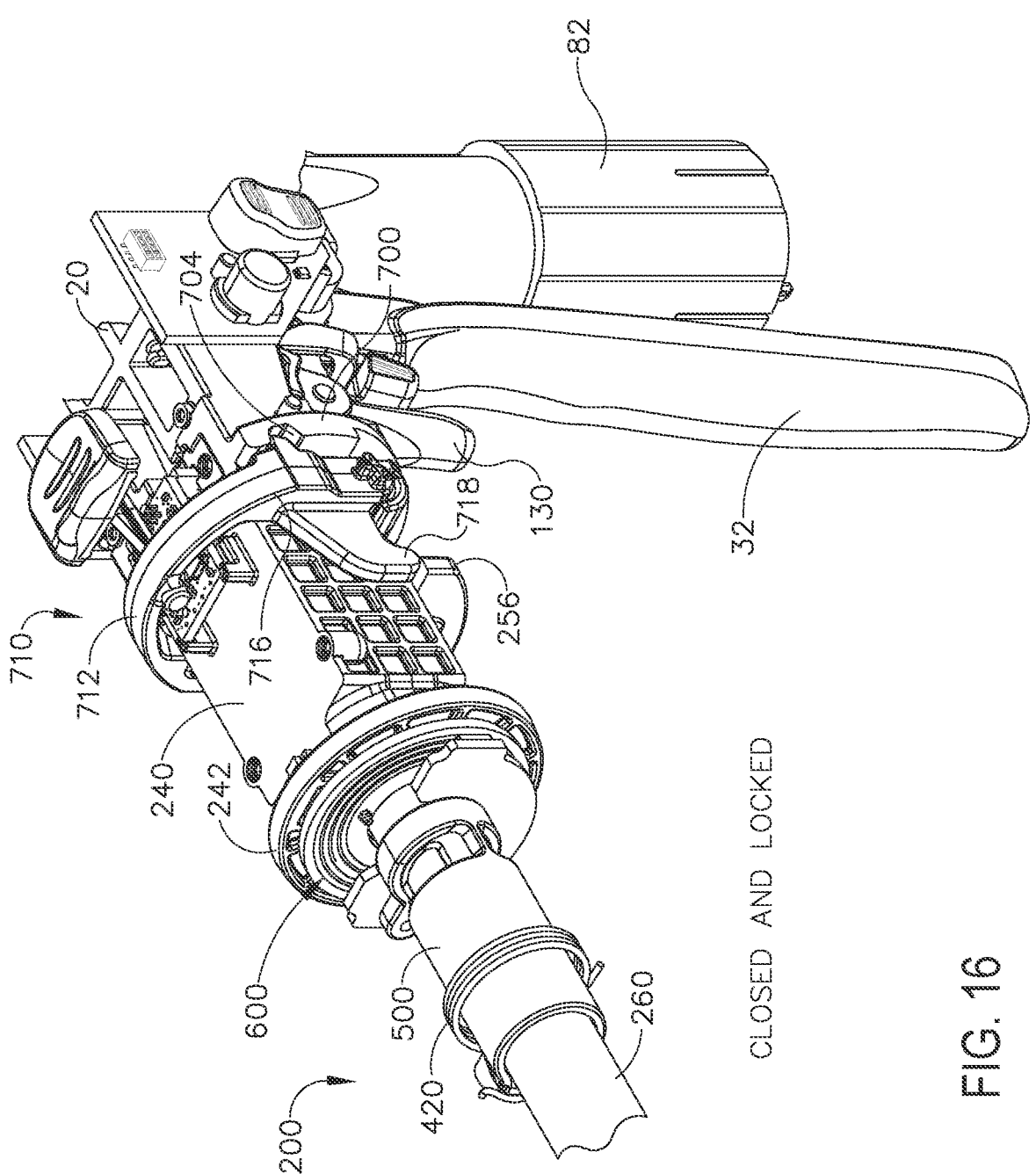
FIG. 16 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position.
Figure 17:
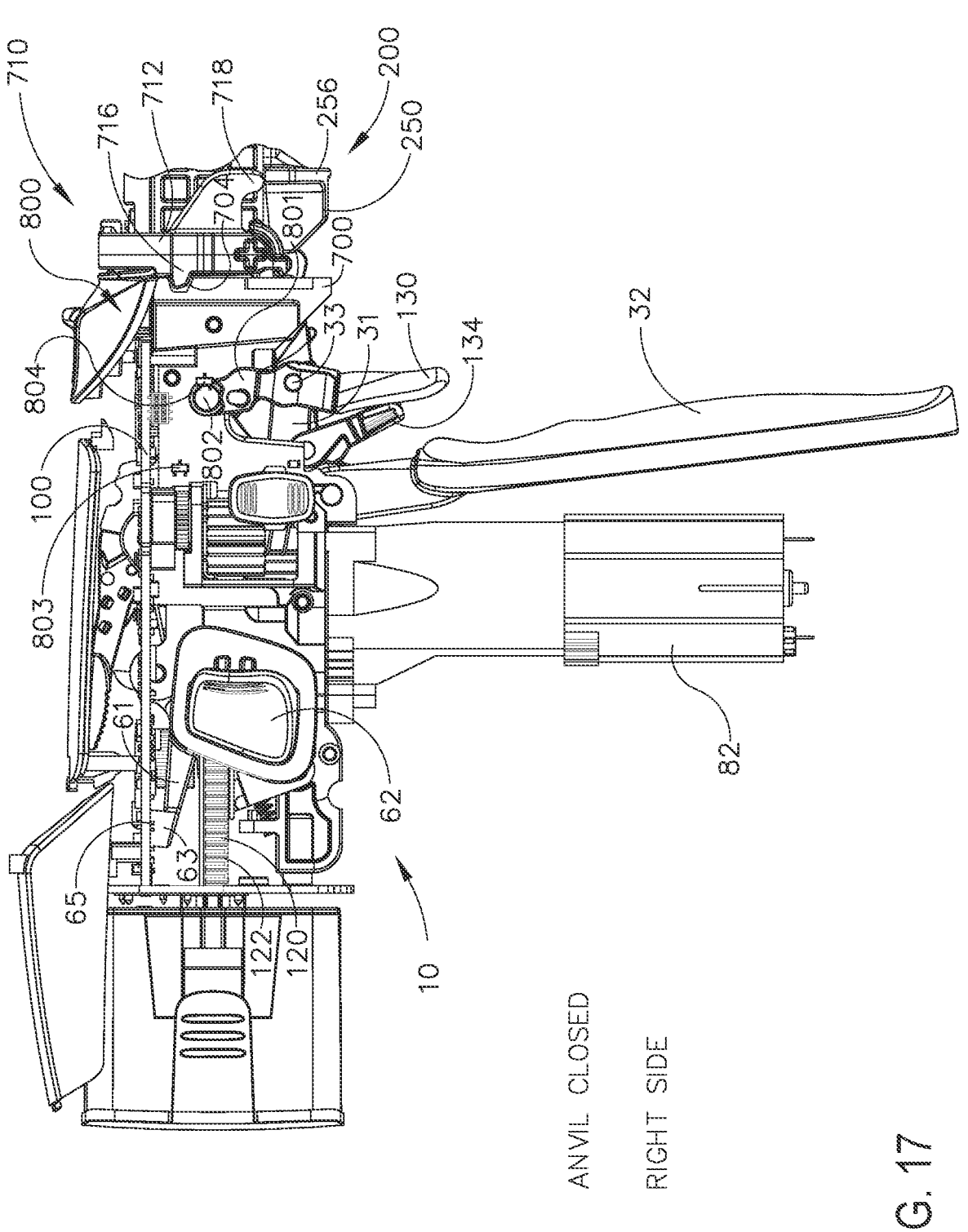
FIG. 17 is a right side elevational view of the interchangeable shaft assembly and surgical instrument of FIG. 16.
Figure 18:
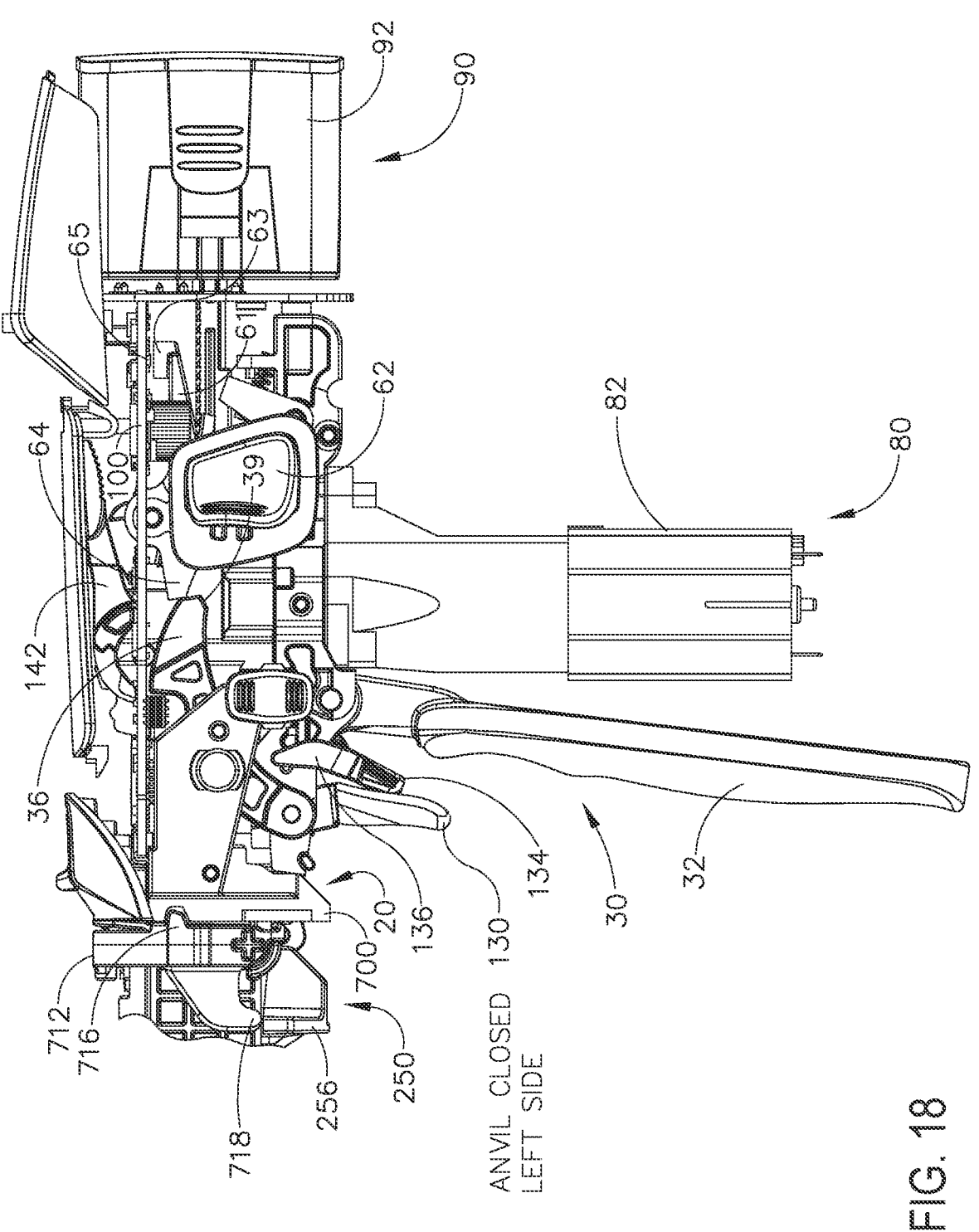
FIG. 18 is a left side elevational view of the interchangeable shaft assembly and surgical instrument of FIGS. 16 and 17.

Further to the above, FIGS. 13-15 illustrate the closure trigger 32 in its unactuated position which is associated with an open, or unclamped, configuration of the shaft assembly 200 in which tissue can be positioned between the jaws of the shaft assembly 200. FIGS. 16-18 illustrate the closure trigger 32 in its actuated position which is associated with a closed, or clamped, configuration of the shaft assembly 200 in which tissue is clamped between the jaws of the shaft assembly 200. Upon comparing FIGS. 14 and 17, the reader will appreciate that, when the closure trigger 32 is moved from its unactuated position (FIG. 14) to its actuated position (FIG. 17), the closure release button 62 is pivoted between a first position (FIG. 14) and a second position (FIG. 17). The rotation of the closure release button 62 can be referred to as being an upward rotation; however, at least a portion of the closure release button 62 is being rotated toward the circuit board 100. Referring to FIG. 4, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor configured to detect the movement of the magnetic element 63. In at least one aspect, a magnetic field sensor 65, for example, can be mounted to the bottom surface of the circuit board 100. The magnetic field sensor 65 can be configured to detect changes in a magnetic field surrounding the magnetic field sensor 65 caused by the movement of the magnetic element 63. The magnetic field sensor 65 can be in signal communication with a microcontroller 1500 (FIG. 19), for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

As used throughout the present disclosure, a magnetic field sensor may be a Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In at least one form, the handle assembly 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle assembly 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As shown in FIG. 4, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle assembly 14 can include a switch which can be configured to reverse the polarity applied to the electric motor 82 by the power source 90. As with the other forms described herein, the handle assembly 14 can also include a sensor that is configured to detect the position of the drive member 120 and/or the direction in which the drive member 120 is being moved.

Actuation of the motor 82 can be controlled by a firing trigger 130 that is pivotally supported on the handle assembly 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 4. When the closure trigger 32 is in the unactuated position, the safety button 134 is contained in the handle assembly 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle assembly 14 can include a closure trigger 32 and a firing trigger 130. Referring to FIGS. 14-18A, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 14) to its actuated position (FIG. 17), the firing trigger 130 can descend downwardly, as outlined above. After the safety button 134 has been moved to its firing position, referring primarily to FIG. 18A, the firing trigger 130 can be depressed to operate the motor of the surgical instrument firing system. In various instances, the handle assembly 14 can include a tracking system, such as system 800, for example, configured to determine the position of the closure trigger 32 and/or the position of the firing trigger 130. With primary reference to FIGS. 14, 17, and 18A, the tracking system 800 can include a magnetic element, such as permanent magnet 802, for example, which is mounted to an arm 801 extending from the firing trigger 130. The tracking system 800 can comprise one or more sensors, such as a first magnetic field sensor 803 and a second magnetic field sensor 804, for example, which can be configured to track the position of the magnet 802.

Upon comparing FIGS. 14 and 17, the reader will appreciate that, when the closure trigger 32 is moved from its unactuated position to its actuated position, the magnet 802 can move between a first position adjacent the first magnetic field sensor 803 and a second position adjacent the second magnetic field sensor 804.

Figure 18A:
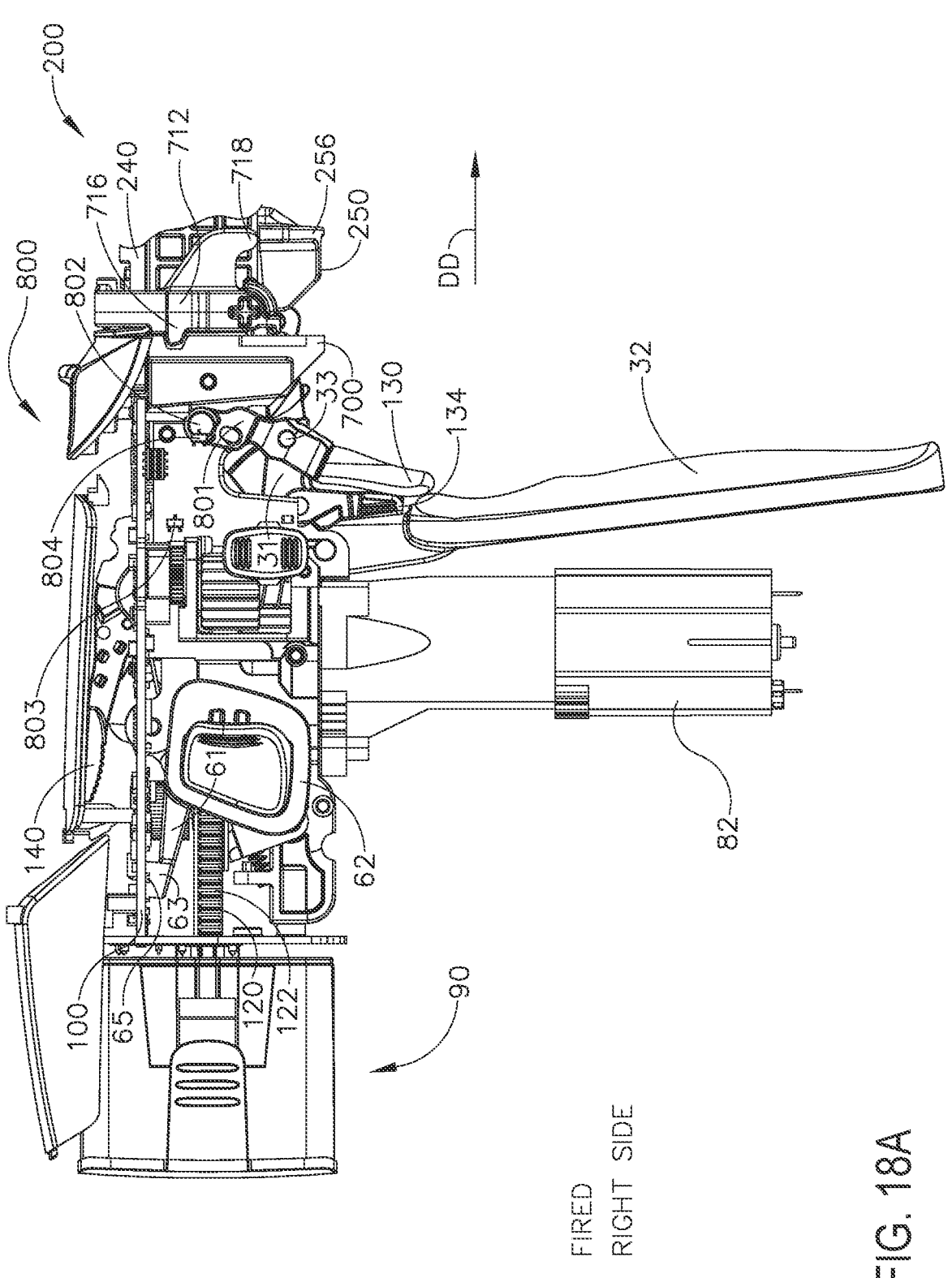
FIG. 18A is a right side elevational view of the interchangeable shaft assembly of FIG. 11 operably coupled to a portion of the surgical instrument of FIG. 1 illustrated with the closure trigger thereof in an actuated position and the firing trigger thereof in an actuated position.

Upon comparing FIGS. 17 and 18A, the reader will further appreciate that, when the firing trigger 130 is moved from an unfired position (FIG. 17) to a fired position (FIG. 18A), the magnet 802 can move relative to the second magnetic field sensor 804. The sensors 803 and 804 can track the movement of the magnet 802 and can be in signal communication with a microcontroller on the circuit board 100. With data from the first sensor 803 and/or the second sensor 804, the microcontroller can determine the position of the magnet 802 along a predefined path and, based on that position, the microcontroller can determine whether the closure trigger 32 is in its unactuated position, its actuated position, or a position therebetween. Similarly, with data from the first sensor 803 and/or the second sensor 804, the microcontroller can determine the position of the magnet 802 along a predefined path and, based on that position, the microcontroller can determine whether the firing trigger 130 is in its unfired position, its fully fired position, or a position therebetween.

As indicated above, in at least one form, the longitudinally movable drive member 120 has a rack of teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 14 that is configured to be manually pivoted into ratcheting engagement with teeth 124 also provided in the drive member 120. Thus, the clinician can manually retract the drive member 120 by using the bailout handle assembly 14 to ratchet the drive member 120 in the proximal direction "PD". U.S. Patent Application Publication No. 2010/0089970, now U.S. Pat. No. 8,608,045 discloses bailout arrangements and other components, arrangements and systems that also may be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, U.S. Patent Application Publication No. 2010/0089970, now U.S. Pat. No. 8,608,045, is hereby incorporated by reference in its entirety.

Figure 7:
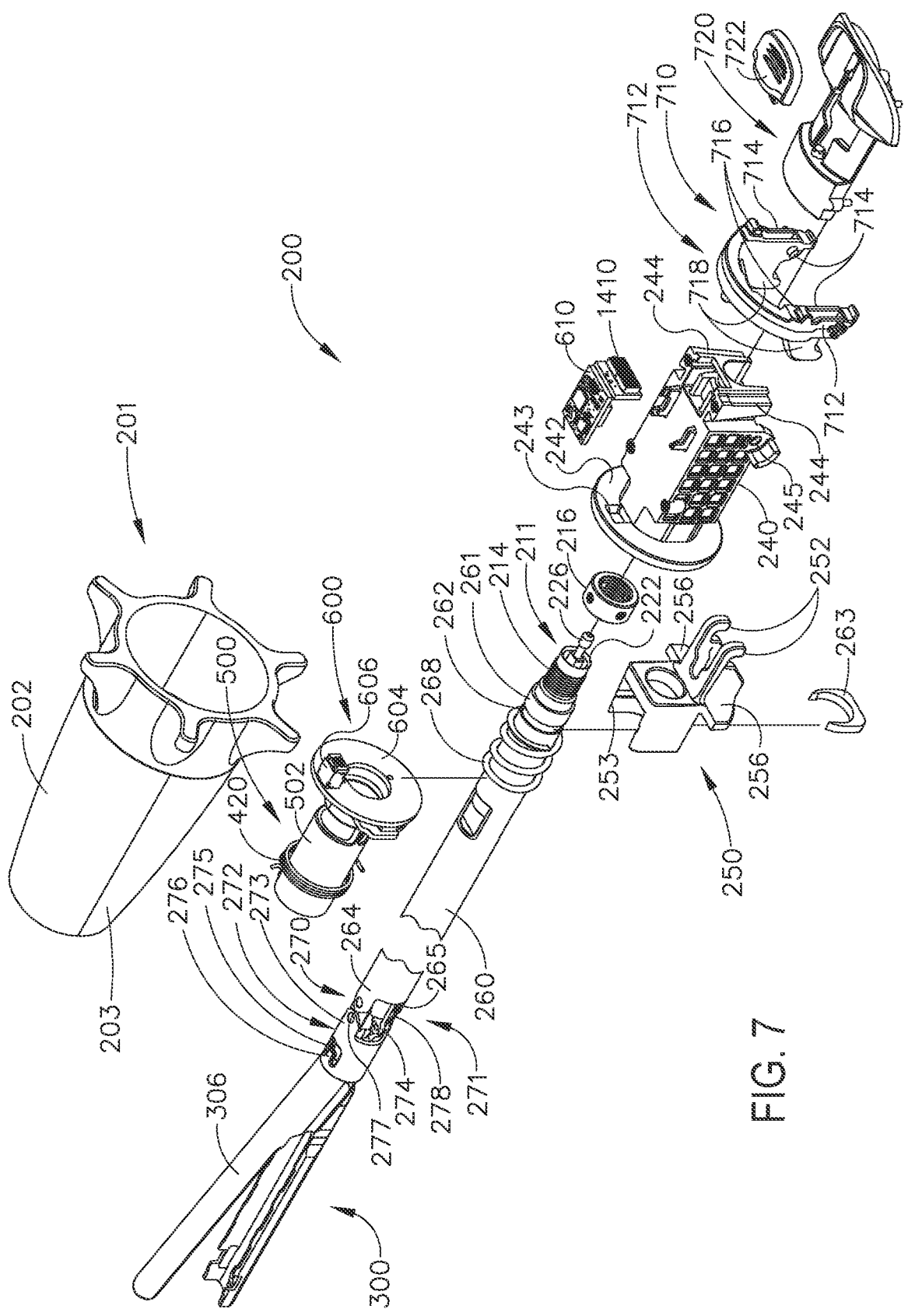
FIG. 7 is an exploded assembly view of one form of an interchangeable shaft assembly.
Figure 8:
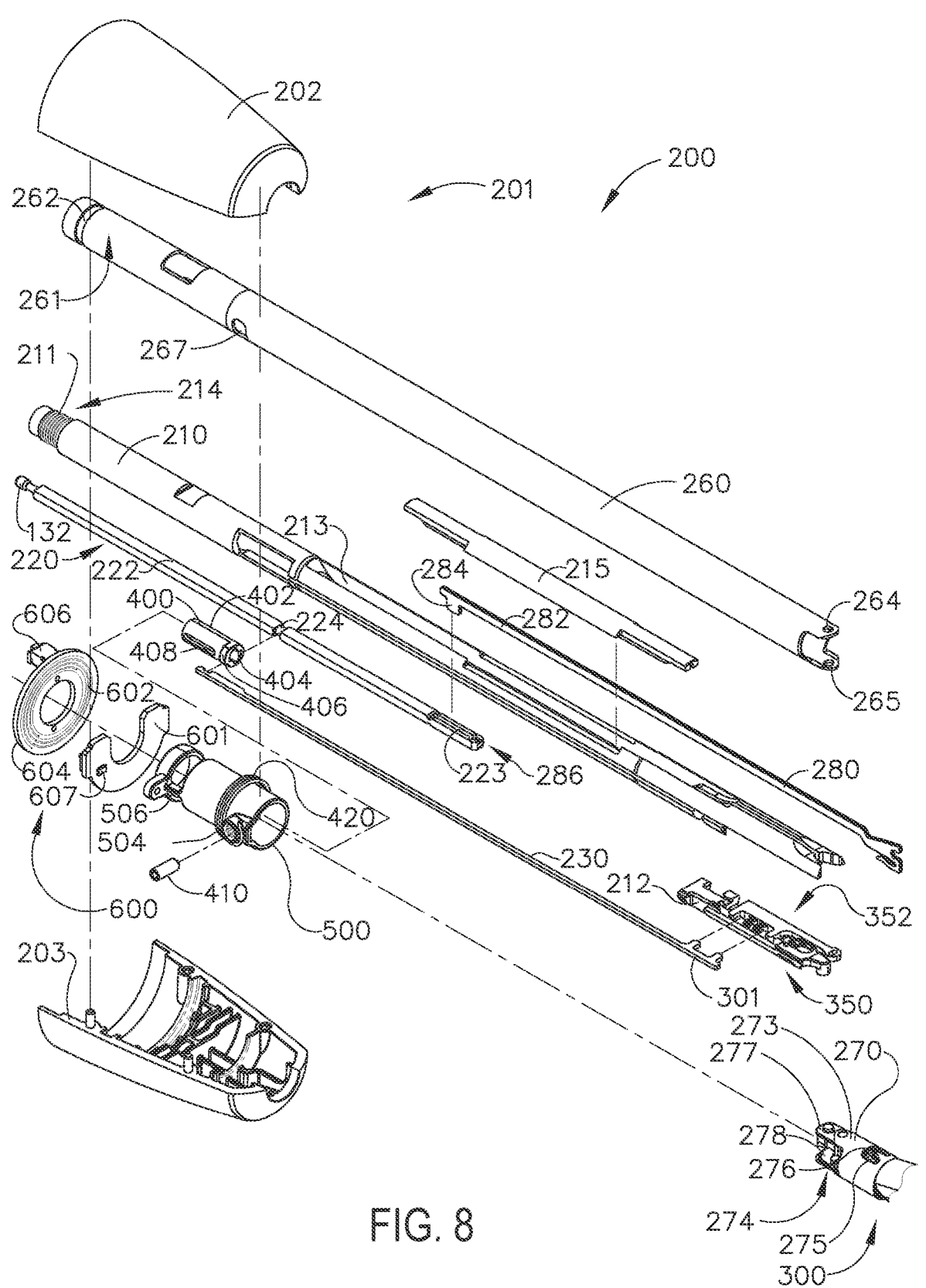
FIG. 8 is another exploded assembly view of portions of the interchangeable shaft assembly of FIG. 7.

Turning now to FIGS. 1 and 7, the interchangeable shaft assembly 200 includes a surgical end effector 300 that comprises an elongated channel 302 that is configured to operably support a staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 8) which can be configured to releasably hold the end effector 300 in a desired position relative to a shaft axis SA-SA. Details regarding the construction and operation of the end effector 300, the articulation joint 270 and the articulation lock 350 are set forth in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As shown in FIGS. 7 and 8, the interchangeable shaft assembly 200 can further include a proximal housing or nozzle 201 comprised of nozzle portions 202 and 203. The interchangeable shaft assembly 200 can further include a closure tube 260 which can be utilized to close and/or open the anvil 306 of the end effector 300. Primarily referring now to FIGS. 8 and 9, the shaft assembly 200 can include a spine 210 which can be configured to fixably support a shaft frame portion 212 of the articulation lock 350. See FIG. 8. The spine 210 can be configured to, one, slidably support a firing member 220 therein and, two, slidably support the closure tube 260 which extends around the spine 210. The spine 210 can also be configured to slidably support a proximal articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. patent application Ser. No. 13/803,086, now U.S. Patent Application Publication No. 2014/0263541. In various circumstances, the spine 210 can comprise a proximal end 211 which is rotatably supported in a chassis 240. In one arrangement, for example, the proximal end 211 of the spine

210 has a thread 214 formed thereon for threaded attachment to a spine bearing 216 configured to be supported within the chassis 240. See FIG. 7. Such an arrangement facilitates rotatable attachment of the spine 210 to the chassis 240 such that the spine 210 may be selectively rotated about a shaft axis SA-SA relative to the chassis 240.

Referring primarily to FIG. 7, the interchangeable shaft assembly 200 includes a closure shuttle 250 that is slidably supported within the chassis 240 such that it may be axially moved relative thereto. As shown in FIGS. 3 and 7, the closure shuttle 250 includes a pair of proximally-protruding hooks 252 that are configured for attachment to the attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. See FIG. 7. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle assembly 14.

In at least one form, the interchangeable shaft assembly 200 may further include an articulation joint 270. Other interchangeable shaft assemblies, however, may not be capable of articulation. As shown in FIG. 7, for example, the articulation joint 270 includes a double pivot closure sleeve assembly 271. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, which has been incorporated by reference herein. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 8.

In use, the closure tube 260 is translated distally (direction "DD") to close the anvil 306, for example, in response to the actuation of the closure trigger 32. The anvil 306 is closed by distally translating the closure tube 260 and thus the shaft closure sleeve assembly 272, causing it to strike a proximal surface on the anvil 360 in the manner described in the aforementioned reference U.S. patent application Ser. No. 13/803,086, now U.S. Patent Application Publication No. 2014/0263541. As was also described in detail in that reference, the anvil 306 is opened by proximally translating the closure tube 260 and the shaft closure sleeve assembly 272, causing tab 276 and the horseshoe aperture 275 to contact and push against the anvil tab to lift the anvil 306. In the anvil-open position, the shaft closure tube 260 is moved to its proximal position.

As indicated above, the surgical instrument 10 may further include an articulation lock 350 of the types and construction described in further detail in U.S. patent application Ser. No. 13/803,086, now U.S. Patent Application Publication No. 2014/0263541, which can be configured and operated to selectively lock the end effector 300 in position. Such arrangement enables the end effector 300 to be rotated, or articulated, relative to the shaft closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 also may be articulated relative to the closure tube 260 by an articulation driver 230.

Figure 9:
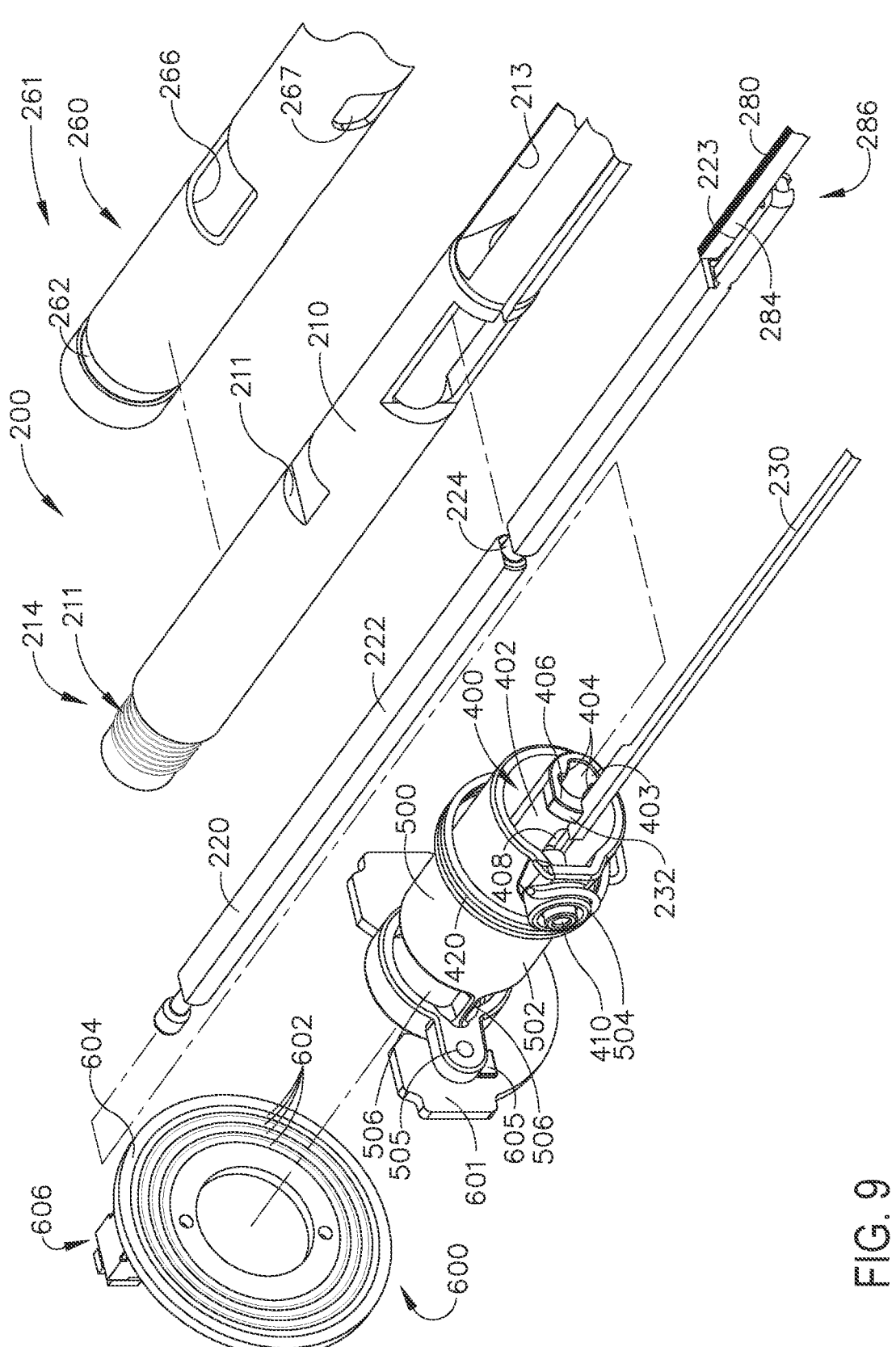
FIG. 9 is another exploded assembly view of portions of the interchangeable shaft assembly of FIGS. 7 and 8.

As was also indicated above, the interchangeable shaft assembly 200 further includes a firing member 220 that is supported for axial travel within the shaft spine 210. The firing member 220 includes an intermediate firing shaft portion 222 that is configured for attachment to a distal cutting portion or knife bar 280. The firing member 220 also may be referred to herein as a "second shaft" and/or a "second shaft assembly". As shown in FIGS. 8 and 9, the intermediate firing shaft portion 222 may include a longitudinal slot 223 in the distal end thereof which can be configured to receive a tab 284 on the proximal end 282 of the distal knife bar 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the end effector 300 without moving, or at least substantially moving, the knife bar 280. Once the end effector 300 has been suitably oriented, the intermediate firing shaft portion 222 can be advanced distally until a proximal sidewall of the longitudinal slot 223 comes into contact with the tab 284 in order to advance the knife bar 280 and fire the staple cartridge positioned within the channel 302 As can be further seen in FIGS. 8 and 9, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and knife bar 280 therein. Further description of the operation of the firing member 220 may be found in U.S. patent application Ser. No. 13/803,086, now U.S. Patent Application Publication No. 2014/0263541.

Further to the above, the shaft assembly 200 can include a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Referring primarily to FIG. 9, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

Figure 10:
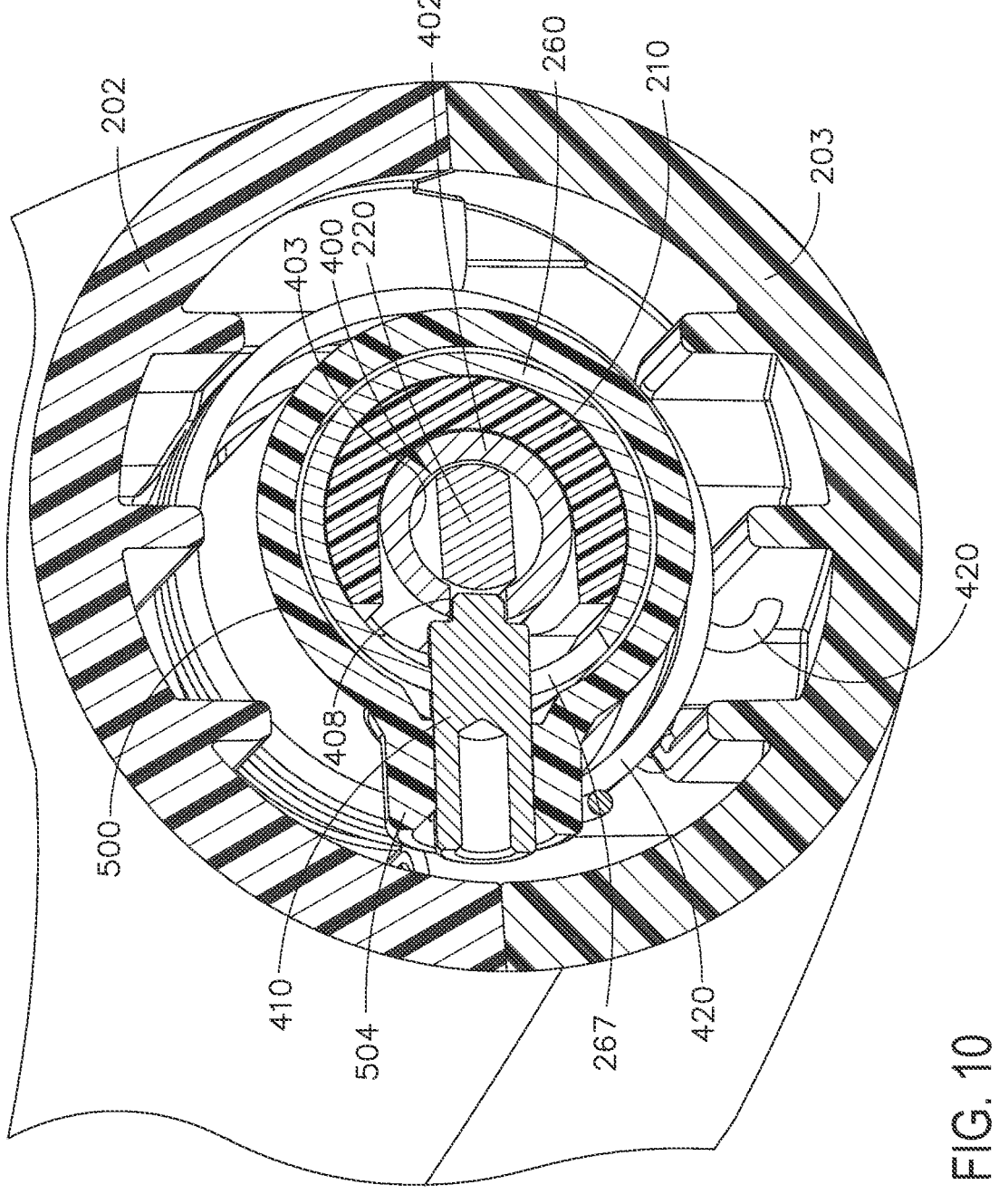
FIG. 10 is a cross-sectional view of a portion of the interchangeable shaft assembly of FIGS. 7-9.

As shown in FIGS. 8-12, the shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 10 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle halves 202, 203 and permit relative rotation, but not translation, between the switch drum 500 and the proximal nozzle 201. As shown in those Figures, the mounts 204 and 205 also extend through openings 266 in the closure tube 260 to be seated in recesses 211 in the shaft spine 210. However, rotation of the nozzle 201 to a point where the mounts 204, 205 reach the end of their respective slots 506 in the switch drum 500 will result in rotation of the switch drum 500 about the shaft axis SA-SA. Rotation of the switch drum 500 will ultimately result in the rotation of eth actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803, 086, now U.S. Patent Application Publication No. 2014/0263541.

As also illustrated in FIGS. 8-12, the shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481, is incorporated by reference in its entirety. Further details regarding slip ring assembly 600 may be found in U.S. patent application Ser. No. 13/803,086, now U.S. Patent Application Publication No. 2014/0263541.

Figure 11:
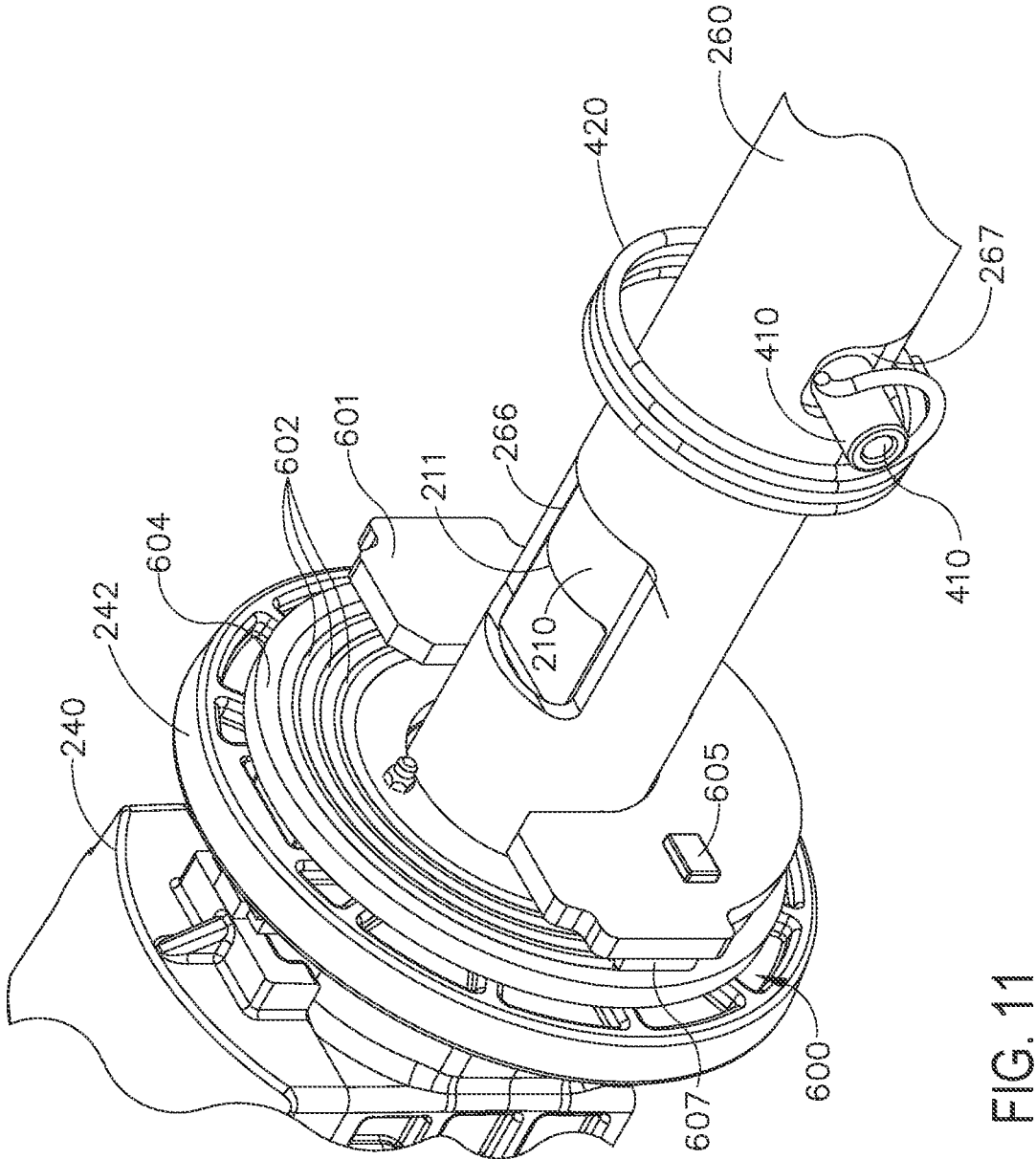
FIG. 11 is a perspective view of a portion of the shaft assembly of FIGS. 7-10 with the switch drum omitted for clarity.
Figure 12:
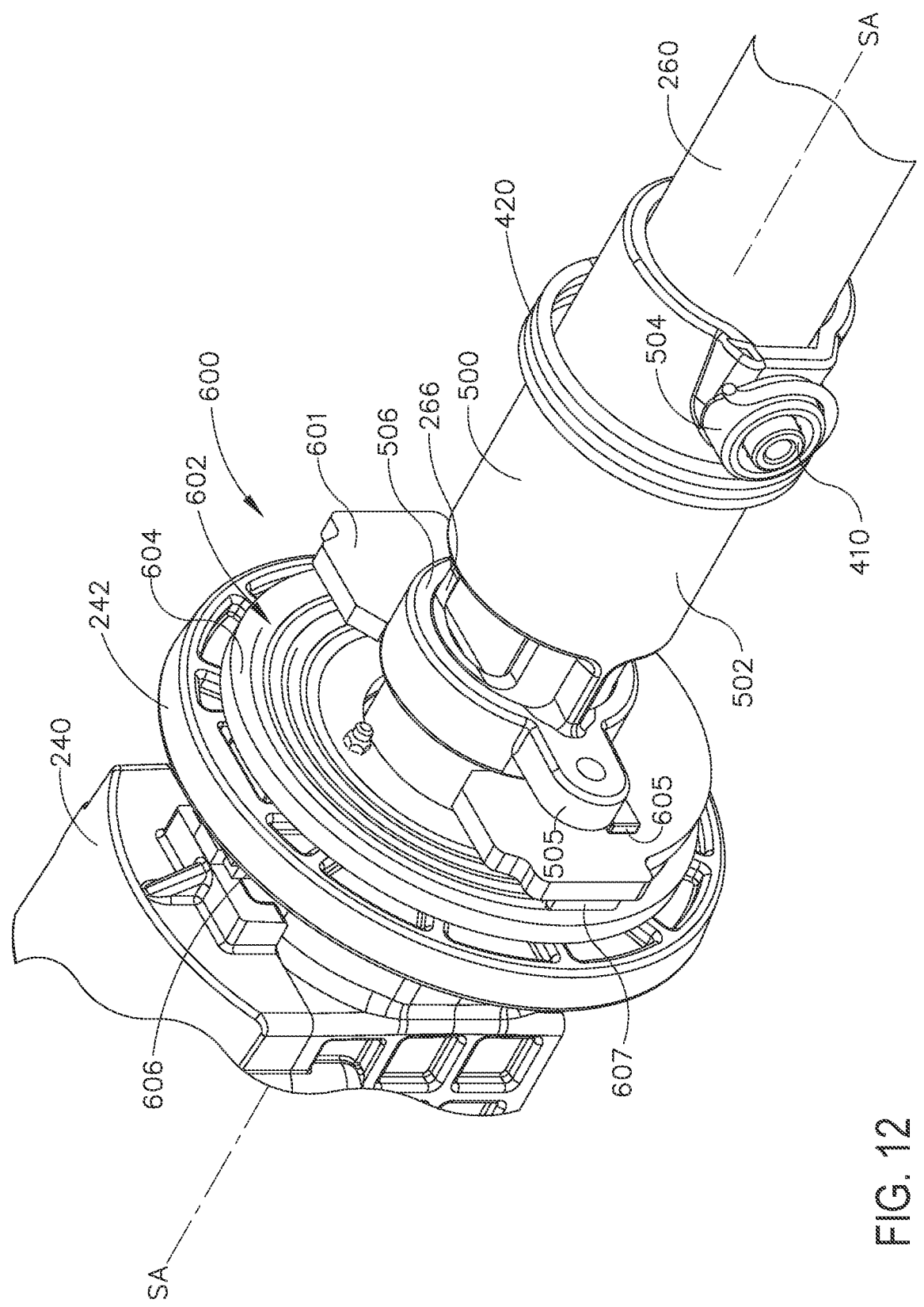
FIG. 12 is another perspective view of the portion of the interchangeable shaft assembly of FIG. 11 with the switch drum mounted thereon.

As discussed above, the shaft assembly 200 can include a proximal portion which is fixably mounted to the handle assembly 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor configured to detect the position of the switch drum 500. Turning now to FIGS. 11 and 12, the distal connector flange 601 can comprise a magnetic field sensor 605, for example, and the switch drum 500 can comprise a magnetic element, such as permanent magnet 505, for example. The magnetic field sensor 605 can be configured to detect the position of the permanent magnet 505. When the switch drum 500 is rotated between its first position and its second position, the permanent magnet 505 can move relative to the magnetic field sensor 605. In various instances, magnetic field sensor 605 can detect changes in a magnetic field created when the permanent magnet 505 is moved. The magnetic field sensor 605 can be in signal communication with the shaft circuit board 610 and/or the handle circuit board 100, for example. Based on the signal from the magnetic field sensor 605, a microcontroller on the shaft circuit board 610 and/or the handle circuit board 100 can determine whether the articulation drive system is engaged with or disengaged from the firing drive system.

Figures 5, 6:
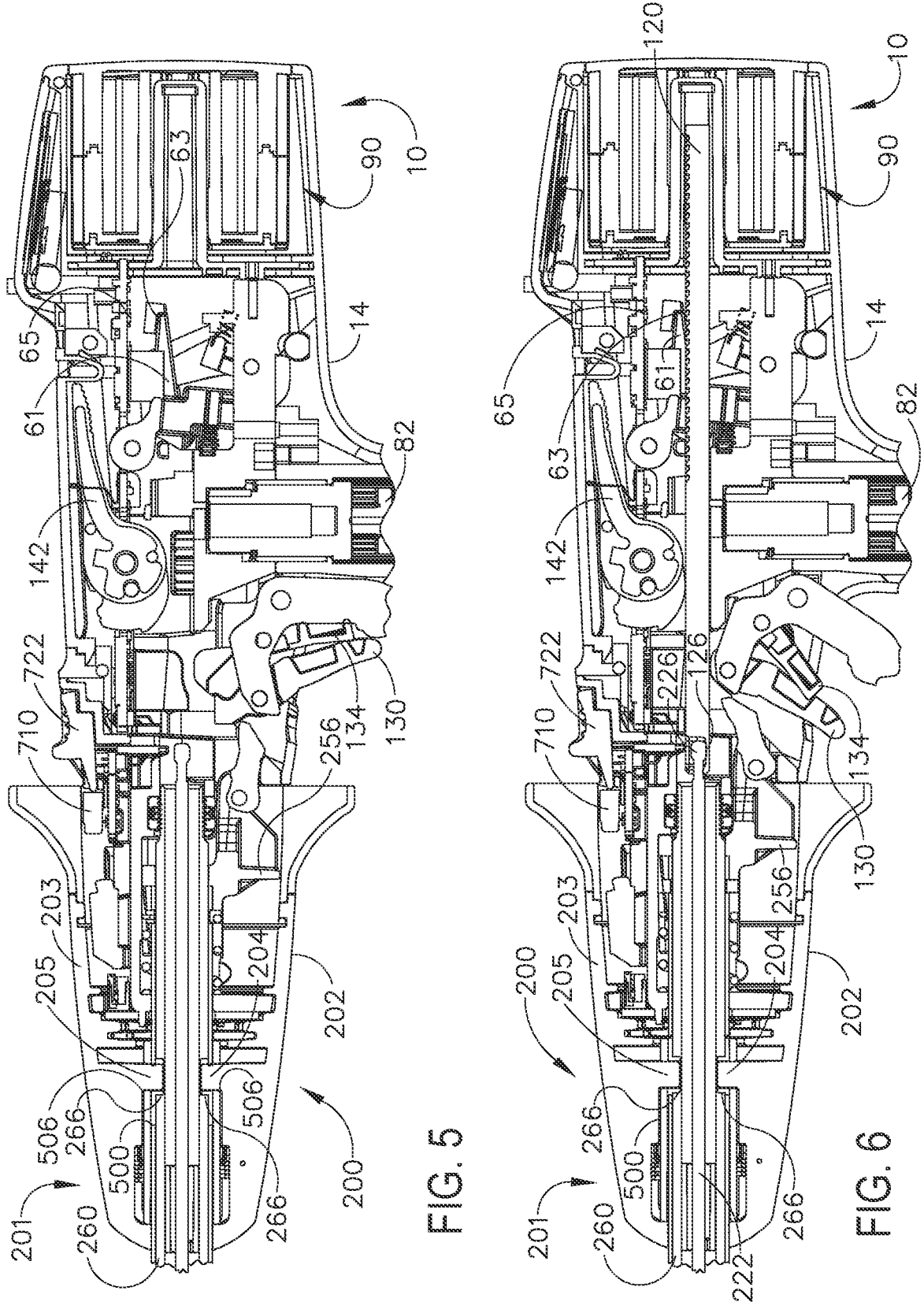
FIG. 5 is a cross-sectional side view of a portion of the surgical instrument of FIG. 4 with the firing trigger in a fully actuated position.
FIG. 6 is another cross-sectional view of a portion of the surgical instrument of FIG. 5 with the firing trigger in an unactuated position.

Referring again to FIGS. 3 and 7, the chassis 240 includes at least one, and preferably two, tapered attachment portions 244 formed thereon that are adapted to be received within corresponding dovetail slots 702 formed within a distal attachment flange portion 700 of the frame 20. Each dovetail slot 702 may be tapered or, stated another way, be somewhat V-shaped to seatingly receive the attachment portions 244 therein. As can be further seen in FIGS. 3 and 7, a shaft attachment lug 226 is formed on the proximal end of the intermediate firing shaft 222. As will be discussed in further detail below, when the interchangeable shaft assembly 200 is coupled to the handle assembly 14, the shaft attachment lug 226 is received in a firing shaft attachment cradle 126 formed in the distal end 125 of the longitudinal drive member 120 as shown in FIGS. 3 and 6, for example.

Various shaft assemblies employ a latch system 710 for removably coupling the shaft assembly 200 to the housing 12 and more specifically to the frame 20. As shown in FIG. 7, for example, in at least one form, the latch system 710 includes a lock member or lock yoke 712 that is movably coupled to the chassis 240. In the illustrated example, for example, the lock yoke 712 has a U-shape with two spaced downwardly extending legs 714. The legs 714 each have a pivot lug 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button in the distal direction which also causes the lock yoke 712 to pivot out of retaining engagement with the distal attachment flange 700 of the frame 20. When the lock yoke 712 is in "retaining engagement" with the distal attachment flange 700 of the frame 20, the lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the shaft assembly 200 from the housing 12. One form of the latch system 710 is configured to prevent such inadvertent detachment.

As can be most particularly seen in FIG. 7, the lock yoke 712 includes at least one and preferably two lock hooks 718 that are adapted to contact corresponding lock lug portions 256 that are formed on the closure shuttle 250. Referring to FIGS. 13-15, when the closure shuttle 250 is in an unactuated position (i.e., the first drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lug portions 256 on the closure shuttle 250. However, when the closure shuttle 250 is moved to an actuated position (i.e., the first drive system 30 is actuated and the anvil 306 is in the closed position), the lock yoke 712 is prevented from being pivoted to an unlocked position. See FIGS. 16-18. Stated another way, if the clinician were to attempt to pivot the lock yoke 712 to an unlocked position or, for example, the lock yoke 712 was in advertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle assembly 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the shaft assembly 200 along an installation axis IA that is perpendicular to the shaft axis SA-SA to seat the attachment portions 244 in "operable engagement" with the corresponding dovetail receiving slots 702. In doing so, the shaft attachment lug 226 on the intermediate firing shaft 222 will also be seated in the cradle 126 in the longitudinally movable drive member 120 and the portions of pin 37 on the second closure link 38 will be seated in the corresponding hooks 252 in the closure yoke 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle assembly 14. A first system can comprise a frame system which couples and/or aligns the frame or spine of the shaft assembly 200 with the frame 20 of the handle assembly 14. Another system can comprise a closure drive system 30 which can operably connect the closure trigger 32 of the handle assembly 14 and the closure tube 260 and the anvil 306 of the shaft assembly 200. As outlined above, the closure tube attachment yoke 250 of the shaft assembly 200 can be engaged with the pin 37 on the second closure link 38. Another system can comprise the firing drive system 80 which can operably connect the firing trigger 130 of the handle assembly 14 with the intermediate firing shaft 222 of the shaft assembly 200.

As outlined above, the shaft attachment lug 226 can be operably connected with the cradle 126 of the longitudinal drive member 120. Another system can comprise an electrical system which can signal to a controller in the handle assembly 14, such as microcontroller, for example, that a shaft assembly, such as shaft assembly 200, for example, has been operably engaged with the handle assembly 14 and/or, two, conduct power and/or communication signals between the shaft assembly 200 and the handle assembly 14. For instance, the shaft assembly 200 can include an electrical connector 1410 that is operably mounted to the shaft circuit board 610. The electrical connector 1410 is configured for mating engagement with a corresponding electrical connector 1400 on the handle control board 100. Further details regaining the circuitry and control systems may be found in U.S. patent application Ser. No. 13/803,086, now U.S. Patent Application Publication No. 2014/0263541, the entire disclosure of which was previously incorporated by reference herein. The fifth system may consist of the latching system for releasably locking the shaft assembly 200 to the handle assembly 14.

Figure 19:
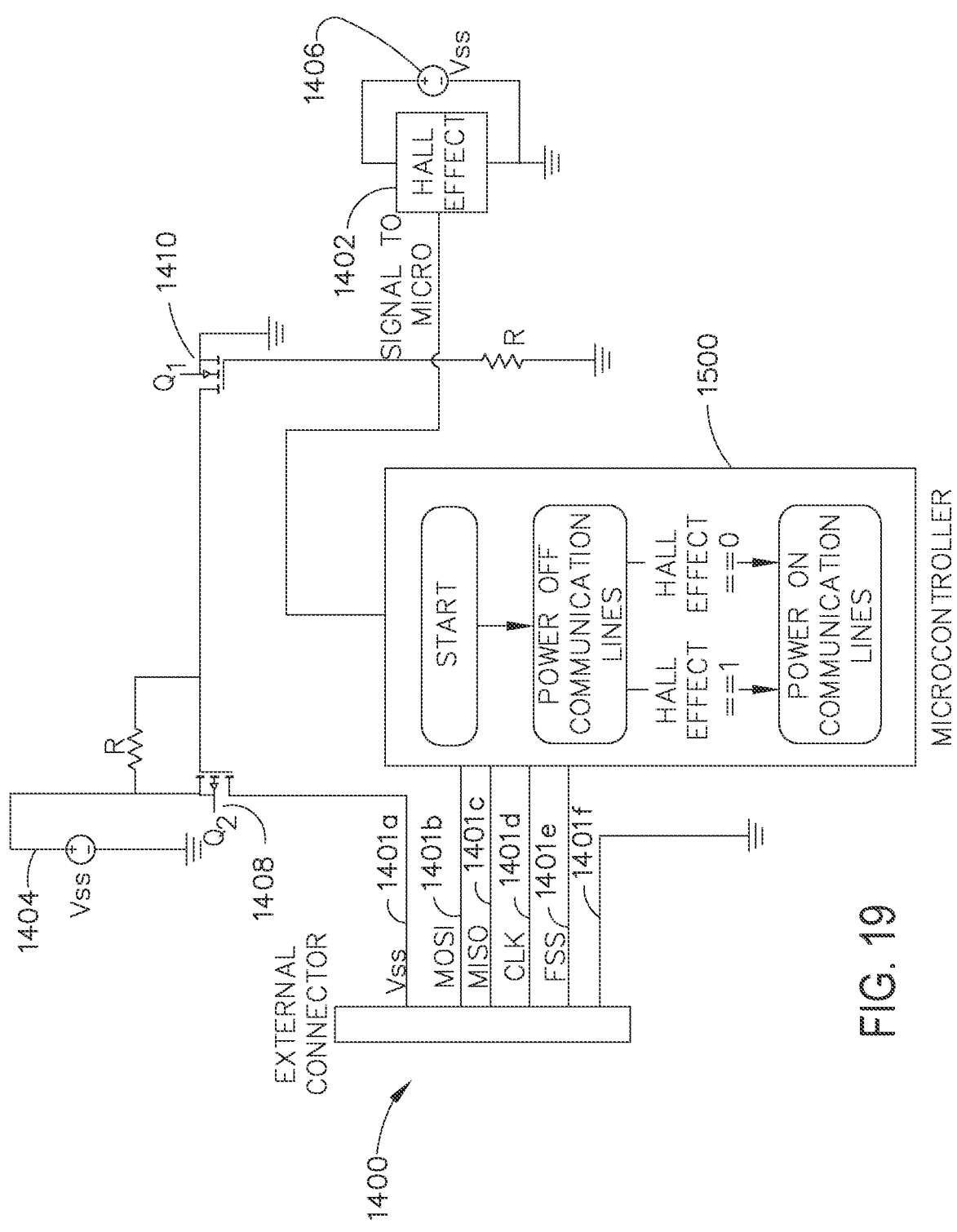
FIG. 19 is a schematic of a system for powering down an electrical connector of a surgical instrument handle when a shaft assembly is not coupled thereto.

Referring again to FIGS. 2 and 3, the handle assembly 14 can include an electrical connector 1400 comprising a plurality of electrical contacts. Turning now to FIG. 19, the electrical connector 1400 can comprise a first contact 1401a, a second contact 1401b, a third contact 1401c, a fourth contact 1401d, a fifth contact 1401e, and a sixth contact 1401f, for example. While the illustrated example utilizes six contacts, other examples are envisioned which may utilize more than six contacts or less than six contacts.

As illustrated in FIG. 19, the first contact 1401a can be in electrical communication with a transistor 1408, contacts 1401b-1401e can be in electrical communication with a microcontroller 1500, and the sixth contact 1401f can be in electrical communication with a ground. In certain circumstances, one or more of the electrical contacts 1401b-1401e may be in electrical communication with one or more output channels of the microcontroller 1500 and can be energized, or have a voltage potential applied thereto, when the handle 1042 is in a powered state. In some circumstances, one or more of the electrical contacts 1401b-1401e may be in electrical communication with one or more input channels of the microcontroller 1500 and, when the handle assembly 14 is in a powered state, the microcontroller 1500 can be configured to detect when a voltage potential is applied to such electrical contacts. When a shaft assembly, such as shaft assembly 200, for example, is assembled to the handle assembly 14, the electrical contacts 1401a-1401f may not communicate with each other. When a shaft assembly is not assembled to the handle assembly 14, however, the electrical contacts 1401a-1401f of the electrical connector 1400 may be exposed and, in some circumstances, one or more of the contacts 1401a-1401f may be accidentally placed in electrical communication with each other. Such circumstances can arise when one or more of the contacts 1401a-1401f come into contact with an electrically conductive material, for example. When this occurs, the microcontroller 1500 can receive an erroneous input and/or the shaft assembly 200 can receive an erroneous output, for example. To address this issue, in various circumstances, the handle assembly 14 may be unpowered when a shaft assembly, such as shaft assembly 200, for example, is not attached to the handle assembly 14.

In other circumstances, the handle 1042 can be powered when a shaft assembly, such as shaft assembly 200, for example, is not attached thereto. In such circumstances, the microcontroller 1500 can be configured to ignore inputs, or voltage potentials, applied to the contacts in electrical communication with the microcontroller 1500, i.e., contacts 1401b-1401e, for example, until a shaft assembly is attached to the handle assembly 14. Even though the microcontroller 1500 may be supplied with power to operate other functionalities of the handle assembly 14 in such circumstances, the handle assembly 14 may be in a powered-down state. In a way, the electrical connector 1400 may be in a powered-down state as voltage potentials applied to the electrical contacts 1401b-1401e may not affect the operation of the handle assembly 14. The reader will appreciate that, even though contacts 1401b-1401e may be in a powered-down state, the electrical contacts 1401a and 1401f, which are not in electrical communication with the microcontroller 1500, may or may not be in a powered-down state. For instance, sixth contact 1401f may remain in electrical communication with a ground regardless of whether the handle assembly 14 is in a powered-up or a powered-down state.

Furthermore, the transistor 1408, and/or any other suitable arrangement of transistors, such as transistor 1410, for example, and/or switches may be configured to control the supply of power from a power source 1404, such as a battery 90 within the handle assembly 14, for example, to the first electrical contact 1401a regardless of whether the handle assembly 14 is in a powered-up or a powered-down state. In various circumstances, the shaft assembly 200, for example, can be configured to change the state of the transistor 1408 when the shaft assembly 200 is engaged with the handle assembly 14. In certain circumstances, further to the below, a magnetic field sensor 1402 can be configured to switch the state of transistor 1410 which, as a result, can switch the state of transistor 1408 and ultimately supply power from power source 1404 to first contact 1401a. In this way, both the power circuits and the signal circuits to the connector 1400 can be powered down when a shaft assembly is not installed to the handle assembly 14 and powered up when a shaft assembly is installed to the handle assembly 14.

In various circumstances, referring again to FIG. 19, the handle assembly 14 can include the magnetic field sensor 1402, for example, which can be configured to detect a detectable element, such as a magnetic element 1407 (FIG. 3), for example, on a shaft assembly, such as shaft assembly 200, for example, when the shaft assembly is coupled to the handle assembly 14. The magnetic field sensor 1402 can be powered by a power source 1406, such as a battery, for example, which can, in effect, amplify the detection signal of the magnetic field sensor 1402 and communicate with an input channel of the microcontroller 1500 via the circuit illustrated in FIG. 19. Once the microcontroller 1500 has a received an input indicating that a shaft assembly has been at least partially coupled to the handle assembly 14, and that, as a result, the electrical contacts 1401a-1401f are no longer exposed, the microcontroller 1500 can enter into its normal, or powered-up, operating state. In such an operating state, the microcontroller 1500 will evaluate the signals transmitted to one or more of the contacts 1401b-1401e from the shaft assembly and/or transmit signals to the shaft assembly through one or more of the contacts 1401b-1401e in normal use thereof. In various circumstances, the shaft assembly 200 may have to be fully seated before the magnetic field sensor 1402 can detect the magnetic element 1407. While a magnetic field sensor 1402 can be utilized to detect the presence of the shaft assembly 200, any suitable system of sensors and/or switches can be utilized to detect whether a shaft assembly has been assembled to the handle assembly 14, for example. In this way, further to the above, both the power circuits and the signal circuits to the connector 1400 can be powered down when a shaft assembly is not installed to the handle assembly 14 and powered up when a shaft assembly is installed to the handle assembly 14.

In various examples, as may be used throughout the present disclosure, any suitable magnetic field sensor may be employed to detect whether a shaft assembly has been assembled to the handle assembly 14, for example. For example, the technologies used for magnetic field sensing include Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 19, the microcontroller 1500 may generally comprise a microprocessor ("processor") and one or more memory units operationally coupled to the processor. By executing instruction code stored in the memory, the processor may control various components of the surgical instrument, such as the motor, various drive systems, and/or a user display, for example. The microcontroller 1500 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the microcontroller 1500 may include a hybrid circuit comprising discrete and integrated circuit elements or components on one or more substrates, for example.

Referring to FIG. 19, the microcontroller 1500 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

As discussed above, the handle assembly 14 and/or the shaft assembly 200 can include systems and configurations configured to prevent, or at least reduce the possibility of, the contacts of the handle electrical connector 1400 and/or the contacts of the shaft electrical connector 1410 from becoming shorted out when the shaft assembly 200 is not assembled, or completely assembled, to the handle assembly 14. Referring to FIG. 3, the handle electrical connector 1400 can be at least partially recessed within a cavity 1409 defined in the handle frame 20. The six contacts 1401a-1401f of the electrical connector 1400 can be completely recessed within the cavity 1409. Such arrangements can reduce the possibility of an object accidentally contacting one or more of the contacts 1401a-1401f. Similarly, the shaft electrical connector 1410 can be positioned within a recess defined in the shaft chassis 240 which can reduce the possibility of an object accidentally contacting one or more of the contacts 1411a-1411f of the shaft electrical connector 1410. With regard to the particular example depicted in FIG. 3, the shaft contacts 1411a-1411f can comprise male contacts. In at least one example, each shaft contact 1411a-1411f can comprise a flexible projection extending therefrom which can be configured to engage a corresponding handle contact 1401a-1401f, for example. The handle contacts 1401a-1401f can comprise female contacts. In at least one example, each handle contact 1401a-1401f can comprise a flat surface, for example, against which the male shaft contacts 1401a-1401f can wipe, or slide, against and maintain an electrically conductive interface therebetween. In various instances, the direction in which the shaft assembly 200 is assembled to the handle assembly 14 can be parallel to, or at least substantially parallel to, the handle contacts 1401a-1401f such that the shaft contacts 1411a-1411f slide against the handle contacts 1401a-1401f when the shaft assembly 200 is assembled to the handle assembly 14. In various alternative examples, the handle contacts 1401a-1401f can comprise male contacts and the shaft contacts 1411a-1411f can comprise female contacts. In certain alternative examples, the handle contacts 1401a-1401f and the shaft contacts 1411a-1411f can comprise any suitable arrangement of contacts.

In various instances, the handle assembly 14 can comprise a connector guard configured to at least partially cover the handle electrical connector 1400 and/or a connector guard configured to at least partially cover the shaft electrical connector 1410. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one example, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 1400, for example. In various instances, the contacts can be transitioned between an unactivated condition and an activated condition. In certain instances, the contacts can be transitioned between a monitored condition, a deactivated condition, and an activated condition. For instance, the microcontroller 1500, for example, can monitor the contacts 1401a-1401f when a shaft assembly has not been assembled to the handle assembly 14 to determine whether one or more of the contacts 1401a-1401f may have been shorted. The microcontroller 1500 can be configured to apply a low voltage potential to each of the contacts 1401a-1401f and assess whether only a minimal resistance is present at each of the contacts. Such an operating state can comprise the monitored condition. In the event that the resistance detected at a contact is high, or above a threshold resistance, the microcontroller 1500 can deactivate that contact, more than one contact, or, alternatively, all of the contacts. Such an operating state can comprise the deactivated condition. If a shaft assembly is assembled to the handle assembly 14 and it is detected by the microcontroller 1500, as discussed above, the microcontroller 1500 can increase the voltage potential to the contacts 1401a-1401f. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

Figure 20:
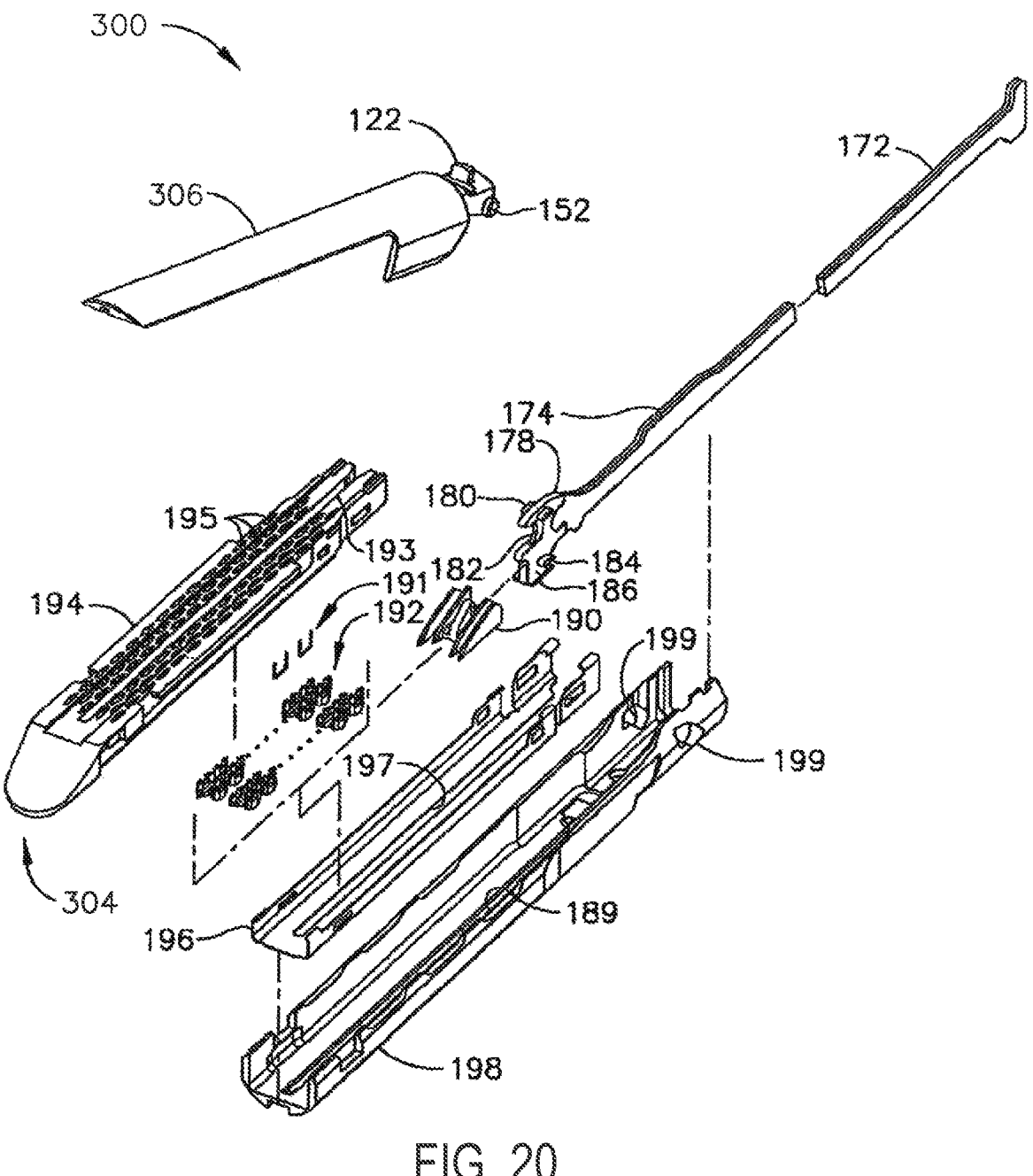
FIG. 20 is an exploded view of one aspect of an end effector of the surgical instrument of FIG. 1.

Referring to FIG. 20, a non-limiting form of the end effector 300 is illustrated. As described above, the end effector 300 may include the anvil 306 and the staple cartridge 304. In this non-limiting example, the anvil 306 is coupled to an elongate channel 198. For example, apertures 199 can be defined in the elongate channel 198 which can receive pins 152 extending from the anvil 306 and allow the anvil 306 to pivot from an open position to a closed position relative to the elongate channel 198 and staple cartridge 304. In addition, FIG. 20 shows a firing bar 172, configured to longitudinally translate into the end effector 300. The firing bar 172 may be constructed from one solid section, or in various examples, may include a laminate material comprising, for example, a stack of steel plates. A distally projecting end of the firing bar 172 can be attached to an E-beam 178 that can, among other things, assist in spacing the anvil 306 from a staple cartridge 304 positioned in the elongate channel 198 when the anvil 306 is in a closed position. The E-beam 178 can also include a sharpened cutting edge 182 which can be used to sever tissue as the E-beam 178 is advanced distally by the firing bar 172. In operation, the E-beam 178 can also actuate, or fire, the staple cartridge 304. The staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the replaceable staple cartridge 304. The wedge sled 190 upwardly cams the staple drivers 192 to force out the staples 191 into deforming contact with the anvil 306 while a cutting surface 182 of the E-beam 178 severs clamped tissue.

Further to the above, the E-beam 178 can include upper pins 180 which engage the anvil 306 during firing. The E-beam 178 can further include middle pins 184 and a bottom foot 186 which can engage various portions of the cartridge body 194, cartridge tray 196 and elongate channel 198. When a staple cartridge 304 is positioned within the elongate channel 198, a slot 193 defined in the cartridge body 194 can be aligned with a slot 197 defined in the cartridge tray 196 and a slot 189 defined in the elongate channel 198. In use, the E-beam 178 can slide through the aligned slots 193, 197, and 189 wherein, as indicated in FIG. 20, the bottom foot 186 of the E-beam 178 can engage a groove running along the bottom surface of channel 198 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the staple cartridge 304 as the firing bar 172 is moved distally to fire the staples from the staple cartridge 304 and/or incise the tissue captured between the anvil 306 and the staple cartridge 304. Thereafter, the firing bar 172 and the E-beam 178 can be retracted proximally allowing the anvil 306 to be opened to release the two stapled and severed tissue portions (not shown).

Figure 21A:
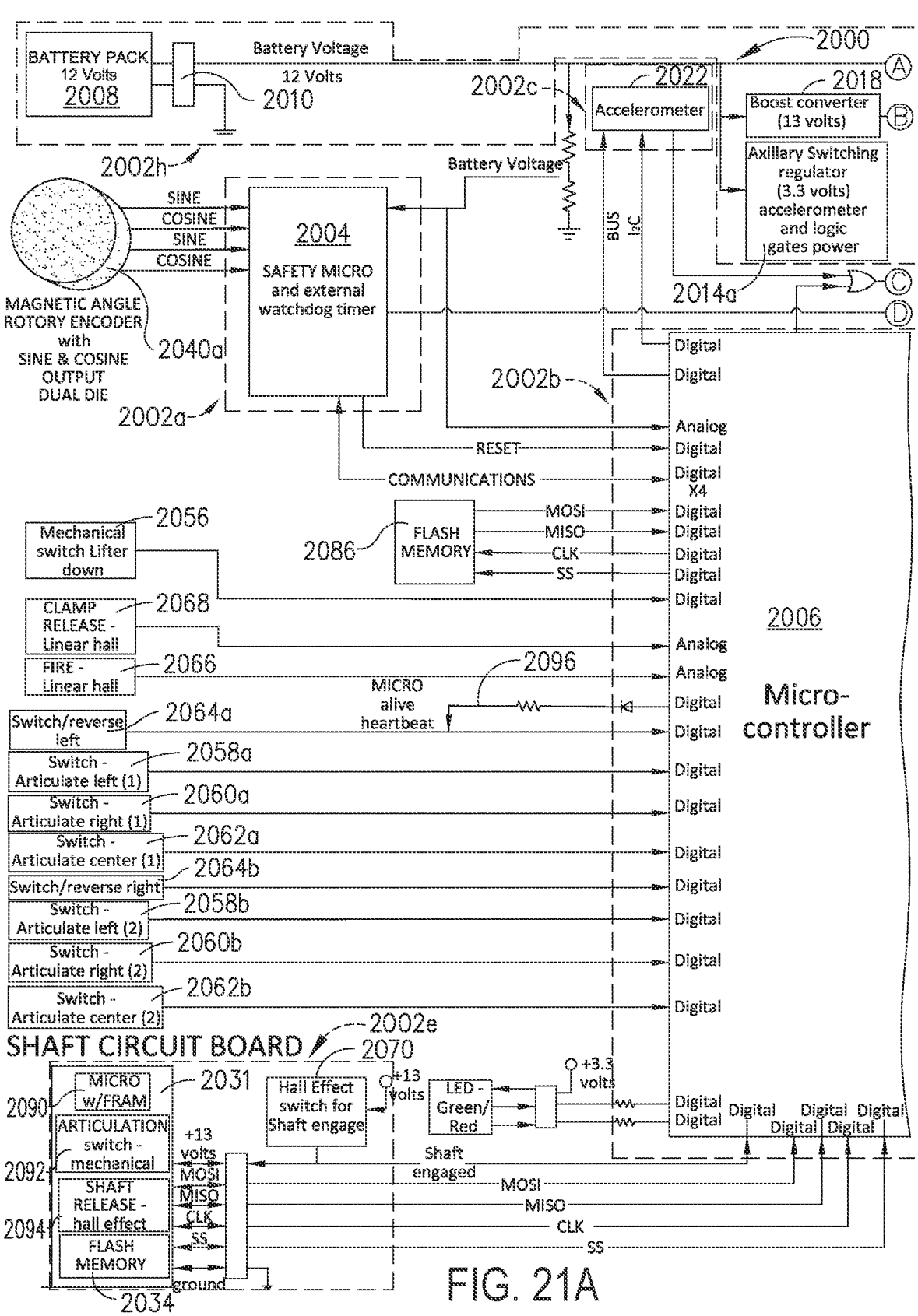
FIGS. 21A-21B is a circuit diagram of the surgical instrument of FIG. 1 spanning two drawings sheets.
Figure 21B:
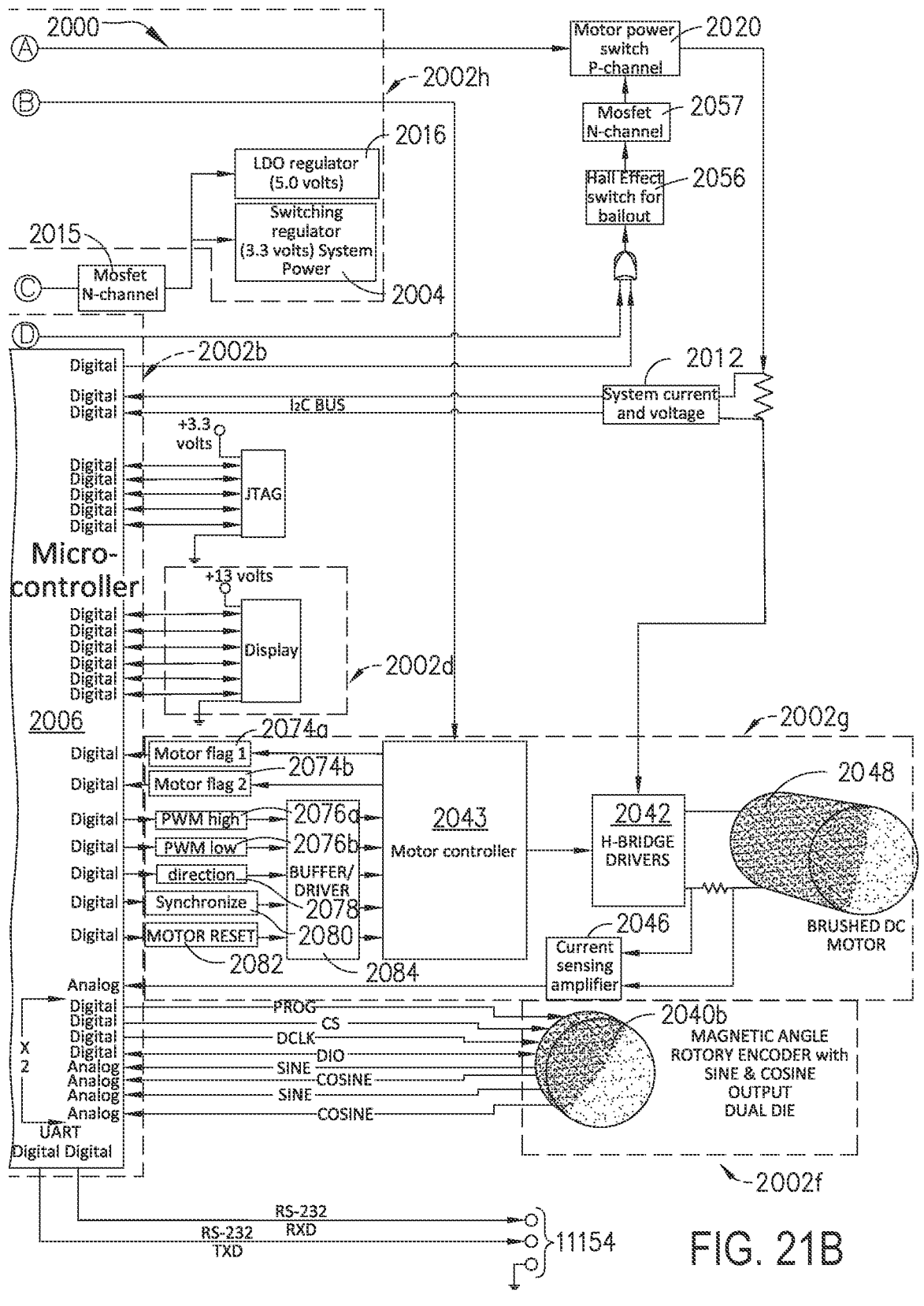

Having described a surgical instrument 10 (FIGS. 1-4) in general terms, the description now turns to a detailed description of various electrical/electronic components of the surgical instrument 10. Turning now to FIGS. 21A-21B, where one example of a segmented circuit 2000 comprising a plurality of circuit segments 2002a-2002g is illustrated. The segmented circuit 2000 comprising the plurality of circuit segments 2002a-2002g is configured to control a powered surgical instrument, such as, for example, the surgical instrument 10 illustrated in FIGS. 1-18A, without limitation. The plurality of circuit segments 2002a-2002g is configured to control one or more operations of the powered surgical instrument 10. A safety processor segment 2002a (Segment 1) comprises a safety processor 2004. A primary processor segment 2002b (Segment 2) comprises a primary processor 2006. The safety processor 2004 and/or the primary processor 2006 are configured to interact with one or more additional circuit segments 2002c-2002g to control operation of the powered surgical instrument 10. The primary processor 2006 comprises a plurality of inputs coupled to, for example, one or more circuit segments 2002c-2002g, a battery 2008, and/or a plurality of switches 2058a-2070. The segmented circuit 2000 may be implemented by any suitable circuit, such as, for example, a printed circuit board assembly (PCBA) within the powered surgical instrument 10. It should be understood that the term processor as used herein includes any microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one aspect, the main processor 2006 may be any single core or multicore processor such as those known under the trade name ARM Cortex by Texas Instruments. In one example, the safety processor 2004 may be a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one example, the safety processor 2004 may be configured specifically for IEC 61508 and ISO 26262 safety critical applications, among others, to provide advanced integrated safety features while delivering scalable performance, connectivity, and memory options.

In certain instances, the main processor 2006 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available for the product datasheet. Other processors may be readily substituted and, accordingly, the present disclosure should not be limited in this context.

In one aspect, the segmented circuit 2000 comprises an acceleration segment 2002c (Segment 3). The acceleration segment 2002c comprises an acceleration sensor 2022. The acceleration sensor 2022 may comprise, for example, an accelerometer. The acceleration sensor 2022 is configured to detect movement or acceleration of the powered surgical instrument 10. In some examples, input from the acceleration sensor 2022 is used, for example, to transition to and from a sleep mode, identify an orientation of the powered surgical instrument, and/or identify when the surgical instrument has been dropped. In some examples, the acceleration segment 2002c is coupled to the safety processor 2004 and/or the primary processor 2006.

In one aspect, the segmented circuit 2000 comprises a display segment 2002d (Segment 4). The display segment 2002d comprises a display connector 2024 coupled to the primary processor 2006. The display connector 2024 couples the primary processor 2006 to a display 2028 through one or more display driver integrated circuits 2026. The display driver integrated circuits 2026 may be integrated with the display 2028 and/or may be located separately from the display 2028. The display 2028 may comprise any suitable display, such as, for example, an organic light-emitting diode (OLED) display, a liquid-crystal display (LCD), and/or any other suitable display. In some examples, the display segment 2002*d* is coupled to the safety processor 2004.

In some aspects, the segmented circuit 2000 comprises a shaft segment 2002*e* (Segment 5). The shaft segment 2002*e* comprises one or more controls for a shaft 2004 coupled to the surgical instrument 10 and/or one or more controls for an end effector 2006 coupled to the shaft 2004. The shaft segment 2002*e* comprises a shaft connector 2030 configured to couple the primary processor 2006 to a shaft PCBA 2031. The shaft PCBA 2031 comprises a first articulation switch 2036, a second articulation switch 2032, and a shaft PCBA EEPROM 2034. In some examples, the shaft PCBA EEPROM 2034 comprises one or more parameters, routines, and/or programs specific to the shaft 2004 and/or the shaft PCBA 2031. The shaft PCBA 2031 may be coupled to the shaft 2004 and/or integral with the surgical instrument 10. In some examples, the shaft segment 2002*e* comprises a second shaft EEPROM 2038. The second shaft EEPROM 2038 comprises a plurality of algorithms, routines, parameters, and/or other data corresponding to one or more shafts 2004 and/or end effectors 2006 which may be interfaced with the powered surgical instrument 10.

In some aspects, the segmented circuit 2000 comprises a position encoder segment 2002*f* (Segment 6). The position encoder segment 2002*f* comprises one or more magnetic rotary position encoders 2040*a*-2040*b*. The one or more magnetic rotary position encoders 2040*a*-2040*b* are configured to identify the rotational position of a motor 2048, a shaft 2004, and/or an end effector 2006 of the surgical instrument 10. In some examples, the magnetic rotary position encoders 2040*a*-2040*b* may be coupled to the safety processor 2004 and/or the primary processor 2006.

In some aspects, the segmented circuit 2000 comprises a motor segment 2002*g* (Segment 7). The motor segment 2002*g* comprises a motor 2048 configured to control one or more movements of the powered surgical instrument 10. The motor 2048 is coupled to the primary processor 2006 by an H-Bridge driver 2042 and one or more H-bridge field-effect transistors (FETs) 2044. The H-bridge FETs 2044 are coupled to the safety processor 2004. A motor current sensor 2046 is coupled in series with the motor 2048 to measure the current draw of the motor 2048. The motor current sensor 2046 is in signal communication with the primary processor 2006 and/or the safety processor 2004. In some examples, the motor 2048 is coupled to a motor electromagnetic interference (EMI) filter 2050.

In some aspects, the segmented circuit 2000 comprises a power segment 2002*h* (Segment 8). A battery 2008 is coupled to the safety processor 2004, the primary processor 2006, and one or more of the additional circuit segments 2002*c*-2002*g*. The battery 2008 is coupled to the segmented circuit 2000 by a battery connector 2010 and a current sensor 2012. The current sensor 2012 is configured to measure the total current draw of the segmented circuit 2000. In some examples, one or more voltage converters 2014*a*, 2014*b*, 2016 are configured to provide predetermined voltage values to one or more circuit segments 2002*a*-2002*g*. For example, in some examples, the segmented circuit 2000 may comprise 3.3V voltage converters 2014*a*-2014*b* and/or 5V voltage converters 2016. A boost converter 2018 is configured to provide a boost voltage up to a predetermined amount, such as, for example, up to 13V. The boost converter 2018 is configured to provide additional voltage and/or current during power intensive operations and prevent brownout or low-power conditions.

In some aspects, the safety segment 2002*a* comprises a motor power interrupt 2020. The motor power interrupt 2020 is coupled between the power segment 2002*h* and the motor segment 2002*g*. The safety segment 2002*a* is configured to interrupt power to the motor segment 2002*g* when an error or fault condition is detected by the safety processor 2004 and/or the primary processor 2006 as discussed in more detail herein. Although the circuit segments 2002*a*-2002*g* are illustrated with all components of the circuit segments 2002*a*-2002*h* located in physical proximity, one skilled in the art will recognize that a circuit segment 2002*a*-2002*h* may comprise components physically and/or electrically separate from other components of the same circuit segment 2002*a*-2002*g*. In some examples, one or more components may be shared between two or more circuit segments 2002*a*-2002*g*.

In some aspects, a plurality of switches 2056-2070 are coupled to the safety processor 2004 and/or the primary processor 2006. The plurality of switches 2056-2070 may be configured to control one or more operations of the surgical instrument 10, control one or more operations of the segmented circuit 2000, and/or indicate a status of the surgical instrument 10. For example, a bail-out door switch 2056 is configured to indicate the status of a bail-out door. A plurality of articulation switches, such as, for example, a left side articulation left switch 2058*a*, a left side articulation right switch 2060*a*, a left side articulation center switch 2062*a*, a right side articulation left switch 2058*b*, a right side articulation right switch 2060*b*, and a right side articulation center switch 2062*b* are configured to control articulation of a shaft 2004 and/or an end effector 2006. A left side reverse switch 2064*a* and a right side reverse switch 2064*b* are coupled to the primary processor 2006. In some examples, the left side switches comprising the left side articulation left switch 2058*a*, the left side articulation right switch 2060*a*, the left side articulation center switch 2062*a*, and the left side reverse switch 2064*a* are coupled to the primary processor 2006 by a left flex connector 2072*a*. The right side switches comprising the right side articulation left switch 2058*b*, the right side articulation right switch 2060*b*, the right side articulation center switch 2062*b*, and the right side reverse switch 2064*b* are coupled to the primary processor 2006 by a right flex connector 2072*b*. In some examples, a firing switch 2066, a clamp release switch 2068, and a shaft engaged switch 2070 are coupled to the primary processor 2006.

In some aspects, the plurality of switches 2056-2070 may comprise, for example, a plurality of handle controls mounted to a handle of the surgical instrument 10, a plurality of indicator switches, and/or any combination thereof. In various examples, the plurality of switches 2056-2070 allow a surgeon to manipulate the surgical instrument, provide feedback to the segmented circuit 2000 regarding the position and/or operation of the surgical instrument, and/or indicate unsafe operation of the surgical instrument 10. In some examples, additional or fewer switches may be coupled to the segmented circuit 2000, one or more of the switches 2056-2070 may be combined into a single switch, and/or expanded to multiple switches. For example, in one example, one or more of the left side and/or right side articulation switches 2058*a*-2064*b* may be combined into a single multi-position switch.

In one aspect, the safety processor 2004 is configured to implement a watchdog function, among other safety operations. The safety processor 2004 and the primary processor 2006 of the segmented circuit 2000 are in signal communication. A microprocessor alive heartbeat signal is provided at output 2096. The acceleration segment 2002*c* comprises an accelerometer 2022 configured to monitor movement of the surgical instrument 10. In various examples, the accelerometer 2022 may be a single, double, or triple axis accelerometer. The accelerometer 2022 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 2022. For example, the accelerometer 2022 at rest on the surface of the earth will measure an acceleration g=9.8 m/s² (gravity) straight upwards, due to its weight. Another type of acceleration that accelerometer 2022 can measure is g-force acceleration. In various other examples, the accelerometer 2022 may comprise a single, double, or triple axis accelerometer. Further, the acceleration segment 2002*c* may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

In one aspect, the safety processor 2004 is configured to implement a watchdog function with respect to one or more circuit segments 2002*c*-2002*h*, such as, for example, the motor segment 2002*g*. In this regards, the safety processor 2004 employs the watchdog function to detect and recover from malfunctions of the primary processor 2006. During normal operation, the safety processor 2004 monitors for hardware faults or program errors of the primary processor 2004 and to initiate corrective action or actions. The corrective actions may include placing the primary processor 2006 in a safe state and restoring normal system operation. In one example, the safety processor 2004 is coupled to at least a first sensor. The first sensor measures a first property of the surgical instrument 10 (FIGS. 1-4). In some examples, the safety processor 2004 is configured to compare the measured property of the surgical instrument 10 to a predetermined value. For example, in one example, a motor sensor 2040*a* is coupled to the safety processor 2004. The motor sensor 2040*a* provides motor speed and position information to the safety processor 2004. The safety processor 2004 monitors the motor sensor 2040*a* and compares the value to a maximum speed and/or position value and prevents operation of the motor 2048 above the predetermined values. In some examples, the predetermined values are calculated based on real-time speed and/or position of the motor 2048, calculated from values supplied by a second motor sensor 2040*b* in communication with the primary processor 2006, and/or provided to the safety processor 2004 from, for example, a memory module coupled to the safety processor 2004.

In some aspects, a second sensor is coupled to the primary processor 2006. The second sensor is configured to measure the first physical property. The safety processor 2004 and the primary processor 2006 are configured to provide a signal indicative of the value of the first sensor and the second sensor respectively. When either the safety processor 2004 or the primary processor 2006 indicates a value outside of an acceptable range, the segmented circuit 2000 prevents operation of at least one of the circuit segments 2002*c*-2002*h*, such as, for example, the motor segment 2002*g*. For example, in the example illustrated in FIGS. 21A-21B, the safety processor 2004 is coupled to a first motor position sensor 2040*a* and the primary processor 2006 is coupled to a second motor position sensor 2040*b*. The motor position sensors 2040*a*, 2040*b* may comprise any suitable motor position sensor, such as, for example, a magnetic angle rotary input comprising a sine and cosine output. The motor position sensors 2040*a*, 2040*b* provide respective signals to the safety processor 2004 and the primary processor 2006 indicative of the position of the motor 2048.

The safety processor 2004 and the primary processor 2006 generate an activation signal when the values of the first motor sensor 2040*a* and the second motor sensor 2040*b* are within a predetermined range. When either the primary processor 2006 or the safety processor 2004 to detect a value outside of the predetermined range, the activation signal is terminated and operation of at least one circuit segment 2002*c*-2002*h*, such as, for example, the motor segment 2002*g*, is interrupted and/or prevented. For example, in some examples, the activation signal from the primary processor 2006 and the activation signal from the safety processor 2004 are coupled to an AND gate. The AND gate is coupled to a motor power switch 2020. The AND gate maintains the motor power switch 2020 in a closed, or on, position when the activation signal from both the safety processor 2004 and the primary processor 2006 are high, indicating a value of the motor sensors 2040*a*, 2040*b* within the predetermined range. When either of the motor sensors 2040*a*, 2040*b* detect a value outside of the predetermined range, the activation signal from that motor sensor 2040*a*, 2040*b* is set low, and the output of the AND gate is set low, opening the motor power switch 2020. In some examples, the value of the first sensor 2040*a* and the second sensor 2040*b* is compared, for example, by the safety processor 2004 and/or the primary processor 2006. When the values of the first sensor and the second sensor are different, the safety processor 2004 and/or the primary processor 2006 may prevent operation of the motor segment 2002*g*.

In some aspects, the safety processor 2004 receives a signal indicative of the value of the second sensor 2040*b* and compares the second sensor value to the first sensor value. For example, in one aspect, the safety processor 2004 is coupled directly to a first motor sensor 2040*a*. A second motor sensor 2040*b* is coupled to a primary processor 2006, which provides the second motor sensor 2040*b* value to the safety processor 2004, and/or coupled directly to the safety processor 2004. The safety processor 2004 compares the value of the first motor sensor 2040 to the value of the second motor sensor 2040*b*. When the safety processor 2004 detects a mismatch between the first motor sensor 2040*a* and the second motor sensor 2040*b*, the safety processor 2004 may interrupt operation of the motor segment 2002*g*, for example, by cutting power to the motor segment 2002*g*.

In some aspects, the safety processor 2004 and/or the primary processor 2006 is coupled to a first sensor 2040*a* configured to measure a first property of a surgical instrument and a second sensor 2040*b* configured to measure a second property of the surgical instrument. The first property and the second property comprise a predetermined relationship when the surgical instrument is operating normally. The safety processor 2004 monitors the first property and the second property. When a value of the first property and/or the second property inconsistent with the predetermined relationship is detected, a fault occurs. When a fault occurs, the safety processor 2004 takes at least one action, such as, for example, preventing operation of at least one of the circuit segments, executing a predetermined operation, and/or resetting the primary processor 2006. For example, the safety processor 2004 may open the motor power switch 2020 to cut power to the motor circuit segment 2002g when a fault is detected.

In one aspect, the safety processor 2004 is configured to execute an independent control algorithm. In operation, the safety processor 2004 monitors the segmented circuit 2000 and is configured to control and/or override signals from other circuit components, such as, for example, the primary processor 2006, independently. The safety processor 2004 may execute a preprogrammed algorithm and/or may be updated or programmed on the fly during operation based on one or more actions and/or positions of the surgical instrument 10. For example, in one example, the safety processor 2004 is reprogrammed with new parameters and/or safety algorithms each time a new shaft and/or end effector is coupled to the surgical instrument 10. In some examples, one or more safety values stored by the safety processor 2004 are duplicated by the primary processor 2006. Two-way error detection is performed to ensure values and/or parameters stored by either of the processors 2004, 2006 are correct.

In some aspects, the safety processor 2004 and the primary processor 2006 implement a redundant safety check. The safety processor 2004 and the primary processor 2006 provide periodic signals indicating normal operation. For example, during operation, the safety processor 2004 may indicate to the primary processor 2006 that the safety processor 2004 is executing code and operating normally. The primary processor 2006 may, likewise, indicate to the safety processor 2004 that the primary processor 2006 is executing code and operating normally. In some examples, communication between the safety processor 2004 and the primary processor 2006 occurs at a predetermined interval. The predetermined interval may be constant or may be variable based on the circuit state and/or operation of the surgical instrument 10.

Figure 22:
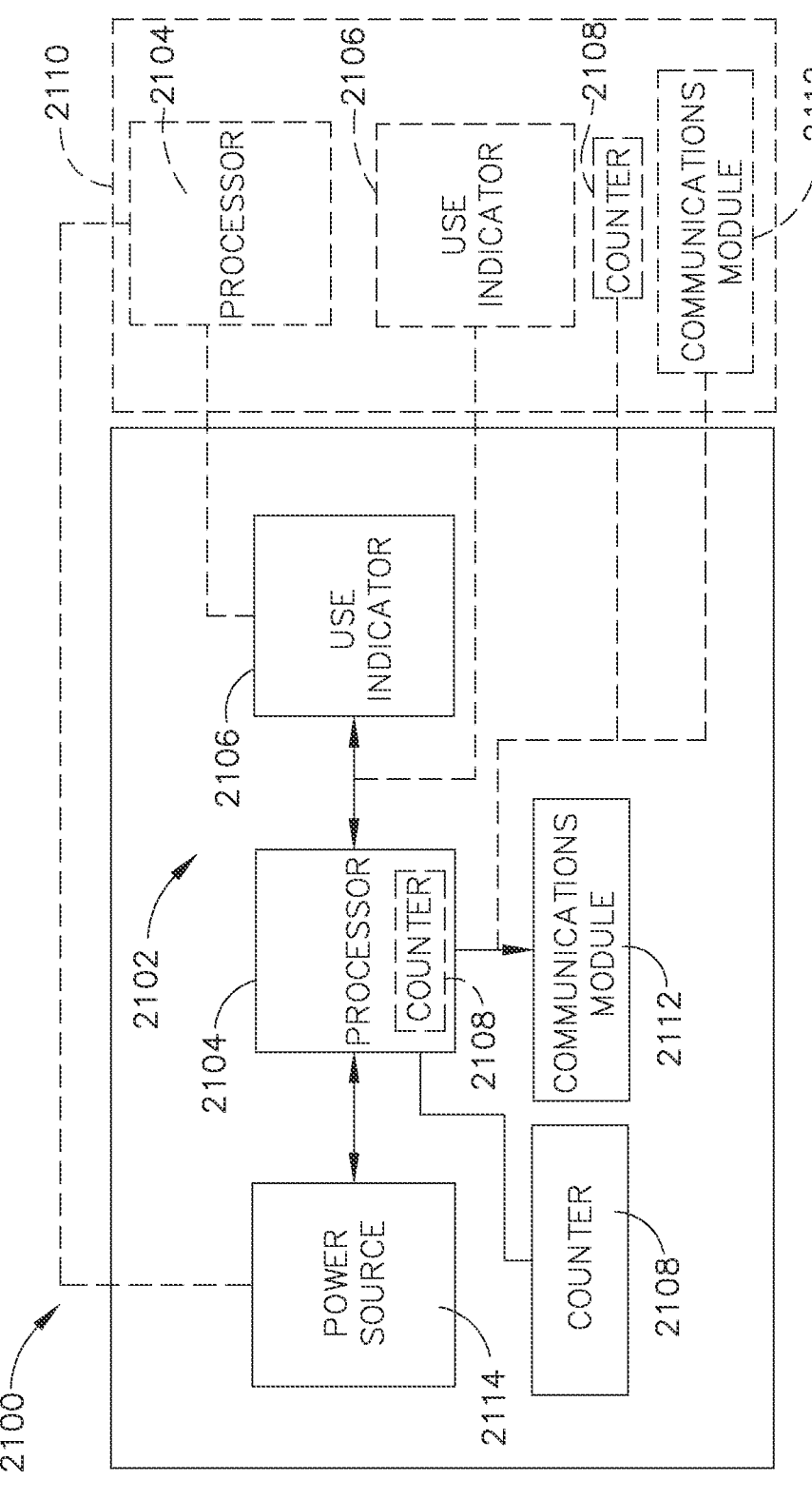
FIG. 22 illustrates one instance of a power assembly comprising a usage cycle circuit configured to generate a usage cycle count of the battery back.

FIG. 22 illustrates one example of a power assembly 2100 comprising a usage cycle circuit 2102 configured to monitor a usage cycle count of the power assembly 2100. The power assembly 2100 may be coupled to a surgical instrument 2110. The usage cycle circuit 2102 comprises a processor 2104 and a use indicator 2106. The use indicator 2106 is configured to provide a signal to the processor 2104 to indicate a use of the battery back 2100 and/or a surgical instrument 2110 coupled to the power assembly 2100. A "use" may comprise any suitable action, condition, and/or parameter such as, for example, changing a modular component of a surgical instrument 2110, deploying or firing a disposable component coupled to the surgical instrument 2110, delivering electrosurgical energy from the surgical instrument 2110, reconditioning the surgical instrument 2110 and/or the power assembly 2100, exchanging the power assembly 2100, recharging the power assembly 2100, and/or exceeding a safety limitation of the surgical instrument 2110 and/or the battery back 2100.

In some instances, a usage cycle, or use, is defined by one or more power assembly 2100 parameters. For example, in one instance, a usage cycle comprises using more than 5% of the total energy available from the power assembly 2100 when the power assembly 2100 is at a full charge level. In another instance, a usage cycle comprises a continuous energy drain from the power assembly 2100 exceeding a predetermined time limit. For example, a usage cycle may correspond to five minutes of continuous and/or total energy draw from the power assembly 2100. In some instances, the power assembly 2100 comprises a usage cycle circuit 2102 having a continuous power draw to maintain one or more components of the usage cycle circuit 2102, such as, for example, the use indicator 2106 and/or a counter 2108, in an active state.

The processor 2104 maintains a usage cycle count. The usage cycle count indicates the number of uses detected by the use indicator 2106 for the power assembly 2100 and/or the surgical instrument 2110. The processor 2104 may increment and/or decrement the usage cycle count based on input from the use indicator 2106. The usage cycle count is used to control one or more operations of the power assembly 2100 and/or the surgical instrument 2110. For example, in some instances, a power assembly 2100 is disabled when the usage cycle count exceeds a predetermined usage limit. Although the instances discussed herein are discussed with respect to incrementing the usage cycle count above a predetermined usage limit, those skilled in the art will recognize that the usage cycle count may start at a predetermined amount and may be decremented by the processor 2104. In this instance, the processor 2104 initiates and/or prevents one or more operations of the power assembly 2100 when the usage cycle count falls below a predetermined usage limit.

The usage cycle count is maintained by a counter 2108. The counter 2108 comprises any suitable circuit, such as, for example, a memory module, an analog counter, and/or any circuit configured to maintain a usage cycle count. In some instances, the counter 2108 is formed integrally with the processor 2104. In other instances, the counter 2108 comprises a separate component, such as, for example, a solid state memory module. In some instances, the usage cycle count is provided to a remote system, such as, for example, a central database. The usage cycle count is transmitted by a communications module 2112 to the remote system. The communications module 2112 is configured to use any suitable communications medium, such as, for example, wired and/or wireless communication. In some instances, the communications module 2112 is configured to receive one or more instructions from the remote system, such as, for example, a control signal when the usage cycle count exceeds the predetermined usage limit.

In some instances, the use indicator 2106 is configured to monitor the number of modular components used with a surgical instrument 2110 coupled to the power assembly 2100. A modular component may comprise, for example, a modular shaft, a modular end effector, and/or any other modular component. In some instances, the use indicator 2106 monitors the use of one or more disposable components, such as, for example, insertion and/or deployment of a staple cartridge within an end effector coupled to the surgical instrument 2110. The use indicator 2106 comprises one or more sensors for detecting the exchange of one or more modular and/or disposable components of the surgical instrument 2110.

In some instances, the use indicator 2106 is configured to monitor single patient surgical procedures performed while the power assembly 2100 is installed. For example, the use indicator 2106 may be configured to monitor firings of the surgical instrument 2110 while the power assembly 2100 is coupled to the surgical instrument 2110. A firing may correspond to deployment of a staple cartridge, application of electrosurgical energy, and/or any other suitable surgical event. The use indicator 2106 may comprise one or more circuits for measuring the number of firings while the power assembly 2100 is installed. The use indicator 2106 provides a signal to the processor 2104 when a single patient procedure is performed and the processor 2104 increments the usage cycle count.

In some instances, the use indicator 2106 comprises a circuit configured to monitor one or more parameters of the power source 2114, such as, for example, a current draw from the power source 2114. The one or more parameters of the power source 2114 correspond to one or more operations performable by the surgical instrument 2110, such as, for example, a cutting and sealing operation. The use indicator 2106 provides the one or more parameters to the processor 2104, which increments the usage cycle count when the one or more parameters indicate that a procedure has been performed.

In some instances, the use indicator 2106 comprises a timing circuit configured to increment a usage cycle count after a predetermined time period. The predetermined time period corresponds to a single patient procedure time, which is the time required for an operator to perform a procedure, such as, for example, a cutting and sealing procedure. When the power assembly 2100 is coupled to the surgical instrument 2110, the processor 2104 polls the use indicator 2106 to determine when the single patient procedure time has expired. When the predetermined time period has elapsed, the processor 2104 increments the usage cycle count. After incrementing the usage cycle count, the processor 2104 resets the timing circuit of the use indicator 2106.

In some instances, the use indicator 2106 comprises a time constant that approximates the single patient procedure time. In one example, the usage cycle circuit 2102 comprises a resistor-capacitor (RC) timing circuit 2506. The RC timing circuit comprises a time constant defined by a resistor-capacitor pair. The time constant is defined by the values of the resistor and the capacitor. In one example, the usage cycle circuit 2552 comprises a rechargeable battery and a clock. When the power assembly 2100 is installed in a surgical instrument, the rechargeable battery is charged by the power source. The rechargeable battery comprises enough power to run the clock for at least the single patient procedure time. The clock may comprise a real time clock, a processor configured to implement a time function, or any other suitable timing circuit.

Referring still to FIG. 22, in some instances, the use indicator 2106 comprises a sensor configured to monitor one or more environmental conditions experienced by the power assembly 2100. For example, the use indicator 2106 may comprise an accelerometer. The accelerometer is configured to monitor acceleration of the power assembly 2100. The power assembly 2100 comprises a maximum acceleration tolerance. Acceleration above a predetermined threshold indicates, for example, that the power assembly 2100 has been dropped. When the use indicator 2106 detects acceleration above the maximum acceleration tolerance, the processor 2104 increments a usage cycle count. In some instances, the use indicator 2106 comprises a moisture sensor. The moisture sensor is configured to indicate when the power assembly 2100 has been exposed to moisture. The moisture sensor may comprise, for example, an immersion sensor configured to indicate when the power assembly 2100 has been fully immersed in a cleaning fluid, a moisture sensor configured to indicate when moisture is in contact with the power assembly 2100 during use, and/or any other suitable moisture sensor.

In some instances, the use indicator 2106 comprises a chemical exposure sensor. The chemical exposure sensor is configured to indicate when the power assembly 2100 has come into contact with harmful and/or dangerous chemicals. For example, during a sterilization procedure, an inappropriate chemical may be used that leads to degradation of the power assembly 2100. The processor 2104 increments the usage cycle count when the use indicator 2106 detects an inappropriate chemical.

In some instances, the usage cycle circuit 2102 is configured to monitor the number of reconditioning cycles experienced by the power assembly 2100. A reconditioning cycle may comprise, for example, a cleaning cycle, a sterilization cycle, a charging cycle, routine and/or preventative maintenance, and/or any other suitable reconditioning cycle. The use indicator 2106 is configured to detect a reconditioning cycle. For example, the use indicator 2106 may comprise a moisture sensor to detect a cleaning and/or sterilization cycle. In some instances, the usage cycle circuit 2102 monitors the number of reconditioning cycles experienced by the power assembly 2100 and disables the power assembly 2100 after the number of reconditioning cycles exceeds a predetermined threshold.

The usage cycle circuit 2102 may be configured to monitor the number of power assembly 2100 exchanges. The usage cycle circuit 2102 increments the usage cycle count each time the power assembly 2100 is exchanged. When the maximum number of exchanges is exceeded the usage cycle circuit 2102 locks out the power assembly 2100 and/or the surgical instrument 2110. In some instances, when the power assembly 2100 is coupled the surgical instrument 2110, the usage cycle circuit 2102 identifies the serial number of the power assembly 2100 and locks the power assembly 2100 such that the power assembly 2100 is usable only with the surgical instrument 2110. In some instances, the usage cycle circuit 2102 increments the usage cycle each time the power assembly 2100 is removed from and/or coupled to the surgical instrument 2110.

In some instances, the usage cycle count corresponds to sterilization of the power assembly 2100. The use indicator 2106 comprises a sensor configured to detect one or more parameters of a sterilization cycle, such as, for example, a temperature parameter, a chemical parameter, a moisture parameter, and/or any other suitable parameter. The processor 2104 increments the usage cycle count when a sterilization parameter is detected. The usage cycle circuit 2102 disables the power assembly 2100 after a predetermined number of sterilizations. In some instances, the usage cycle circuit 2102 is reset during a sterilization cycle, a voltage sensor to detect a recharge cycle, and/or any suitable sensor. The processor 2104 increments the usage cycle count when a reconditioning cycle is detected. The usage cycle circuit 2102 is disabled when a sterilization cycle is detected. The usage cycle circuit 2102 is reactivated and/or reset when the power assembly 2100 is coupled to the surgical instrument 2110. In some instances, the use indicator comprises a zero power indicator. The zero power indicator changes state during a sterilization cycle and is checked by the processor 2104 when the power assembly 2100 is coupled to a surgical instrument 2110. When the zero power indicator indicates that a sterilization cycle has occurred, the processor 2104 increments the usage cycle count.

A counter 2108 maintains the usage cycle count. In some instances, the counter 2108 comprises a non-volatile memory module. The processor 2104 increments the usage cycle count stored in the non-volatile memory module each time a usage cycle is detected. The memory module may be accessed by the processor 2104 and/or a control circuit, such as, for example, the control circuit 200. When the usage cycle count exceeds a predetermined threshold, the processor 2104 disables the power assembly 2100. In some instances, the usage cycle count is maintained by a plurality of circuit components. For example, in one instance, the counter 2108 comprises a resistor (or fuse) pack. After each use of the power assembly 2100, a resistor (or fuse) is burned to an open position, changing the resistance of the resistor pack. The power assembly 2100 and/or the surgical instrument 2110 reads the remaining resistance. When the last resistor of the resistor pack is burned out, the resistor pack has a predetermined resistance, such as, for example, an infinite resistance corresponding to an open circuit, which indicates that the power assembly 2100 has reached its usage limit. In some instances, the resistance of the resistor pack is used to derive the number of uses remaining.

In some instances, the usage cycle circuit 2102 prevents further use of the power assembly 2100 and/or the surgical instrument 2110 when the usage cycle count exceeds a predetermined usage limit. In one instance, the usage cycle count associated with the power assembly 2100 is provided to an operator, for example, utilizing a screen formed integrally with the surgical instrument 2110. The surgical instrument 2110 provides an indication to the operator that the usage cycle count has exceeded a predetermined limit for the power assembly 2100, and prevents further operation of the surgical instrument 2110.

In some instances, the usage cycle circuit 2102 is configured to physically prevent operation when the predetermined usage limit is reached. For example, the power assembly 2100 may comprise a shield configured to deploy over contacts of the power assembly 2100 when the usage cycle count exceeds the predetermined usage limit. The shield prevents recharge and use of the power assembly 2100 by covering the electrical connections of the power assembly 2100.

In some instances, the usage cycle circuit 2102 is located at least partially within the surgical instrument 2110 and is configured to maintain a usage cycle count for the surgical instrument 2110. FIG. 22 illustrates one or more components of the usage cycle circuit 2102 within the surgical instrument 2110 in phantom, illustrating the alternative positioning of the usage cycle circuit 2102. When a predetermined usage limit of the surgical instrument 2110 is exceeded, the usage cycle circuit 2102 disables and/or prevents operation of the surgical instrument 2110. The usage cycle count is incremented by the usage cycle circuit 2102 when the use indicator 2106 detects a specific event and/or requirement, such as, for example, firing of the surgical instrument 2110, a predetermined time period corresponding to a single patient procedure time, based on one or more motor parameters of the surgical instrument 2110, in response to a system diagnostic indicating that one or more predetermined thresholds are met, and/or any other suitable requirement. As discussed above, in some instances, the use indicator 2106 comprises a timing circuit corresponding to a single patient procedure time. In other instances, the use indicator 2106 comprises one or more sensors configured to detect a specific event and/or condition of the surgical instrument 2110.

In some instances, the usage cycle circuit 2102 is configured to prevent operation of the surgical instrument 2110 after the predetermined usage limit is reached. In some instances, the surgical instrument 2110 comprises a visible indicator to indicate when the predetermined usage limit has been reached and/or exceeded. For example, a flag, such as a red flag, may pop-up from the surgical instrument 2110, such as from the handle, to provide a visual indication to the operator that the surgical instrument 2110 has exceeded the predetermined usage limit. As another example, the usage cycle circuit 2102 may be coupled to a display formed integrally with the surgical instrument 2110. The usage cycle circuit 2102 displays a message indicating that the predetermined usage limit has been exceeded. The surgical instrument 2110 may provide an audible indication to the operator that the predetermined usage limit has been exceeded. For example, in one instance, the surgical instrument 2110 emits an audible tone when the predetermined usage limit is exceeded and the power assembly 2100 is removed from the surgical instrument 2110. The audible tone indicates the last use of the surgical instrument 2110 and indicates that the surgical instrument 2110 should be disposed or reconditioned.

In some instances, the usage cycle circuit 2102 is configured to transmit the usage cycle count of the surgical instrument 2110 to a remote location, such as, for example, a central database. The usage cycle circuit 2102 comprises a communications module 2112 configured to transmit the usage cycle count to the remote location. The communications module 2112 may utilize any suitable communications system, such as, for example, wired or wireless communications system. The remote location may comprise a central database configured to maintain usage information. In some instances, when the power assembly 2100 is coupled to the surgical instrument 2110, the power assembly 2100 records a serial number of the surgical instrument 2110. The serial number is transmitted to the central database, for example, when the power assembly 2100 is coupled to a charger. In some instances, the central database maintains a count corresponding to each use of the surgical instrument 2110. For example, a bar code associated with the surgical instrument 2110 may be scanned each time the surgical instrument 2110 is used. When the use count exceeds a predetermined usage limit, the central database provides a signal to the surgical instrument 2110 indicating that the surgical instrument 2110 should be discarded.

The surgical instrument 2110 may be configured to lock and/or prevent operation of the surgical instrument 2110 when the usage cycle count exceeds a predetermined usage limit. In some instances, the surgical instrument 2110 comprises a disposable instrument and is discarded after the usage cycle count exceeds the predetermined usage limit. In other instances, the surgical instrument 2110 comprises a reusable surgical instrument which may be reconditioned after the usage cycle count exceeds the predetermined usage limit. The surgical instrument 2110 initiates a reversible lockout after the predetermined usage limit is met. A technician reconditions the surgical instrument 2110 and releases the lockout, for example, utilizing a specialized technician key configured to reset the usage cycle circuit 2102.

Figure 23:
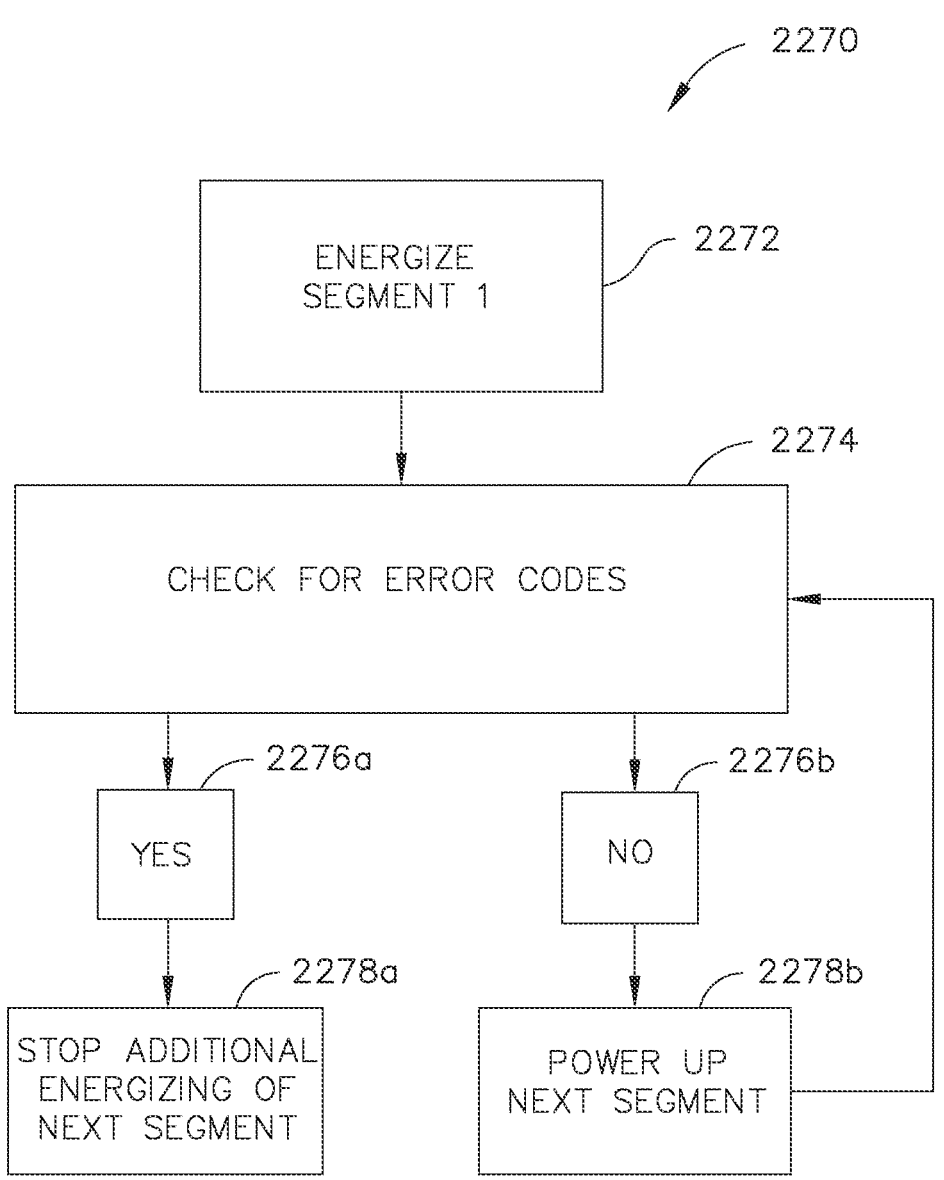
FIG. 23 illustrates one aspect of a process for sequentially energizing a segmented circuit.

In some aspects, the segmented circuit 2000 is configured for sequential start-up. An error check is performed by each circuit segment 2002a-2002g prior to energizing the next sequential circuit segment 2002a-2002g. FIG. 23 illustrates one example of a process for sequentially energizing a segmented circuit 2270, such as, for example, the segmented circuit 2000. When a battery 2008 is coupled to the segmented circuit 2000, the safety processor 2004 is energized 2272. The safety processor 2004 performs a self-error check 2274. When an error is detected 2276a, the safety processor stops energizing the segmented circuit 2000 and generates an error code 2278a. When no errors are detected 2276b, the safety processor 2004 initiates 2278b power-up of the primary processor 2006. The primary processor 2006 performs a self-error check. When no errors are detected, the primary processor 2006 begins sequential power-up of each of the remaining circuit segments 2278b. Each circuit segment is energized and error checked by the primary processor 2006. When no errors are detected, the next circuit segment is energized 2278*b*. When an error is detected, the safety processor 2004 and/or the primary process stops energizing the current segment and generates an error 2278*a*. The sequential start-up continues until all of the circuit segments 2002*a*-2002*g* have been energized. In some examples, the segmented circuit 2000 transitions from sleep mode following a similar sequential power-up process 11250.

Figure 24:
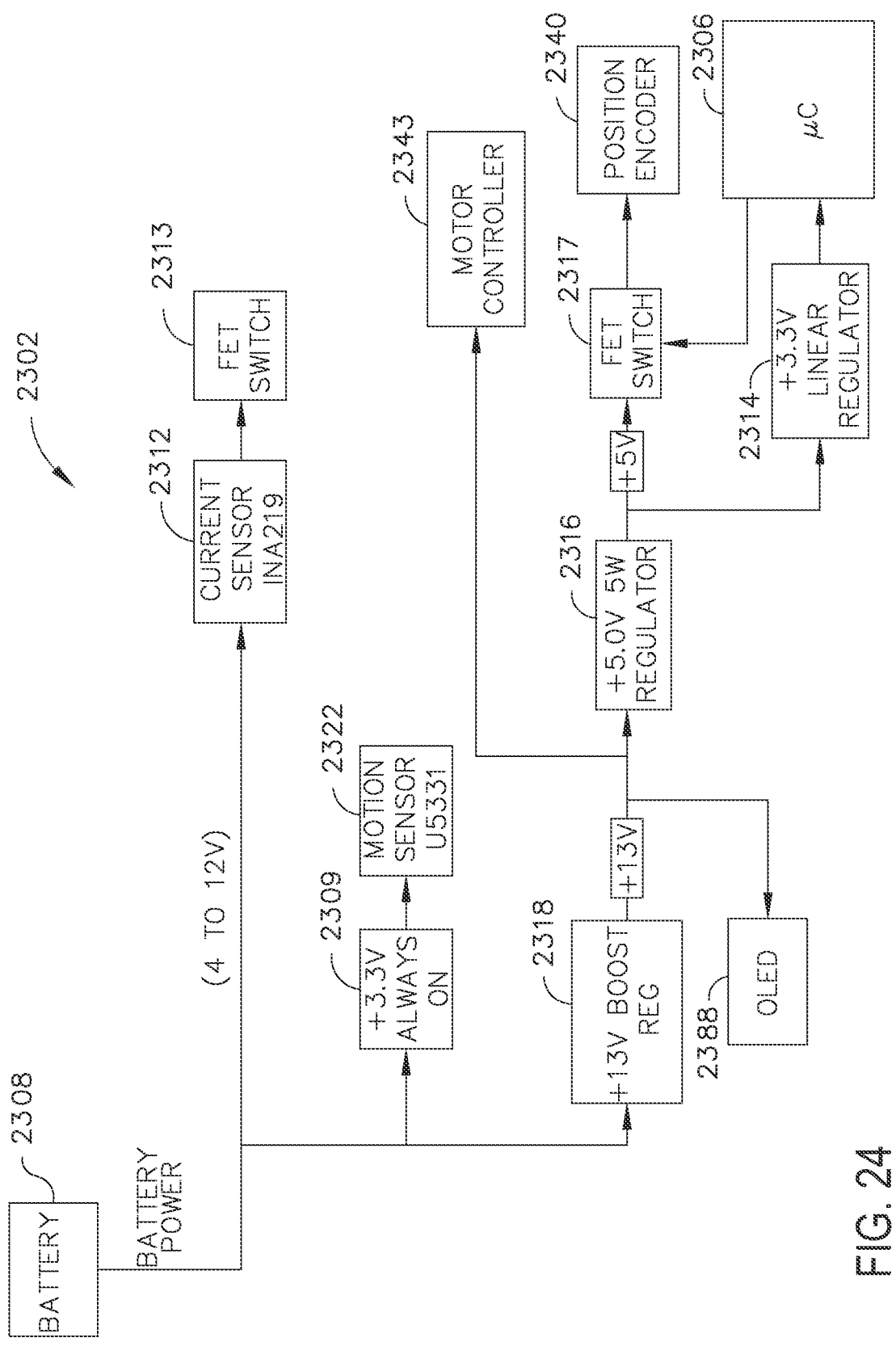
FIG. 24 illustrates one aspect of a power segment comprising a plurality of daisy chained power converters.

FIG. 24 illustrates one aspect of a power segment 2302 comprising a plurality of daisy chained power converters 2314, 2316, 2318. The power segment 2302 comprises a battery 2308. The battery 2308 is configured to provide a source voltage, such as, for example, 12V. A current sensor 2312 is coupled to the battery 2308 to monitor the current draw of a segmented circuit and/or one or more circuit segments. The current sensor 2312 is coupled to an FET switch 2313. The battery 2308 is coupled to one or more voltage converters 2309, 2314, 2316. An always on converter 2309 provides a constant voltage to one or more circuit components, such as, for example, a motion sensor 2322. The always on converter 2309 comprises, for example, a 3.3V converter. The always on converter 2309 may provide a constant voltage to additional circuit components, such as, for example, a safety processor (not shown). The battery 2308 is coupled to a boost converter 2318. The boost converter 2318 is configured to provide a boosted voltage above the voltage provided by the battery 2308. For example, in the illustrated example, the battery 2308 provides a voltage of 12V. The boost converter 2318 is configured to boost the voltage to 13V. The boost converter 2318 is configured to maintain a minimum voltage during operation of a surgical instrument, for example, the surgical instrument 10 (FIGS. 1-4). Operation of a motor can result in the power provided to the primary processor 2306 dropping below a minimum threshold and creating a brownout or reset condition in the primary processor 2306. The boost converter 2318 ensures that sufficient power is available to the primary processor 2306 and/or other circuit components, such as the motor controller 2343, during operation of the surgical instrument 10. In some examples, the boost converter 2318 is coupled directly one or more circuit components, such as, for example, an OLED display 2388.

The boost converter 2318 is coupled to one or more step-down converters to provide voltages below the boosted voltage level. A first voltage converter 2316 is coupled to the boost converter 2318 and provides a first stepped-down voltage to one or more circuit components. In the illustrated example, the first voltage converter 2316 provides a voltage of 5V. The first voltage converter 2316 is coupled to a rotary position encoder 2340. A FET switch 2317 is coupled between the first voltage converter 2316 and the rotary position encoder 2340. The FET switch 2317 is controlled by the processor 2306. The processor 2306 opens the FET switch 2317 to deactivate the position encoder 2340, for example, during power intensive operations. The first voltage converter 2316 is coupled to a second voltage converter 2314 configured to provide a second stepped-down voltage. The second stepped-down voltage comprises, for example, 3.3V. The second voltage converter 2314 is coupled to a processor 2306. In some examples, the boost converter 2318, the first voltage converter 2316, and the second voltage converter 2314 are coupled in a daisy chain configuration. The daisy chain configuration allows the use of smaller, more efficient converters for generating voltage levels below the boosted voltage level. The examples, however, are not limited to the particular voltage range(s) described in the context of this specification.

Figure 25:
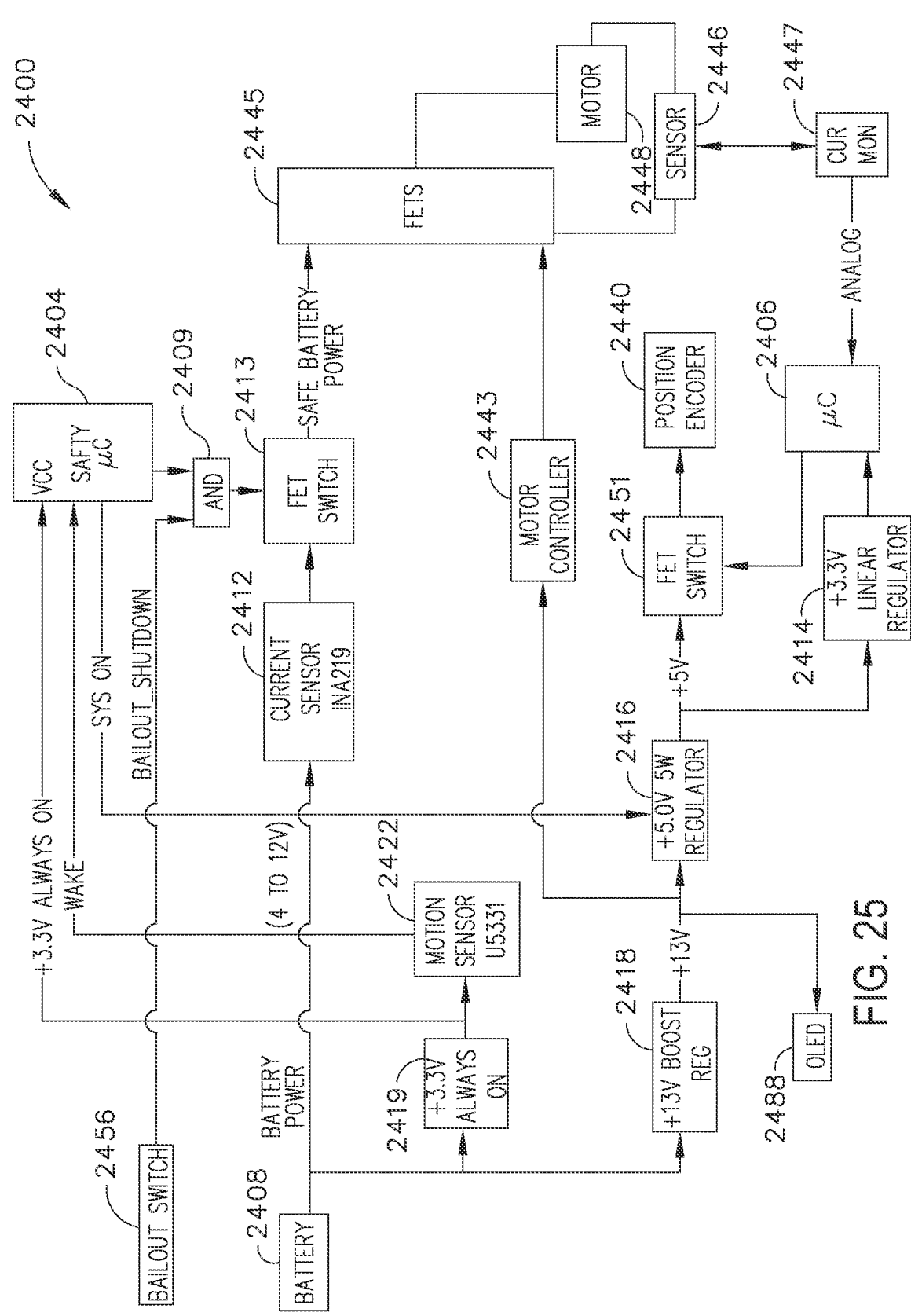
FIG. 25 illustrates one aspect of a segmented circuit configured to maximize power available for critical and/or power intense functions.

FIG. 25 illustrates one aspect of a segmented circuit 2400 configured to maximize power available for critical and/or power intense functions. The segmented circuit 2400 comprises a battery 2408. The battery 2408 is configured to provide a source voltage such as, for example, 12V. The source voltage is provided to a plurality of voltage converters 2409, 2418. An always-on voltage converter 2409 provides a constant voltage to one or more circuit components, for example, a motion sensor 2422 and a safety processor 2404. The always-on voltage converter 2409 is directly coupled to the battery 2408. The always-on converter 2409 provides a voltage of 3.3V, for example. The examples, however, are not limited to the particular voltage range(s) described in the context of this specification.

The segmented circuit 2400 comprises a boost converter 2418. The boost converter 2418 provides a boosted voltage above the source voltage provided by the battery 2408, such as, for example, 13V. The boost converter 2418 provides a boosted voltage directly to one or more circuit components, such as, for example, an OLED display 2488 and a motor controller 2443. By coupling the OLED display 2488 directly to the boost converter 2418, the segmented circuit 2400 eliminates the need for a power converter dedicated to the OLED display 2488. The boost converter 2418 provides a boosted voltage to the motor controller 2443 and the motor 2448 during one or more power intensive operations of the motor 2448, such as, for example, a cutting operation. The boost converter 2418 is coupled to a step-down converter 2416. The step-down converter 2416 is configured to provide a voltage below the boosted voltage to one or more circuit components, such as, for example, 5V. The step-down converter 2416 is coupled to, for example, a FET switch 2451 and a position encoder 2440. The FET switch 2451 is coupled to the primary processor 2406. The primary processor 2406 opens the FET switch 2451 when transitioning the segmented circuit 2400 to sleep mode and/or during power intensive functions requiring additional voltage delivered to the motor 2448. Opening the FET switch 2451 deactivates the position encoder 2440 and eliminates the power draw of the position encoder 2440. The examples, however, are not limited to the particular voltage range(s) described in the context of this specification.

The step-down converter 2416 is coupled to a linear converter 2414. The linear converter 2414 is configured to provide a voltage of, for example, 3.3V. The linear converter 2414 is coupled to the primary processor 2406. The linear converter 2414 provides an operating voltage to the primary processor 2406. The linear converter 2414 may be coupled to one or more additional circuit components. The examples, however, are not limited to the particular voltage range(s) described in the context of this specification.

The segmented circuit 2400 comprises a bailout switch 2456. The bailout switch 2456 is coupled to a bailout door on the surgical instrument 10. The bailout switch 2456 and the safety processor 2404 are coupled to an AND gate 2419. The AND gate 2419 provides an input to a FET switch 2413. When the bailout switch 2456 detects a bailout condition, the bailout switch 2456 provides a bailout shutdown signal to the AND gate 2419. When the safety processor 2404 detects an unsafe condition, such as, for example, due to a sensor mismatch, the safety processor 2404 provides a shutdown signal to the AND gate 2419. In some examples, both the bailout shutdown signal and the shutdown signal are high during normal operation and are low when a bailout condition or an unsafe condition is detected. When the output of the AND gate 2419 is low, the FET switch 2413 is opened and operation of the motor 2448 is prevented. In some examples, the safety processor 2404 utilizes the shutdown signal to transition the motor 2448 to an off state in sleep mode. A third input to the FET switch 2413 is provided by a current sensor 2412 coupled to the battery 2408. The current sensor 2412 monitors the current drawn by the circuit 2400 and opens the FET switch 2413 to shut-off power to the motor 2448 when an electrical current above a predetermined threshold is detected. The FET switch 2413 and the motor controller 2443 are coupled to a bank of FET switches 2445 configured to control operation of the motor 2448.

A motor current sensor 2446 is coupled in series with the motor 2448 to provide a motor current sensor reading to a current monitor 2447. The current monitor 2447 is coupled to the primary processor 2406. The current monitor 2447 provides a signal indicative of the current draw of the motor 2448. The primary processor 2406 may utilize the signal from the motor current 2447 to control operation of the motor, for example, to ensure the current draw of the motor 2448 is within an acceptable range, to compare the current draw of the motor 2448 to one or more other parameters of the circuit 2400 such as, for example, the position encoder 2440, and/or to determine one or more parameters of a treatment site. In some examples, the current monitor 2447 may be coupled to the safety processor 2404.

In some aspects, actuation of one or more handle controls, such as, for example, a firing trigger, causes the primary processor 2406 to decrease power to one or more components while the handle control is actuated. For example, in one example, a firing trigger controls a firing stroke of a cutting member. The cutting member is driven by the motor 2448. Actuation of the firing trigger results in forward operation of the motor 2448 and advancement of the cutting member. During firing, the primary processor 2406 closes the FET switch 2451 to remove power from the position encoder 2440. The deactivation of one or more circuit components allows higher power to be delivered to the motor 2448. When the firing trigger is released, full power is restored to the deactivated components, for example, by closing the FET switch 2451 and reactivating the position encoder 2440.

In some aspects, the safety processor 2404 controls operation of the segmented circuit 2400. For example, the safety processor 2404 may initiate a sequential power-up of the segmented circuit 2400, transition of the segmented circuit 2400 to and from sleep mode, and/or may override one or more control signals from the primary processor 2406. For example, in the illustrated example, the safety processor 2404 is coupled to the step-down converter 2416. The safety processor 2404 controls operation of the segmented circuit 2400 by activating or deactivating the step-down converter 2416 to provide power to the remainder of the segmented circuit 2400.

Figure 26:
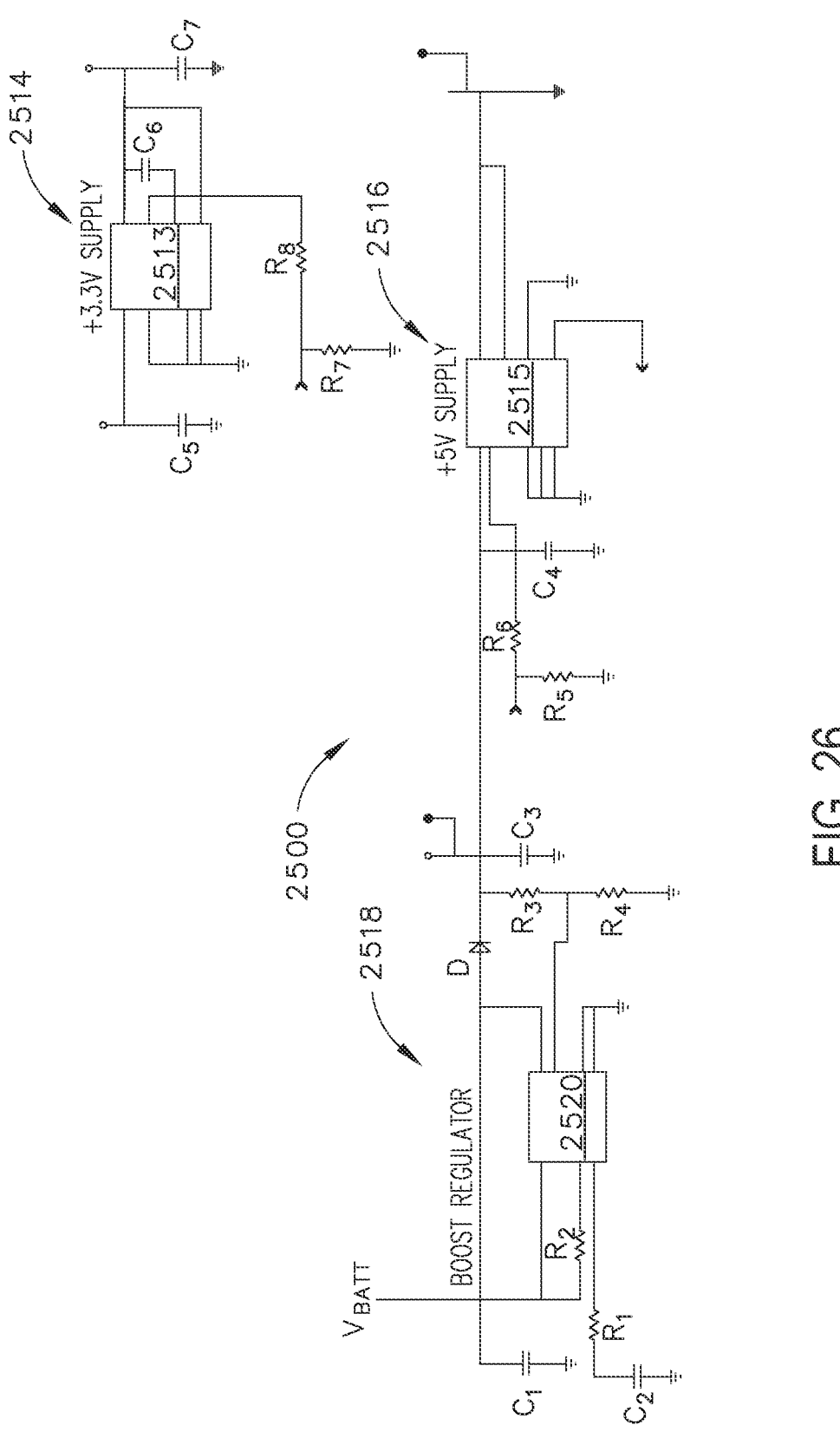
FIG. 26 illustrates one aspect of a power system comprising a plurality of daisy chained power converters configured to be sequentially energized.

FIG. 26 illustrates one aspect of a power system 2500 comprising a plurality of daisy chained power converters 2514, 2516, 2518 configured to be sequentially energized. The plurality of daisy chained power converters 2514, 2516, 2518 may be sequentially activated by, for example, a safety processor during initial power-up and/or transition from sleep mode. The safety processor may be powered by an independent power converter (not shown). For example, in one example, when a battery voltage $V_{BATT}$ is coupled to the power system 2500 and/or an accelerometer detects movement in sleep mode, the safety processor initiates a sequential start-up of the daisy chained power converters 2514, 2516, 2518. The safety processor activates the 13V boost section 2518. The boost section 2518 is energized and performs a self-check. In some examples, the boost section 2518 comprises an integrated circuit 2520 configured to boost the source voltage and to perform a self check. A diode D prevents power-up of a 5V supply section 2516 until the boost section 2518 has completed a self-check and provided a signal to the diode D indicating that the boost section 2518 did not identify any errors. In some examples, this signal is provided by the safety processor. The examples, however, are not limited to the particular voltage range(s) described in the context of this specification.

The 5V supply section 2516 is sequentially powered-up after the boost section 2518. The 5V supply section 2516 performs a self-check during power-up to identify any errors in the 5V supply section 2516. The 5V supply section 2516 comprises an integrated circuit 2515 configured to provide a step-down voltage from the boost voltage and to perform an error check. When no errors are detected, the 5V supply section 2516 completes sequential power-up and provides an activation signal to the 3.3V supply section 2514. In some examples, the safety processor provides an activation signal to the 3.3V supply section 2514. The 3.3V supply section comprises an integrated circuit 2513 configured to provide a step-down voltage from the 5V supply section 2516 and perform a self-error check during power-up. When no errors are detected during the self-check, the 3.3V supply section 2514 provides power to the primary processor. The primary processor is configured to sequentially energize each of the remaining circuit segments. By sequentially energizing the power system 2500 and/or the remainder of a segmented circuit, the power system 2500 reduces error risks, allows for stabilization of voltage levels before loads are applied, and prevents large current draws from all hardware being turned on simultaneously in an uncontrolled manner. The examples, however, are not limited to the particular voltage range(s) described in the context of this specification.

In one aspect, the power system 2500 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 27:
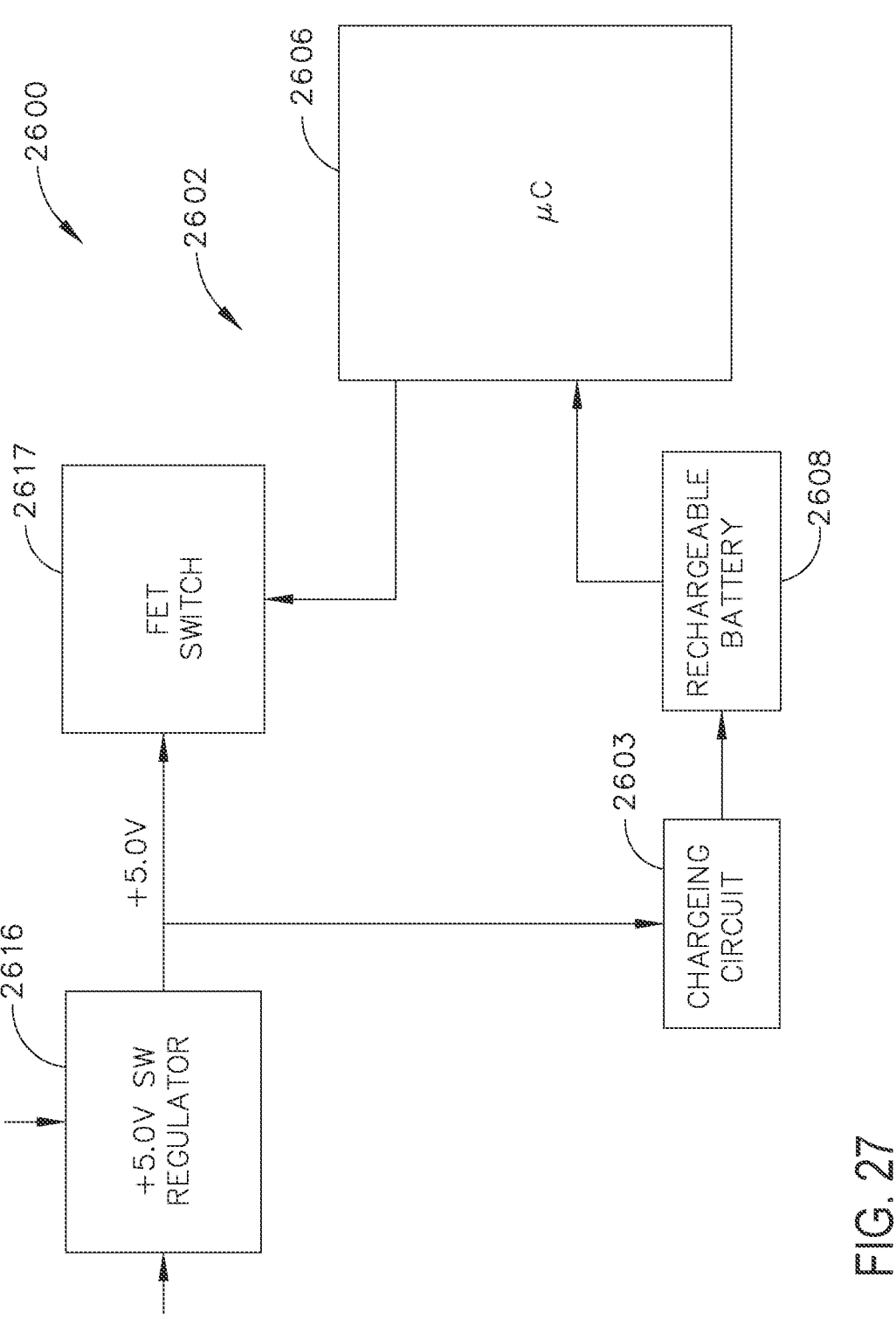
FIG. 27 illustrates one aspect of a segmented circuit comprising an isolated control section.

FIG. 27 illustrates one aspect of a segmented circuit 2600 comprising an isolated control section 2602. The isolated control section 2602 isolates control hardware of the segmented circuit 2600 from a power section (not shown) of the segmented circuit 2600. The control section 2602 comprises, for example, a primary processor 2606, a safety processor (not shown), and/or additional control hardware, for example, a FET Switch 2617. The power section comprises, for example, a motor, a motor driver, and/or a plurality of motor MOSFETS. The isolated control section 2602 comprises a charging circuit 2603 and a rechargeable battery 2608 coupled to a 5V power converter 2616. The charging circuit 2603 and the rechargeable battery 2608 isolate the primary processor 2606 from the power section. In some examples, the rechargeable battery 2608 is coupled to a safety processor and any additional support hardware. Isolating the control section 2602 from the power section allows the control section 2602, for example, the primary processor 2606, to remain active even when main power is removed, provides a filter, through the rechargeable battery

2608, to keep noise out of the control section 2602, isolates the control section 2602 from heavy swings in the battery voltage to ensure proper operation even during heavy motor loads, and/or allows for real-time operating system (RTOS) to be used by the segmented circuit 2600. In some examples, the rechargeable battery 2608 provides a stepped-down voltage to the primary processor, such as, for example, 3.3V. The examples, however, are not limited to the particular voltage range(s) described in the context of this specification.

Figure 28A:
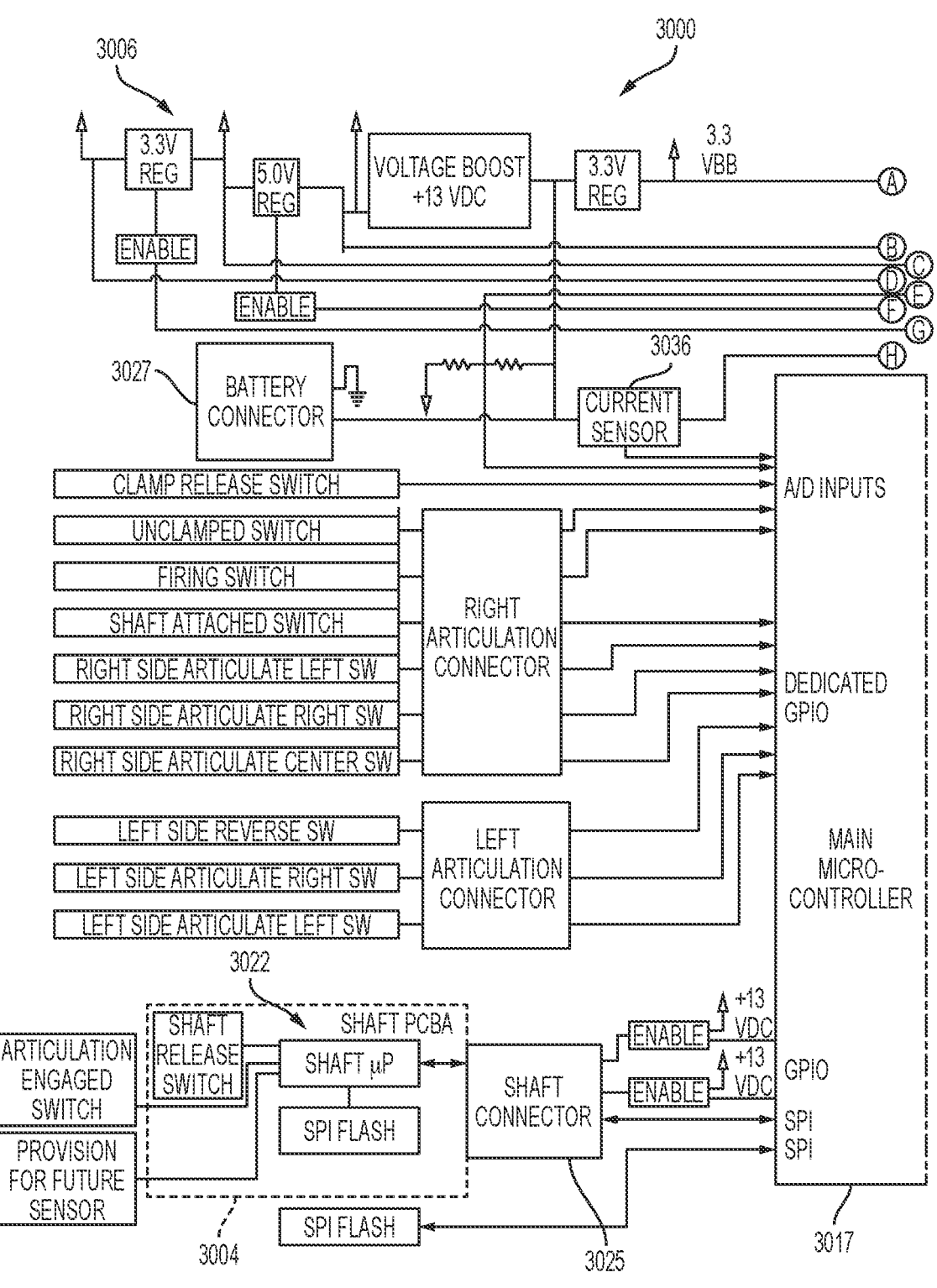
FIGS. 28A and 28B, is a circuit diagram of the surgical instrument of FIG. 1.
Figure 28B:
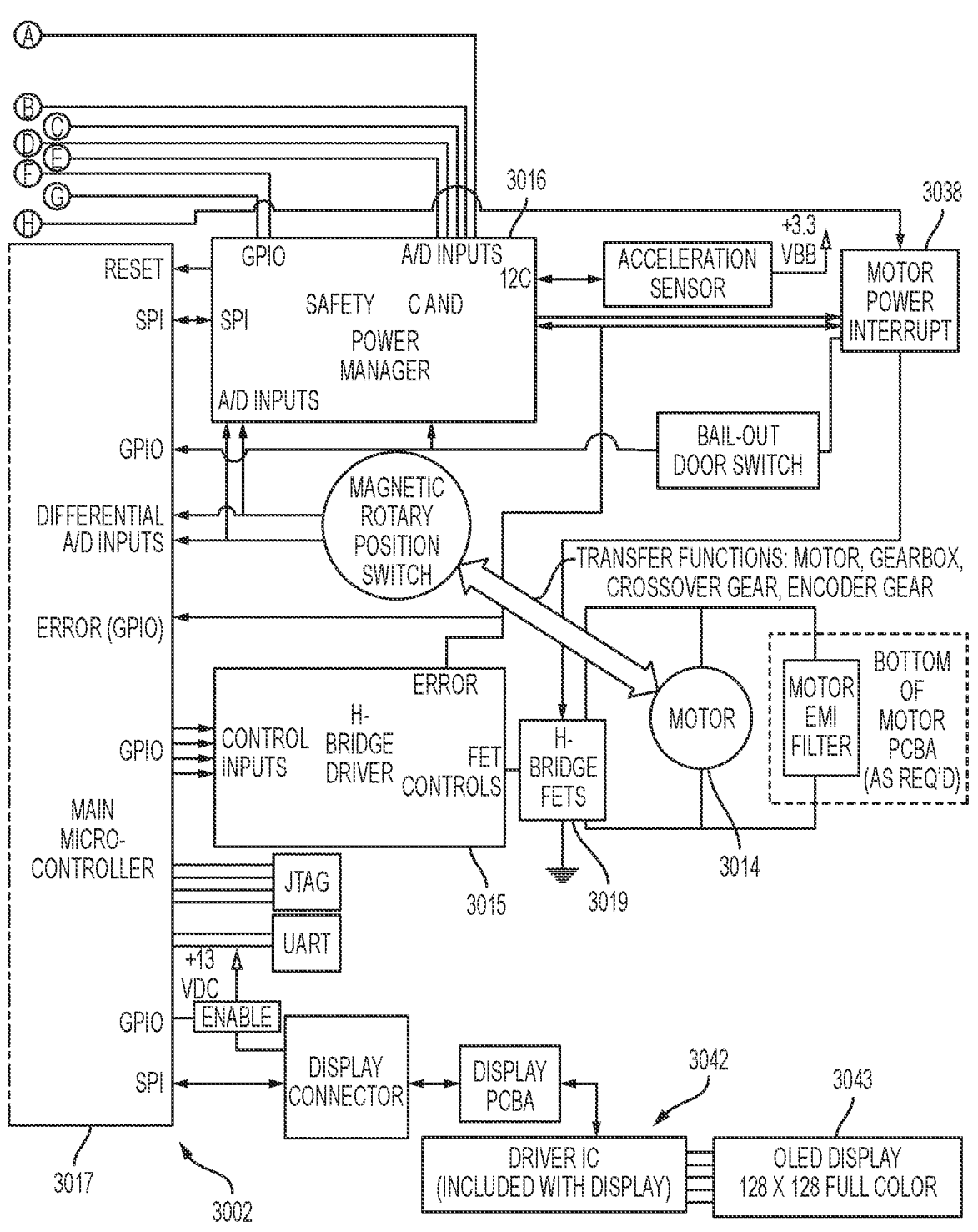

FIGS. 28A and 28B illustrate another aspect of a control circuit 3000 configured to control the powered surgical instrument 10, illustrated in FIGS. 1-18A. As shown in FIGS. 18A, 28B, the handle assembly 14 may include a motor 3014 which can be controlled by a motor driver 3015 and can be employed by the firing system of the surgical instrument 10. In various forms, the motor 3014 may be a DC brushed driving motor having a maximum rotation of, approximately, 25,000 RPM, for example. In other arrangements, the motor 3014 may include a brushless motor, a cordless motor, a synchronous motor, a stepper motor, or any other suitable electric motor. In certain circumstances, the motor driver 3015 may comprise an H-Bridge FETs 3019, as illustrated in FIGS. 28A and 28B, for example. The motor 3014 can be powered by a power assembly 3006, which can be releasably mounted to the handle assembly 14. The power assembly 3006 is configured to supply control power to the surgical instrument 10. The power assembly 3006 may comprise a battery which may include a number of battery cells connected in series that can be used as the power source to power the surgical instrument 10. In such configuration, the power assembly 3006 may be referred to as a battery pack. In certain circumstances, the battery cells of the power assembly 3006 may be replaceable and/or rechargeable. In at least one example, the battery cells can be Lithium-Ion batteries which can be separably couplable to the power assembly 3006.

Examples of drive systems and closure systems that are suitable for use with the surgical instrument 10 are disclosed in U.S. Provisional Patent Application Ser. No. 61/782,866, entitled CONTROL SYSTEM OF A SURGICAL INSTRU-MENT, and filed Mar. 14, 2013, the entire disclosure of which is incorporated by reference herein in its entirety. For example, the electric motor 3014 can include a rotatable shaft (not shown) that may operably interface with a gear reducer assembly that can be mounted in meshing engage-ment with a set, or rack, of drive teeth on a longitudinally-movable drive member. In use, a voltage polarity provided by the battery can operate the electric motor 3014 to drive the longitudinally-movable drive member to effectuate the end effector 300. For example, the motor 3014 can be configured to drive the longitudinally-movable drive mem-ber to advance a firing mechanism to fire staples into tissue captured by the end effector 300 from a staple cartridge assembled with the end effector 300 and/or advance a cutting member to cut tissue captured by the end effector 300, for example.

As illustrated in FIGS. 28A and 28B and as described below in greater detail, the power assembly 3006 may include a power management controller which can be con-figured to modulate the power output of the power assembly 3006 to deliver a first power output to power the motor 3014 to advance the cutting member while the interchangeable shaft 200 is coupled to the handle assembly 14 (FIG. 1) and to deliver a second power output to power the motor 3014 to advance the cutting member while the interchangeable shaft assembly 200 is coupled to the handle assembly 14, for example. Such modulation can be beneficial in avoiding transmission of excessive power to the motor 3014 beyond the requirements of an interchangeable shaft assembly that is coupled to the handle assembly 14.

In certain circumstances, the interface 3024 can facilitate transmission of the one or more communication signals between the power management controller 3016 and the shaft assembly controller 3022 by routing such communi-cation signals through a main controller 3017 residing in the handle assembly 14 (FIG. 1), for example. In other circum-stances, the interface 3024 can facilitate a direct line of communication between the power management controller 3016 and the shaft assembly controller 3022 through the handle assembly 14 while the shaft assembly 200 (FIG. 1) and the power assembly 3006 are coupled to the handle assembly 14.

In one instance, the main microcontroller 3017 may be any single core or multicore processor such as those known under the trade name ARM Cortex by Texas Instruments. In one instance, the surgical instrument 10 (FIGS. 1-4) may comprise a power management controller 3016 such as, for example, a safety microcontroller platform comprising two microcontroller-based families such as TMS570 and RM4x known under the trade name Hercules ARM Cortex R4, also by Texas Instruments. Nevertheless, other suitable substi-tutes for microcontrollers and safety processor may be employed, without limitation. In one instance, the safety processor 2004 (FIG. 21A) may be configured specifically for IEC 61508 and ISO 26262 safety critical applications, among others, to provide advanced integrated safety features while delivering scalable performance, connectivity, and memory options.

In certain instances, the microcontroller 3017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with Stellar-isWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

Figure 29:
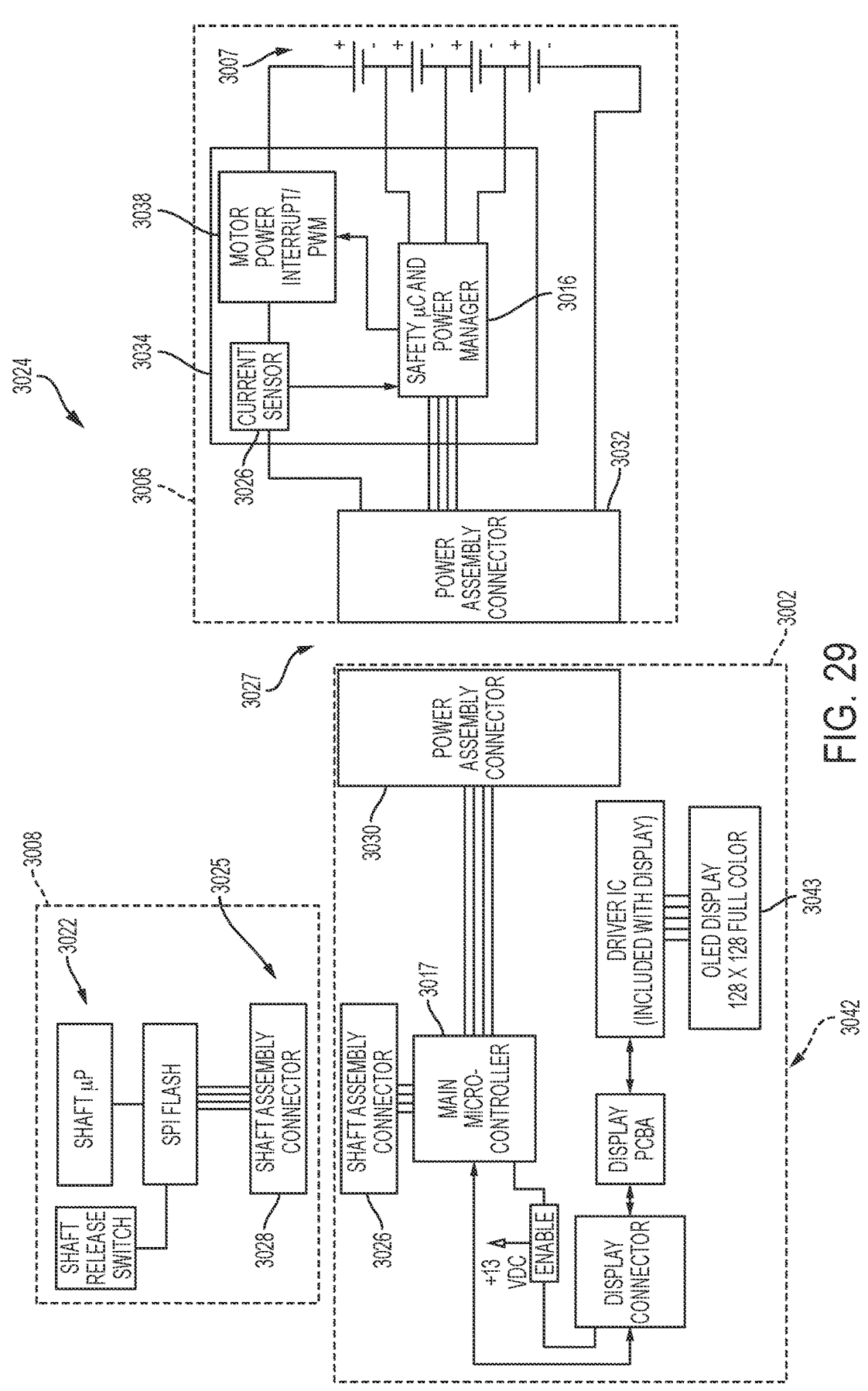
FIG. 29 is a block diagram the surgical instrument of FIG. 1 illustrating interfaces between the handle assembly 14 and the power assembly and between the handle assembly 14 and the interchangeable shaft assembly.

FIG. 29 is a block diagram the surgical instrument of FIG. 1 illustrating interfaces between the handle assembly 14 (FIG. 1) and the power assembly and between the handle assembly 14 and the interchangeable shaft assembly. As shown in FIG. 29, the power assembly 3006 may include a power management circuit 3034 which may comprise the power management controller 3016, a power modulator 3038, and a current sense circuit 3036. The power manage-ment circuit 3034 can be configured to modulate power output of the battery 3007 based on the power requirements of the shaft assembly 200 (FIG. 1) while the shaft assembly 200 and the power assembly 3006 are coupled to the handle assembly 14. For example, the power management control-ler 3016 can be programmed to control the power modulator 3038 of the power output of the power assembly 3006 and the current sense circuit 3036 can be employed to monitor power output of the power assembly 3006 to provide feed-back to the power management controller 3016 about the power output of the battery 3007 so that the power management controller 3016 may adjust the power output of the power assembly 3006 to maintain a desired output.

It is noteworthy that the power management controller 3016 and/or the shaft assembly controller 3022 each may comprise one or more processors and/or memory units which may store a number of software modules. Although certain modules and/or blocks of the surgical instrument 14 (FIG. 1) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 10 (FIGS. 1-4) may comprise an output device 3042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 3042 may comprise a display 3043 which may be included in the handle assembly 14 (FIG. 1). The shaft assembly controller 3022 and/or the power management controller 3016 can provide feedback to a user of the surgical instrument 10 through the output device 3042. The interface 3024 can be configured to connect the shaft assembly controller 3022 and/or the power management controller 3016 to the output device 3042. The reader will appreciate that the output device 3042 can instead be integrated with the power assembly 3006. In such circumstances, communication between the output device 3042 and the shaft assembly controller 3022 may be accomplished through the interface 3024 while the shaft assembly 200 is coupled to the handle assembly 14.

Having described a surgical instrument 10 (FIGS. 1-4) and various control circuits 2000, 3000 for controlling the operation thereof, the disclosure now turns to various specific configurations of the surgical instrument 10 and control circuits 2000 (or 3000).

In various aspects the present disclosure provides techniques for data storage and usage. In one aspect, data storage and usage is based on multiple levels of action thresholds. Such thresholds include upper and lower ultimate threshold limits, ultimate threshold that shuts down motor or activates return is current, pressure, firing load, torque is exceeded, and alternatively, while running within the limits the device automatically compensates for loading of the motor.

In one aspect, the instrument 10 (described in connection with FIGS. 1-29) can be configured to monitor upper and lower ultimate threshold limits to maintain minimum and maximum closure clamp loads within acceptable limits. If a minimum is not achieved the instrument 10 cannot start or if it drops below minimum a user action is required. If the clamp load is at a suitable level but drops under minimum during firing, the instrument 10 can adjust the speed of the motor or warn the user. If the minimum limit is breached during operation the unit could give a warning that the firing may not be completely as anticipated. The instrument 10 also can be configured to monitor when the battery voltage drops below the lower ultimate limit the remaining battery power is only direct able towards returning the device to the I-beam parked state. The opening force on the anvil can be employed to sense jams in the end effector. Alternatively, the instrument 10 can be configured to monitor when the motor current goes up or the related speed goes down, then the motor control increases pulse width or frequency modulation to keep speed constant.

In another aspect, the instrument 10 can (FIG. 1) be configured to detect an ultimate threshold of current draw, pressure, firing load, torque such that when any of these thresholds are exceeded, the instrument 10 shuts down the motor or causes the motor to return the knife to a pre-fired position. A secondary threshold, which is less than the ultimate threshold, may be employed to alter the motor control program to accommodate changes in conditions by changing the motor control parameters. A marginal threshold can be configured as a step function or a ramp function based on a proportionate response to another counter or input. For example, in the case of sterilization, no changes between 0-200 sterilization cycles, slow motor 1% per use from 201-400 sterilization cycles, and prevent use over 400 sterilization cycles. The speed of the motor also can be varied based on tissue gap and current draw.

There are many parameters that could influence the ideal function of a powered reusable stapler device. Most of these parameters have an ultimate maximum and/or minimum threshold beyond which the device should not be operated. Nevertheless, there are also marginal limits that may influence the functional operation of the device. These multiple limits, from multiple parameters may provide an overlying and cumulative effect on the operations program of the device.

Accordingly, the present disclosure relates to surgical instruments and, in various circumstances, to surgical stapling and cutting instruments and staple cartridges therefor that are designed to staple and cut tissue.

Efficient performance of an electromechanical device depends on various factors. One is the operational envelope, i.e., range of parameters, conditions and events in which the device carries out its intended functions. For example, for a device powered by a motor driven by electrical current, there may be an operational region above a certain electrical current threshold where the device runs more inefficiently than desired. Put another way, there may be an upper "speed limit" above which there is decreasing efficiency. Such an upper threshold may have value in preventing substantial inefficiencies or even device degradation.

There may be thresholds within an operational envelope, however, that may form regions exploitable to enhance efficiency within operational states. In other words, there may be regions where the device can adjust and perform better within a defined operational envelope (or sub-envelope). Such a region can be one between a marginal threshold and an ultimate threshold. In addition, these regions may comprise "sweet spots" or a predetermined optional range or point. These regions also may comprise a large range within which performance is judged to be adequate.

An ultimate threshold can be defined, above which or below which an action or actions could be taken (or refrained from being taken) such as stopping the device. In addition, a marginal threshold or thresholds can be defined, above which or below which an action or actions could be taken (or refrained from being taken). By way of non-limiting example, a marginal threshold can be set to define where the current draw of the motor exceeds 75% of an ultimate threshold. Exceeding the marginal threshold can result, for example, in the device's beginning to slow motor speed at an increasing rate as it continues to climb toward the ultimate threshold.

Various mechanisms can be employed to carry out the adjustment(s) taken as a result of exceeding a threshold. For example, the adjustment can reflect a step function. It can also reflect a ramped function. Other functions can be utilized.

In various aspects, to enhance performance by additional mechanisms, an overlaying threshold can be defined. An overlaying threshold can comprise one or more thresholds defined by multiple parameters. An overlaying threshold can result in one or more thresholds being an input into the generation of another threshold or thresholds. An overlaying threshold can be predetermined or dynamically generated such as at runtime. The overlaying threshold may come into effect when you the threshold is defined by multiple inputs. For example, as the number of sterilization cycles exceeds 300 (the marginal threshold) but not 500 (the ultimate threshold) the device runs the motor slower. Then as the current draw exceeds its 75% marginal threshold it multiples the slow down going even slower.

Figure 30:
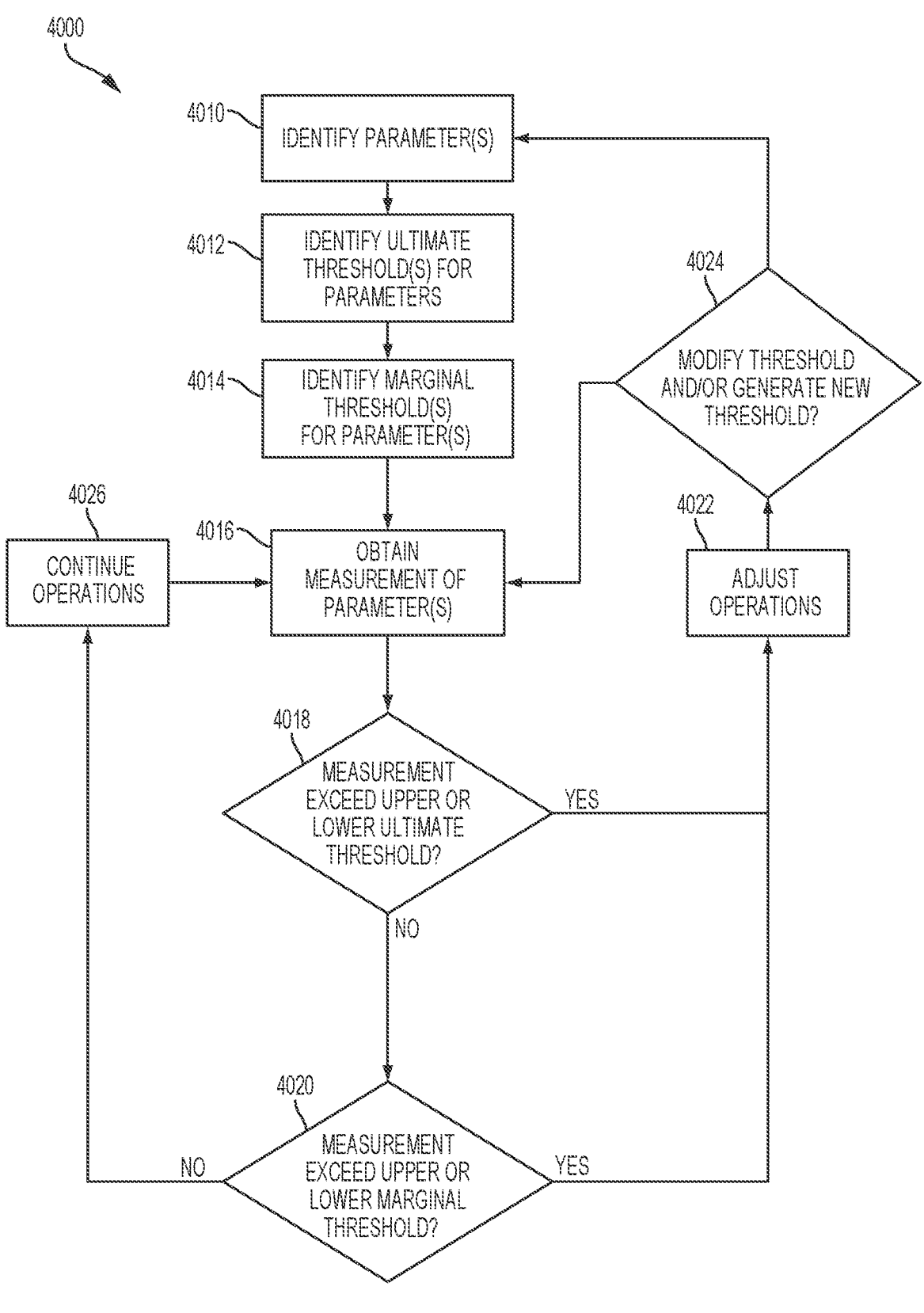
FIG. 30 illustrates one aspect of a process for utilizing thresholds to modify operations of a surgical instrument.

FIG. 30 is a logic diagram disclosing aspects of a multiple-level threshold system wherein a threshold rules framework 4000. Parameters can be identified 4010, such parameters representing quantities, amounts, states, events or more. For example, parameters identified can include one or more of current, voltage, tissue pressure, tissue thickness, jaw closure rate, tissue creep rate, firing load, knife thickness, torque, or battery usage. An ultimate threshold or thresholds for these parameters can be identified 4012. For instance, a predetermined current draw can be identified. As but one example, an ultimate electrical current draw threshold may be defined as 100% of a selected current magnitude. There can be an upper ultimate threshold, a lower ultimate threshold, multiple lower or upper ultimate thresholds depending on the circumstances, or a range defining an ultimate threshold. It will be appreciated that an "ultimate" threshold can be defined and/or calibrated in such a way as to remain essentially a unitary threshold but embody various action triggers. A marginal threshold or thresholds can be identified 4014. If the marginal threshold is exceeded, a motor control program can alter operations to accommodate change.

One or more thresholds can be monitored an acted on during a single surgical procedure, wherein the thresholds are independent of each other with no interaction. In addition, there can be an interactive association between thresholds of two or more parameters. For example, a marginal threshold for a parameter based on current draw can be 75% of the ultimate threshold. In addition, in connection with a parameter based on number of sterilization cycles, a marginal threshold may be set at 200 sterilization cycles, and an ultimate threshold at sterilization 400 cycles. Motor use can proceed normally from 0-199 cycles, and then slow by 1% from 200 cycles to 399. At cycle 400, motor use can be prevented. It will be appreciated, however, that there can be an interactive effect. In other words, because motor speed is reduced by 1% due to exceeding the sterilization cycle threshold, the current draw threshold can be correspondingly adjusted. This interactive effect can result in the motor running more slowly than it would if either input were considered independently.

Thus, the value of one threshold can be an input into the value of another threshold, or one threshold can be completely independent of another threshold. Where two or more thresholds are activated, it can be considered that there can be an overlaying threshold. As a result, multiple thresholds, defining multiple boundaries and limits, can have an overlaying or cumulative effect on operations of instrument 10 (FIGS. 1-4). And, one threshold in a multiple-threshold operation scenario can have a cause-and-effect with another threshold, or there may be no cause-and-effect and the thresholds may exist independent of each other.

In addition, a threshold can be dynamically set and/or reset depending on conditions experienced during surgery or other conditions. In other words, prior to a given surgical procedure, a module or modules can be preprogrammed into instrument 10 (FIGS. 1-4) or uploaded as needed. Also, a threshold can be dynamically determined, or uploaded, during a surgical procedure.

Turning briefly now to FIG. 1, numerous parameters can be assigned thresholds. Thus, in examples thresholds may be assigned based on tissue gap between the anvil 306 and staple cartridge 304, or anvil 306 and second jaw member 302, of an end effector 300, and motor speed varied thereby. In addition, in example thresholds based on current can vary motor speed control. Further, in various examples ultimate, marginal and overlaying thresholds can be established in connection with closure clamp loads in furtherance of an acceptable operating range. Plus, in various examples opening force on an anvil 306 can help to detect a jam. Further, in various examples if a minimum threshold is not achieved, the system may be prevented from starting or if it drops below a minimum then a user action can be required.

Still with reference to FIG. 1, in various aspects, it can be determined whether clamp load is acceptable and when clamp load drops under a minimum threshold during firing the speed of the motor can be adjusted and/or the clinician warned. In various examples, when a minimum threshold is exceeded during operation, instrument 10 can give a warning that the firing may not be completely as anticipated. Moreover, in various examples thresholds can be assigned wherein if battery charge falls below a threshold then remaining battery charge can be used to return the device to a parked state with respect to the I-beam.

However, thresholds can be referenced even during operations that do not exceed a threshold. Thus, for example, instrument 10 can, while running "within limits", compensate for the loading of the motor. For instance, if current goes up or related speed goes down, then motor control can increase pulse width or frequency modulation to help to maintain a constant speed. In other words, measures can be taken to improve and/or optimize operations of instrument 10 even while running "within limits."

In addition, dynamically during a surgical procedure, a threshold can be modified, or a new threshold generated. This can occur after several events including adjusting operations of the instrument 10.

Turning now back to FIG. 30, in various aspects a parameter or parameters are identified 4010. Further, an ultimate threshold or thresholds for a given parameter(s) are identified 4012. In addition, a marginal threshold or thresholds for a given parameter(s) are identified 4014. Measures 4010, 4012, and 4014 can be accomplished prior to the procedure, during the procedure, or both.

Measurements of a parameter(s) are obtained 4016. It can be determined whether the measurement of a given parameter exceeds an upper or lower ultimate threshold for the parameter 4018. When the answer is no, it can be determined whether the measurement of a given parameter exceeds an upper or lower marginal threshold for the parameter 4020.

When the answer is no, operations can be continued 4026. And, measurements of a given parameter(s) can be again obtained.

When, however, the answer is yes to whether the measurement of a given parameter exceeds an upper or lower ultimate threshold for the parameter 4018, control can pass to where operations can be adjusted 4022. Many types of adjustments can be made. One example is to vary motor speed. It can be determined whether to modify a given threshold and/or generate a new threshold 4024. This can occur after operations have been adjusted 4022.

After operations are adjusted, it can be determined whether to modify a threshold or generate a new threshold. For example, a marginal threshold initially set at 75% can be set to a different value. In addition, a new threshold on the same parameter, or a new threshold on a new parameter, can be generated if desired.

Upon determining whether to modify a threshold or generate a new one, control can pass back to step 4016 where measurement of a parameter(s) is obtained. In addition, control can proceed to identify 4010 parameters.

When the answer to whether the measurement exceeds an upper or lower ultimate threshold is no, however, then it can be determined when the measurement exceeds an upper or lower marginal threshold. When the answer is yes, then operations can be adjusted 4022 and control proceed as above. When the answer is no, operations can be continued 4026 and control proceed to measuring a parameter(s).

It will be appreciated that the sequence of steps can be varied and is not limited to that specifically disclosed in FIG. 30. As just one example, after obtaining measurement of a parameter(s) 4016, it can then be determined whether a marginal threshold is exceeded 4020. In addition, an overlaying threshold can expressly be identified and considered in the course of the flow.

Figure 31:
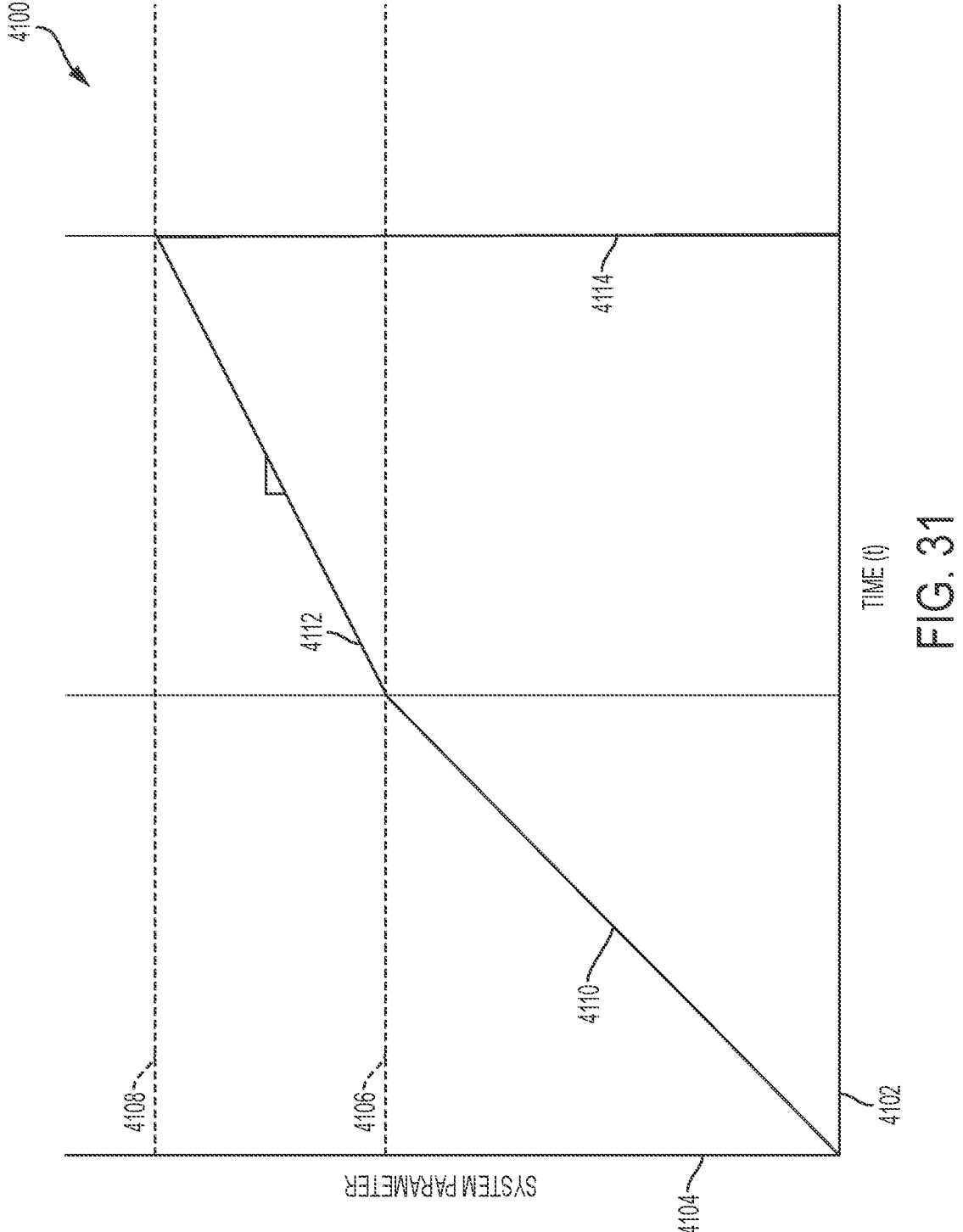
FIG. 31 illustrates an example graph showing modification of operations of a surgical instrument describing a linear function.

FIG. 31 is a graphical representation 4100 of instrument system parameters versus time depicting how, in one aspect, instrument system parameters can be adjusted in the event that a threshold is reached. Time (t) is shown along a horizontal (x) axis 4102 and the instrument System Parameter is shown along a vertical (y) axis 4104, marginal threshold 4104 and ultimate threshold 4106. In the graphical representation 4100 depicted in FIG. 34, the y-axis parameter 4102 is the one to which a threshold of instrument system parameter is assigned and the x-axis 4102 represents time. At a certain time during operation of instrument 10 (FIGS. 1-4), as evidenced by function 4110, a measurement can indicate that marginal threshold 4106 is reached. At this point, operations of the instrument 10 (FIGS. 1-4) can be adjusted. For example, when the y-axis 4104 parameter is electrical current draw by a motor, a function can be imposed on the subsequent electrical current draw and limit current in some fashion. In one example, the function can represent a linear progression 4112. At a certain time in the course of operation, an ultimate threshold 4108 can be reached. At this point, electrical current can be discontinued 4114. Accordingly, an adjustment mechanism can be accomplished via a linear function. An additional perspective with which to view the operational adjustment is that there can be a square-wave multiplier change.

Figure 32:
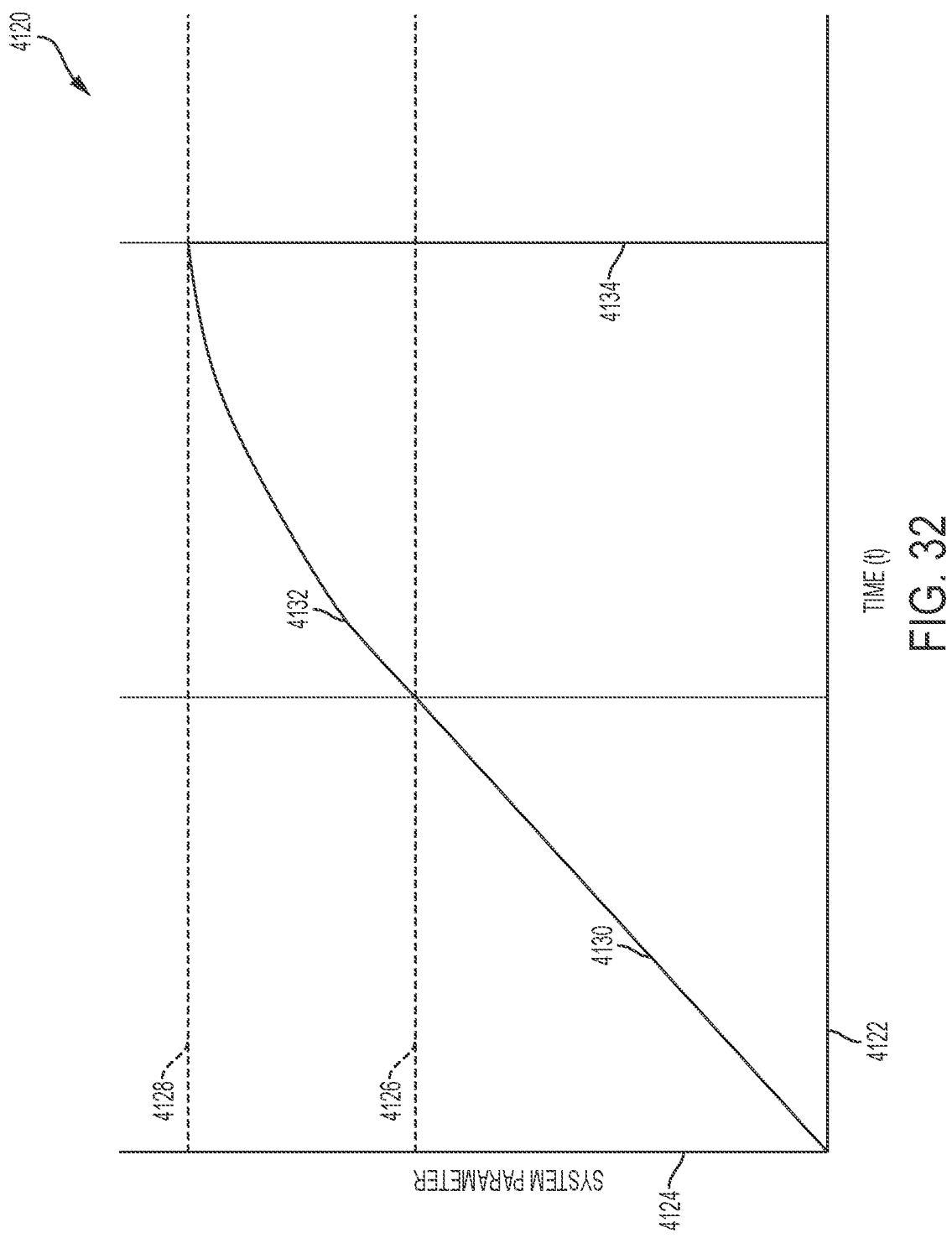
FIG. 32 illustrates an example graph showing modification of operations of a surgical instrument describing a non-linear function.

FIG. 32 is a graphical representation 4120 of instrument system parameter depicting how, in another aspect, a system parameter can be adjusted in the event that a threshold is reached. Time (t) is shown along a horizontal (x) axis 4122 and the number of Instrument Operations is shown along a vertical (y) axis 4124, marginal threshold 4126 and ultimate threshold 4128. Here the y-axis 4124 parameter is the one to which a threshold is assigned. At a certain time during operation of instrument 10 (FIGS. 1-4), a measurement can indicate that the marginal threshold 4126 is reached during the course of operation 4130. At this point, operations of the instrument 10 can be adjusted. For example, when the y-axis 4124 parameter is electrical current draw by a motor, a limit can be placed on the subsequent current draw representing a non-linear progression 4132. At a certain time after this, an ultimate threshold 4128 can be reached. At this point, current can be discontinued 4134. Accordingly, an adjustment mechanism can be accomplished via a non-linear function 4132, with a variable slope. An additional perspective with which to view the operational adjustment is that there is an exponential multiplier change; here, the closer the y-axis 4124 parameter comes to the ultimate threshold 4128, the rate at which current increases diminishes.

Figure 33:
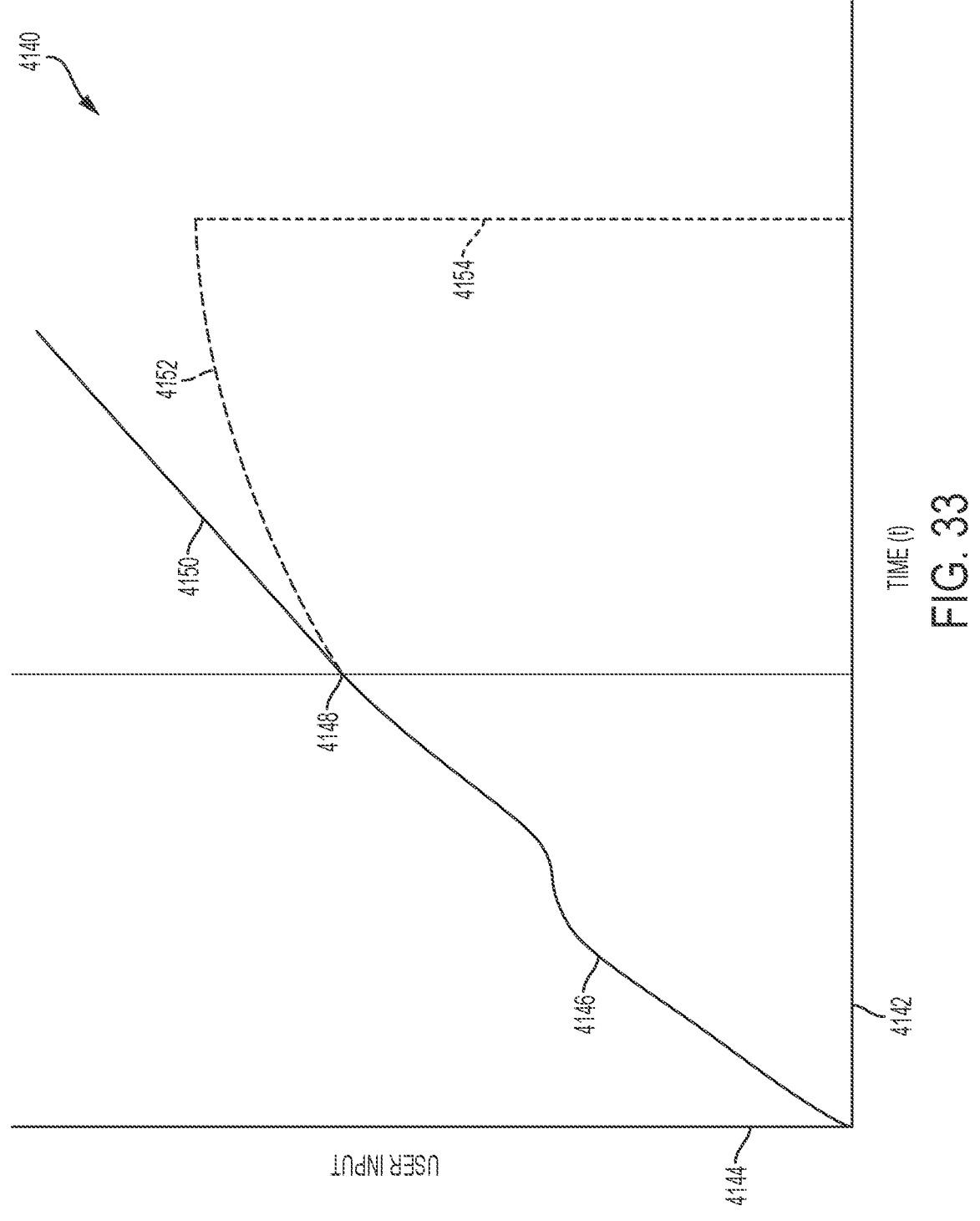
FIG. 33 illustrates an example graph showing modification of operations of a surgical instrument based on an expected user input parameter.

FIG. 33 is a graphical representation 4140 that represents one aspect wherein a response by instrument 10 (FIGS. 1-4) to clinician input (User Input) is detected and then a modification is made. Time (t) is shown along a horizontal (x) axis 4142 and User Input is represented along a vertical (y) axis 4144. In other words, a clinician, in performing a procedure, can actuate a response by instrument 10 such as depressing closure trigger 32 (FIG. 1) which may for example cause motor operation 4146. As motor speed increases there may or not be a threshold reached. At a certain point, however, here represented by the divergence point 4148 of curves 4150 and 4152, it can be determined that motor speed has reached an actual level, or a future level be predicted, that is or will be suboptimal or otherwise undesirable. At this point, rather than following the actual or expected speed curve 4150, instrument 10 can employ a control measure such as an algorithm to adapt or otherwise modify the output, thus regulating the motor. At a certain point, motor actuation can be discontinued 4154. In other words, instrument 10 can take an actual or expected y-axis parameter and, determining that such actual or expected measurement is excessive, employ an algorithm to modify such parameter. Put another way, measured clinician behavior can comprise a value for a threshold or thresholds.

Figure 34:
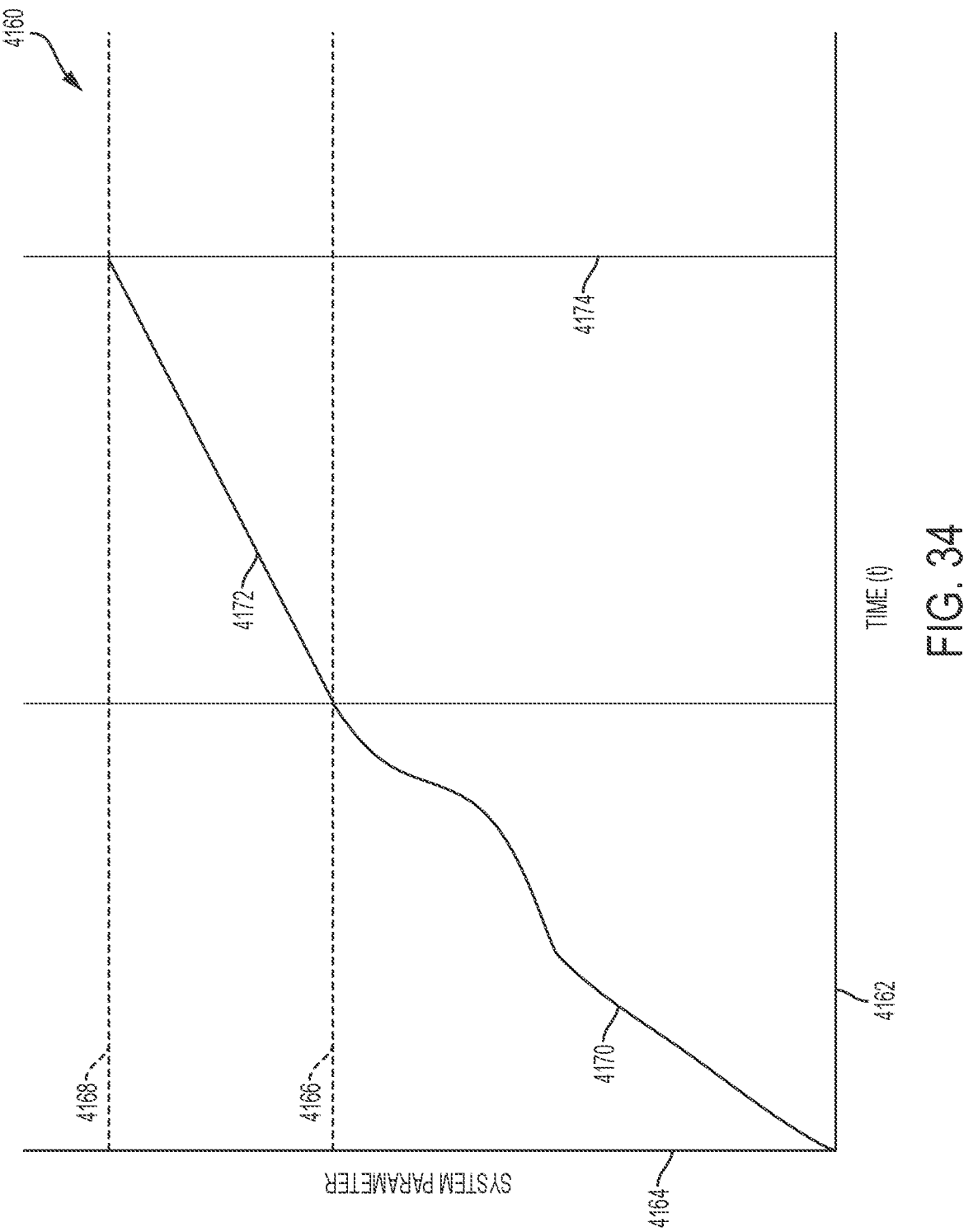
FIG. 34 illustrates an example graph showing modification of velocity of a drive based on detection of a threshold.

FIG. 34 is a graphical representation 4160 of instrument system parameters that represents one aspect wherein instrument 10 (FIGS. 1-4) detects whether a marginal threshold 4166 or ultimate threshold 4168 is reached, and responds accordingly. Time (t) is shown along the horizontal (x) axis 4162 and instrument System Parameters is shown along the vertical (y) axis 4164. For example, here the vertical (y) axis 4154 parameter can be the velocity of a drive, such as a closure drive system 30 (FIG. 1) or firing drive system 80 (FIG. 1). Instrument 10 can check whether during the course of operation 4170 a marginal threshold 4166 velocity is reached. When the marginal threshold 4166 is reached, a control measure such as an algorithm can be used to adapt or otherwise modify the velocity 4172. The modified velocity 4172 can be given by a linear or non-linear function. And, at an ultimate threshold, power to the motor can be discontinued 4174.

It will be appreciated that where FIG. 33 can represent a situation where an actual or predicted value is evaluated, whether or not an express threshold is provided, FIG. 34 is a graphical representation where thresholds are provided. It can be appreciated, however, that a threshold or thresholds can be implicitly given to FIG. 33 with equivalent results, insofar as a predetermined or dynamically determined value can serve as a functional equivalent of a threshold, or trigger actions associated with a threshold or thresholds. There may be two or more ceiling or floor values that can serve as such threshold functional equivalents.

Figure 35:
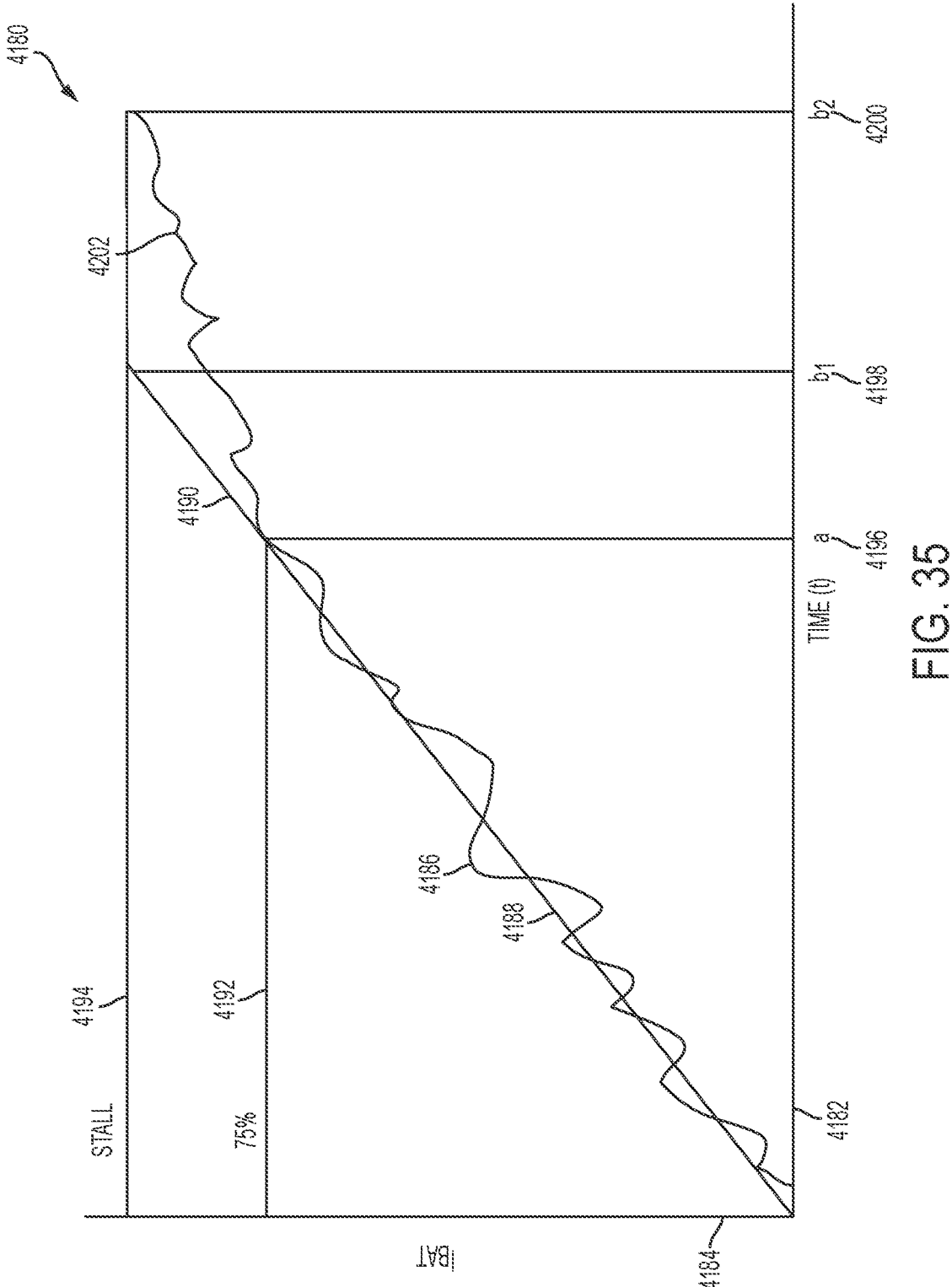
FIG. 35 illustrates an example graph showing modification in connection with operations based on battery current based on detection of a threshold.

Turning to another example using thresholds, FIG. 35 is a graphical representation 4180 of battery current versus time, where Time (t) is shown along the horizontal (x) axis 4182 and battery current $I_{BAT}$ is shown along the vertical (y) axis 4184. In one example battery current $I_{BAT}$ 4184 is monitored under varying operational conditions. As motor speed increases, current drawn 4186 from a battery 90 (FIG. 4) increases. Current drawn can increase in a non-linear manner depending on several factors; however, instrument 10 (FIGS. 1-4) can resolve the current drawn into a linear function 4188. The linear function can be based on (1) averaging overall current, (2) be based on a prediction of future current based on past and/or present current, both (1) and (2), or another function. Linear function 4188 can be extended out theoretically to linear function 4190, which is an extrapolated extension with the same slope as linear function 4188.

Once linear function 4188 reaches a marginal threshold 4192, instrument 10 (FIGS. 1-4) can take action to modify the response. Here the marginal threshold is given as 75% of an ultimate threshold 4194 wherein the ultimate threshold represents a motor stall; however, it will be appreciated that the selection of the marginal threshold or ultimate threshold can be made based on multiple factors. In other words, marginal threshold 4192 can be reached at time "a" 4196. If adjustments are not made, it is expected that motor stall would occur at time "b1" 4198. However, due to adjustments made by instrument 10, the actual motor stall will not occur until time "b2" 4200. It is possible that a stall might not occur at all, because the more graduated rise may help to prevent such an event. Function 4202, which is implemented via a control measure, can be based on slowing the motor, or another adjustment. It can manifest as a stepped, ramped or further function.

Employing the thresholds herein can give the clinician greater time to react and adapt, maintain a desired efficiency of the instrument, and prolong battery life. Thus, utilizing thresholds can provide multiple benefits in connection with ease of clinician use and protection of the instrument itself.

Figure 36:
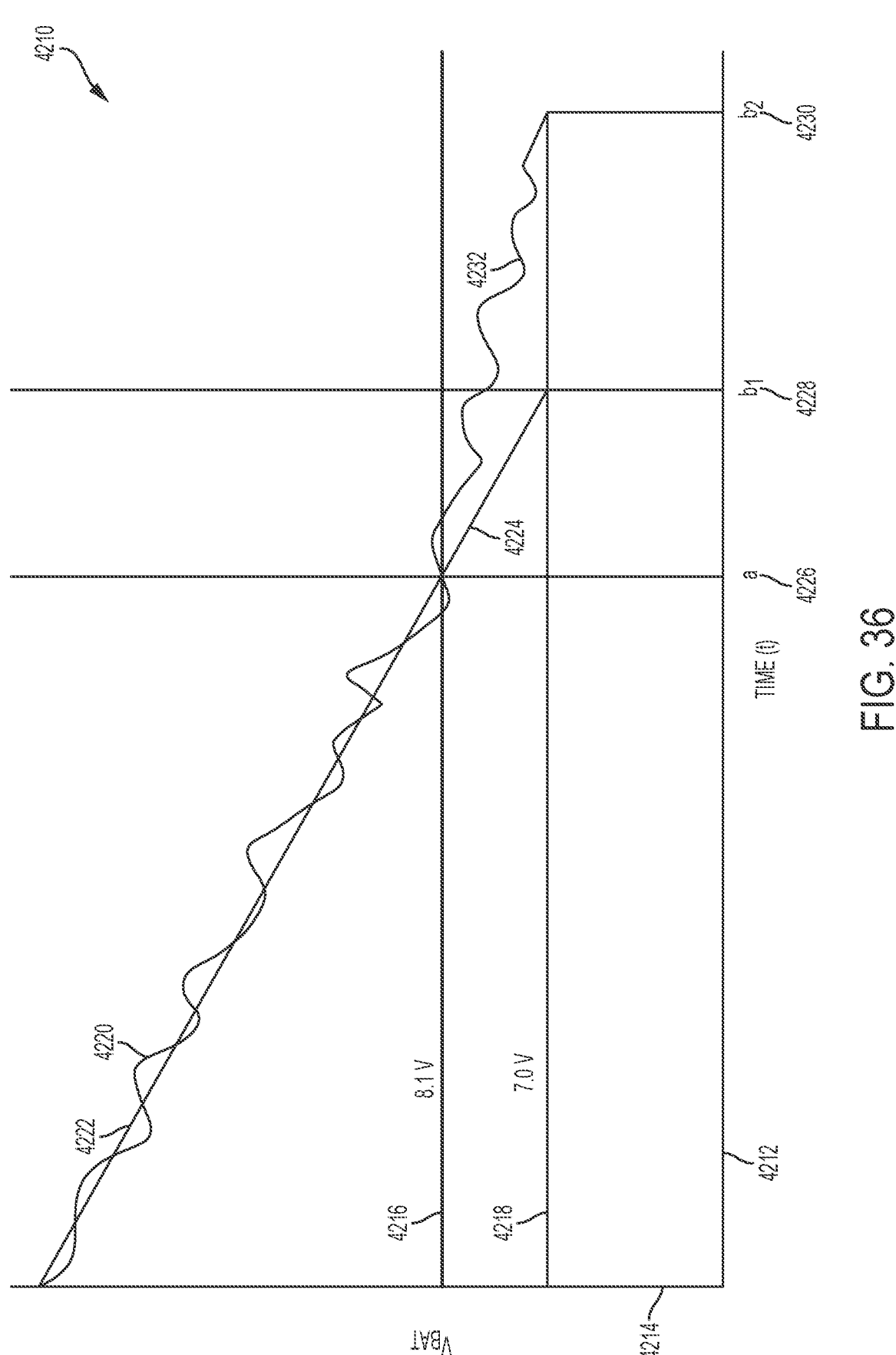
FIG. 36 illustrates an example graph showing modification in connection with operations based on battery voltage based on detection of a threshold.

Turning to another aspect, FIG. 36 is a graphical representation 4210 of battery voltage that shows Time (t) along the horizontal (x) axis 4212 and battery voltage VBAT along the vertical (y) axis 4214. In one example a threshold can be set in connection with battery voltage VBAT 4214. Here a marginal threshold 4216 can be set at 8.1V. Additionally, an ultimate threshold 4218 can be set at 7.0V. During the course of operation of instrument 10 (FIGS. 1-4), voltage can decrease over time. The curve described by measuring the voltage decrease 4220 is not necessarily linear. However, instrument 10 can resolve the voltage decrease into a linear function 4222. The linear function can be based on (1) averaging overall voltage, (2) be based on a prediction of future voltage based on past and/or present voltage, both (1) and (2), or another function. Linear function 4222 can be extrapolated out theoretically to linear function 4224, which has the same slope as linear function 4222.

Once linear function 4222 reaches a marginal threshold 4216, instrument 10 can take action to modify the response. Marginal threshold 4216 is reached at time "a" 4226. If adjustments are not made, it is expected that a depleted battery condition would occur at time "b1" 4228. However, due to adjustments made by instrument 10 (FIGS. 1-4), the actual depleted battery condition will not occur until time "b2" 4230. Again, it is possible that it may not occur at all. Function 4232, which can be implemented via a control measure, can be based on slowing the motor, or another adjustment. It can manifest as a stepped, ramped or further function.

Figure 37:
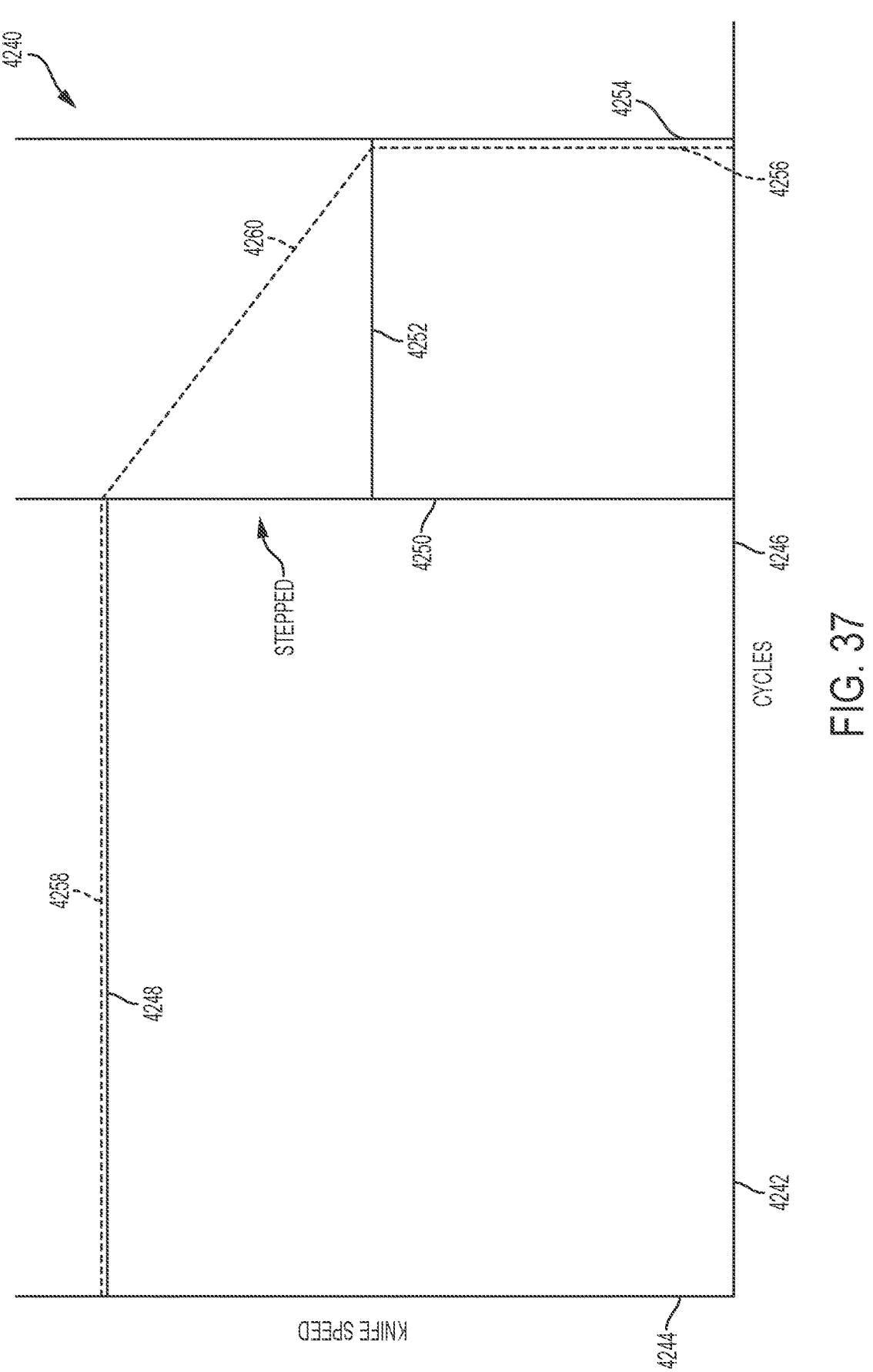
FIG. 37 illustrates an example graph showing modification of knife speed based on detection of a cycle threshold.

FIG. 37 is a graphical representation 4240 of knife speed versus number of cycles where and Cycles is shown along the horizontal (x) axis 4242 and Knife Speed is shown along the vertical (y) axis 4244. As shown in the example illustrated by FIG. 37, thresholds can be employed to adjust speed of a knife 280 (FIG. 8) based on the number of cycles. Relevant cycles can refer to an amount of firings performed by instrument 10 (FIGS. 1-4), sterilization cycles performed by instrument 10, or other measured events. An objective of managing instrument operation by this threshold mechanism is to maximize the likelihood that an incision will be effective, taking into account potential blunting of the knife 280 edge after multiple uses. In this example, firing of the knife can be initialized based on an expected speed. However, once a marginal threshold 4246 is reached based on number of cycles, speed can be reduced from speed 4248 to 4252, such as in a stepped manner 4250. Thus, once marginal threshold 4760 is exceeded, knife 280 will fire at a progressively lower speed. This will occur for a given number of cycles 4246 until ultimate threshold 4254 is reached. At this point, knife speed will be stepped down 4256 even more or of course instrument 10 can alert the clinician that it may be undesirable to incise with the knife, and can lock out firing. It will be understood that function 4248 shows employing a stepped function once a threshold 4246 is reached, and function 4258 shows employing a ramped function 4260 once a threshold 4246 is reached. Additional functions can be employed.

Further, it will be appreciated that the thresholds given in FIG. 37 have been defined on the x-axis 4711, whereas prior figures have shown thresholds on the y-axis 4712. It will also be appreciated that there can be an additional axis or axes taken into account, i.e., a z-axis or further axes, wherein the interrelationship of multiple variables can be considered. Further, thresholds from a first parameter can be considered along with thresholds from a second parameter, and one threshold can comprise an input into another threshold, and vice versa.

When a threshold is exceeded, the clinician can be notified. This can be based on a feedback system. In certain instances, the feedback system may comprise one or more visual feedback systems such as display screens, backlights, and/or LEDs, for example. In certain instances, the feedback system may comprise one or more audio feedback systems such as speakers and/or buzzers, for example. In certain instances, the feedback system may comprise one or more haptic feedback systems, for example. In certain instances, the feedback system may comprise combinations of visual, audio, and/or tactile feedback systems, for example. Such feedback can serve to alert or warn the clinician.

Figure 38:
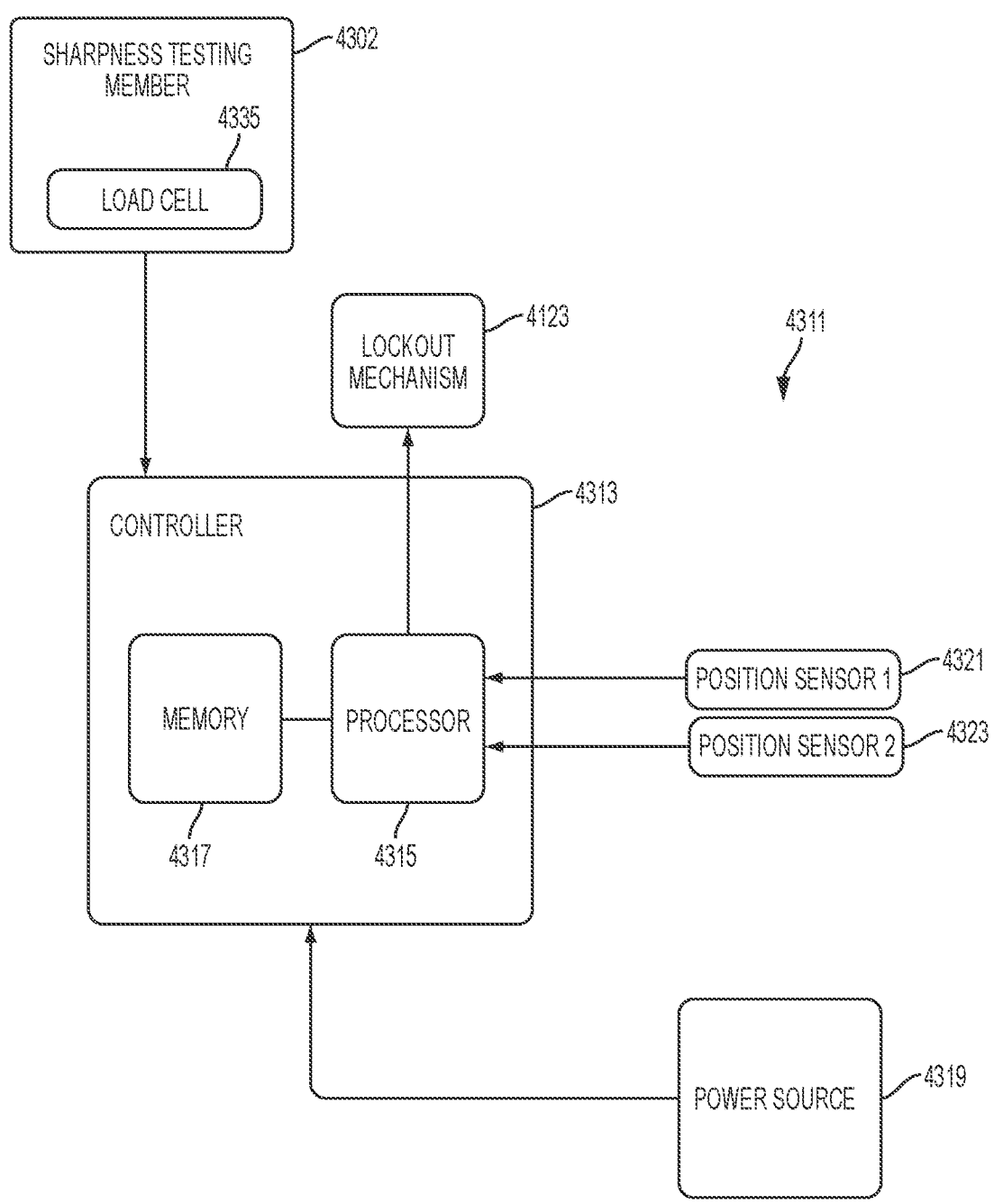
FIG. 38 illustrates a logic diagram of a system for evaluating sharpness of a cutting edge of a surgical instrument according to various aspects.

FIG. 38 illustrates a logic diagram of a system 4311 for evaluating sharpness of a cutting edge 182 (FIG. 20) of a surgical instrument 10 (FIGS. 1-4) according to various examples. FIG. 38 illustrates a sharpness testing system 4311 for evaluating sharpness of a cutting edge of a surgical instrument 10 according to various examples. In certain instances, the system 4311 can evaluate the sharpness of the cutting edge 182 by testing the ability of the cutting edge 182 to be advanced through a sharpness testing member 4302. For example, the system 4311 can be configured to observe the time period the cutting edge 182 takes to fully transect and/or completely pass through at least a predetermined portion of a sharpness testing member 4302. If the observed time period exceeds a predetermined threshold, the module 4310 may conclude that the sharpness of the cutting edge 182 has dropped below an acceptable level, for example.

In one aspect, the sharpness testing member 4302 can be employed to test the sharpness of the cutting edge 182 (FIG. 20). In certain instances, the sharpness testing member 4302 can be attached to and/or integrated with the cartridge body 194 (FIG. 20) of the staple cartridge 304 (FIGS. 1, 2, and 20), for example. In certain instances, the sharpness testing member 4302 can be disposed in the proximal portion of the staple cartridge 304, for example. In certain instances, the sharpness testing member 4302 can be disposed onto a cartridge deck or cartridge body 194 of the staple cartridge 304, for example.

In certain instances, a load cell 4335 can be configured to monitor the force (Fx) applied to the cutting edge 182 (FIG. 20) while the cutting edge 182 is engaged and/or in contact with the sharpness testing member 4302, for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. The load cell 4335 of the sharpness testing member 4302 may be employed to measure the force (Fx) applied to the cutting edge 182 while the cutting edge 182 travels a predefined distance (D) through the sharpness testing member 4302 may be employed to determine the sharpness of the cutting edge 182.

In certain instances, the module 4311 may include a microcontroller 4313 ("controller") which may include a microprocessor 4315 ("processor") and one or more computer readable mediums or memory units 4317 ("memory"). In certain instances, the memory 4317 may store various program instructions, which when executed may cause the processor 4315 to perform a plurality of functions and/or calculations described herein. In certain instances, the memory 4317 may be coupled to the processor 4315, for example. A power source 4319 can be configured to supply power to the controller 4313, for example. In certain instances, the power source 4319 may comprise a battery (or "battery pack" or "power pack"), such as a Li ion battery, for example. In certain instances, the battery pack may be configured to be releasably mounted to the handle 14. A number of battery cells connected in series may be used as the power source 4319. In certain instances, the power source 4319 may be replaceable and/or rechargeable, for example.

In certain instances, the processor 4313 can be operably coupled to the feedback system and/or the lockout mechanism 4123, for example.

The module 4311 may comprise one or more position sensors. Example position sensors and positioning systems suitable for use with the present disclosure are described in U.S. patent application Ser. No. 13/803,210, entitled SENSOR ARRANGEMENTS FOR ABSOLUTE POSITIONING SYSTEM FOR SURGICAL INSTRUMENTS, and filed Mar. 14, 2013, now U.S. Pat. No. 9,808,244, the disclosure of which is hereby incorporated by reference herein in its entirety. In certain instances, the module 4311 may include a first position sensor 4321 and a second position sensor 4323. In certain instances, the first position sensor 4321 can be employed to detect a first position of the cutting edge 182 (FIG. 20) at a proximal end of a sharpness testing member 4302, for example; and the second position sensor 4323 can be employed to detect a second position of the cutting edge 182 at a distal end of a sharpness testing member 4302, for example.

In certain instances, the position sensors 4321 and 4323 can be employed to provide first and second position signals, respectively, to the microcontroller 4313. It will be appreciated that the position signals may be analog signals or digital values based on the interface between the microcontroller 4313 and the position sensors 4321 and 4323. In one example, the interface between the microcontroller 4313 and the position sensors 4321 and 4323 can be a standard serial peripheral interface (SPI), and the position signals can be digital values representing the first and second positions of the cutting edge 182, as described above.

Further to the above, the processor 4315 may determine the time period between receiving the first position signal and receiving the second position signal. The determined time period may correspond to the time it takes the cutting edge 182 (FIG. 20) to advance through a sharpness testing member 4302 from the first position at a proximal end of the sharpness testing member 4302, for example, to a second position at a distal end of the sharpness testing member 4302, for example. In at least one example, the controller 4313 may include a time element which can be activated by the processor 4315 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4313 can compare the time period it takes the cutting edge 182 (FIG. 20) to advance from the first position to the second position to a predefined threshold value to assess whether the sharpness of the cutting edge 182 has dropped below an acceptable level, for example. In certain instances, the controller 4313 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 39:
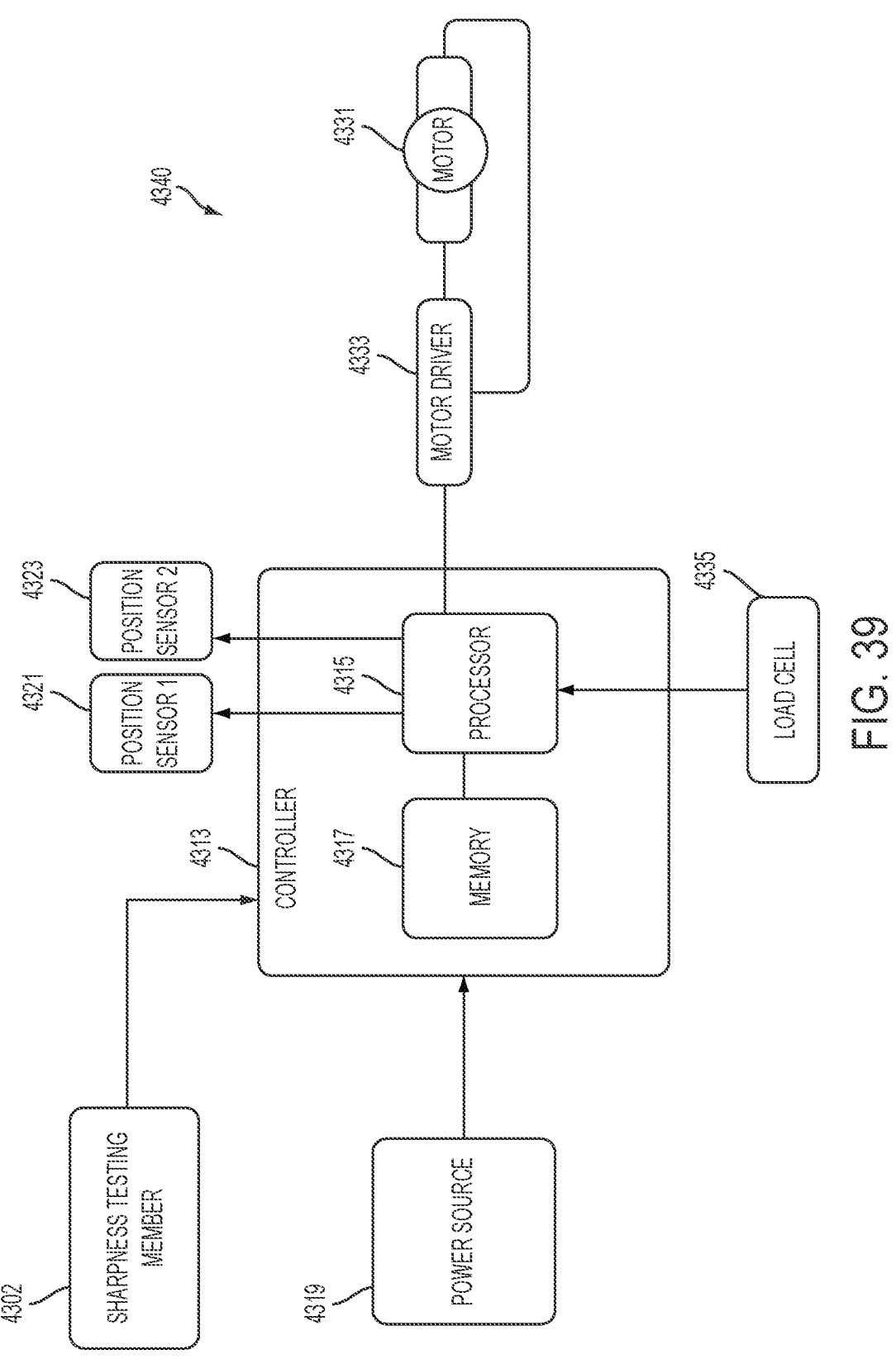
FIG. 39 illustrates a logic diagram of a system for determining the forces applied against a cutting edge of a surgical instrument by a sharpness testing member at various sharpness levels according to various aspects.

FIG. 39 illustrates a logic diagram of a system 4340 for determining the forces applied against a cutting edge of a surgical instrument 10 (FIGS. 1-4) by a sharpness testing member 4302 at various sharpness levels according to various aspects. Referring to FIG. 39, in various instances, an electric motor 4331 can drive the firing bar 172 (FIG. 20) to advance the cutting edge 182 (FIG. 20) during a firing stroke and/or to retract the cutting edge 182 during a return stroke, for example. A motor driver 4333 can control the electric motor 4331; and a microcontroller such as, for example, the microcontroller 4313 can be in signal communication with the motor driver 4333. As the electric motor 4331 advances the cutting edge 182, the microcontroller 4313 can determine the current drawn by the electric motor 4331, for example. In such instances, the force required to advance the cutting edge 182 can correspond to the current drawn by the electric motor 4331, for example. Referring still to FIG. 39, the microcontroller 4313 of the surgical instrument 10 can determine if the current drawn by the electric motor 4331 increases during advancement of the cutting edge 182 and, if so, can calculate the percentage increase of the current.

In certain instances, the current drawn by the electric motor 4331 may increase significantly while the cutting edge 182 (FIG. 20) is in contact with the sharpness testing member 4302 due to the resistance of the sharpness testing member 4302 to the cutting edge 182. For example, the current drawn by the electric motor 4331 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the motor 4331 while the cutting edge is in contact with the sharpness testing member 4302 can increase as the sharpness of the cutting edge 182 decreases from repetitive use, for example.

In certain instances, the determined value of the percentage increase of the current drawn by the motor 4331 can be the maximum detected percentage increase of the current drawn by the motor 4331. In various instances, the microcontroller 4313 can compare the determined value of the percentage increase of the current drawn by the motor 4331 to a predefined threshold value of the percentage increase of the current drawn by the motor 4331. If the determined value exceeds the predefined threshold value, the microcontroller 4313 may conclude that the sharpness of the cutting edge 182 has dropped below an acceptable level, for example.

In certain instances, as illustrated in FIG. 39, the processor 4315 can be in communication with the feedback system and/or the lockout mechanism for example. In certain instances, the processor 4315 can employ the feedback system to alert a user if the determined value of the percentage increase of the current drawn by the motor 4331 exceeds the predefined threshold value, for example. In certain instances, the processor 4315 may employ the lockout mechanism to prevent advancement of the cutting edge 182 (FIG. 20) if the determined value of the percentage increase of the current drawn by the motor 4331 exceeds the predefined threshold value, for example. In certain instances, the system 4311 may include a first position sensor 4321 and a second position sensor 4323. The surgical instrument 10 (FIGS. 1-4) may include a load cell 4335.

In various instances, the microcontroller 4313 can utilize an algorithm to determine the change in current drawn by the electric motor 4331. For example, a current sensor can detect the current drawn by the electric motor 4331 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Figure 40:
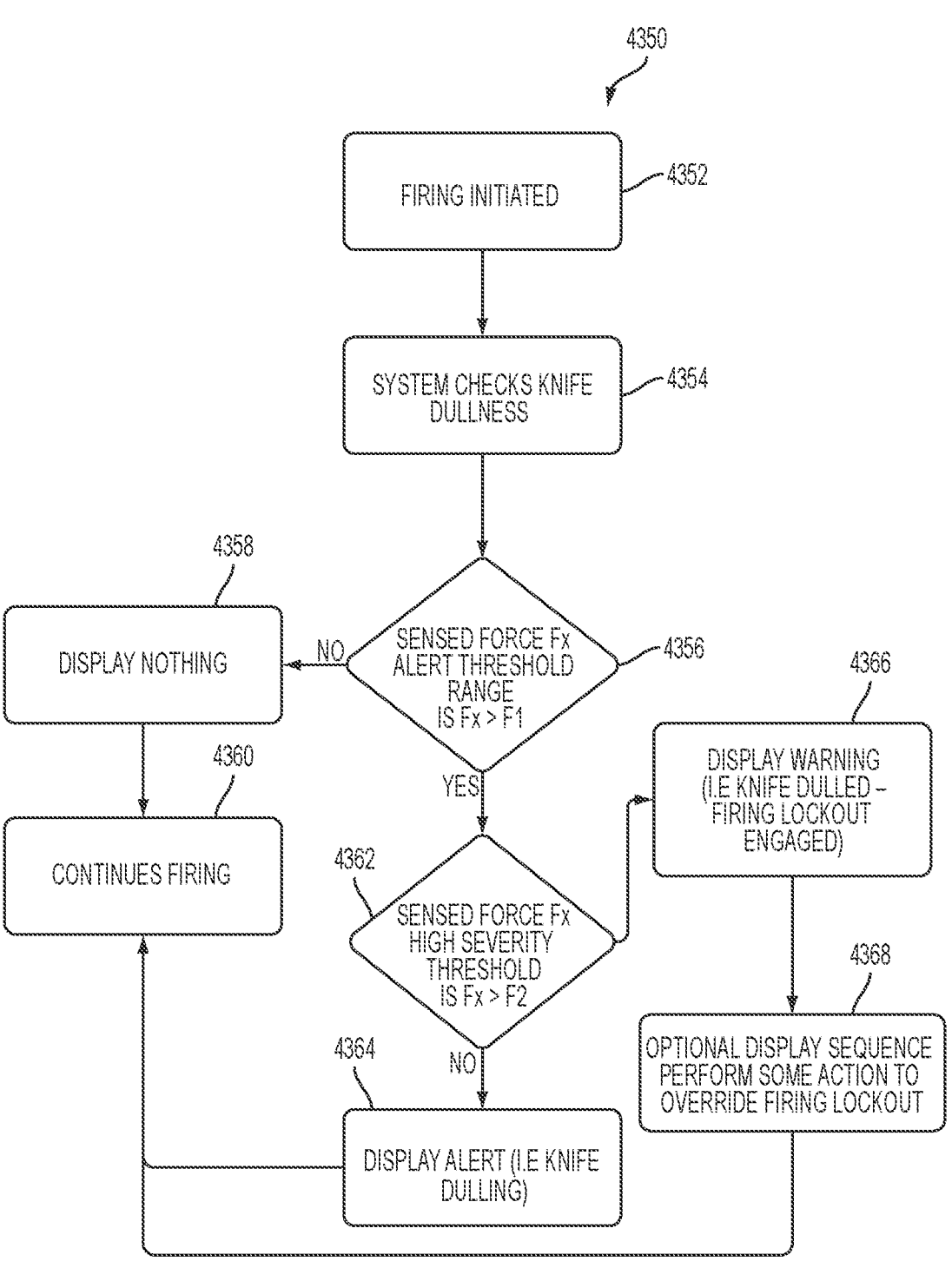
FIG. 40 illustrates a flow chart of a method for determining whether a cutting edge of a surgical instrument is sufficiently sharp to transect tissue captured by the surgical instrument according to various aspects.

FIG. 40 illustrates a logic diagram 4350 of a method for determining whether a cutting edge of a surgical instrument 10 (FIGS. 1-4) is sufficiently sharp to transect tissue captured by the surgical instrument 10 according to various aspects. Referring to FIG. 40, the logic diagram 4350 depicts a method for evaluating the sharpness of the cutting edge 182 (FIG. 20) of the surgical instrument 10; and various responses are outlined in the event the sharpness of the cutting edge 182 drops to and/or below an alert threshold and/or a high severity threshold, for example. In various instances, a microcontroller such as, for example, the microcontroller 4313 can be configured to implement the method 4350 depicted in FIG. 40. In certain instances, the surgical instrument 10 may include a load cell 4335, as illustrated in FIGS. 38 and 39, and the microcontroller 4313 may be in communication with the load cell 4335. In certain instances, the load cell 4335 may include a force sensor such as, for example, a strain gauge, which can be operably coupled to the firing bar 172, for example. In certain instances, the microcontroller 4313 may employ the load cell 4335 to monitor the force (Fx) applied to the cutting edge 182 as the cutting edge 182 is advanced during a firing stroke.

In various instances, the method 4350 begins by initiating 4352 firing of the surgical instrument 10 (FIGS. 1-4). Before, during, and/or after firing of the surgical instrument 10 is initiated 4352, a system checks 4354 the dullness of the cutting edge 182 by monitoring a force (Fx). The reader will appreciate that the force (Fx) is applied by the sharpness testing member 4302 to the cutting edge 182 while the cutting edge 182 is engaged and/or in contact with the sharpness testing member 4302, and, the force (Fx) may depend, at least in part, on the sharpness of the cutting edge 182. In certain instances, a decrease in the sharpness of the cutting edge 182 can result in an increase in the force (Fx) required for the cutting edge 182 to cut or pass through sharpness testing member 4302.

The system senses 4356 the force (Fx) applied by the sharpness testing member 4302 to the cutting edge 182 (FIG. 20). When the force (Fx) sensed 4356 stays within an alert threshold range a display will display 4358 nothing and firing 4360 of the surgical instrument 10 (FIGS. 1-4) will proceed. When the force (Fx) sensed 4356 is outside the alert threshold range, the system 4354 will then determine if the force (Fx) is outside a high severity threshold range. The display will display 4364 an alert to the user of the surgical instrument 10 that the cutting edge 182 is dulling. At this stage, the user is aware that the cutting edge 182 is dulling and may need replaced. When the force (Fx) is sensed 4362 to be greater than the high severity threshold range, the display displays 4366 a warning indicating the force (Fx) applied to the cutting edge 182 is greater than the high severity threshold and that the cutting edge 182 is dull. If the cutting edge is determined to be dull, a firing lockout system may be engaged. The display may display 4368 an optional display sequence to allow the user of the surgical instrument 10 to override the firing lockout system and continue firing 4360 this surgical instrument 10.

In certain instances, the load cell 4335 (FIGS. 38, 39) can be configured to monitor the force (Fx) applied to the cutting edge 182 (FIG. 20) while the cutting edge 182 is engaged and/or in contact with the sharpness testing member 4302 (FIGS. 38, 39), for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. For example, as illustrated graphically in FIG. 41, graphs 4336, 4338, and 4342 represent, respectively, the force (Fx) applied to the cutting edge 182 while the cutting edge 182 travels a predefined distance (D) through three identical, or at least substantially identical, sharpness testing members 4302. The graph 4336 corresponds to a first sharpness of the cutting edge 182; the graph 4338 corresponds to a second sharpness of the cutting edge 182; and the graph 4342 corresponds to a third sharpness of the cutting edge 182. The first sharpness is greater than the second sharpness, and the second sharpness is greater than the third sharpness.

Figure 41:
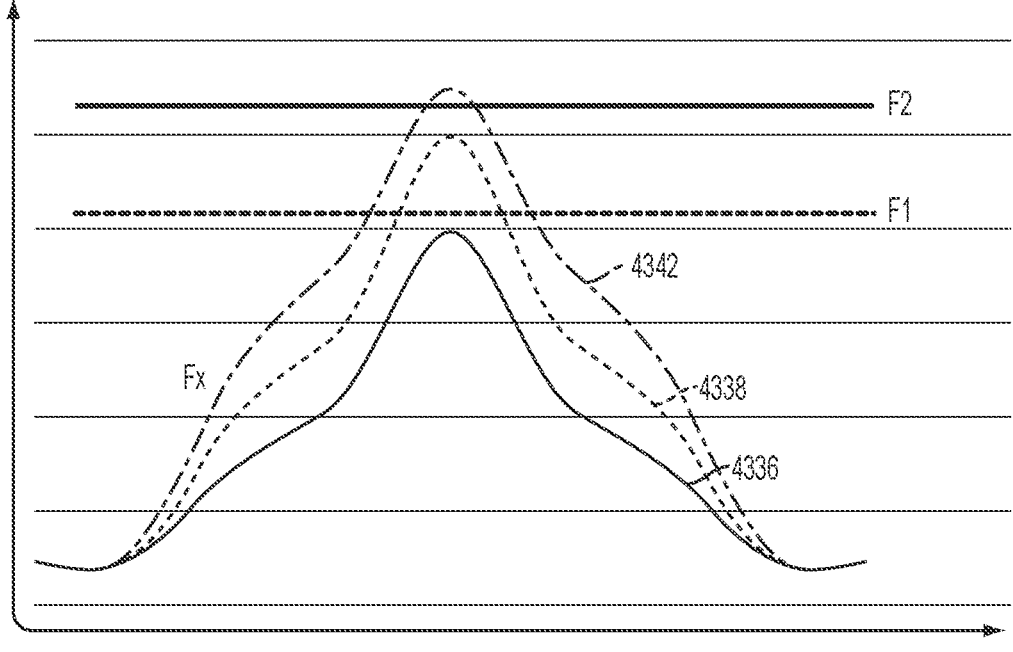
FIG. 41 illustrates a chart of the forces applied against a cutting edge of a surgical instrument by a sharpness testing member at various sharpness levels according to various embodiments.

In certain instances, the microcontroller 4313 (FIGS. 38, 39) may compare a maximum value of the monitored force (Fx) applied to the cutting edge 182 (FIG. 20) to one or more predefined threshold values. In certain instances, as illustrated in FIG. 41, the predefined threshold values may include an alert threshold (F1) and/or a high severity threshold (F2). In certain instances, as illustrated in the graph 4336 of FIG. 41, the monitored force (Fx) can be less than the alert threshold (F1), for example. In such instances, as illustrated in FIG. 41, the sharpness of the cutting edge 182 is at a good level and the microcontroller 4313 may take no action to alert a user as to the status of the cutting edge 182 or may inform the user that the sharpness of the cutting edge 182 is within an acceptable range.

In certain instances, as illustrated in the graph 4338 of FIG. 41, the monitored force (Fx) can be more than the alert threshold (F1) but less than the high severity threshold (F2), for example. In such instances, as illustrated in FIG. 40, the sharpness of the cutting edge 182 (FIG. 2) can be dulling but still within an acceptable level. The microcontroller 4313 may take no action to alert a user as to the status of the cutting edge 182. Alternatively, the microcontroller 4313 (FIGS. 38, 39) may inform the user that the sharpness of the cutting edge 182 is within an acceptable range. Alternatively or additionally, the microcontroller 4313 may determine or estimate the number of cutting cycles remaining in the lifecycle of the cutting edge 182 and may alert the user accordingly.

In certain instances, the memory 4317 (FIGS. 38, 39) may include a database or a table that correlates the number of cutting cycles remaining in the lifecycle of the cutting edge 182 (FIG. 20) to predetermined values of the monitored force (Fx). The processor 4315 (FIGS. 38, 39) may access the memory 4317 to determine the number of cutting cycles remaining in the lifecycle of the cutting edge 182 which correspond to a particular measured value of the monitored force (Fx) and may alert the user to the number of cutting cycles remaining in the lifecycle of the cutting edge 182, for example.

In certain instances, as illustrated in the graph 4342 of FIG. 41, the monitored force (Fx) can be more than the high severity threshold (F2), for example. In such instances, as illustrated in FIG. 40, the sharpness of the cutting edge 182 can be below an acceptable level. In response, the microcontroller 4313 may employ the feedback system to warn the user that the cutting edge 182 is too dull for safe use, for example. In certain instances, the microcontroller 4313 may employ the lockout mechanism to prevent advancement of the cutting edge 182 upon detection that the monitored force (Fx) exceeds the high severity threshold (F2), for example. In certain instances, the microcontroller 4313 may employ the feedback system to provide instructions to the user for overriding the lockout mechanism, for example.

Figure 42:
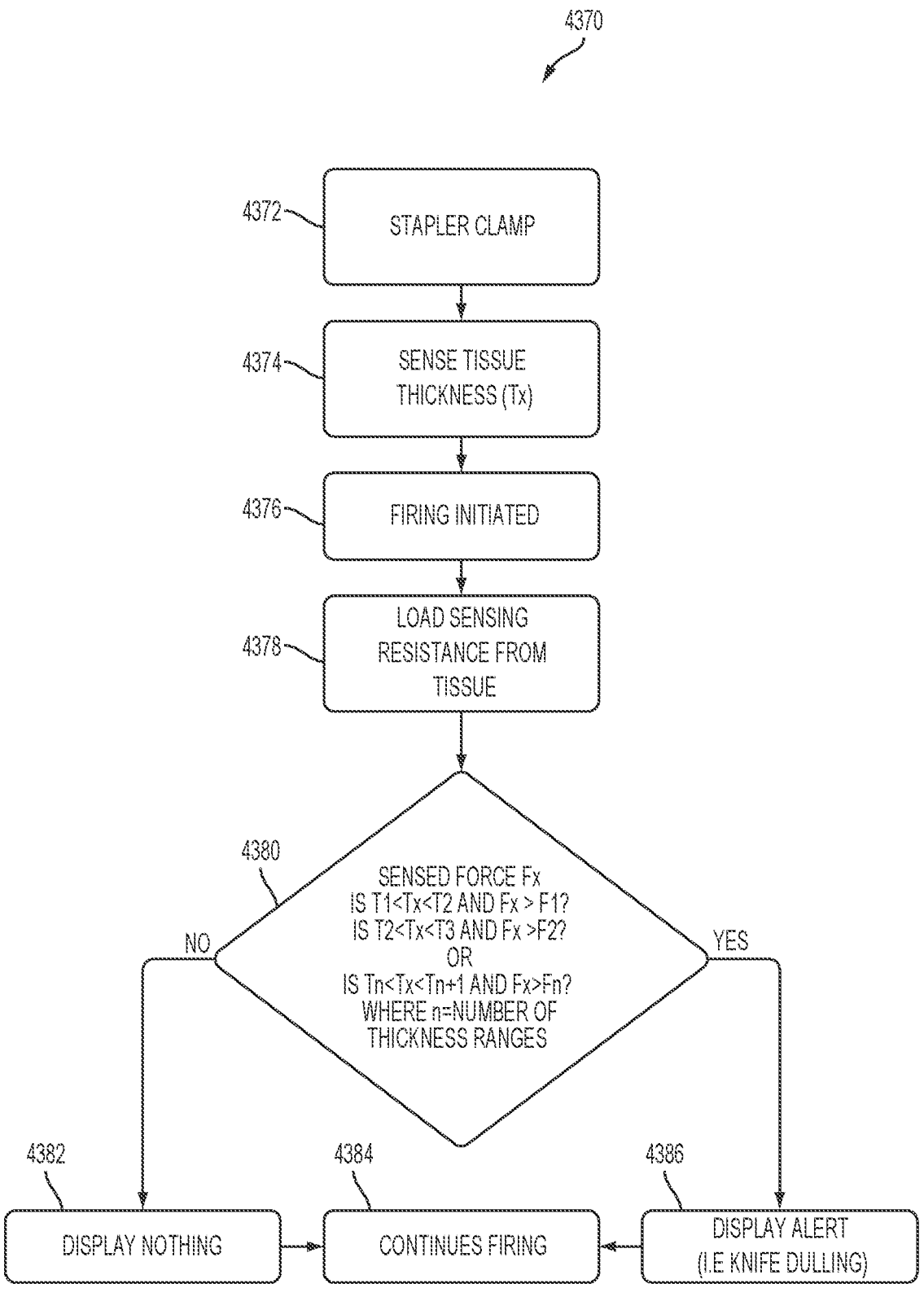
FIG. 42 illustrates a flow chart outlining a method for determining whether a cutting edge of a surgical instrument is sufficiently sharp to transect tissue captured by the surgical instrument according to various embodiments.

Referring now to FIG. 42, a method 4370 is depicted for determining whether a cutting edge such as, for example, the cutting edge 182 (FIG. 20) is sufficiently sharp to be employed in transecting a tissue of a particular tissue thickness that is captured by the end effector 300 (FIG. 1), for example. In certain instances, the microcontroller 4313 can be implemented to perform the method 4370 depicted in FIG. 42, for example. As described above, repetitive use of the cutting edge 182 may dull or reduce the sharpness of the cutting edge 182 which may increase the force required for the cutting edge 182 to transect the captured tissue. In other words, the sharpness level of the cutting edge 182 can be defined by the force required for the cutting edge 182 to transect the captured tissue, for example. The reader will appreciate that the force required for the cutting edge 182 to transect a captured tissue also may depend on the thickness of the captured tissue. In certain instances, the greater the thickness of the captured tissue, the greater the force required for the cutting edge 182 to transect the captured tissue at the same sharpness level, for example.

In certain instances, the cutting edge 182 (FIG. 20) may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example. In certain instances, the memory 4317 (FIGS. 38, 39) can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, when the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

The method 4370 shown in FIG. 42 begins with clamping 4372 the tissue. Once the tissue to be transected is clamped, the thickness of the tissue is sensed 4374. After the tissue thickness is sensed 4374, firing of the surgical instrument can be initiated 4376 by the user. Once the surgical instrument begins firing, the force (Fx) applied to the cutting edge 182 (FIG. 20) is sensed 4378. The force (Fx) and the tissue thickness (Tx) is then compared 4380 to predetermined tissue thickness ranges and force ranges required to adequately transect the predetermined tissue thicknesses. For example, if the force (Fx) sensed is greater than a predetermined force range required to adequately transect tissue at the tissue thickness (Tx) that was sensed for the tissue clamped, a display will display 4386 an alert to the user that the cutting edge 182 is dulling. When the force (Fx) sensed is within the predetermined force range required to adequately transect tissue at the tissue thickness (Tx) that was sensed for the tissue clamped, the display may display 4382 nothing. In both instances, the surgical instrument continues 4384 firing to transect the tissue.

In various aspects, the present disclosure provides techniques for determining tissue compression and additional techniques to control the operation of the instrument 10 (described in connection with FIGS. 1-29) in response to the tissue compression. In one example, the cartridges may be configured to define variable compression algorithm which drives instrument 10 to close differently based on intended tissue type and thickness. In another example, the instrument 10 learns from surgeon use and original tissue compression profile to adapt closure based on load experienced during firing. When the instrument 10 experiences tissue compression loads that are dramatically different that those experienced for this cartridge type the instrument highlights this to the user.

Active adjustment of a motor control algorithm over time as the instrument become acclimated to the hospital's usage can improve the life expectancy of a rechargeable battery as well as adjust to tissue/procedure requirements of minimizing tissue flow, thus improving staple formation in the tissue seal.

Accordingly, the present disclosure relates to surgical instruments and, in various circumstances, to surgical stapling and cutting instruments and staple cartridges therefor that are designed to staple and cut tissue. For example, in various aspects the present disclosure provides an endosurgical instrument configured to sense the cartridge type or tissue gap to enable the handle to adjust the closure and firing algorithms to adjust for intended tissue properties. This adaptive algorithm adjustment can "learn" from the user's operations allowing the device to react and benefit two different systems. The first benefit provided by the disclosed adaptive algorithm includes tissue flow and staple formation. As the device learns the users' basic habits and step timings, the device can adjust the closure speed and firing speed to provide a more consistent and reliable output. The second benefit provided by the disclosed adaptive algorithm is related to the battery pack. As the device learns how many firings and what conditions the instrument was used, the device can adjust motor current needs/speed in a predefined manner to prolong battery life. There is a substantially small likelihood that a device used in a hospital that performs predominantly bariatric procedures would be operated in a manner similar to a device used in a hospital that performs mostly colorectal or thoracic procedures. Thus, when the device is used to perform substantially similar procedure, over time, the device is configured to learn and adjust its operational algorithm to maintain within the "ideal" discharge and tissue flow envelopes.

Safe and effective surgery requires due knowledge of, and respect for, the tissue involved. Clinicians are mindful that adjustments made during surgery may be beneficial. These adjustments include mechanisms to detect and promote desirable staple formation.

Endosurgical instruments can generate, monitor and process a substantial amount of data during their use in connection with a surgical procedure. Such data can be obtained from the surgical instrument itself, including battery usage. Additionally, data can be obtained from the properties of the tissue with which the surgical instrument interacts, including properties such as tissue compression. Further, data can be obtained from the clinician's interaction with the surgical instrument itself. The repository of data so obtained can be processed and, where desired, the surgical instrument can be designed to adapt to circumstances so as to promote a safe and effective outcome to the current surgical procedure, as well as lay the foundation for more generalized productive use by multiple clinicians. Such adaptive adjustments—both during a surgical procedure, and wherein the instrument "learns" based on usage patterns drawn from multiple surgical procedures—can provide numerous mechanisms to enhance the overall patient-care environment.

Figure 43:
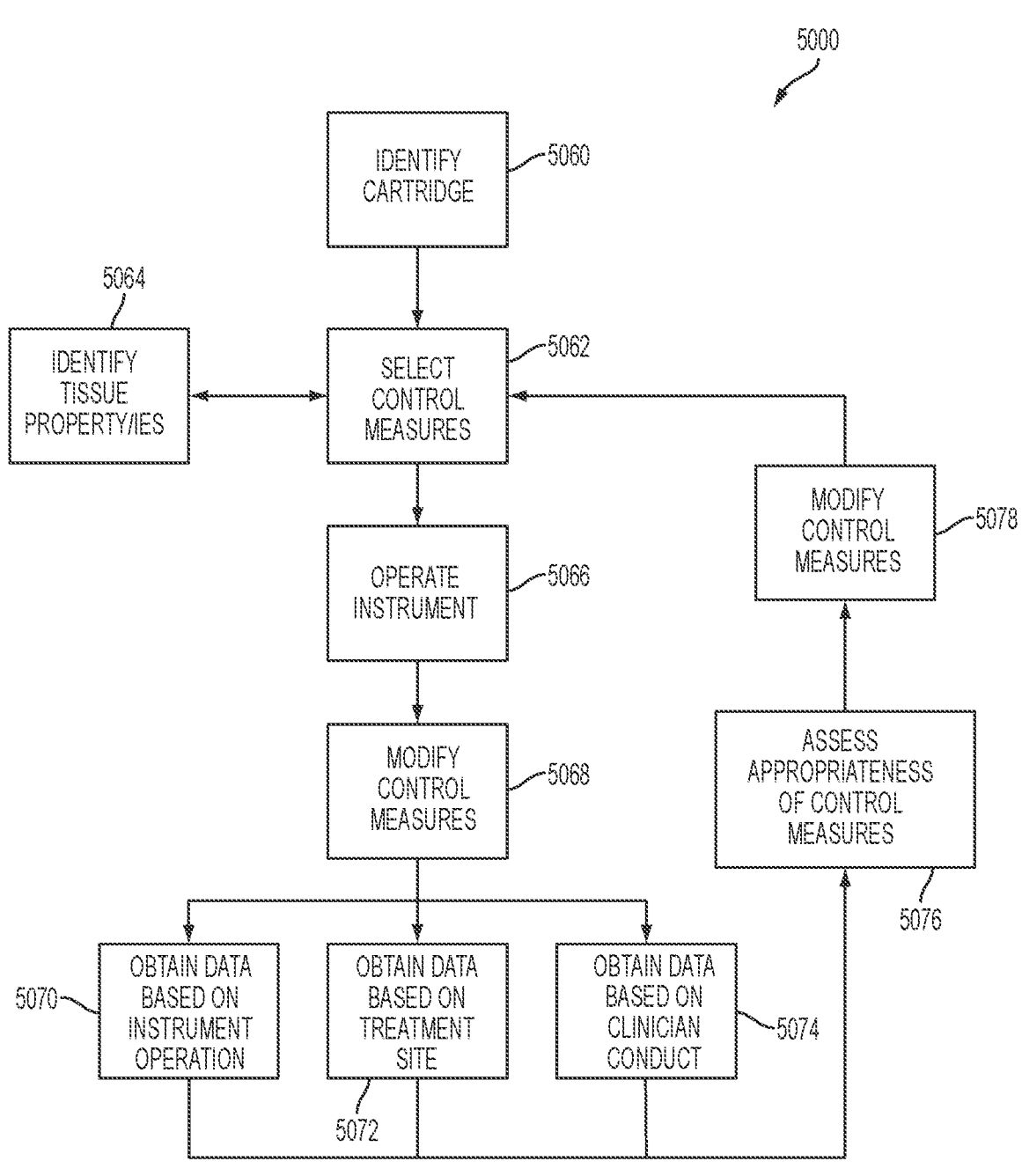
FIG. 43 illustrates one aspect of a process for adapting operations of a surgical instrument.

FIG. 43 illustrates one aspect of a process for adapting operations of a surgical instrument. As shown in FIG. 43, in various examples, an adaptive algorithm framework 5000 is provided. A staple cartridge can be identified 5060. Control measures, such as algorithms, can be selected 5062 based on the cartridge identified. These algorithms may include one or more variable compression algorithms that drives instrument 10 (FIGS. 1-4) to close in a different manner based on an expected tissue type and/or thickness. Tissue properties can be identified 5064 as an aid to selection of control measures. The clinician can operate 5066 instrument 10 to carry out a surgical procedure, including but not limited to stapling and/or incising tissue. Control measures can be modified 5068, with or without reference to data observed or generated during the course of a surgical procedure.

A surgical procedure can entail generating a significant amount of data on parameters. By way of non-limiting example, these parameters can include those associated with surgical instrument 10 (FIGS. 1-4) itself and its functionality, including but not limited to: speed of closure of the anvil 306 (FIG. 1) and staple cartridge 304 (FIG. 1), or speed of closure of anvil 306 and second jaw member 302 (FIG. 1); gap (e.g., distance) between anvil 306 and staple cartridge 304, or anvil 306 and second jaw member 302; voltage; current; motor(s') speed; power management, e.g., battery use; or sensor operation and accuracy.

Additional parameters that may be generated and observed in connection with a surgical procedure can also include those derived from the tissue being operated upon, including but not limited to: tissue compression; tissue thickness; tissue flow; tissue creep; tissue pressure; tissue stabilization; whether end effector 300 (FIG. 1) clamps a full or partial bite of tissue, and whether such partial bite is proximal or distal; speed of closure drive system 30 (FIG. 1); speed of firing drive system 80 (FIG. 4); staple performance; and/or determination if the tissue profile is consistent with healthy tissue or diseased tissue.

Further parameters that may be generated and observed in connection with a surgical procedure can also include those derived from the clinician, such as frequency of actuating closure trigger 32 (FIG. 1) by clinician; force applied on closure trigger 32 by clinician; frequency of actuating firing trigger 130 (FIG. 4) by clinician; force applied on firing trigger 130 by clinician; and/or step timing by clinician.

Even more, parameters can include to what extent the instrument 10: experiences tissue compression loads different from those expected for the cartridge type; experiences a wait period (such as for tissue creep) different from that expected; experiences a firing speed different from that expected; has undergone one or more sterilization cycles; and/or experiences different or similar patterns of use based on the clinical setting. For example, there may be meaningful differences among use of the instrument in a setting directed primarily to bariatric, colorectal, or thoracic procedures respectively.

On top of these, parameters can include accuracy and appropriateness of control measures themselves, such as algorithms, used in connection with operating the instrument. Feedback loops and/or logic paths can be developed that include one or more of algorithms, data based on instrument operation 5070, data based on the treatment site 5072, data based on clinician conduct 5074, and more. Added parameters can be considered and developed.

It will be apparent that there are numerous data resources that can be derived from a single surgical procedure. These data resources can be analyzed in various manners including as a single data point, a plurality of data points, a range or ranges, as a range or ranges, or based on added metrics such as rate of change of current, voltage, speed, or other parameter. Taking into account one, or many, of these data resources can enhance the safety and effectiveness of a single procedure.

In addition, these data resources can enhance the safety and effectiveness of future procedures by the same clinician to the extent that the surgical instrument can "learn" the basic habits and step timings of the clinician. In addition, data can be aggregated from multiple clinicians, further enabling the successful calibration of the surgical instrument in the context of the surgical procedure. It can be appreciated that the hospital or health center in which the data is compiled can develop a unique profile that can further enhance health outcomes. In addition, battery life can be prolonged, as it is learned how many firings and under what conditions the surgical instrument 10 is used. Thus, arrangements to adapt to numerous battery usage metrics are contemplated in examples.

Instrument 10 (FIGS. 1-4) can determine whether, based on data obtained 5070, 5072, 5074, a control measure is appropriate or not by various mechanisms. One mechanism is by identifying a predetermined value or values. Such value or values can comprise an acceptable, or expected, parameter. If data obtained 5070, 5072, 5074 leads to a determination that an acceptable range has been exceeded, then a new control measure(s) can be identified 5076 and control measures can be modified 5078 including setting forth a new acceptable value. Exceeding a range can be considered to mean going above a range, below or range, or otherwise going beyond a range. The second control measure can be a minor adaptation of the first control measure, or it can be an entirely new control measure. It will also be appreciated that the predetermined acceptable range can be a single data point, multiple data points, a function or other calculable equation, or any mechanism by which it can be determined that a measurement, property or other metric that can be resolvable into a calculable value differs from an actual, expected or predicted value. It is also understood that a control measure can be compared with another control measure, and the differential effectiveness of each determined, thus forming an input into another determination of whether and which control measures to adopt. Put another way, success of control measures can represent an input.

In addition, expected values for parameters can be embedded in control measures. In other words, an expected set of values for a tissue property can be embedded in a control measure that has been associated with instrument 10 (FIGS. 1-4). Thus, it will be evident that numerous expected values for numerous parameters can be populated into numerous control measures. These expected values can be referenced during operations of the instrument in order to determine control measures carried out by instrument 10. Further, observed values can be detected and analyzed by instrument 10 during operation. These observed values can be referenced and help determine the course of selection of current and future control measures of the instrument 10 during the procedure, and also programmed into instrument 10 to set new or modified benchmarks to help determine an acceptable range or ranges of control measures. Further predictions can be made during operation of the instrument 10. The predictions can inform the processing and analysis of measurements, can lead to modifying control measures, and generally adapting to operational circumstances.

Thus, data can be obtained from multiple sources. One source is data based on operation of the instrument (e.g., closure speed) 5070. Another source of data can be that derived from the treatment site 5072 (e.g., tissue thickness). A further source of data can be that based on clinician conduct 5074 (e.g., firing habits). Once this data 5070, 5072, 5074 is obtained, the appropriateness of control measures can be assessed 5076. For example, a certain tissue type may have been expected, and this tissue type was experienced during the procedure. However, it may be that the exudation resulting from clamping was heavier than anticipated. Also, it may be that the clinician has a habit of applying more pressure than may be desirable on the firing trigger 130 (FIG. 1). In short, there may be many data sources that can be consulted to analyze, improve on and potentially optimize efficacy of current and future uses of the instrument. As a result, control measures can be modified 5078 during and/or after a procedure for maximum success.

In one aspect, surgical instrument 10 (FIGS. 1-4) can comprise a plurality of modules, based on control mechanisms configurable from a controller and/or other processor, memory, and other systems therein for transmission, communication and processing of data. One of multiple possible modules can be based on a feedback system, as generalized and/or customized for a specific purpose or system. In addition, it will be apparent that there will be a processor 4315 (FIGS. 38, 39) and memory 4317 (FIGS. 38, 39) in operative communication with the surgical instrument 10 that can permit the functionality discussed herein.

Figure 44:
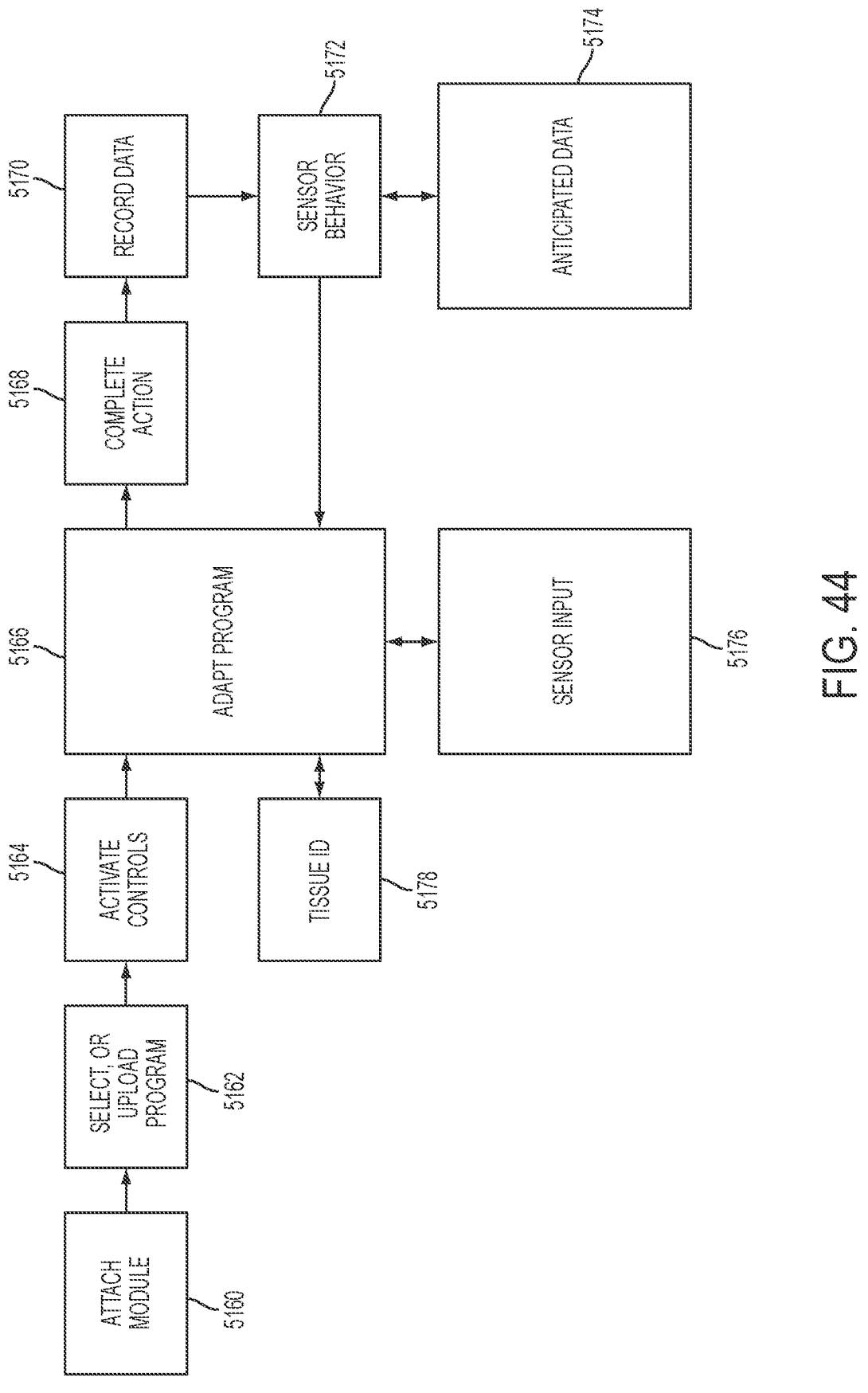
FIG. 44 illustrates one aspect of a process for adapting operations of a surgical instrument.

FIG. 44 illustrates one aspect of a process for adapting operations of a surgical instrument. As depicted in FIG. 44, a module can be attached 5160 or otherwise loaded to instrument 10 (FIGS. 1-4). The module can contain a program that is selected or uploaded 5162. Controls can be activated 5164 such that they can be ready to operate instrument 10. During or after usage of instrument 10, a program, including control measures, can be adapted 5166. For example, this can include adjusting the data rate within the instrument 10 or with respect to remote operation of the instrument 10. This can include adjusting speed, such as speed by which anvil 306 (FIG. 1) and cartridge 304 (FIG. 1) engage in a closure motion. This can also include a pulse from an emitter and sensor or to apply a pulse of electrical current to tissue, and the timing of such pulse. This can include adjusting a program to adapt to acceleration, such as acceleration of the instrument 10 if dropped, or transition from a sleep mode. A program can be adapted to handle an actual and/or expected load based on clamping force.

Instrument 10 (FIGS. 1-4) can be employed to complete an action 5168, for example to carry out a stapling procedure. Data can be recorded 5170 in appropriate memory locations of instrument 10. Sensor behavior 5172 can be assessed, such as to what extent a sensor accurately measured and/or measures a parameter. Anticipated data can be assessed 5174, including but not limited to tissue properties, wait period and firing speed. Foregoing mechanisms disclosed herein can provide an input to adapt a program 5166 further. In addition, a tissue identification 5178 can be performed, based on historical, actual or expected tissue properties, and this can provide an input to adapt a program 5166 further. In addition, tissue identification 5178 properties can be updated. Moreover, measured sensor input 5176 during a procedure can be used as an additional input to adapt a program 5166 further; such sensor measurements can include those of the gap between anvil 306 and cartridge 304, obtaining a derivative measurement including a derivative of a function, current, or torque.

Figure 45:
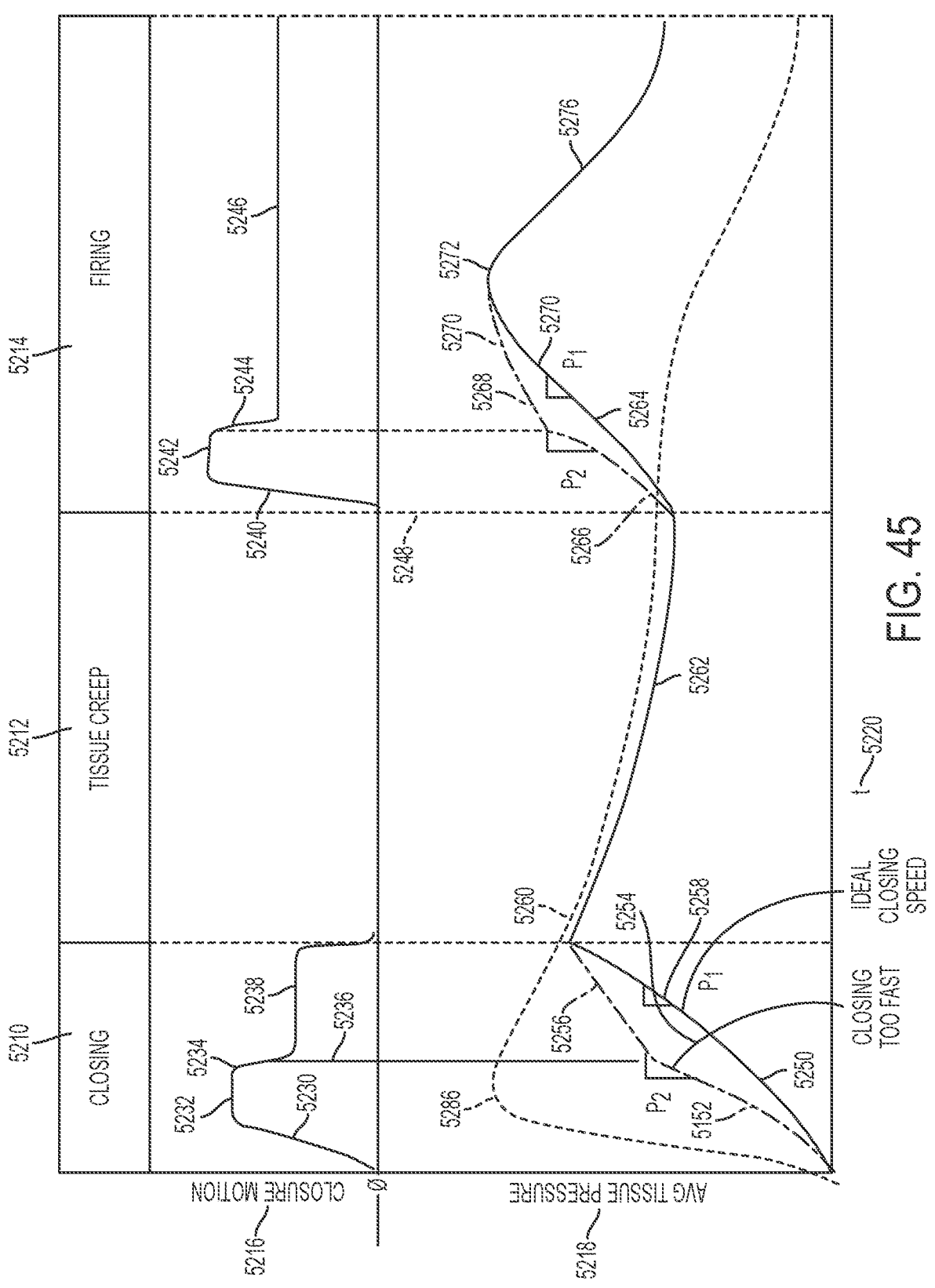
FIG. 45 illustrates one aspect of a mechanism for adapting operations of a surgical instrument in the context of closure motion and tissue pressure.

FIG. 45 illustrates one aspect of a mechanism for adapting operations of a surgical instrument in the context of closure motion and tissue pressure. In various aspects, closure motion 5216 can be adjusted based on a parameter. An example parameter can be average tissue pressure 5218. FIG. 45 is a diagram that illustrates three phases of carrying out a procedure with instrument 10 (FIGS. 1-4). Time (t) is shown along a bottom horizontal axis 5220, a bottom vertical axis represents average tissue pressure 5218 applied to tissue clamped between the jaw members of the end effector. A top vertical axis represents closure motion 5216 of the anvil 306 (FIG. 1) towards the cartridge 304 (FIG. 1) to engage tissue therebetween in a closure motion. A top horizontal axis represents closing 5210 of the anvil 306 (FIG. 1) of end effector to engage a cartridge 304 (FIG. 1) or second jaw member 302 (FIG. 1), tissue creep 5212 wherein material is allowed to exudate from the tissue section held within end effector 300 (FIG. 1), and firing 5214, which can comprise deploying a staple cartridge 304, applying electrosurgical energy, incising tissue, or other suitable surgical event. An anvil 306 can begin to close on a second jaw member 302, which is configured to receive a staple cartridge 304 therein. As anvil 306 closes toward cartridge 304 during a clamping operation, tissue pressure is determined by one or more mechanisms, such as by reference to one or more sensors. A plurality of sensors may comprise one or more identical sensors and/or different sensors. The plurality of sensors may comprise, for example, magnetic sensors, such as a magnetic field sensor, strain gauges, pressure sensors, inductive sensors, such as an eddy current sensor, resistive sensors, capacitive sensors, optical sensors, and/or any other suitable sensors or combination thereof.

During the closing phase 5210, the closure motion 5216 versus time of the jaw members is compared with average tissue pressure 5218 versus time. A first average tissue pressure versus time curve, represented by a dashed line includes three segments, includes a first segment 5286 during the closing phase 5210 of the anvil 306 (FIG. 1) towards the cartridge 304 (FIG. 1) to apply pressure against the tissue grasped therebetween. A second segment 5260 represents the tissue pressure during the tissue creep 5212 phase where the anvil 304 has stopped moving and the tissue is given an opportunity to creep. A third segment represents the tissue pressure during the firing phase during which the staples are deployed to seal the tissue ahead of advancement of the cutting member to cut the tissue.

A second average tissue pressure versus time curve, represented by a dashed-dot line, represents a typical curve observed when the anvil 306 (FIG. 1) is closing too fast 5254. This is represented by the first segment 5152 where the slope P2 of the average tissue pressure 5218 versus time is too steep during the closure motion curve segment 5230 during the acceleration of the closure motion and curve segment 5234 when the closure motion 5216 remains steady until a threshold 5236 average tissue slope 5218 is detected at which time the closure motion drops to a lower constant value shown by curve segment 5238 at which time the slope of the average tissue pressure 5216 curve segment 5256 decreases to reflect the slower closure motion 5216.

A third "ideal" tissue pressure versus time curve 5258 having an ideal slope is represented by a solid line curve segment 5250.

The tissue creep 5212 phase is entered after the tissue is grasped and the average tissue pressure reaches a predetermined threshold and the closure motion 5216 stops such that the jaw members, e.g., anvil 306 (FIG. 1) and cartridge 304 (FIG. 1), hold the tissue therebetween for a predetermined time before initiating the firing 5214 phase in which the staples and knife are deployed. During the tissue creep 5212 phase the average tissue pressure drops over the time period between closing 5210 and firing 5214 phases. The dashed-dot curve (adjusted closing too fast curve) and solid curve (ideal closing speed) segments 5262 overlap.

At a predetermined time 5248, the firing 5214 phase initiates. A typical firing 5214 cycle, is represented by the dashed line average tissue pressure curve segment 5266. An ideal firing 5214 cycle is represented by the solid line average tissue pressure curve segment 5264 where the slope P1 increases 5270, reaches a peak 5272, and then gently decreases 5276. When the firing 5214 phase moves too rapidly as indicated by curve segment 5240, the slope P2 of the dashed-dot line average tissue pressure curve 5266 rises too steeply. When a predetermined slope threshold is detected, the firing speed is maintained constant as represented by firing curve speed segment 5242 and the slope 5270 of the dashed-dot line average tissue pressure curve 5266 decreases. After a predetermined time, the firing speed drops to a lower speed as represented by the firing speed curve segment 5246. After allowing for system response times, the dashed-dot line coincides with the solid line during the lower firing speed 5246.

Closure motion 5216, such as speed of closure, or another measured rate related to closure, can be determined. As the clamping operation progresses, and a parameter increases 5230, average tissue pressure is being measured. The parameter in question can be but is not limited to speed. Average tissue pressure can be plotted graphically. A curve 5252 described by such graph can be plotted. At a certain point closure motion 5216 can be steady 5232. However, a tissue pressure reading can suggest that the closure motion rate is too fast 5254 as indicated by, for example, the slope of curve 5252. It can also be the case that the closure motion rate was too fast, or is predicted to be too fast in the future. This can occur during a period where closure rate is steady 5232, or during a period where closure rate drops 5234 such as where thick, fluid-filled or unexpectedly dense tissue is encountered, among other reasons. Fluid in tissue could cause thickness to increase temporarily, causing undesirable staple deployment. To the extent that it is detected that the slope of average tissue pressure curve 5218 is growing too steep, adjustments can be made. It will also be appreciated that, independent of or in conjunction with slope, a secondary calculation can be made based on the observed parameters suggesting that the closure rate is too fast. An adjustment can be made, such as by decreasing the rate of change of closure motion 5216. For example, an ideal closing speed can be referenced based on stored control measures or dynamically obtained control measures, or both. An average tissue pressure curve reflecting such ideal closing speed 5258 can be referenced.

Accordingly, curve 5258 can influence closure motion 5216 such that the rate of closure is decreased 5238 or otherwise modified to adapt to circumstances encountered during a surgical procedure. It will be understood that an ideal closing speed can represent an optimal closing speed, or one within a range of adequate closing speeds.

Compression of clamped tissue can precede the firing 5214 phase. It may be desired that compression reach a certain average tissue pressure, and/or that the tissue is considered stabilized such that firing 5214 can be warranted. A measured tissue pressure can be reached at a point, for example, representing the intersection of curve 5252 and 5250. Upon reaching this point, the tissue can be allowed to stabilize and the exudate seep from the tissue. Tissue, in part because it is composed of solid and liquid material, tends to elongate when compressed; one way to account for this property is "tissue creep". When tissue is compressed, a certain amount of tissue creep 5212 can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep 5212 prior to firing 5214.

Upon reaching a desirable point, firing 5214 can be commenced. Firing 5214 can comprise one or more actions or events, including deployment of an I-beam and/or other firing member towards and/or within end effector 300 (FIG. 1). An I-beam can comprise a cutting member deployable therein. The cutting member can comprise, for example, an I-Beam configured for simultaneously cutting of a tissue section located between an anvil 306 (FIG. 1) and a staple cartridge 304 (FIG. 1) and deploying staples from the staple cartridge 304.

During firing 5214, average tissue pressure can ascend along curve 5266, comparable with the rate of closure motion 5216. A slope can be calculated for average tissue pressure during firing 5214. The slope can be evaluated to be steeper than desired, perhaps due to an increasing rate of average tissue pressure change in combination with a stable firing rate 5242. If this condition or another condition provided for is detected, instrument 10 (FIGS. 1-4) can have the capability to adapt. Measures can be implemented to modify the firing curve 5268 such that a peak can be reached that would be similar to or identical to that obtainable from a more desirable tissue pressure curve 5274.

Accordingly, similar to adaptive mechanisms employed in connection with closing 5210, adaptive measures can be employed in connection with firing 5214.

Tissue-pressure curve 5286 can be referenced which can track a desired tissue-creep rate after reference to an ideal closing speed. Tissue-pressure curve 5286 can be programmed to operate in conjunction with, or be extrapolated from, the closing phase 5210 or firing phase 5214. Additionally, a given tissue type can be referenced that would give certain characteristics when surgical operations are carried out thereon, such characteristics embodying curve 5286. It will be appreciated that various purposes can be fulfilled by referencing tissue-pressure curve 5286, or another tissue-pressure curve, that might be considered an "ideal", desired, or otherwise "reference curve". Such a reference curve can assist in improving closing 5210, tissue creep 5212, and/or firing 5214. Such a reference curve or curves can be stored in instrument 10 (FIGS. 1-4) or be developed dynamically, or both, and can account for varying thickness of a tissue portion, and many other factors.

Figures 46, 47:
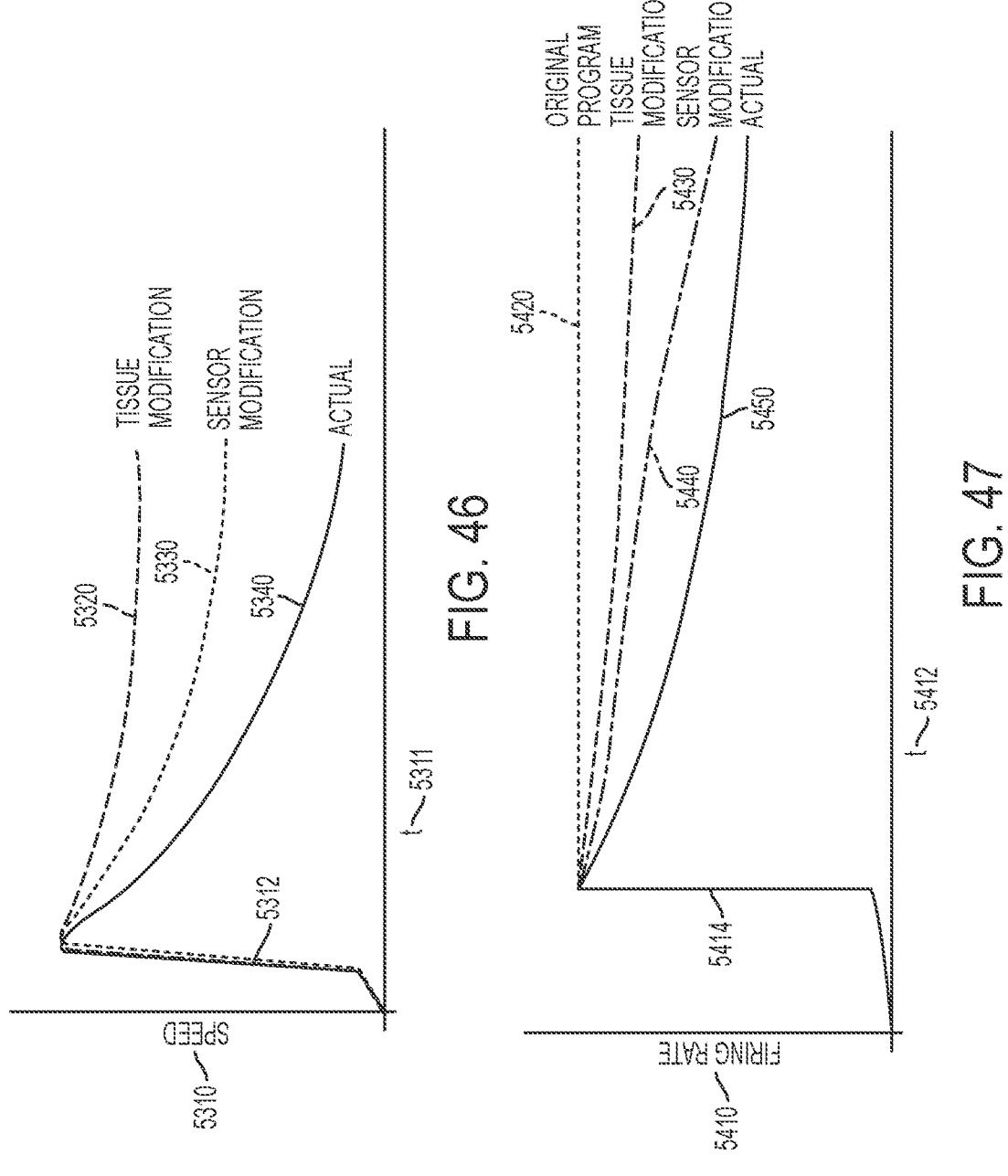
FIG. 46 illustrates one aspect of a mechanism for adapting speed associated with a parameter of a surgical instrument in the context of tissue modification and sensor modification.
FIG. 47 illustrates one aspect of a mechanism for adapting firing rate associated with a parameter of a surgical instrument in the context of tissue modification and sensor modification.

In accordance with aspects, FIG. 46 illustrates adaptive mechanisms that can influence actual behavior of instrument 10 (FIGS. 1-4) in the process of carrying out a surgical procedure. Speed 5310 can be enumerated on the vertical (y) axis and time 5311 (*t*) is represented along the horizontal axis. Speed 5310 can represent speed of the motor, speed of closure of end effector 300 (FIG. 1), speed of firing rate, or another speed. As speed increases 5312, sensors can obtain measurements of various parameters. Based on control measures derived from stored algorithms, or dynamically generated algorithms, or both, one or more modifications can be made. One modification can be a tissue modification 5320 that will influence operation of instrument 10 such that speed is upwardly or downwardly adjusted in order to obtain a more desirable set of conditions. An additional modification can be a sensor modification 5330. Sensor modification 5330 can influence the characteristics or values of data transmitted to microcontroller 1500 (FIG. 19) and operatively associated memory units. Microcontroller 1500 can monitor and obtain data from sensors associated with for example end effector 300. Sensor modification can also influence parameter readings at one or more added sensor(s). For example, a primary sensor such as a magnetic field sensor located for example at a distal portion of anvil 306 (FIG. 1) can indicate a certain thickness of a bite of tissue; however, reference to a secondary sensor such as a strain gauge can be factored in such that the measured Hall effect voltage can be adjusted. As a result, inputs such as tissue modification 5320 and sensor modification 5330 can influence an actual speed 5340 that is adjusted to take into account one or both.

Additionally, in accordance with aspects, FIG. 47 illustrates adaptive mechanisms that can influence actual behavior of a firing rate 5410 in the process of carrying out a surgical procedure. Firing rate 5410 can be enumerated on the vertical (y) axis and time 5412 (*t*) is represented along the horizontal (x) axis. Firing rate 5410 can represent a rate at which a firing member 220 (FIGS. 1 and 7) is longitudinally deployed, a rate at which tissue is incised, and/or a rate at which staples are deployed. In various examples, a firing rate 5410 value can ascend, upon actuation of a firing mechanism. Based on control measures derived from predetermined algorithms, or dynamically generated algorithms, or both, one or more modifications can be made to an original program in the memory that can define the firing rate (here, a steady firing rate 5420). One modification can be a tissue modification 5430 that can influence operation of instrument such that speed is upwardly or downwardly adjusted in order to obtain a more desirable set of conditions. An additional modification can be a sensor modification 5440. Sensor modification 5440 can influence the characteristics or values of data transmitted to microcontroller 1500 from sensors associated with for example end effector 300 (FIG. 1). Sensor modification 5440 can also influence parameter readings at one or more added sensor(s). For example, a primary sensor such as a magnetic field sensor on end effector 300 can indicate a certain thickness of a bite of tissue; however, reference to a secondary sensor such as a strain gauge can be factored in such that the measured Hall effect voltage can be adjusted. As a result, inputs such as tissue modification 5430 and sensor modification 5440 can influence an actual speed 5450 that is adjusted to take into account one or both.

Inputs can be given their actual weight, i.e., without selective weighting. However, in various aspects one or more inputs may not be weighted equally. Certain inputs may be given more weight than other inputs.

Figure 48:
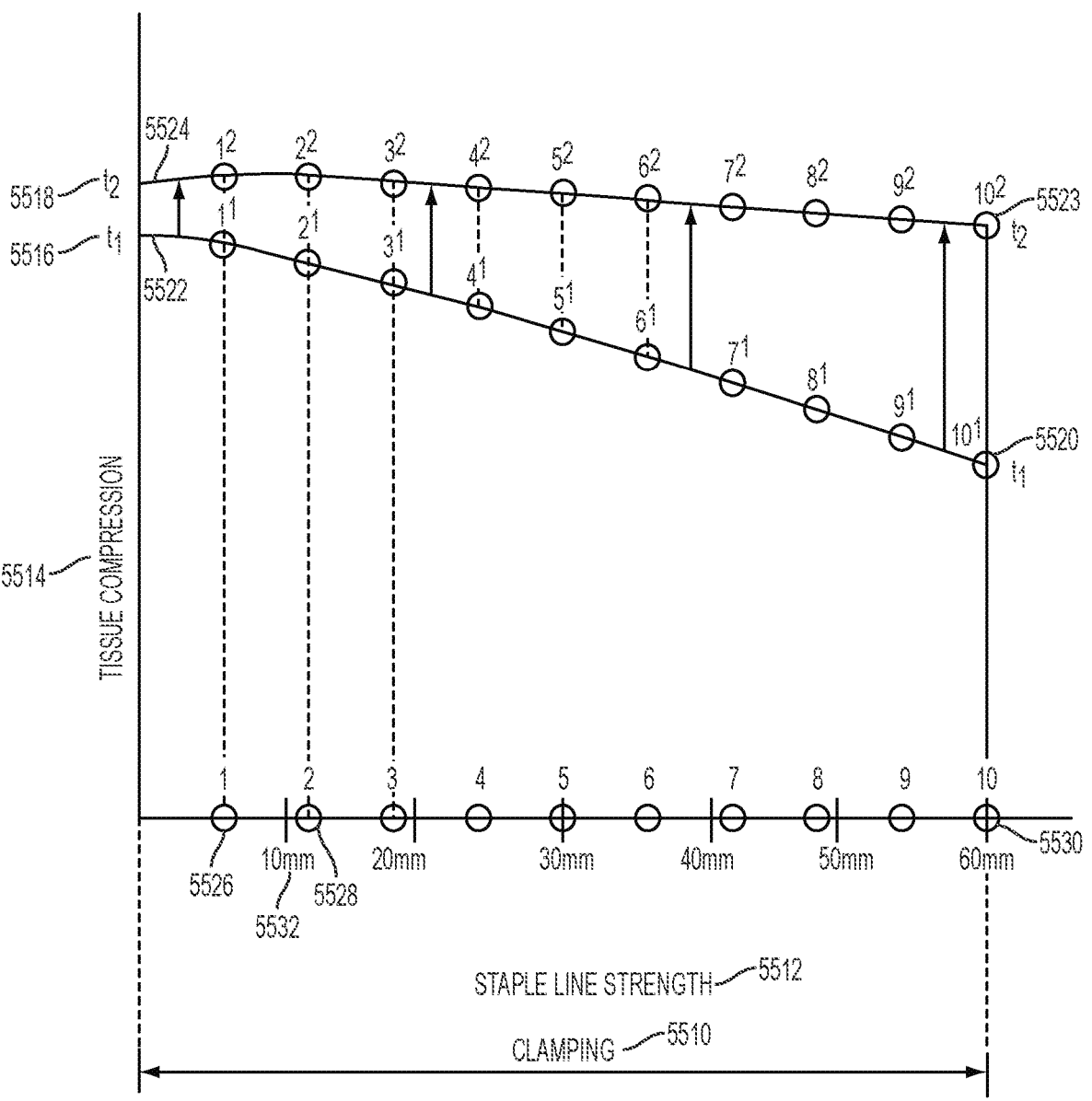
FIG. 48 illustrates one aspect of a mechanism for adapting operations associated with a surgical instrument in the context of tissue compression during a clamping phase.
Figure 49:
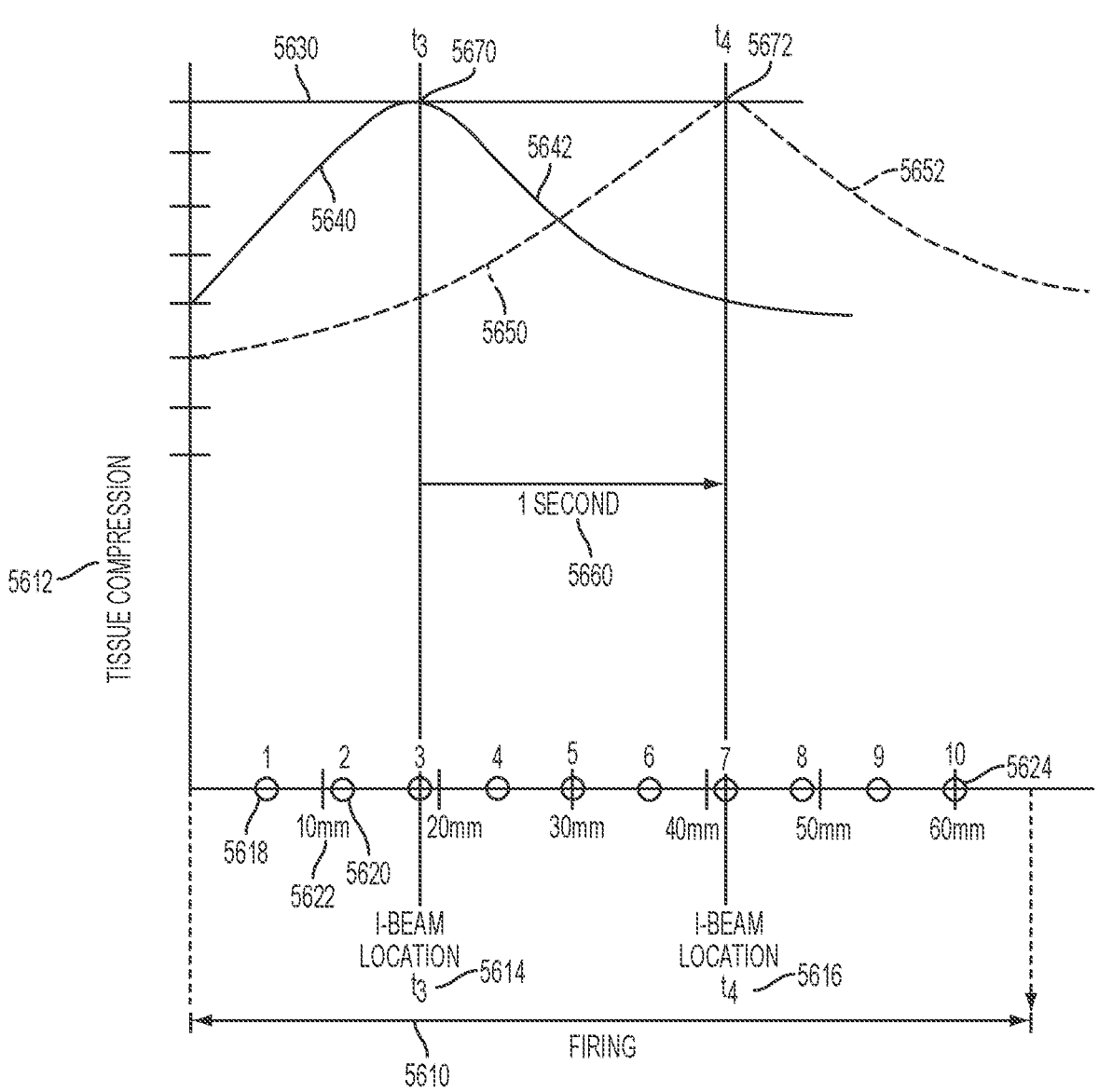
FIG. 49 illustrates one aspect of a mechanism for adapting operations associated with a surgical instrument in the context of tissue compression during a firing phase.

Adequate staple formation is a key consideration. Factors that influence staple formation include finding desirable operational envelopes based on tissue compression. FIGS. 48 and 49 illustrate example scenarios where a parameter such as differential tissue compression, as measured by impedance sensors, can result in adaptive firing procedures. FIG. 48 illustrates clamping 5510 operations where tissue compression 5514 is shown along the vertical (y) axis and staple cartridge size 5532 (mm) is shown along the horizontal (x) axis. Measurements from an end effector 300 (FIG. 1) can embrace a tissue portion of length up to 60 mm in this example, though it can be of a greater length in other examples. Tissue compression within the clamping end effector 300 can be measured by impedance sensors positioned, for example, every 6 mm, such as from 6 mm-60 mm. An impedance measurement can be taken at each sensor. During a surgical procedure, tissue can be compressed within end effector 300. Impedance measurements can be taken at times t1 5516 and t2 5518. At time t1 5516, a curve 5522 can be described toward 5520 by monitoring impedance measurements from one more of the impedance sensors (including impedance sensors 5526, 5528 and 5530). It will be appreciated that there may be ten impedance sensors as shown in the example, but there may be more or fewer. At a second time, t2 5518, a curve 5524 can be described toward 5523 by monitoring the same impedance measurements from one more of the impedance sensors (including impedance sensors 5526, 5528 and 5530). Impedance can be measured based on values from one or more of the impedance sensors, along a curve toward 5524. Comparing the impedance values for a given sensor from t1 and t2 can reveal a differential based on staple line length 5512. There may be multiple reasons. One reason can be that the clamped tissue exhibits different compression properties at different locations along staple line length 5512. An additional reason can be that there is a different tissue thickness; in other words, the tissue may exhibit pre-clamping thickness of a profile seen in FIG. 51. Further, tissue creep may have played a role. It is possible that all these reasons contribute to the observed properties, or there are other reasons. In any event, differential tissue compression over time can be observed.

FIG. 49 can illustrate a firing operation 5610, including but not limited to a firing operation based on FIG. 48. In FIG. 49, tissue compression 5612 is shown along a vertical (y) axis and staple cartridge size 5622 (mm) is shown along the horizontal (x) axis. As the I-beam traverses the tissue, tissue compression 5612 measurements are taken by monitoring impedance measurements from one more of the impedance sensors (including impedance sensors 5618, 5620 and 5624). During firing, tissue compression 5612 can rise to a threshold 5630 and then peak at time t3 5670 relative to I-beam location 5614. Subsequently, tissue compression falls between t3 5670 and t4 5672 (e.g., 1 second 5660) relative to I-beam location 5616. This operation can describe a rising curve 5640 and a falling curve 5642. It also may be observed that under certain circumstances a rising curve 5640 can exhibit a convex complexion, and a falling curve a concave complexion 5642. It may be predicted that an I-beam may take more time to traverse tissue with certain characteristics, e.g., thicker tissue, diseased tissue, etc. Accordingly, a different tissue compression profile may be prescribed such that tissue compression measurements observe a second curve 5650, 5652. In addition, second curve 5650, 5652 may result where there is a differential thickness of the pre-clamped tissue, such as that seen in FIG. 51. Portion 5810 is thinner than portion 5812. Traversing thicker tissue can act to slow the relative speed of the I-Beam, leading to different tissue compression measurements over time, and accordingly variable tissue profiles.

Accordingly, a differential in tissue compression measurements between t1 and t2 can lead to an adaptive response whereby control measures adjust a curve of tissue compression during a firing phase 5610. It will be appreciated, then, that the curve peaking at t4 can represent an adaptive curve based on tissue properties that can lead to improved results from the surgical procedure, battery usage, and other operations where an adaptive response can be used.

The shape of the curve can have significance. For example, a convex curve can reflect a rising tissue compression profile during a firing phase 5610. A concave curve can reflect a falling tissue compression profile during a firing phase 5610. A peak tissue compression measurement 5670, 5672 can fall between respective concave and convex curves. (For purposes of this disclosure, a perspective based on which concavity or convexity is found is based on viewing from a higher value on the y-axis than the peak of the curve.)

Figure 50:
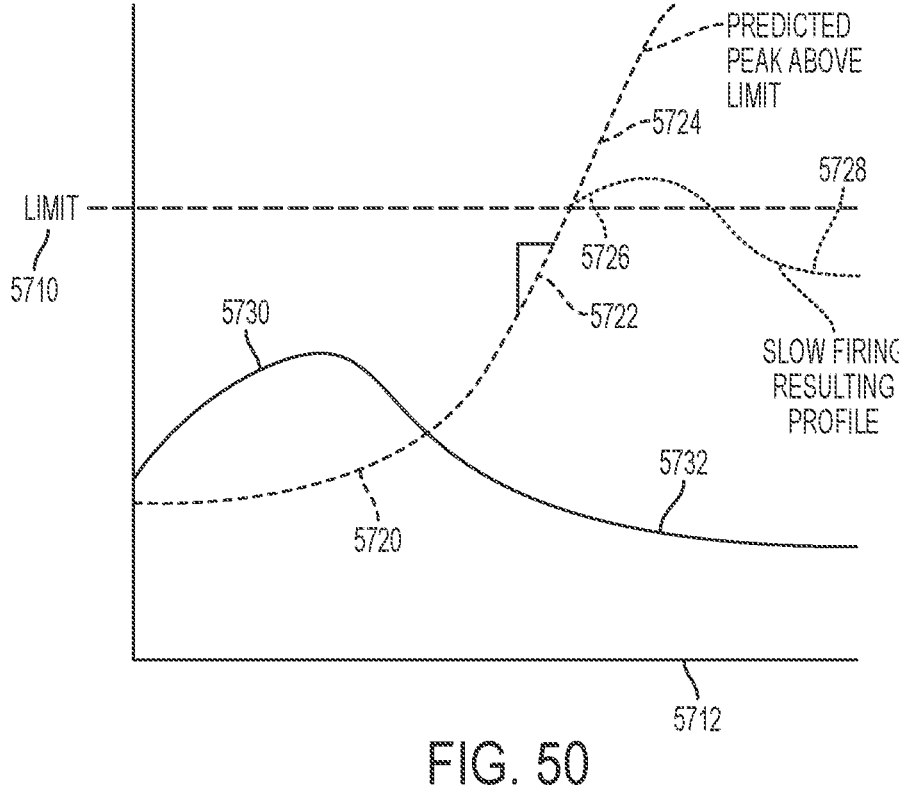
FIG. 50 illustrates one aspect of a mechanism for adapting operations associated with a surgical instrument in the context of slowing a firing event where a peak is predicted above a limit.

In conjunction with FIGS. 48 and 49, or as independent examples, control measures can wholly or partially adjust firing in order to prevent a parameter from rising above a certain limit. FIG. 50 shows an example scenario. A first curve 5730, 5732 can be a predicted firing profile stored by instrument 10 (FIGS. 1-4) for a given type of tissue. It will be seen that the vertical (y) axis parameter, such as tissue compression, over time (t) along the horizontal (x) axis 5172 can rise as in curve 5730, then fall as in curve 5732. However, it is possible that the values associated with the predicted firing profile diverge, during operation, from values actually observed during the surgical procedure. As a result, instrument 10 can take measures to adapt. For example, the observed measurements can fall along curve 5720, with a slower rate of rise but projected higher peak. Thus, the y-axis parameter can continue to rise. Under certain circumstances, it can be predicted that the curve for the y-axis parameter could breach predetermined, or dynamically determined, limit 5710 prior to reaching its peak. This prediction can be made based on a slope 5722 of the curve, in combination or not with input from the x-axis 5172 parameter (e.g., time). If it is determined that the peak is predicted to be above the limit 5726, or other portions of curve 5724 will breach the limit 5710, instrument 10 could adapt firing in order to provide for a slower firing rate. Doing so can result in the y-axis measurement falling along an adaptive curve 5728 based on slower firing. The adaptive curve can rise above the limit, or be constrained from doing by adapting operations accordingly.

Figure 51:
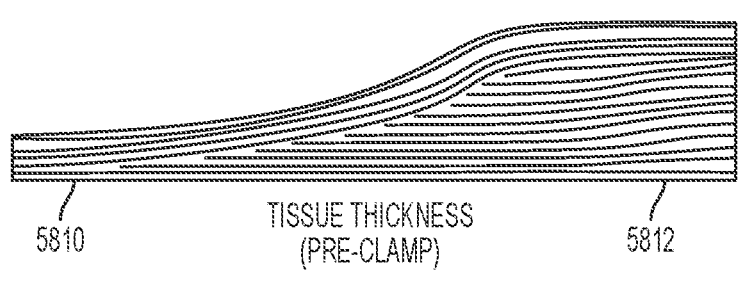
FIG. 51 illustrates a portion of tissue having a disparity in thickness.

FIG. 51 illustrates a portion of tissue prior to clamping. It can be seen that one end of the tissue 5810 is thinner than the other end 5812. In such circumstances, there can be differential forces and timings exerted by end effector 300 (FIG. 1) on the tissue, and by the tissue on end effector 300. The thickness disparity can be taken into account by instrument 10 (FIGS. 1-4) in adapting to such thickness. It may be the case that this tissue portion is similar to the one considered in connection with FIGS. 48-49. It also may be the case that another tissue portion is illustrated in connection with FIGS. 48-49, to show more general applicability. It may further be the case that FIG. 50 is a graphical representation of adaptive operations performed in connection with a tissue portion like that in FIG. 51; again, it also may be the case that FIG. 50 can show more generally adaptive operations in response to detecting measurement of certain parameters during the course of a surgical procedure and adjusting accordingly.

In various aspects, the present disclosure provides an instrument 10 (described in connection with FIGS. 1-29) configured to sense tissue compression when tissue is clamped between the jaw members of the end effector, such as, for example, between the anvil and the staple cartridge. In one example, the instrument 10 (FIGS. 1-4) can be configured to sense tissue contact in one of the jaw members such as the anvil and/or the staple cartridge. In another example, the instrument 10 can be configured to sense the pressure applied to the tissue by the jaw members. In yet another example, the instrument 10 can be configured to measure the electrical impedance (resistance) through the tissue between the jaw members. This may be achieved by embedding micro electrodes in at least one of the jaw members to drive a low amplitude, low energy, RF signal through the tissue to enable a nontherapeutic measurement of tissue impedance. The energy level is kept low enough to avoid therapeutic tissue effects such as coagulation, sealing, welding, or cautery. Further, the instrument 10 can include devices to produce two distinct measures from a single set of energized and return paths. In one example, multiple frequency signals can be overlaid to measure impedance in different places simultaneously. This can include a single active electrode with the channel and the anvil grounded through isolated paths with filters for different frequency RF signals. Otherwise, two isolated return paths with independent filters, which are part of the handle electronics system can be used. In another example, the sequential impedance measurements would be multiplexed at variable RF frequencies.

RF technology has been used in endocutters for some time. The challenge in employing the technology is in the delivery of high density RF energy and shorting between the jaw members of the end effector. Despite the shortcomings of using RF energy therapeutically, RF technology can be effectively employed sub-therapeutically to sense tissue compression rather than actually coagulating, sealing, or cauterizing tissue. In the sub-therapeutic sense, the endo-surgical device can employ RF energy to sense internal tissue parameters and adjust the deployment of staples rather and being employed as an adjunct to the stapling operation to assist in sealing the tissue prior to cutting the tissue with a knife.

RF technology used in endosurgical medical devices, and for example, in RF endocutters, may introduce the challenges of handling high densities of energy and dealing with shorting. However, RF technology may be less challenging if used merely to sense tissue compression rather than, for example, cauterizing tissue. RF technology may be used as a way for medical devices, such as endocutters, to sense internal tissue parameters such as compression, and adjust stapling deployment in response. RF electrode and cautery devices may utilize the same electrodes for sensing tissue impedance as they do to melt tissue. These same electrodes may be implemented with significantly less electrical and power requirements as a tissue compression sensor system.

RF electrodes and cautery devices can utilize the same electrodes for sensing tissue impedance as they do to weld the tissue by applying energy thereto. Nevertheless, in the an endocutter instrument context, the RF electrodes can be employed to as a tissue compression sensor system with significantly less electronics and power needs relative to a fully equipped electrosurgical device. A single energized electrode on the cartridge, for example, or perhaps an isolated knife, can be used to make multiple tissue compression measurements simultaneously. If multiple RF signals are overlaid or multiplexed they can be transmitted down the single power conductor and then allowed to return on either the channel frame or the anvil of the device. If a filter is provided in the anvil and channel contacts before they join the common return path, the tissue impedance for both paths can be differentiated. This would provide a measure of through tissue versus lateral tissue compression. This filtered approach may be implemented proximal and distal as opposed to vertical and lateral depending on the placement of the filters and the location of the metallic electrically conductive return paths. The smaller frequency generator and signal processor may be implemented in a small package form factor on an existing circuit board or a sub circuit board without the need for extensive extra cost associated with an RF sealing/cauterization system.

Figure 52:
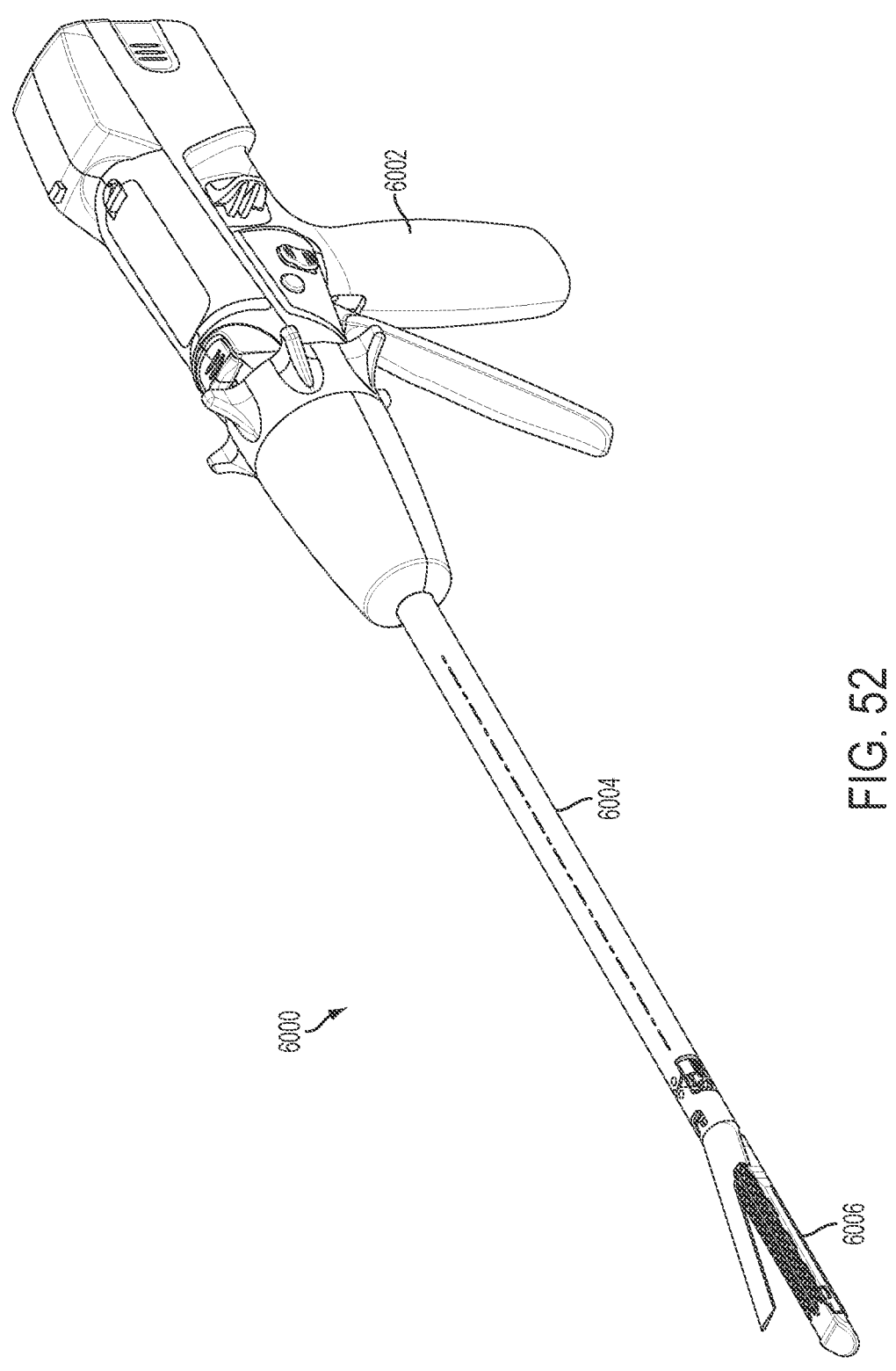
FIG. 52 depicts an example medical device that can include one or more aspects of the present disclosure.
Figure 53A:
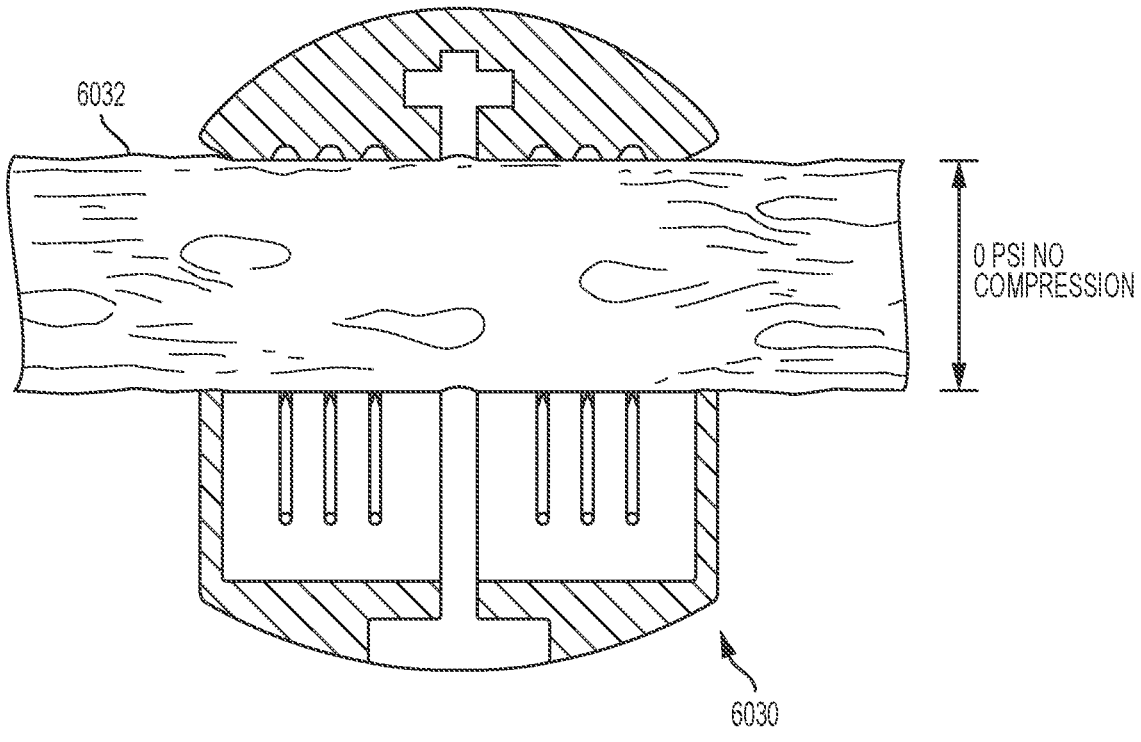
FIG. 53A depicts an example end-effector of a medical device surrounding tissue in accordance with one or more aspects of the present disclosure.
Figure 53B:
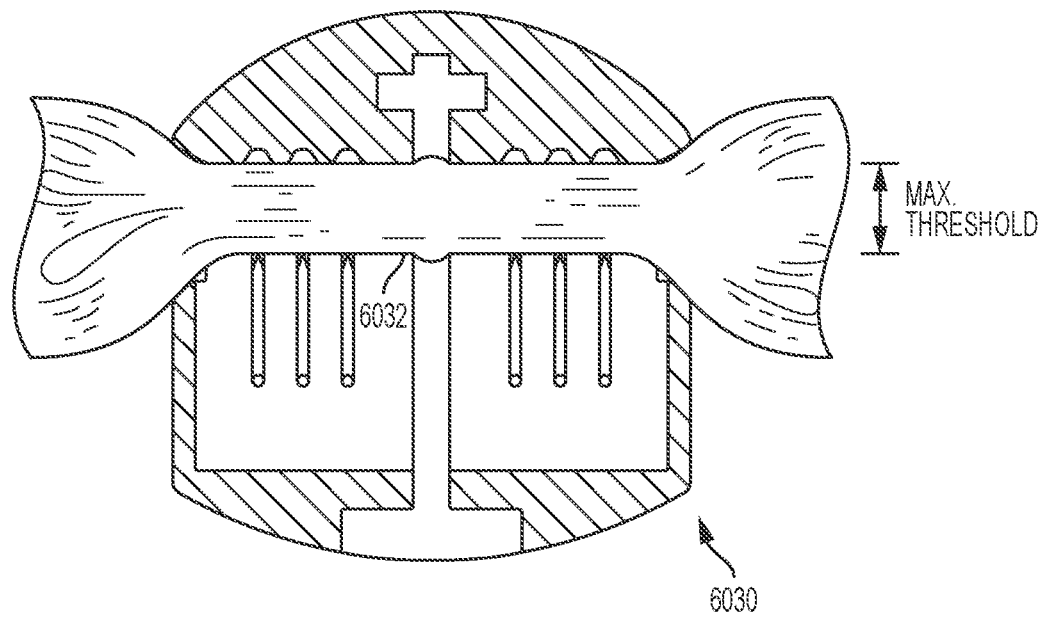
FIG. 53B depicts an example end-effector of a medical device compressing tissue in accordance with one or more aspects of the present disclosure.

Referring to FIG. 52, an endocutter 6000 may include a handle component 6002, a shaft component 6004, and an end-effector component 6006. The endocutter 6000 is similarly constructed and equipped as the motor-driven surgical cutting and fastening instrument 10 described in connection with FIGS. 1-29. Accordingly, for conciseness and clarity the details of operation and construction will not be repeated here. The end-effector 6006 may be used to compress, cut, or staple tissue. Referring now to FIG. 53A, an end-effector 6030 may be positioned by a physician to surround tissue 6032 prior to compression, cutting, or stapling. As shown in FIG. 53A, no compression may be applied to the tissue while preparing to use the end-effector. Referring now to FIG. 53B, by engaging the handle (e.g., handle 6002) of the endocutter, the physician may use the end-effector 6030 to compress the tissue 6032. In one aspect, the tissue 6032 may be compressed to its maximum threshold, as shown in FIG. 53B.

Figure 54A:
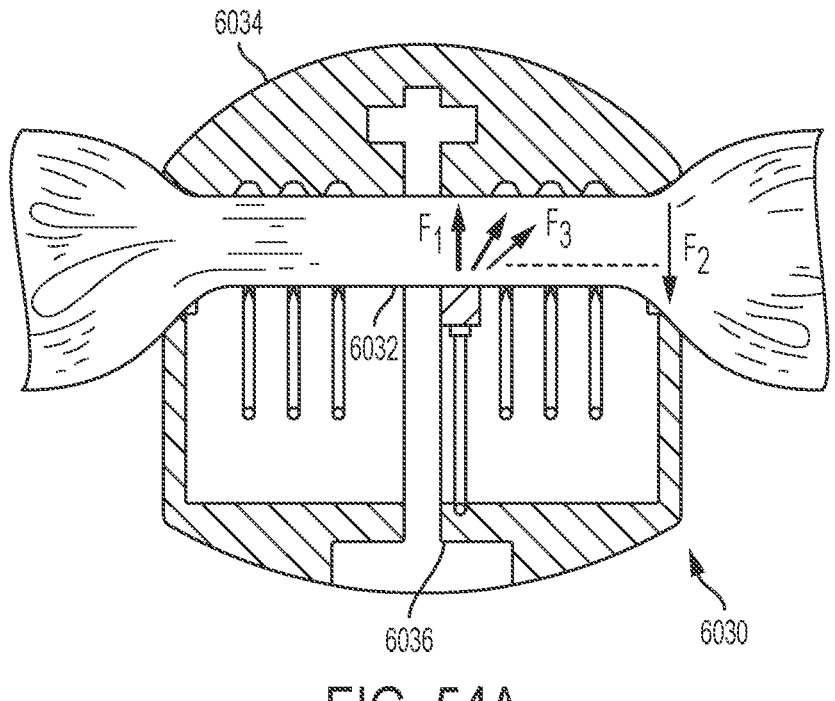
FIG. 54A depicts example forces exerted by an end-effector of a medical device compressing tissue in accordance with one or more aspects of the present disclosure.
Figure 54B:
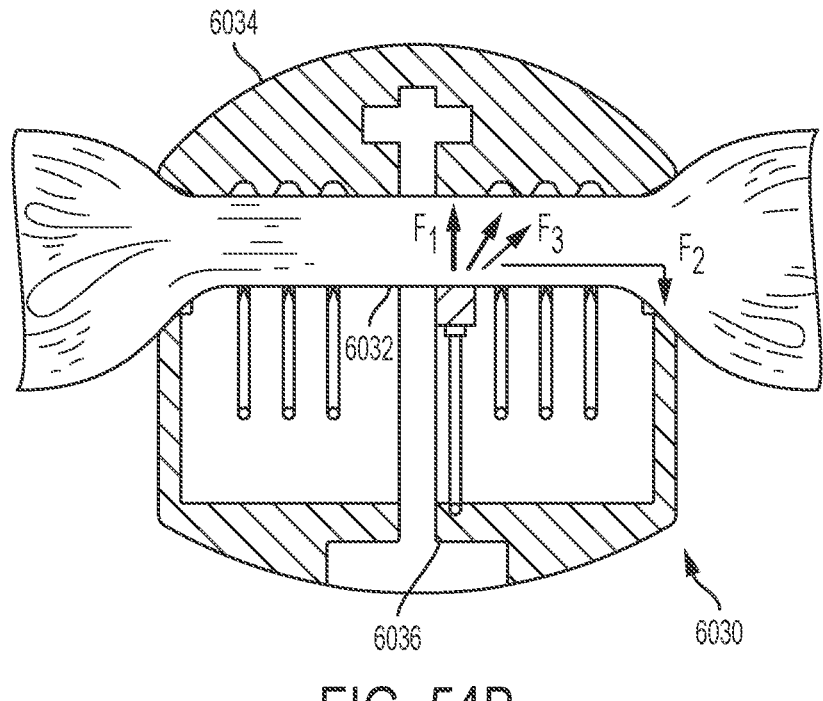
FIG. 54B also depicts example forces exerted by an end-effector of a medical device compressing tissue in accordance with one or more aspects of the present disclosure.

Referring to FIG. 54A, various forces may be applied to the tissue 6032 by the end-effector 6030. For example, vertical forces F1 and F2 may be applied by the anvil 6034 and the channel frame 6036 of the end-effector 6030 as tissue 6032 is compressed between the two. Referring now to FIG. 54B, various diagonal and/or lateral forces also may be applied to the tissue 6032 when compressed by the end-effector 6030. For example, force F3 may be applied. For the purposes of operating a medical device such as endocutter 6000, it may be desirable to sense or calculate the various forms of compression being applied to the tissue by the end-effector. For example, knowledge of vertical or lateral compression may allow the end-effector to more precisely or accurately apply a staple operation or may inform the operator of the endocutter such that the endocutter can be used more properly or safely.

The compression through tissue 6032 may be determined from an impedance of tissue 6032. At various levels of compression, the impedance Z of tissue 6032 may increase or decrease. By applying a voltage V and a current I to the tissue 6032, the impedance Z of the tissue 6032 may be determined at various levels of compression. For example, impedance Z may be calculated by dividing the applied voltage V by the current I.

Figure 55:
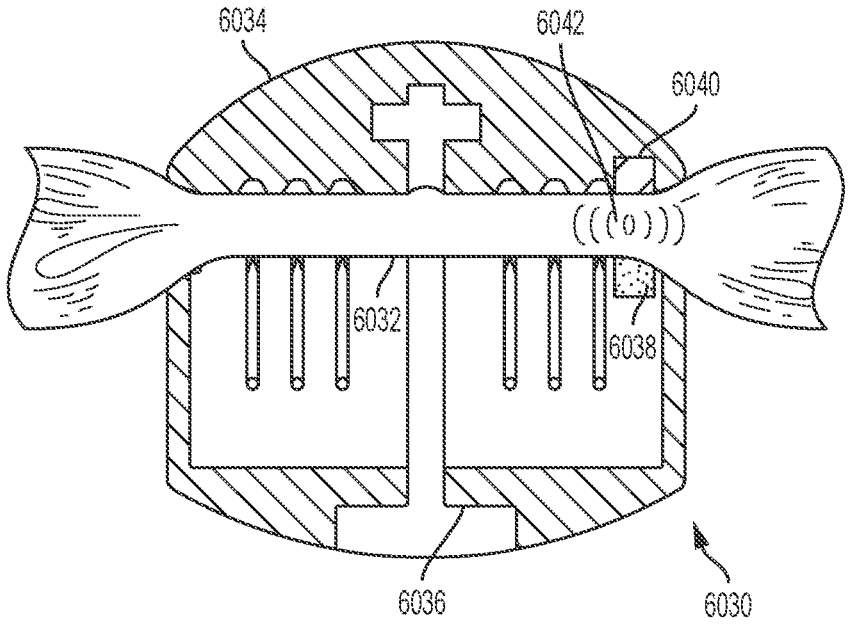
FIG. 55 depicts an example tissue compression sensor system in accordance with one or more aspects of the present disclosure.

Referring now to FIG. 55, in one aspect, an RF electrode 6038 may be positioned on the end-effector 6030 (e.g., on a staple cartridge, knife, or channel frame of the end-effector 6030). Further, an electrical contact 6040 may be positioned on the anvil 6034 of the end-effector 6030. In one aspect, the electrical contact may be positioned on the channel frame of the end-effector. As the tissue 6032 is compressed between the anvil 6034 and, for example, the channel frame 6036 of the end-effector 6030, an impedance Z of the tissue 6032 changes. The vertical tissue compression 6042 caused by the end-effector 6030 may be measured as a function of the impedance Z of the tissue 6032.

Figure 56:
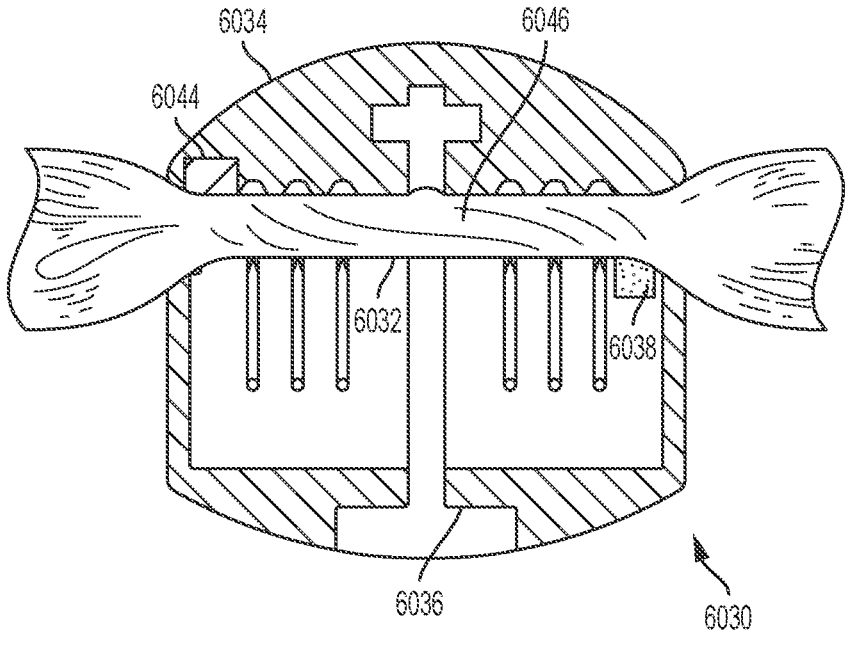
FIG. 56 also depicts an example tissue compression sensor system in accordance with one or more aspects of the present disclosure.

Referring now to FIG. 56, in one aspect, an electrical contact 6044 may be positioned on an opposite end of the anvil 6034 of the end-effector 6030 as the RF electrode 6038 is positioned. As the tissue 6032 is compressed between the anvil 6034 and, for example, the channel frame 6036 of the end-effector 6030, an impedance Z of the tissue 6032 changes. The lateral tissue compression 6046 caused by the end-effector 6030 may be measured as a function of the impedance Z of the tissue 6032.

Figure 57:
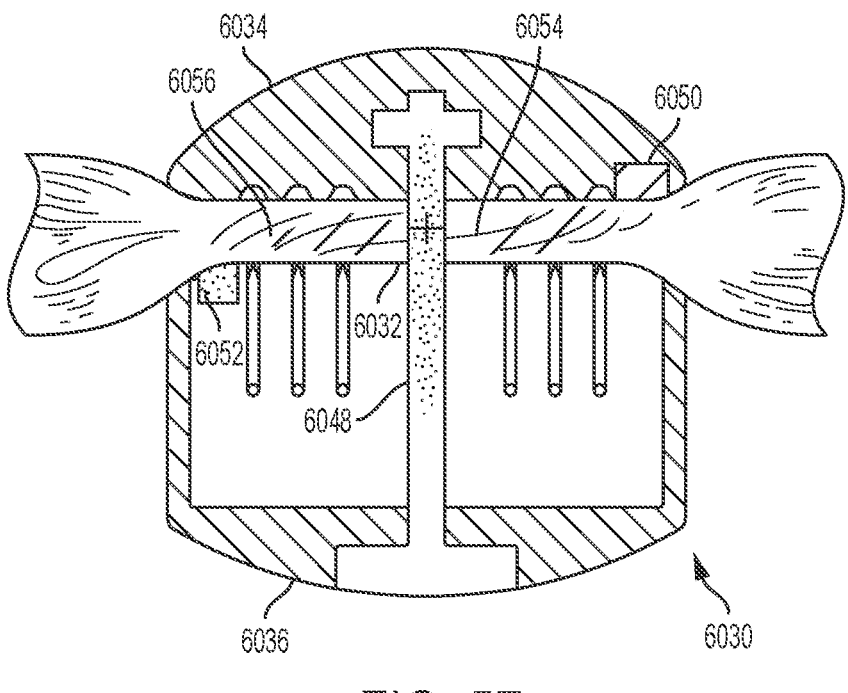
FIG. 57 also depicts an example tissue compression sensor system in accordance with one or more aspects of the present disclosure.

Referring now to FIG. 57, in one aspect, electrical contact 6050 may be positioned on the anvil 6034 and electrical contact 6052 may be positioned on an opposite end of the end-effector 6030 at channel frame 6036. RF electrode 6048 may be positioned laterally to the central to the end-effector 6030. As the tissue 6032 is compressed between the anvil 6034 and, for example, the channel frame 6036 of the end-effector 6030, an impedance Z of the tissue 6032 changes. The lateral compression or angular compressions 6054 and 6056 on either side of the RF electrode 6048 may be caused by the end-effector 6030 and may be measured as a function of different impedances Z of the tissue 6032, based on the relative positioning of the RF electrode 6048 and electrical contacts 6050 and 6052.

Figure 58:
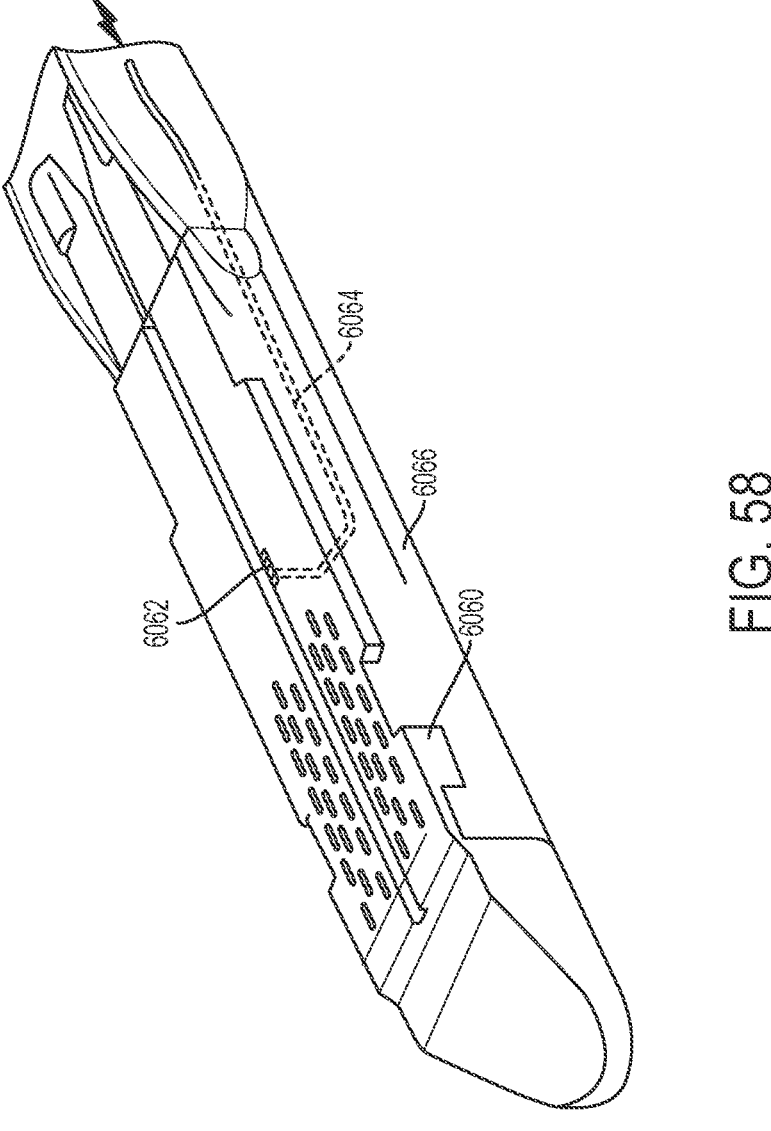
FIG. 58 depicts an example end-effector channel frame in accordance with one or more aspects of the present disclosure.

In accordance with one or more of the techniques and features described in the present disclosure, and as discussed above, an RF electrode may be used as an RF sensor. Referring now to FIG. 58, in one aspect, an RF sensor 6062 may be positioned on a staple cartridge 6060 inserted into a channel frame 6066 an end-effector. The RF electrode may run from a power line 6064 which may be powered by a power source in a handle (e.g., handle 6002) of an endocutter.

Figure 59:
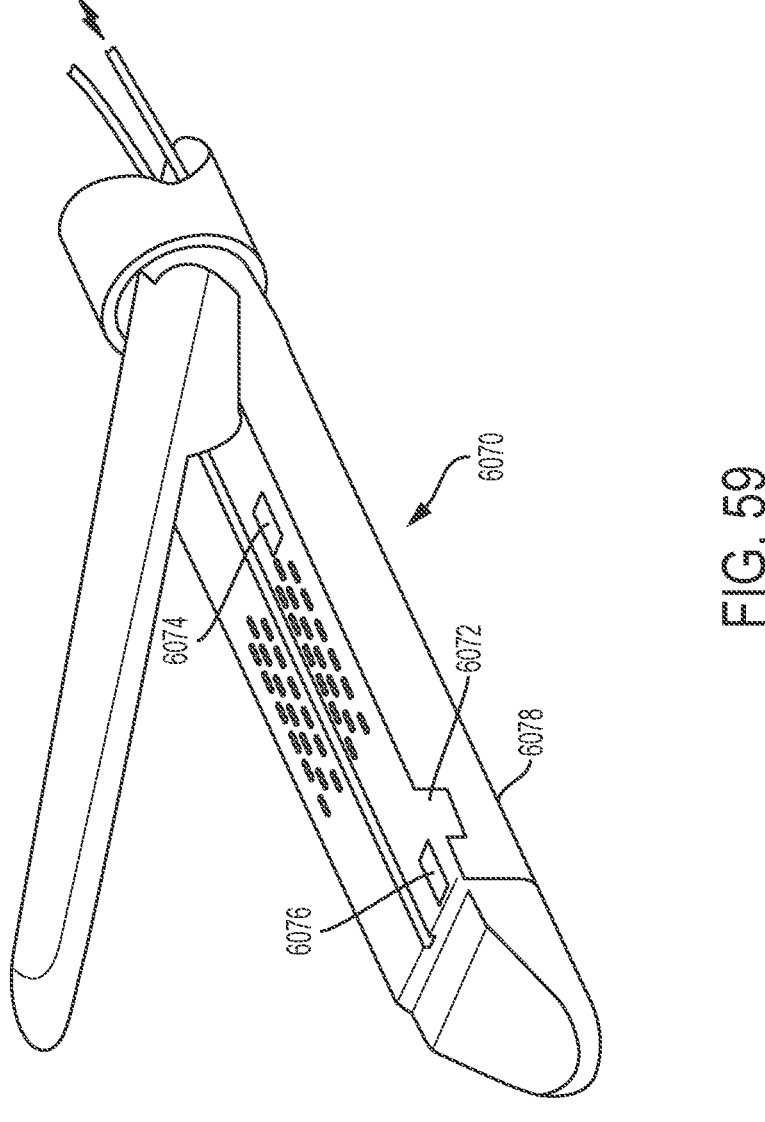
FIG. 59 depicts an example end-effector in accordance with one or more aspects of the present disclosure.

Referring now to FIG. 59, in one aspect, RF electrodes 6074 and 6076 may be positioned on a staple cartridge 6072 inserted into a channel frame 6078 of end-effector 6070. As shown, RF electrode 6074 may be placed in a proximal position of the end-effector relative to an endocutter handle. Further, RF electrode 6076 may be placed in a distal position of the end-effector relative to the endocutter handle. RF electrodes 6074 and 6076 may be utilized to measure vertical, lateral, proximal, or distal compression at different points in a tissue based on the position of one or more electrical contacts on the end-effector.

Figure 60:
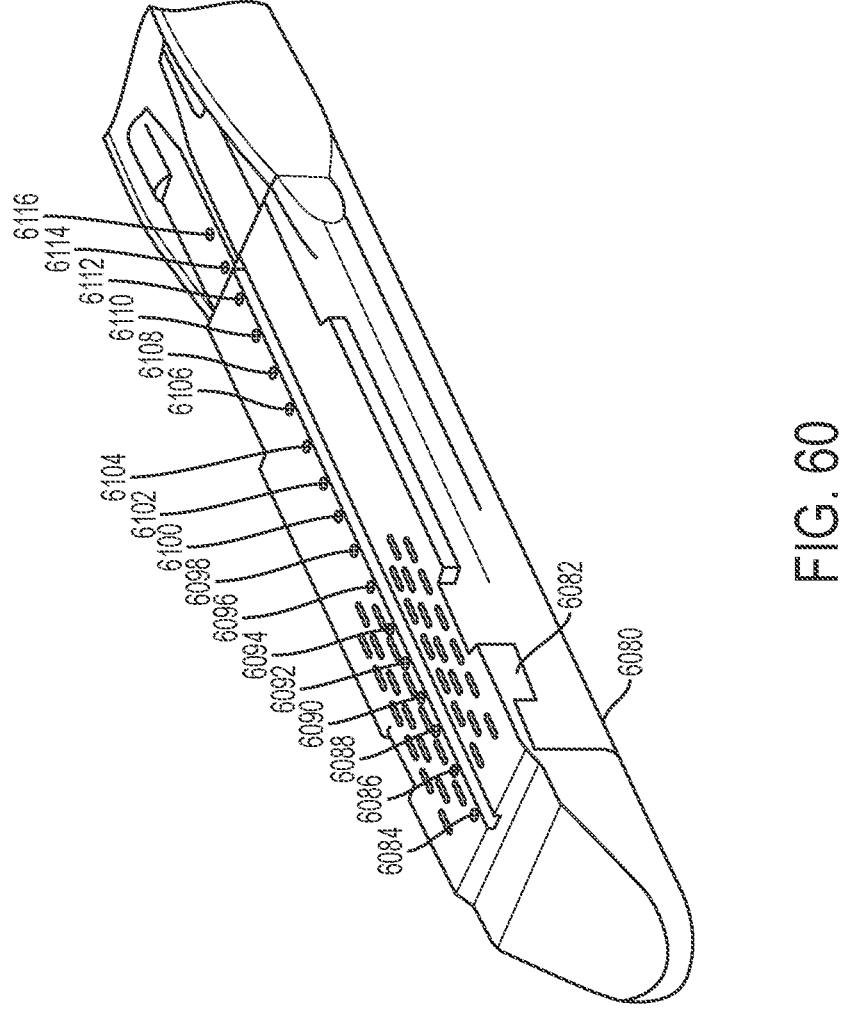
FIG. 60 also depicts an example end-effector channel frame in accordance with one or more aspects of the present disclosure.
Figure 61:
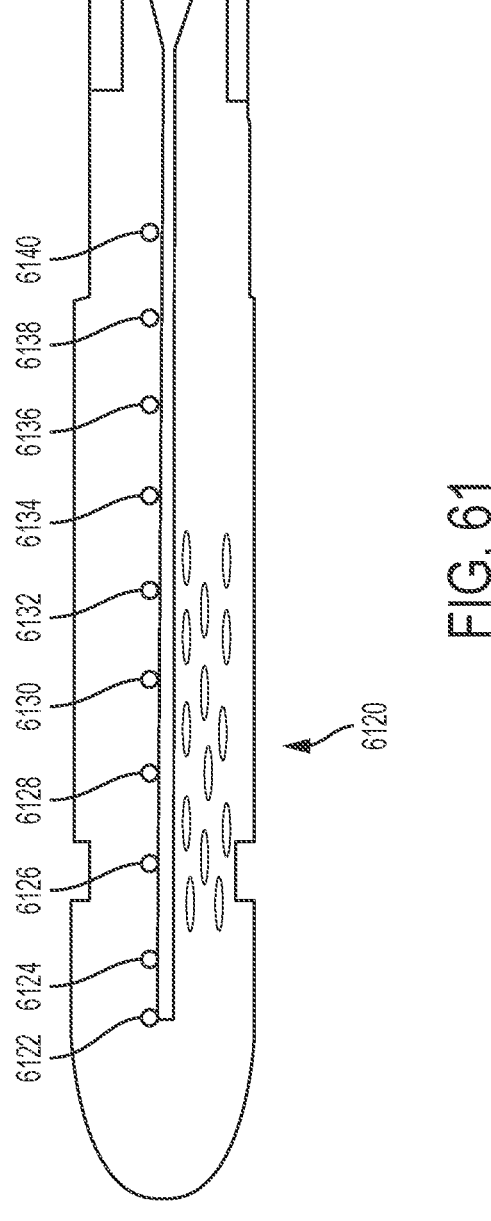
FIG. 61 also depicts an example end-effector channel frame in accordance with one or more aspects of the present disclosure.
Figure 62:
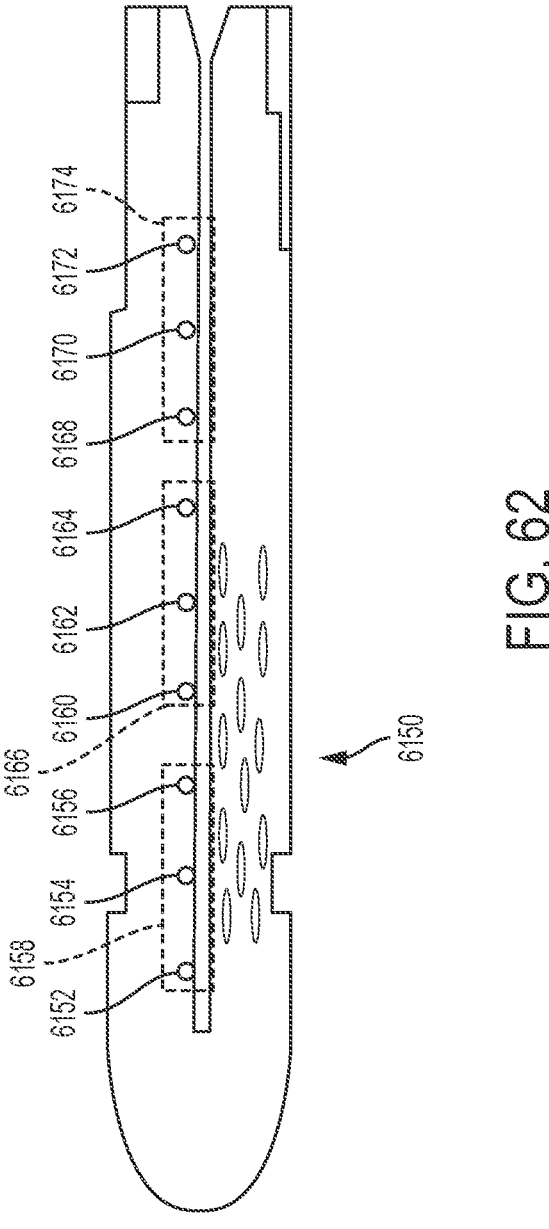
FIG. 62 also depicts an example end-effector channel frame in accordance with one or more aspects of the present disclosure.

Referring now to FIG. 60, in one aspect, RF electrodes 6084-6116 may be positioned on staple cartridge 6082 inserted into the channel frame 6080 (or other component of an end-effector) based on various points for which compression information is desired. Referring now to FIG. 61, in one aspect, RF electrodes 6122-6140 may be positioned on staple cartridge 6120 at discrete points for which compression information is desired. Referring now to FIG. 62, RF electrodes 6152-6172 may be positioned at different points in multiple zones of a staple cartridge based on how accurate or precise the compression measurements should be. For example, RF electrodes 6152-6156 may be positioned in zone 6158 of staple cartridge 6150 depending on how accurate or precise the compression measurements in zone 6158 should be. Further, RF electrodes 6160-6164 may be positioned in zone 6166 of staple cartridge 6150 depending on how accurate or precise the compression measurements in zone 6166 should be. Additionally, RF electrodes 6168-6172 may be positioned in zone 6174 of staple cartridge 6150 depending on how accurate or precise the compression measurements in zone 6174 should be.

Figure 63:
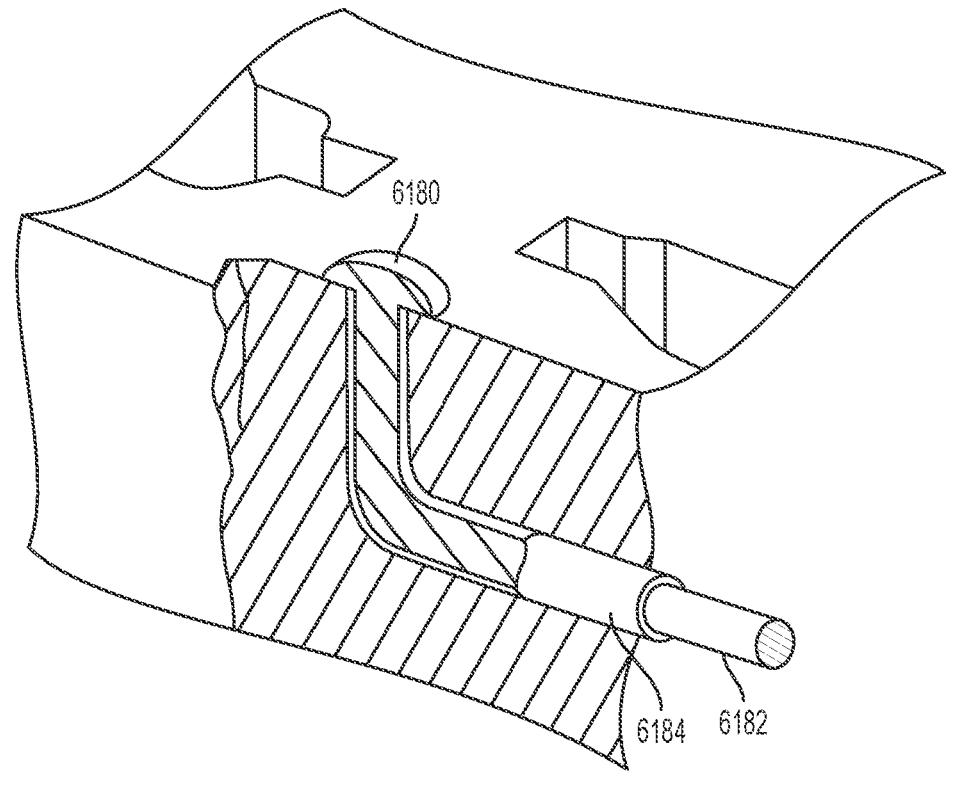
FIG. 63 depicts an example electrode in accordance with one or more aspects of the present disclosure.

The RF electrodes discussed herein may be wired through a staple cartridge inserted in the channel frame. Referring now to FIG. 63, in one aspect, an RF electrode may have a stamped "mushroom head" 6180 of about 1.0 mm in diameter. While the RF electrode may have the stamped "mushroom head" of about 1.0 mm in diameter, this is intended to be a non-limiting example and the RF electrode may be differently shaped and sized depending on each particular application or design. The RF electrode may be connected to, fastened to, or may form, a conductive wire 6182. The conductive wire 182 may be about 0.5 mm in diameter, or may have a larger or smaller diameter based on a particular application or design. Further, the conductive wire may have an insulative coating 6184. In one example, the RF electrode may protrude through a staple cartridge, channel frame, knife, or other component of an end-effector.

Figure 64:
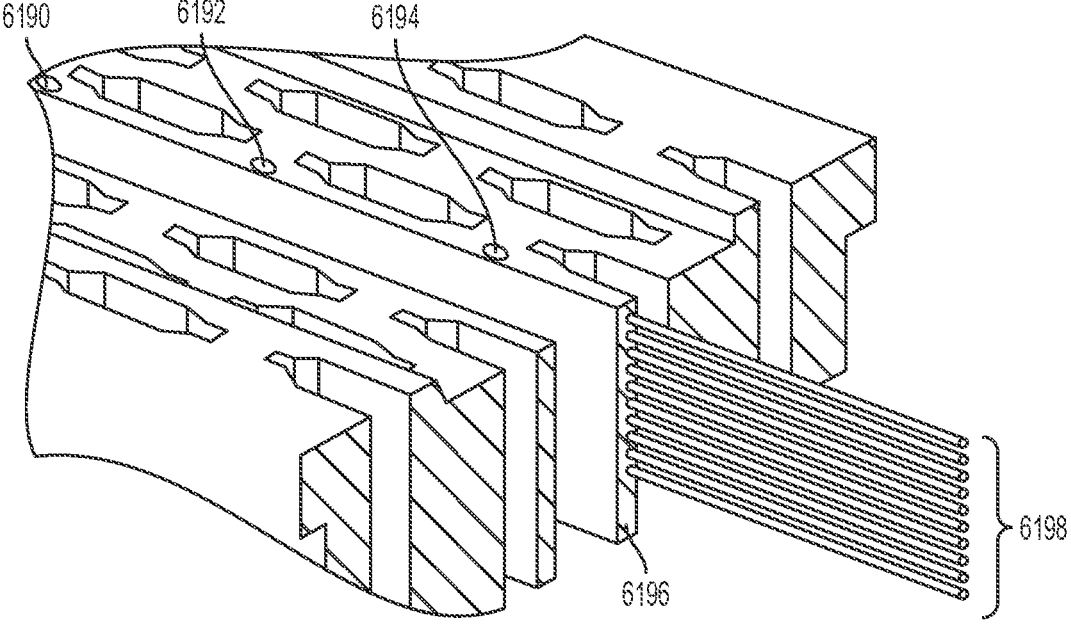
FIG. 64 depicts an example electrode wiring system in accordance with one or more aspects of the present disclosure.

Referring now to FIG. 64, the RF electrodes may be wired through a single wall or through multiple walls of a staple cartridge or channel frame of an end-effector. For example, RF electrodes 6190-6194 may be wired through wall 6196 of the staple cartridge or channel frame of an end-effector. One or more of wires 6198 may be connected to, fastened to, or be part of, RF electrodes 6190-6194 and may run through wall 6196 from a power source in, e.g., a handle of an endocutter.

Figure 65:
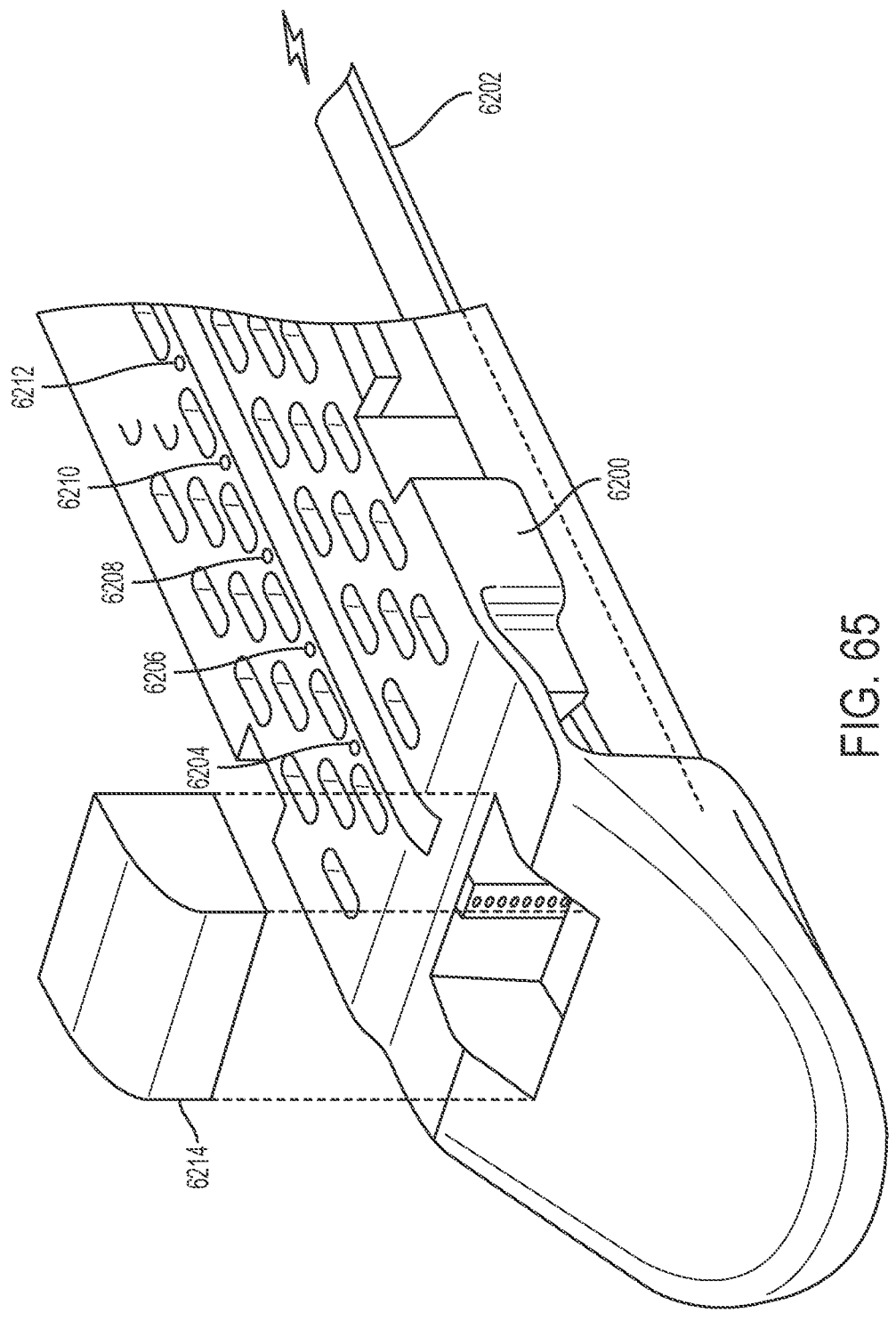
FIG. 65 also depicts an example end-effector channel frame in accordance with one or more aspects of the present disclosure.
Figure 66:
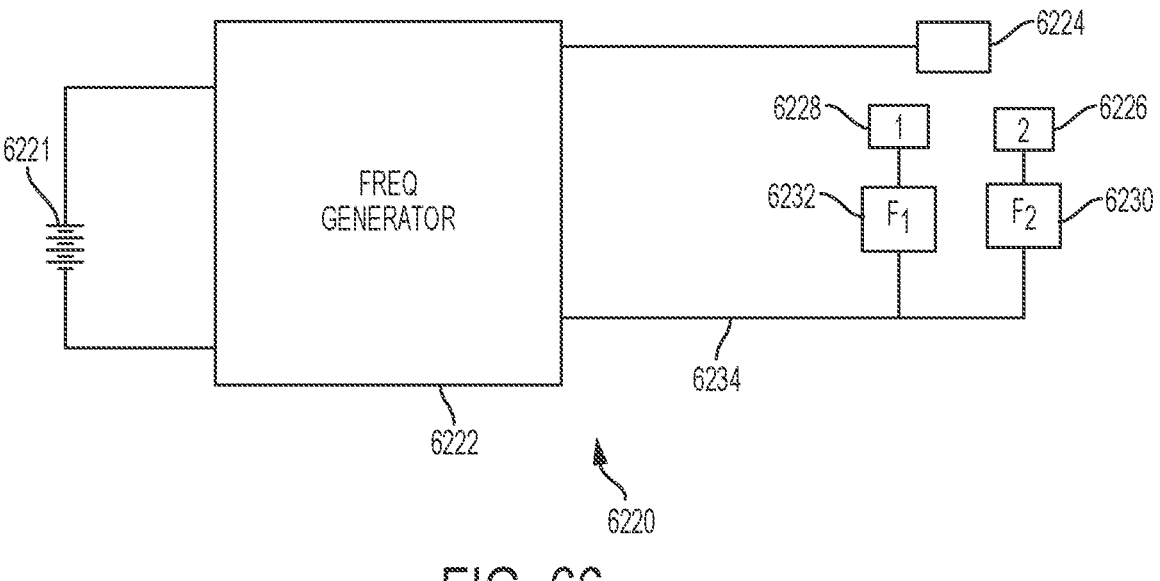
FIG. 66 is an example circuit diagram in accordance with one or more aspects of the present disclosure.

Referring now to FIG. 65, the power source may be in communication with the RF electrodes or may provide power to the RF electrodes through a wire or cable. The wire or cable may join each individual wire and lead to the power source. For example, RF electrodes 6204-6212 may receive power from a power source through wire or cable 6202, which may run through staple cartridge 6200 or a channel frame of an end-effector. In one example, each of RF electrodes 6204-6212 may have its own wire that runs to or through wire or cable 6202. The staple cartridge 6200 or channel frame may also may include a controller 6214, such as the controller 2006 shown in connection with FIGS. 21A, 21B, or other controllers 2606 or 3017 shown in connection with FIGS. 27-29, for example. It will be appreciated that the controller 6214 should be suitably sized to fit in the staple cartridge 6200 or channel frame form factor. Also, the controller In various aspects, the tissue compression sensor system described herein for use with medical devices may include a frequency generator. The frequency generator may be located on a circuit board of the medical device, such as an endocutter. For example the frequency generator may be located on a circuit board in a shaft or handle of the endocutter. Referring now to FIG. 66, an example circuit diagram 6220 in accordance with one example of the present disclosure is shown. As shown, frequency generator 6222 may receive power or current from a power source 6221 and may supply one or more RF signals to one or more RF electrodes 6224. As discussed above, the one or more RF electrodes may be positioned at various locations or components on an end-effector or endocutter, such as a staple cartridge or channel frame. One or more electrical contacts, such as electrical contacts 6226 or 6228 may be positioned on a channel frame or an anvil of an end-effector. Further, one or more filters, such as filters 6230 or 6232 may be communicatively coupled to the electrical contacts 6226 or 6228 as shown in FIG. 66. The filters 6230 and 6232 may filter one or more RF signals supplied by the frequency generator 6222 before joining a single return path 6234. A voltage V and a current I associated with the one or more RF signals may be used to calculate an impedance Z associated with a tissue that may be compressed and/or communicatively coupled between the one or more RF electrodes 6224 and the electrical contacts 6226 or 6228.

Figure 67:
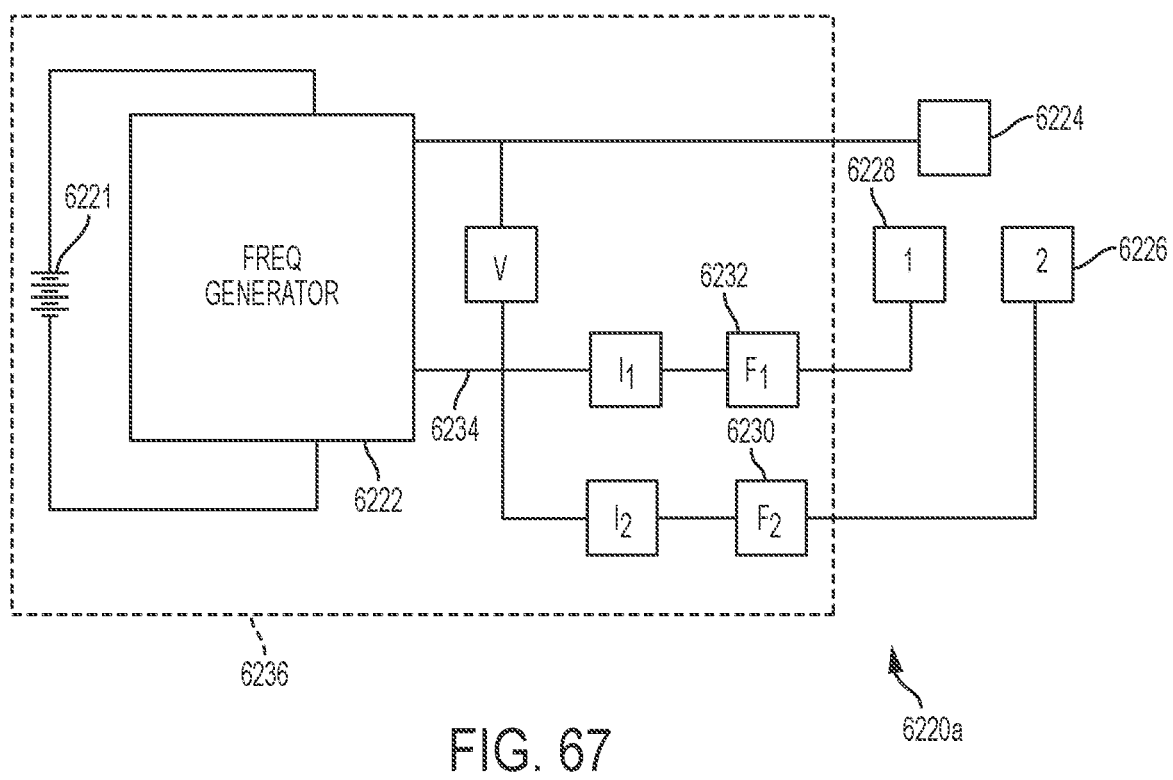
FIG. 67 is also an example circuit diagram in accordance with one or more aspects of the present disclosure.

Referring now to FIG. 67, various components of the tissue compression sensor system described herein may be located in a handle 6236 of an endocutter. For example, as shown in circuit diagram 6220a, frequency generator 6222 may be located in the handle 6236 and receives power from power source 6221. Also, current I1 and current I2 may be measured on a return path corresponding to electrical contacts 6228 and 6226. Using a voltage V applied between the supply and return paths, impedances Z1 and Z2 may be calculated. Z1 may correspond to an impedance of a tissue compressed and/or communicatively coupled between one or more of RF electrodes 6224 and electrical contact 6228. Further, Z2 may correspond to an impedance of a tissue compressed and/or communicatively coupled between one or more of RF electrodes 6224 and electrical contact 6226. Applying the formulas Z1=V/I1 and Z2=V/I2, impedances Z1 and Z2 corresponding to different compression levels of a tissue compressed by an end-effector may be calculated.

Figure 68:
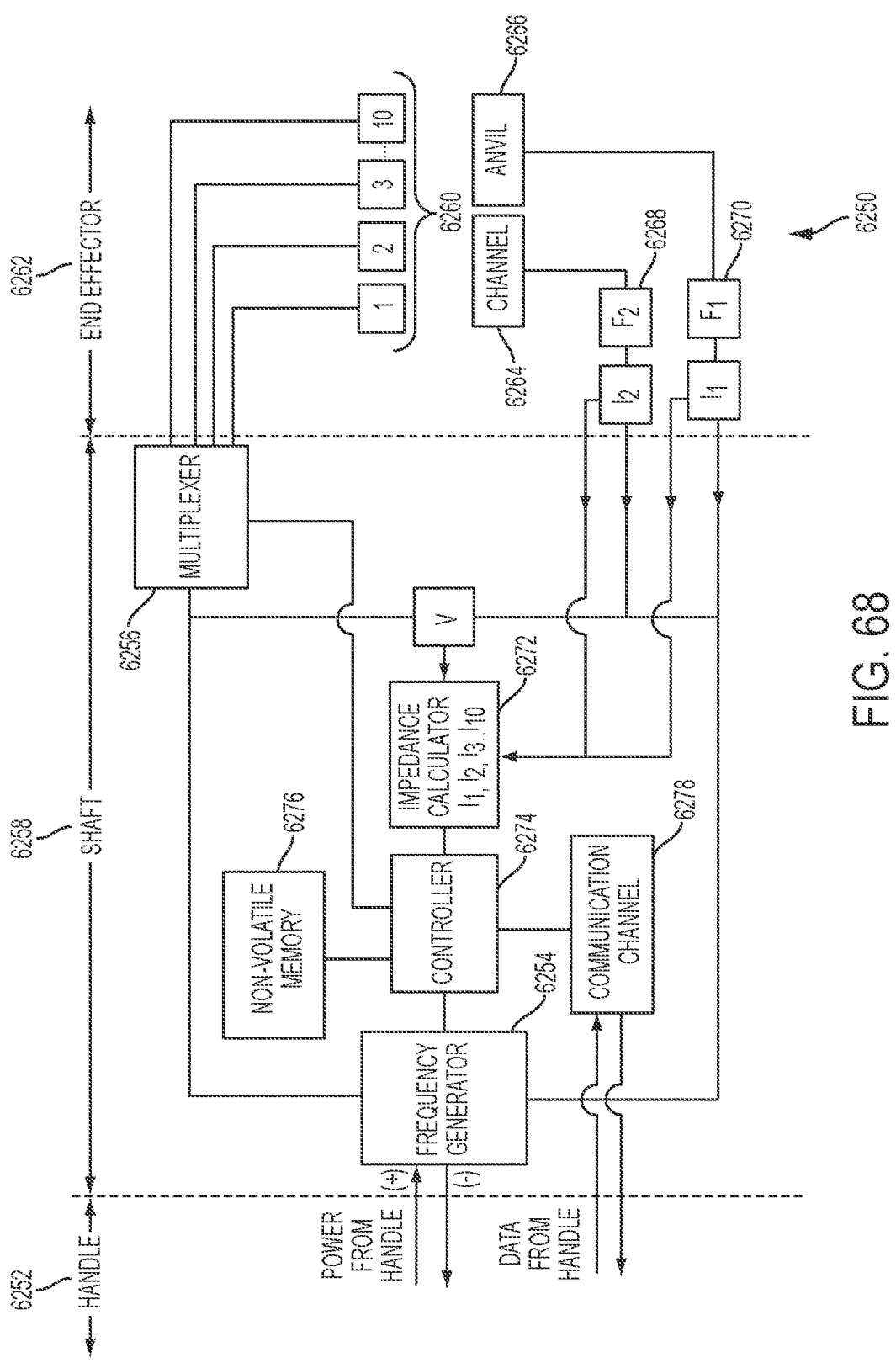
FIG. 68 is also an example circuit diagram in accordance with one or more aspects of the present disclosure.

Referring now to FIG. 68, one or more aspects of the present disclosure are described in circuit diagram 6250. In an implementation, a power source at a handle 6252 of an endocutter may provide power to a frequency generator 6254. The frequency generator 6254 may generate one or more RF signals. The one or more RF signals may be multiplexed or overlaid at a multiplexer 6256, which may be in a shaft 6258 of the endocutter. In this way, two or more RF signals may be overlaid (or, e.g., nested or modulated together) and transmitted to the end-effector. The one or more RF signals may energize one or more RF electrodes 6260 at an end-effector 6262 (e.g., positioned in a staple cartridge) of the endocutter. A tissue (not shown) may be compressed and/or communicatively coupled between the one or more of RF electrodes 6260 and one or more electrical contacts. For example, the tissue may be compressed and/or communicatively coupled between the one or more RF electrodes 6260 and the electrical contact 6264 positioned in a channel frame of the end-effector 6262 or the electrical contact 6266 positioned in an anvil of the end-effector 6262. A filter 6268 may be communicatively coupled to the electrical contact 6264 and a filter 6270 may be communicatively coupled to the electrical contact 6266.

A voltage V and a current I associated with the one or more RF signals may be used to calculate an impedance Z associated with a tissue that may be compressed between the staple cartridge (and communicatively coupled to one or more RF electrodes 6260) and the channel frame or anvil (and communicatively coupled to one or more of electrical contacts 6264 or 6266).

In one aspect, various components of the tissue compression sensor system described herein may be located in a shaft 6258 of the endocutter. For example, as shown in circuit diagram 6250 (and in addition to the frequency generator 6254), an impedance calculator 6272, a controller 6274, a non-volatile memory 6276, and a communication channel 6278 may be located in the shaft 6258. In one example, the frequency generator 6254, impedance calculator 6272, controller 6274, non-volatile memory 6276, and communication channel 6278 may be positioned on a circuit board in the shaft 6258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 6264 and 6266. Using a voltage V applied between the supply and return paths, impedances Z1 and Z2 may be calculated. Z1 may correspond to an impedance of a tissue compressed and/or communicatively coupled between one or more of RF electrodes 6260 and electrical contact 6264. Further, Z2 may correspond to an impedance of the tissue compressed and/or communicatively coupled between one or more of RF electrodes 6260 and electrical contact 6266. Applying the formulas Z1=V/I1 and Z2=V/I2, impedances Z1 and Z2 corresponding to different compressions of a tissue compressed by an end-effector 6262 may be calculated. In example, the impedances Z1 and Z2 may be calculated by the impedance calculator 6272. The impedances Z1 and Z2 may be used to calculate various compression levels of the tissue.

Figure 69:
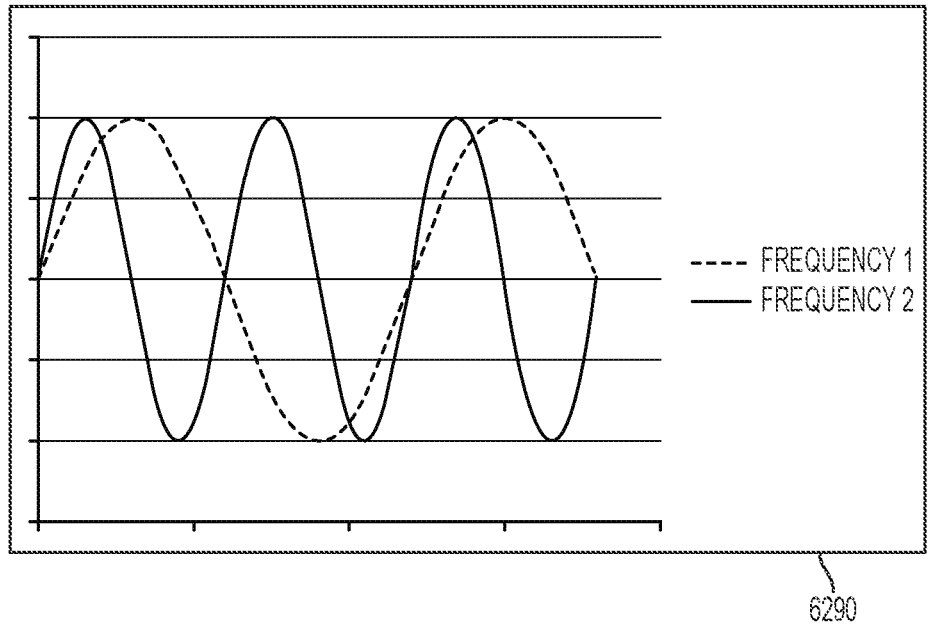
FIG. 69 is graph depicting an example frequency modulation in accordance with one or more aspects of the present disclosure.
Figure 70:
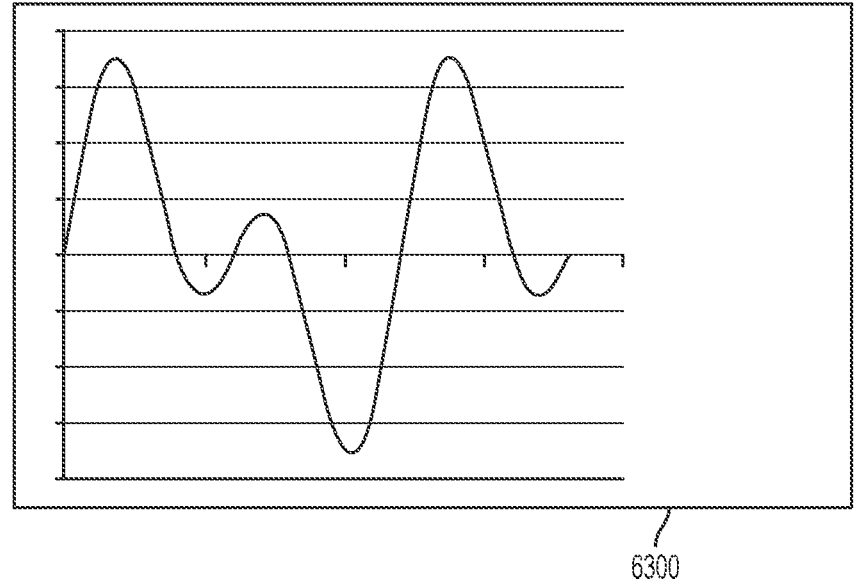
FIG. 70 is graph depicting a compound RF signal in accordance with one or more aspects of the present disclosure.
Figure 71:
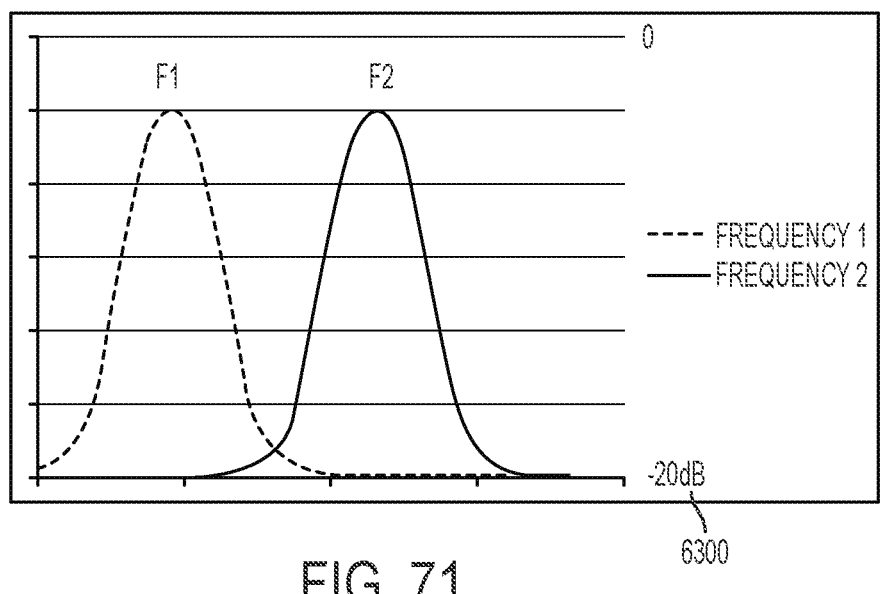
FIG. 71 is graph depicting filtered RF signals in accordance with one or more aspects of the present disclosure.

Referring now to FIG. 69, a frequency graph 6290 is shown. The frequency graph 6290 shows a frequency modulation to nest two RF signals. The two RF signals may be nested before reaching RF electrodes at an end-effector as described above. For example, an RF signal with Frequency 1 and an RF signal with Frequency 2 may be nested together. Referring now to FIG. 70, the resulting nested RF signal is shown in frequency graph 6300. The compound signal shown in frequency graph 6300 includes the two RF signals of frequency graph 6290 compounded. Referring now to FIG. 71, a frequency graph 6310 is shown. Frequency graph 6310 shows the RF signals with Frequencies 1 and 2 after being filtered (by, e.g., filters 6268 and 6270). The resulting RF signals can be used to make separate impedance calculations or measurements on a return path, as described above.

In one aspect, filters 6268 and 6270 may be High Q filters such that the filter range may be narrow (e.g., Q=10). Q may be defined by the Center frequency (Wo)/Bandwidth (BW) where Q=Wo/BW. In one example, Frequency 1 may be 150 kHz and Frequency 2 may be 300 kHz. A viable impedance measurement range may be 100 kHz-20 MHz. In various examples, other sophisticated techniques, such as correlation, quadrature detection, etc., may be used to separate the RF signals.

Using one or more of the techniques and features described herein, a single energized electrode on a staple cartridge or an isolated knife of an end-effector may be used to make multiple tissue compression measurements simultaneously. If two or more RF signals are overlaid or multiplexed (or nested or modulated), they may be transmitted down a single power side of the end-effector and may return on either the channel frame or the anvil of the end-effector. If a filter were built into the anvil and channel contacts before they join a common return path, the tissue impedance represented by both paths could be differentiated. This may provide a measure of vertical tissue vs lateral tissue compression. This approach also may provide proximal and distal tissue compression depending on placement of the filters and location of the metallic return paths. A frequency generator and signal processor may be located on one or more chips on a circuit board or a sub board (which may already exist in an endocutter).

In various aspects, the present disclosure provides techniques for monitoring the speed and precision incrementing of the drive motor in the instrument 10 (described in connection with FIGS. 1-29). In one example, a magnet can be placed on a planet frame of one of the stages of gear reduction with an inductance sensor on the gear housing. In another example, placing the magnet and magnetic field sensor on the last stage would provide the most precise incremental movement monitoring.

Conventional motor control systems employ encoders to detect the location and speed of the motor in hand held battery powered endosurgical instruments such as powered endocutter/stapler devices. Precision operation of endocutter/stapler devices relies in part on the ability to verify the motor operation under load. Simple sensor implementations may be employed to achieve verify the motor operation under load.

Accordingly, the present disclosure includes a magnetic body on one of the planetary carriers of a gear reduction system or employ brushless motor technology. Both approaches involve the placement of an inductance sensor on the outside housing of the motor or planetary gear system. In the case of a brushless motor there are electromagnetic field coils (windings, inductors, etc.) arrayed radially around the center magnetic shaft of the motor. The coils are sequentially activated and deactivated to drive the central motor shaft. One or more inductance sensors can be placed outside of the motor and adjacent to at least some of the coils to sense the activation/deactivation cycles of the motor windings to determine the number times the shaft has been rotated. Alternatively, a permanent magnet can be placed on one of the planetary carriers and the inductance sensor can be placed adjacent to the radial path of the planetary carrier to measure the number of times that stage of the gear train is rotated. This implementation can be applied to any rotational components in the system with increasingly more resolution possible in regions with a relatively large number of rotations during function, or as the rotational components become closer (in terms of number of connections) to the end effector depending on the design. The gear train sensing method may be preferred since it actually measures rotation of one of the stages whereas the motor sensing method senses the number of times the motor has been commanded to energize, rather than the actual shaft rotation. For example, if the motor is stalled under high load, the motor sensing method would not be able to detect the lack of rotation because it senses only the energizing cycles not shaft rotation. Nevertheless, both techniques can be employed in a cost effective manner to sense motor rotation.

During stapling, for example, tissue is firmly clamped between opposing jaws before a staple is driven into the clamped tissue. Tissue compression during clamping can cause fluid to be displaced from the compressed tissue, and the rate or amount of displacement varies depending on tissue type, tissue thickness, the surgical operation (e.g., clamping pressure and clamping time). In various instances, fluid displacement between the opposing jaws of an end effector may contribute to malformation (e.g., bending) of staples between the opposing jaws. Accordingly, in various instances, it may be desirable to control the firing stroke, e.g., to control the firing speed, in relationship to the detected fluid flow, or lack thereof, intermediate opposing jaws of a surgical end effector.

Accordingly, also provided herein are methods, devices, and systems for monitoring speed and incremental movement of a surgical instrument drive train, which in turn provides information about the operational velocity of the device (e.g., jaw closure, stapling). In accordance with the present examples, the instrument 10 (FIGS. 1-4) does not include a motor encoder. Rather, the instrument 10 is equipped with a motor 7012 shown in FIG. 72, which illustrates a speed sensor assembly for a power train 7010 of the motor 7012, in accordance with an illustrative example. The speed sensor assembly can include a motor 7012 having an output shaft 7014 that is coupled directly or indirectly to a drive shaft. In some examples, the output shaft is connected to a gear reduction assembly, such as the planetary gear train 7020 shown in FIG. 72.

Figure 72:
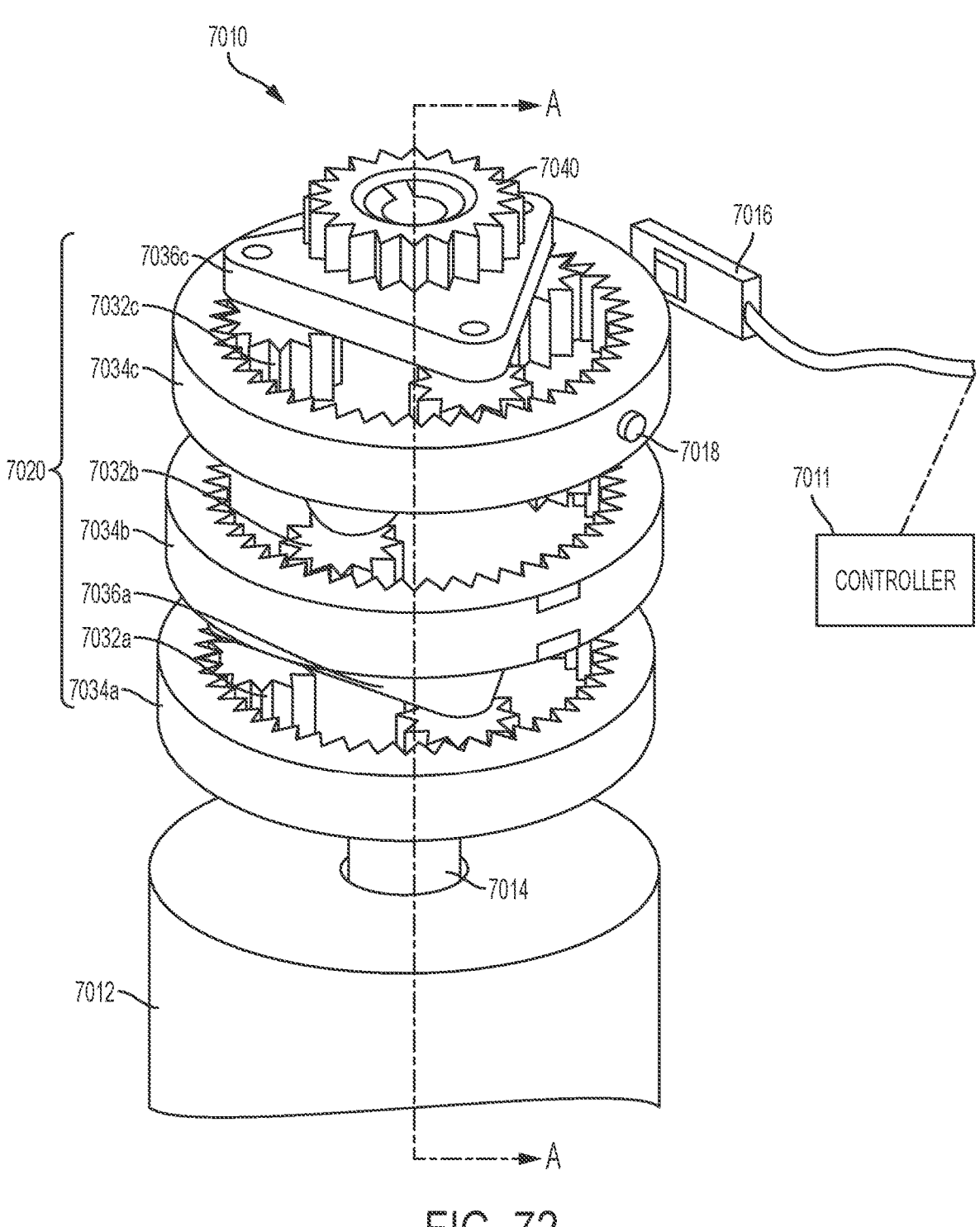
FIG. 72 is a plan view of a speed sensor assembly for a surgical instrument power train.

With continued reference to FIG. 72, the speed sensor assembly further includes at least one sensor 7016 that detects the rotational speed of any suitable component of the system. For example, the sensor may be a proximity sensor, such as an induction sensor, which detects movement of one or more detectable elements 7018 affixed to any rotating part of the gear reduction assembly. In FIG. 72, which is exemplary, the detectable element is affixed to the last stage annular gear 7034c and the sensor is positioned adjacent the radial path of the detectable element so as to detect movement of the detectable element. FIG. 72 is exemplary only—rotating components vary depending on design—and the sensor(s) can be affixed to any rotating component of the gear reduction assembly. For example, in another example, a detectable element is associated with the carrier gear of the final stage or even the drive gear. In some examples, a detectable element is located outside of the gear reduction assembly, such as on the driveshaft between gear reduction assembly and the end effector. In some example, a detectable element is located on a rotating component in the final gear reduction at the end effector.

With continued reference to FIG. 72, in one aspect motor 7012 is rotationally coupled to a gear reduction assembly, such as a planetary gear train 7020. However, any suitable gear reduction or transmission can be used and/or the motor can be coupled directly to a drive shaft (e.g., direct drive). The planetary gear train can include 1, 2, 3, 4, 5, or more stages. The planetary gear train illustrated in FIG. 72 has three stages. The planetary gear train is driven by a sun gear (7042 in FIG. 73) attached directly or indirectly to the motor output shaft 7014. The sun gear drives one or more first stage planet gears 7032a, which in turn engage a first stage annular gear 7034a. Any number of planet gears can be used such as, for example, 1, 2, 3, 4, 5 or more planet gears. First stage planet gears 7032a communicate with a first stage carrier 7036a, which includes or connects to a second stage sun gear (7038a in FIG. 73) that drives the second stage.

Similar to the first stage, the second stage includes one or more planet gears 7032b, an annular gear 7034b, and a carrier 7036b that includes or connects to a third stage sun gear (7038b in FIG. 73) that drives the third stage. Likewise, the third stage includes one or more planet gears 7032c, an annular gear 7034c, and a carrier 7036c. The final stage in the planetary gear train assembly is connected to a drive gear 7040, which can be the final effector in the gear reduction assembly, depending on design. The use of three planetary gear stages is exemplary only. Any suitable type of gear reduction assembly can be used in accordance with the present disclosure.

The sensor 7016 can be mounted in or near the gear reduction assembly in, near, or adjacent the radial path of detectable element 7018. The sensor can be any suitable sensor type capable of detecting rotational speed without an encoder. The sensor is used in conjunction with a detectable element capable of being detected by the sensor. For example, in some examples, the sensor is an inductance sensor and the detectable element is a metallic element. The inductance sensor can be configured to detect a change in inductance caused by a metallic object or magnet passing adjacent the inductive sensor. In some examples, the sensor is a magnetic field sensor, and the detectable element is a magnetic element. A magnetic field sensor can be configured to detect changes in a magnetic field surrounding the magnetic field sensor caused by the movement of the magnetic element.

Detectable elements can be affixed or integral with any rotating part or particular stage of the gear reduction assembly to measure the number of times that the part or stage rotates. For example, a single detectable element could be placed on drive gear 7040. Each complete rotation of the drive gear would cause the detectable element to pass the sensor one time, resulting in one detected rotation. In some examples, multiple detectable elements 7018 can be used within the same gear reduction assembly, by placing a plurality of detectable elements (e.g., 2, 3, 4, 5 or more) on the same component (e.g., a gear) and/or by placing one or more detectable elements on a plurality of different components (e.g., on two different gears). Placing multiple sensors equally spaced on a single component can provide refined information about incremental rotations. Similarly, resolution of speed monitoring can be increased by placing a detectable element(s) on a component that rotates more quickly relative to other components and/or by placing the detectable element closer (in terms of number of connections) to the end effector depending on the design. Using multiple detectable elements on different components provides a redundant, fail-safe system should one sensor or detectable element fail.

Sensors should be located close enough to detectable elements to ensure that each revolution of a detectable element is captured by its associated sensor. Multiple sensors can be placed in the same radial path of a detectable element. In addition, if detectable elements are placed on a plurality of different components (e.g., two different gears), a sensor can be placed adjacent the radial path of each detectable element. The sensor 7016 is in data communication with a controller 7011 such as the microcontroller 1500 (FIG. 19) or microcontroller 2006 (FIGS. 21A, 21B), processor 2104 (FIG. 22), or controller 2606 and 3017 shown in FIGS. 27-29, which is programmed to translate the number and/or rate of detection events into a speed reading useful to the user, such as using the speed indicator display shown in FIGS. 88-90.

Figure 73:
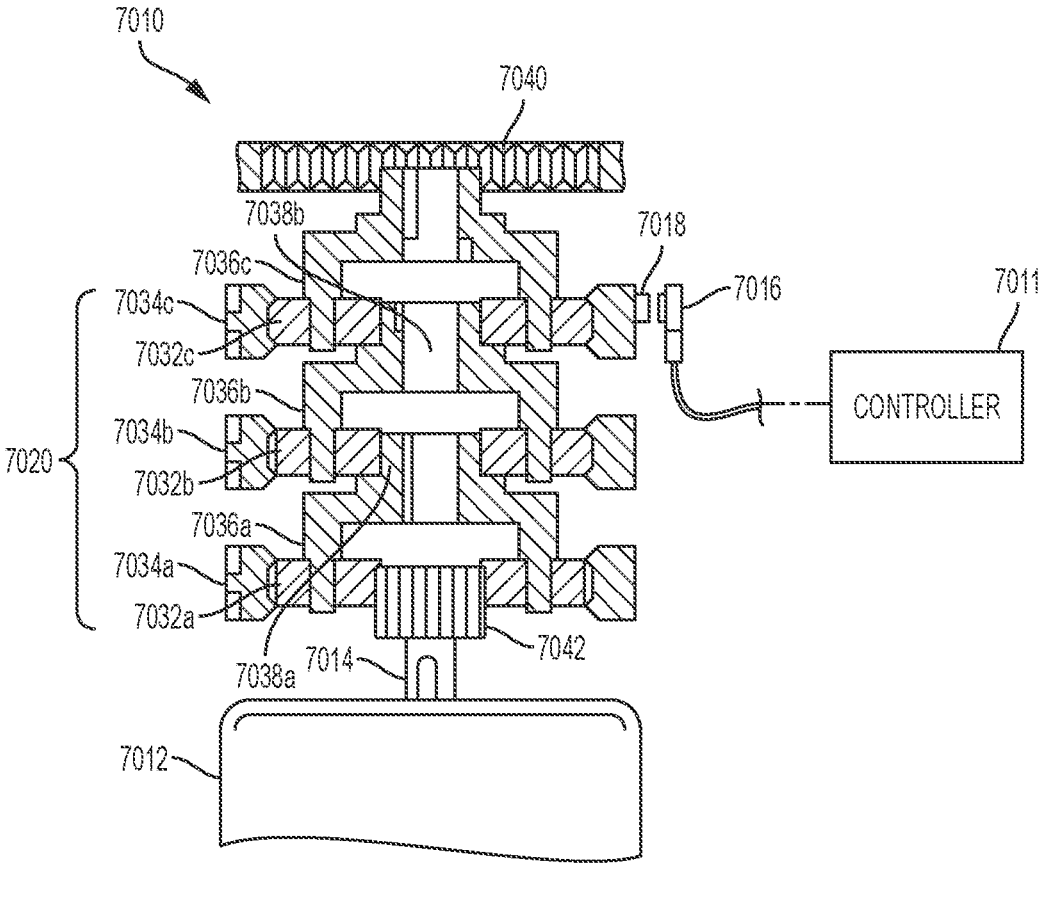
FIG. 73 is a longitudinal cross section through plane A of FIG. 71.

FIG. 73 shows a longitudinal cross section through plane A of FIG. 72. Clearly visible in FIG. 73 is sun gear 7042 coupled to output shaft 7014.

Figure 74:
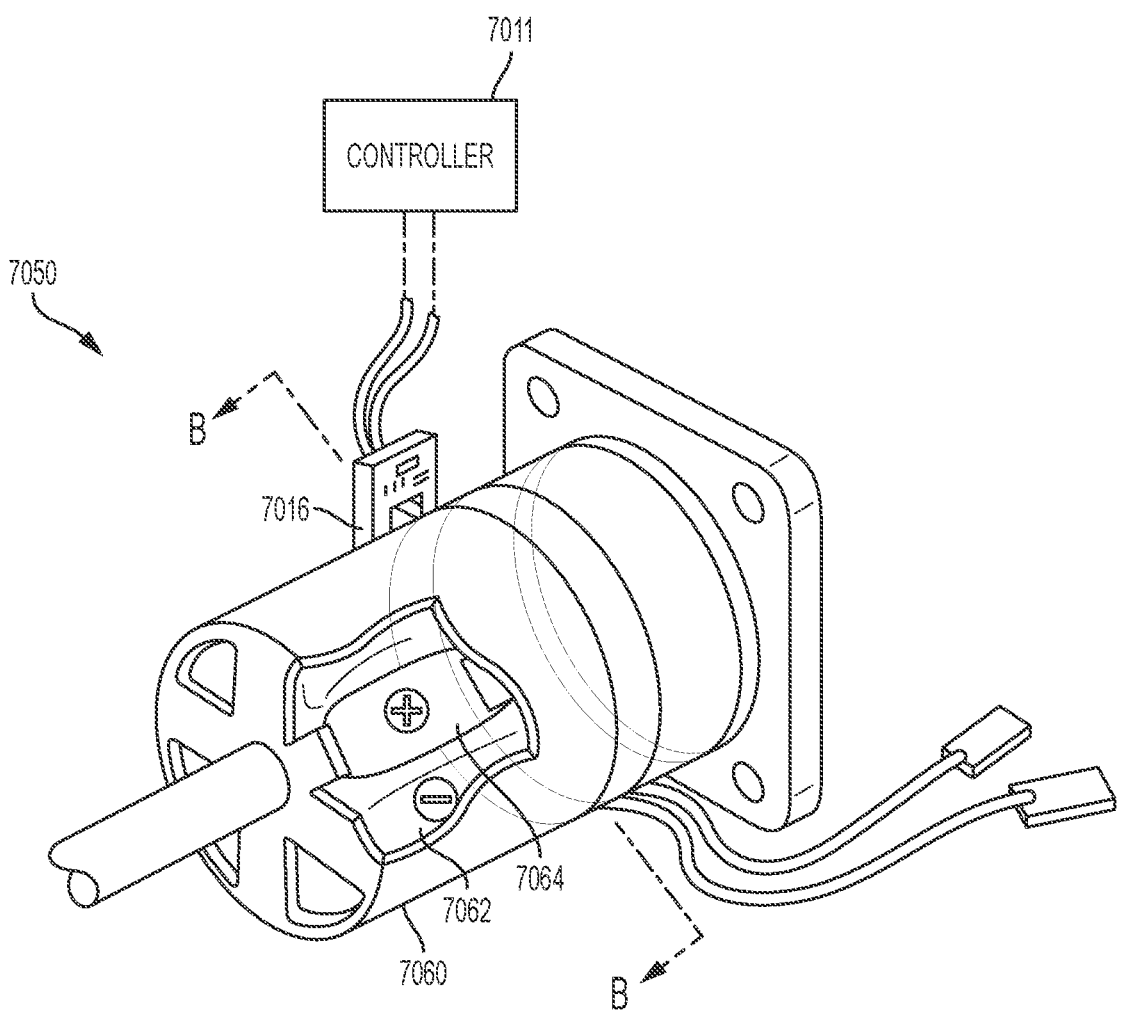
FIG. 74 is a perspective view of a speed sensor assembly for a brushless motor.

FIG. 74 illustrates a speed sensor assembly for 7050 for directly sensing the rotational speed of a brushless motor 7060, in accordance with an illustrative aspect. A brushless motor typically comprises electromagnetic field coils 7062, 7064 arrayed radially around a central magnetic shaft (7066 in FIG. 75). Negative 7062 and positive 7064 coils are alternately arranged around the central magnetic shaft, and these coils are sequentially activated and deactivated to drive the central magnetic shaft. One or more sensors 7016 can be placed adjacent these coils on the outside of the motor to monitor motor speed. The sensor induction field 7068 is affected each time an electromagnetic field coil passes the sensor. The sensor is in data communication with a controller 7011, such as the microcontroller 1500 (FIG. 19) or microcontroller 2006 (FIGS. 21A, 21B), processor 2104 (FIG. 22), or controller 2606 and 3017 shown in FIGS. 27-29, for example, which is programmed to translate the number and/or rate of detection events into a speed reading useful to the user, such as using a speed indicator display shown in FIGS. 88-90.

If the motor stalls, for example under high load, the sensor 7016 may still detect activation of the coils, which the sensor 7016 would interpret as motor rotation even though the motor is stalled. As a result, under certain operational circumstances, motor speed could be an inaccurate readout for operational tool speed. In one example, speed is measured using one or more sensors 7016 on the gear reduction assembly because this measures the actual speed of the gear assembly, or a stage of the gear assembly, rather than the speed of the motor. In addition, the closer the detectable element(s) and associated sensor(s) are to the end effector, the more likely the sensed speed accurately reflects operational tool speed. The ability to verify motor operation under load is important for precision operation of surgical instruments, such as staplers.

Figure 75:
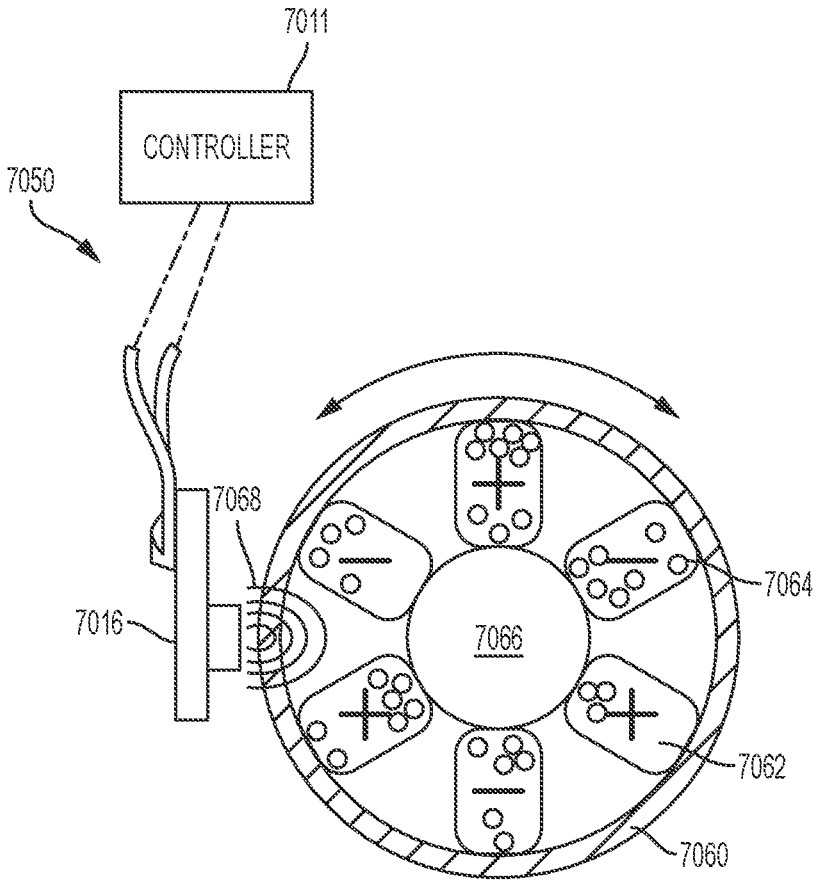
FIG. 75 is a transverse cross section through plane B of FIG. 73.

FIG. 75 illustrates a transverse cross section through plane B of the motor assembly shown in FIG. 74. The central magnetic shaft 7066 is visible in FIG. 75.

Sensor 7016 is in data communication with a controller 7011, such as the microcontroller 1500 (FIG. 19) or microcontroller 2006 (FIGS. 21A, 21B), processor 2104 (FIG. 22), or controller 2606 and 3017 shown in FIGS. 27-29, which is programmed to translate the number and/or rate of detection events into a speed reading useful to the user. The controller 7011 also can regulate motor speed to ensure safe operating parameters and/or to ensure that a constant speed and/or acceleration are maintained for particular surgical applications.

Various functions may be implemented utilizing the circuitry previously described, [For]] for example, the motor may be controlled with a motor controller 7011 similar those described in connection with FIGS. 21A, 21B, 24, 25, 28A, 28B, and 29, where the encoder is replaced with the monitoring speed control and precision incrementing of motor systems for powered surgical instruments described in connection with FIGS. 72-75. For example, the position encoder 2340 shown in FIG. 24 can be replaced with the sensor 7016 shown in FIGS. 72-75 coupled to the microcontroller 2306 in FIG. 24. Similarly, the position encoder 2440 shown in FIG. 25 can be replaced with the sensor 7016 shown in FIGS. 72-75 coupled to the microcontroller 2406 in FIG. 25.

In one aspect, the present disclosure provides an instrument 10 (described in connection with FIGS. 1-29) configured with various sensing systems. Accordingly, for conciseness and clarity the details of operation and construction will not be repeated here. In one aspect, the sensing system includes a viscoelasticity/rate of change sensing system to monitor knife acceleration, rate of change of impedance, and rate of change of tissue contact. In one example, the rate of change of knife acceleration can be used as a measure of for tissue type. In another example, the rate of change of impedance can be measures with a pulse sensor ad can be employed as a measure for compressibility. Finally, the rate of change of tissue contact can be measured with a sensor based on knife firing rate to measure tissue flow.

The rate of change of a sensed parameter or stated otherwise, how much time is necessary for a tissue parameter to reach an asymptotic steady state value, is a separate measurement in itself and may be more valuable than the sensed parameter it was derived from. To enhance measurement of tissue parameters such as waiting a predetermined amount of time before making a measurement, the present disclosure provides a novel technique for employing the derivate of the measure such as the rate of change of the tissue parameter.

The derivative technique or rate of change measure becomes most useful with the understanding that there is no single measurement that can be employed alone to dramatically improve staple formation. It is the combination of multiple measurements that make the measurements valid. In the case of tissue gap it is helpful to know how much of the jaw is covered with tissue to make the gap measure relevant. Rate of change measures of impedance may be combined with strain measurements in the anvil to relate force and compression applied to the tissue grasped between the jaw members of the end effector such as the anvil and the staple cartridge. The rate of change measure can be employed by the endosurgical device to determine the tissue type and not merely the tissue compression. Although stomach and lung tissue sometimes have similar thicknesses, and even similar compressive properties when the lung tissue is calcified, an instrument may be able to distinguish these tissue types by employing a combination of measurements such as gap, compression, force applied, tissue contact area, and rate of change of compression or rate of change of gap. If any of these measurements were used alone, the endo-surgical it may be difficult for the endosurgical device to distinguish one tissue type form another. Rate of change of compression also may be helpful to enable the device to determine if the tissue is "normal" or if some abnormality exists. Measuring not only how much time has passed but the variation of the sensor signals and determining the derivative of the signal would provide another measurement to enable the endosurgical device to measure the signal. Rate of change information also may be employed in determining when a steady state has been achieved to signal the next step in a process. For example, after clamping the tissue between the jaw members of the end effector such as the anvil and the staple cartridge, when tissue compression reaches a steady state (e.g., about 15 seconds), an indicator or trigger to start firing the device can be enabled.

Also provided herein are methods, devices, and systems for time dependent evaluation of sensor data to determine stability, creep, and viscoelastic characteristics of tissue during surgical instrument operation. A surgical instrument 10, such as the stapler illustrated in FIG. 1, can include a variety of sensors for measuring operational parameters, such as jaw gap size or distance, firing current, tissue compression, the amount of the jaw that is covered by tissue, anvil strain, and trigger force, to name a few. These sensed measurements are important for automatic control of the surgical instrument and for providing feedback to the clinician.

The examples shown in connection with FIGS. 52-71 may be employed to measure the various derived parameters such as gap distance versus time, tissue compression versus time, and anvil strain versus time. Motor current may be monitored employing the current sensor 2312 in series with the battery 2308 as described in connection with FIG. 24, the current sensor 2412 in series with the battery 2408 shown in FIG. 25, or the current sensor 3026 in FIG. 29.

Figures 76, 77:
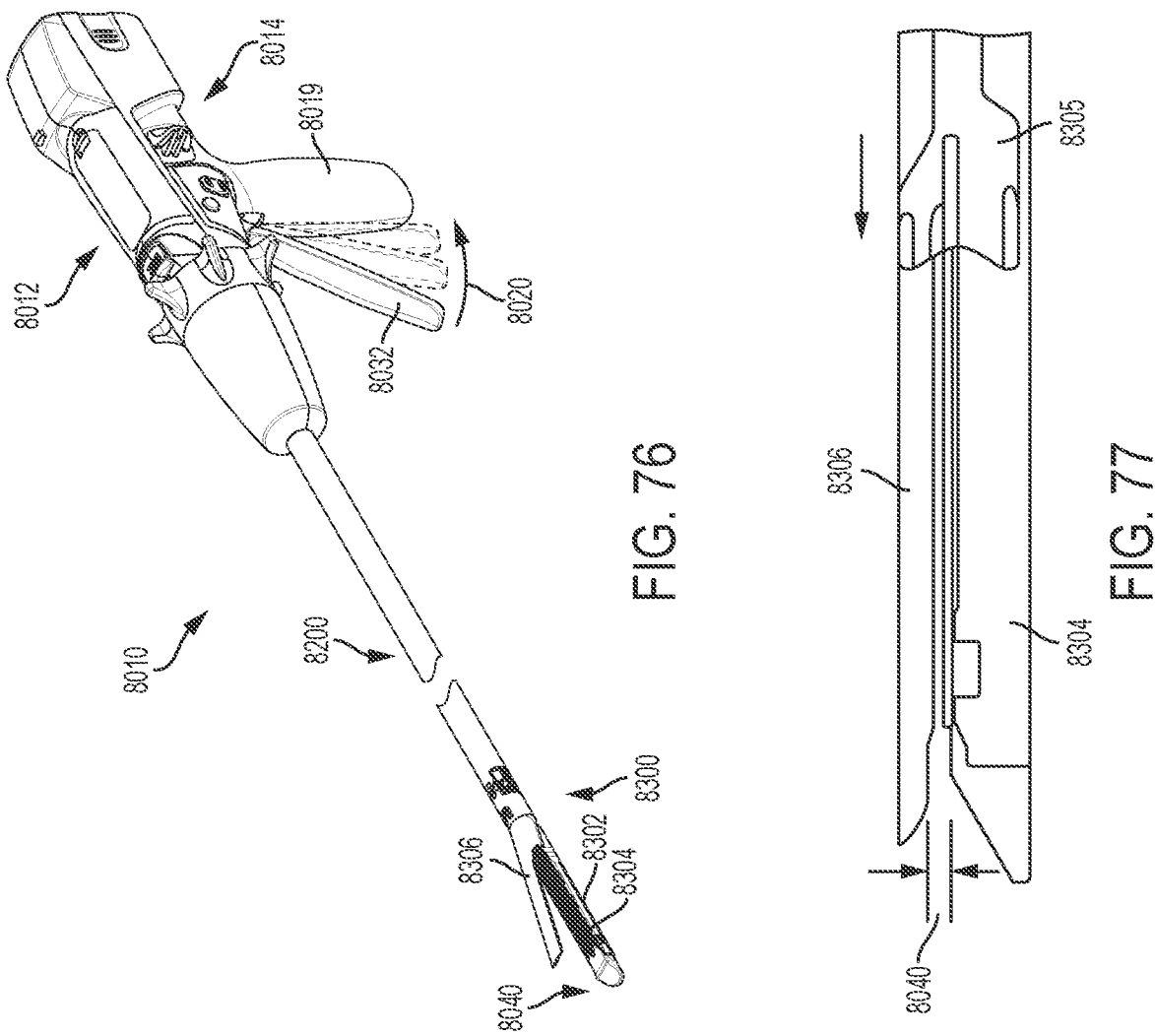
FIG. 76 is a perspective view of a surgical instrument with an articulable, interchangeable shaft.
FIG. 77 is a side view of the tip of the surgical instrument shown in FIG. 76.

Turning now to FIG. 76, a motor-driven surgical cutting and fastening instrument 8010 is depicted that may or may not be reused. The motor-driven surgical cutting and fastening instrument 8010 is similarly constructed and equipped as the motor-driven surgical cutting and fastening instrument 10 described in connection with FIGS. 1-29. In the example illustrated in FIG. 76, the instrument 8010 includes a housing 8012 that comprises a handle assembly 8014 that is configured to be grasped, manipulated and actuated by the clinician. The housing 8012 is configured for operable attachment to an interchangeable shaft assembly 8200 that has a surgical end effector 8300 operably coupled thereto that is configured to perform one or more surgical tasks or procedures. Since the motor-driven surgical cutting and fastening instrument 8010 is similarly constructed and equipped as the motor-driven surgical cutting and fastening instrument 10 described in connection with FIGS. 1-29, for conciseness and clarity the details of operation and construction will not be repeated here.

The housing 8012 depicted in FIG. 76 is shown in connection with an interchangeable shaft assembly 8200 that includes an end effector 8300 that comprises a surgical cutting and fastening device that is configured to operably support a surgical staple cartridge 8304 therein. The housing 8012 may be configured for use in connection with interchangeable shaft assemblies that include end effectors that are adapted to support different sizes and types of staple cartridges, have different shaft lengths, sizes, and types, etc.

In addition, the housing 8012 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 76 illustrates the surgical instrument 8010 with an interchangeable shaft assembly 8200 operably coupled thereto. In the illustrated arrangement, the handle housing forms a pistol grip portion 8019 that can be gripped and manipulated by the clinician. The handle assembly 8014 operably supports a plurality of drive systems therein that are configured to generate and apply various control motions to corresponding portions of the interchangeable shaft assembly that is operably attached thereto. Trigger 8032 is operably associated with the pistol grip for controlling various of these control motions.

With continued reference to FIG. 76, the interchangeable shaft assembly 8200 includes a surgical end effector 8300 that comprises an elongated channel 8302 that is configured to operably support a staple cartridge 8304 therein. The end effector 8300 may further include an anvil 8306 that is pivotally supported relative to the elongated channel 8302.

The inventors have discovered that derived parameters can be even more useful for controlling a surgical instrument, such as the instrument illustrated in FIG. 76, than the sensed parameter(s) upon which the derived parameter is based. Non-limiting examples of derived parameters include the rate of change of a sensed parameter (e.g., jaw gap distance) and how much time elapses before a tissue parameter reaches an asymptotic steady state value (e.g., 15 seconds). Derived parameters, such as rate of change, are particularly useful because they dramatically improve measurement accuracy and also provide information not otherwise evident directly from sensed parameters. For example, impedance (i.e., tissue compression) rate of change can be combined with strain in the anvil to relate compression and force, which enables the microcontroller to determine the tissue type and not merely the amount of tissue compression. This example is illustrative only, and any derived parameters can be combined with one or more sensed parameters to provide more accurate information about tissue types (e.g., stomach vs. lung), tissue health (calcified vs. normal), and operational status of the surgical device (e.g., clamping complete). Different tissues have unique viscoelastic properties and unique rates of change, making these and other parameters discussed herein useful indicia for monitoring and automatically adjusting a surgical procedure.

Figure 78A:
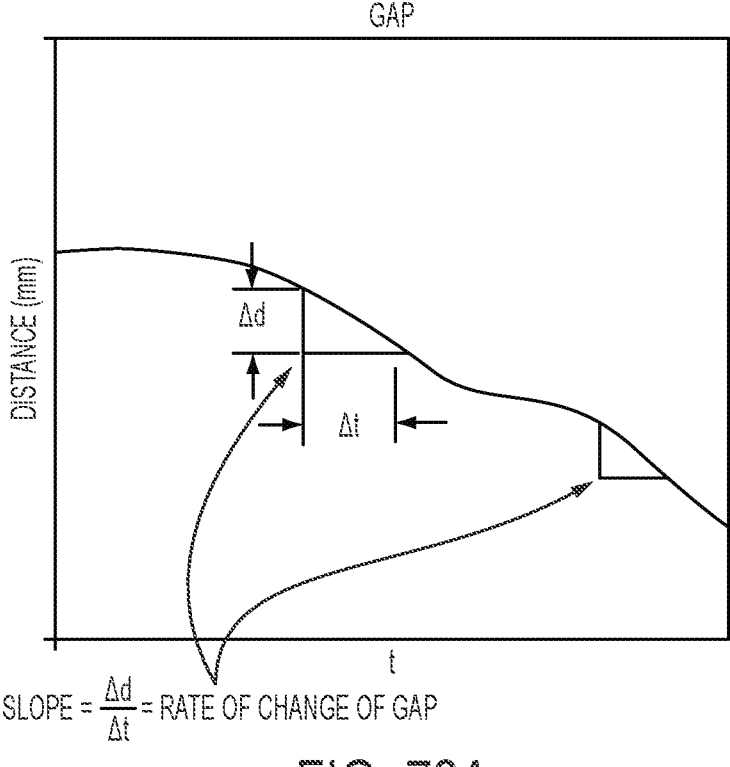
FIGS. 78A-78E are graphs plotting gap size over time (FIG. 78A), firing current over time (FIG. 78B), tissue compression over time (FIG. 78C), anvil strain over time (FIG. 78D), and trigger force over time (FIG. 78E)

FIGS. 78A-78E show exemplary sensed parameters as well as parameters derived therefrom. FIG. 78A is an illustrative graph showing gap distance over time, where the gap is the space between the jaws being occupied by clamped tissue. The vertical (y) axis is distance and the horizontal (x) axis is time. Specifically, referring to FIGS. 76 and 77, the gap distance 8040 is the distance between the anvil 8306 and the elongate channel 8302 of the end effector. In the open jaw position, at time zero, the gap 8040 between the anvil 8306 and the elongate member is at its maximum distance. The width of the gap 8040 decreases as the anvil

8306 closes, such as during tissue clamping. The gap distance rate of change can vary because tissue has non-uniform resiliency. For example, certain tissue types may initially show rapid compression, resulting in a faster rate of change. However, as tissue is continually compressed, the viscoelastic properties of the tissue can cause the rate of change to decrease until the tissue cannot be compressed further, at which point the gap distance will remain substantially constant. The gap decreases over time as the tissue is squeezed between the anvil 8306 and the staple cartridge 8304 of the end effector 8040. The one or more sensors described in connection with FIGS. 50-68 and FIG. 84 may be adapted and configured to measure the gap distance "d" between the anvil 8306 and the staple cartridge 8304 over time "t" as represented graphically in FIG. 78A. The rate of change of the gap distance "d" over time "t" is the Slope of the curve shown in FIG. 78A, where Slope=Δd/Δt.

Figure 78B:
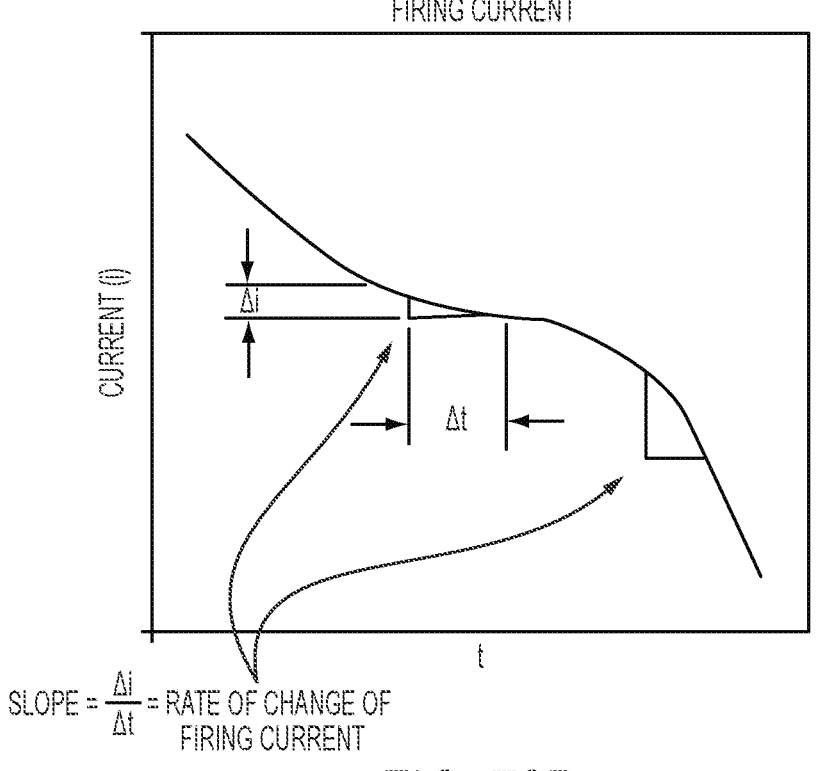

FIG. 78B is an illustrative graph showing firing current of the end effector jaws. The vertical (y) axis is current and the horizontal (x) axis is time. As discussed herein, the surgical instrument and/or the microcontroller, as shown in FIGS. 21-29, thereof can include a current sensor that detects the current utilized during various operations, such as clamping, cutting, and/or stapling tissue. For example, when tissue resistance increases, the instrument's electric motor can require more current to clamp, cut, and/or staple the tissue. Similarly, if resistance is lower, the electric motor can require less current to clamp, cut, and/or staple the tissue. As a result, firing current can be used as an approximation of tissue resistance. The sensed current can be used alone or more preferably in conjunction with other measurements to provide feedback about the target tissue. Referring still to FIG. 78B, during some operations, such as stapling, firing current initially is high at time zero but decreases over time. During other device operations, current may increase over time if the motor draws more current to overcome increasing mechanical load. In addition, the rate of change of firing current is can be used as an indicator that the tissue is transitioning from one state to another state. Accordingly, firing current and, in particular, the rate of change of firing current can be used to monitor device operation. The firing current decreases over time as the knife cuts through the tissue. The rate of change of firing current can vary if the tissue being cut provides more or less resistance due to tissue properties or sharpness of the knife 8305 (FIG. 77). As the cutting conditions vary, the work being done by the motor varies and hence will vary the firing current over time. A current sensor may be may be employed to measure the firing current over time while the knife 8305 is firing as represented graphically in FIG. 78B. For example, the motor current may be monitored employing the current sensor 2312 in series with the battery 2308 as described in connection with FIG. 24, the current sensor 2412 in series with the battery 2408 shown in FIG. 25, or the current sensor 3026 shown in FIG. 29. The current sensors 2312, 2314, 3026 may be adapted and configured to measure the motor firing current "i" over time "t" as represented graphically in FIG. 78B. The rate of change of the firing current "i" over time "t" is the Slope of the curve shown in FIG. 78B, where Slope=Δi/Δt.

Figure 78C:
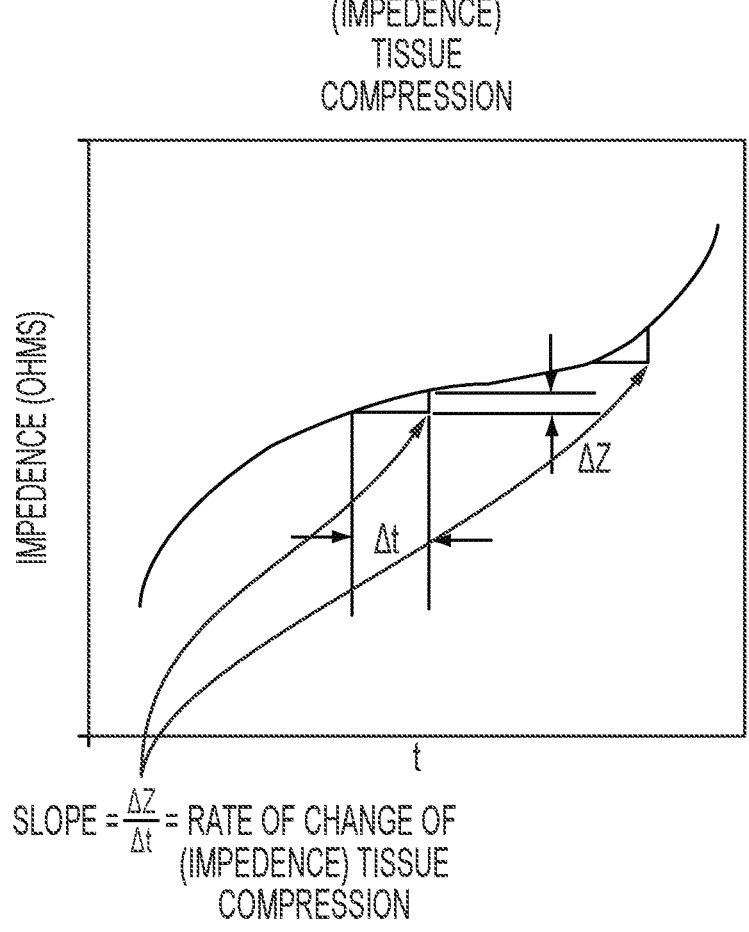

FIG. 78C is an illustrative graph of impedance over time. The vertical (y) axis is impedance and the horizontal (x) axis is time. At time zero, impedance is low but increases over time as tissue pressure increases under manipulation (e.g., clamping and stapling). The rate of change varies over time as because as the tissue between the anvil 8306 and the staple cartridge 8304 of the end effector 8040 is severed by the knife or is sealed using RF energy between electrodes located between the anvil 8306 and the staple cartridge 8304 of the end effector 8040. For example, as the tissue is cut the electrical impedance increases and reaches infinity when the tissue is completely severed by the knife. Also, if the end effector 8040 includes electrodes coupled to an RF energy source, the electrical impedance of the tissue increases as energy is delivered through the tissue between the anvil 8306 and the staple cartridge 8304 of the end effector 8040. The electrical impedance increase as the energy through the tissue dries out the tissue by vaporizing moistures in the tissue. Eventually, when a suitable amount of energy is delivered to the tissue, the impedance increases to a very high value or infinity when the tissue is severed. In addition, as illustrated in FIG. 78C, different tissues can have unique compression properties, such as rate of compression, that distinguish tissues. The tissue impedance can be measured by driving a sub-therapeutic RF current through the tissue grasped between the first and second jaw members 9014, 9016. One or more electrodes can be positioned on either or both the anvil 8306 and the staple cartridge 8304. The tissue compression/impedance of the tissue between the anvil 8306 and the staple cartridge 8304 can be measured over time as represented graphically in FIG. 78C. The sensors described in connection with FIGS. 50-68 and 84 may be adapted and configured to measure tissue compression/impedance. The sensors may be adapted and configured to measure tissue impedance "Z" over time "t" as represented graphically in FIG. 78C. The rate of change of the tissue impedance "Z" over time "t" is the Slope of the curve shown in FIG. 78C, where Slope=ΔZ/Δt.

Figure 78D:
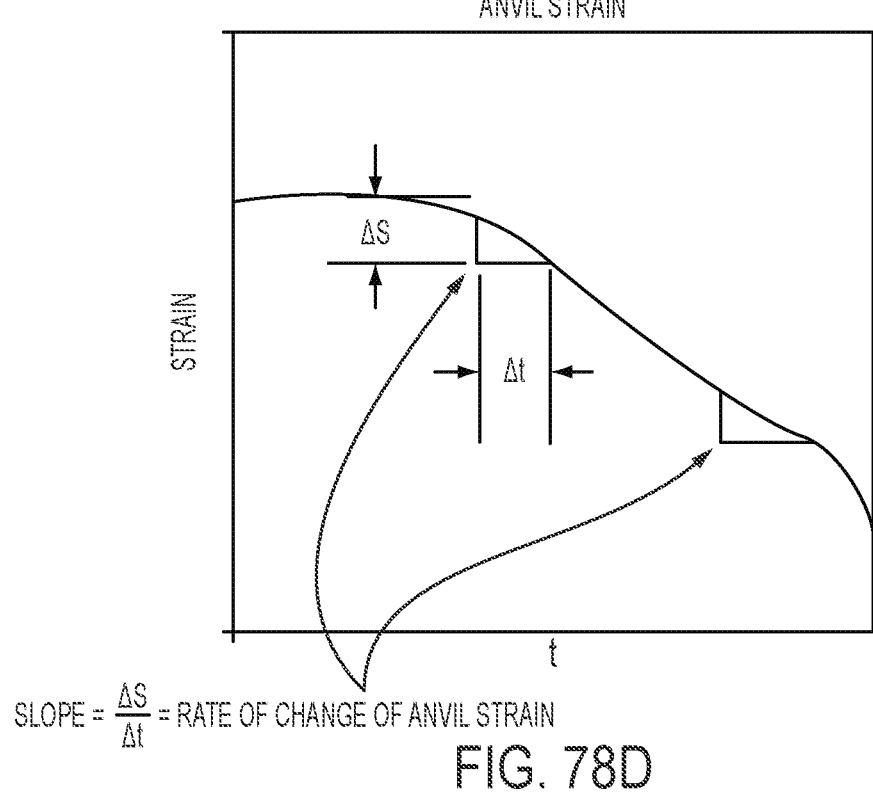

FIG. 78D is an illustrative graph of anvil 8306 (FIGS. 76, 77) strain over time. The vertical (y) axis is strain and the horizontal (x) axis is time. During stapling, for example, anvil 8306 strain initially is high but decreases as the tissue reaches a steady state and exerts less pressure on the anvil 8306. The rate of change of anvil 8306 strain can be measured by a pressure sensor or strain gauge positioned on either or both the anvil 8306 and the staple cartridge 8304 (FIGS. 76, 77) to measure the pressure or strain applied to the tissue grasped between the anvil 8306 and the staple cartridge 8304. The anvil 8306 strain can be measured over time as represented graphically in FIG. 78D. The rate of change of strain "S" over time "t" is the Slope of the curve shown in FIG. 78D, where Slope=ΔS/Δt.

Figure 78E:
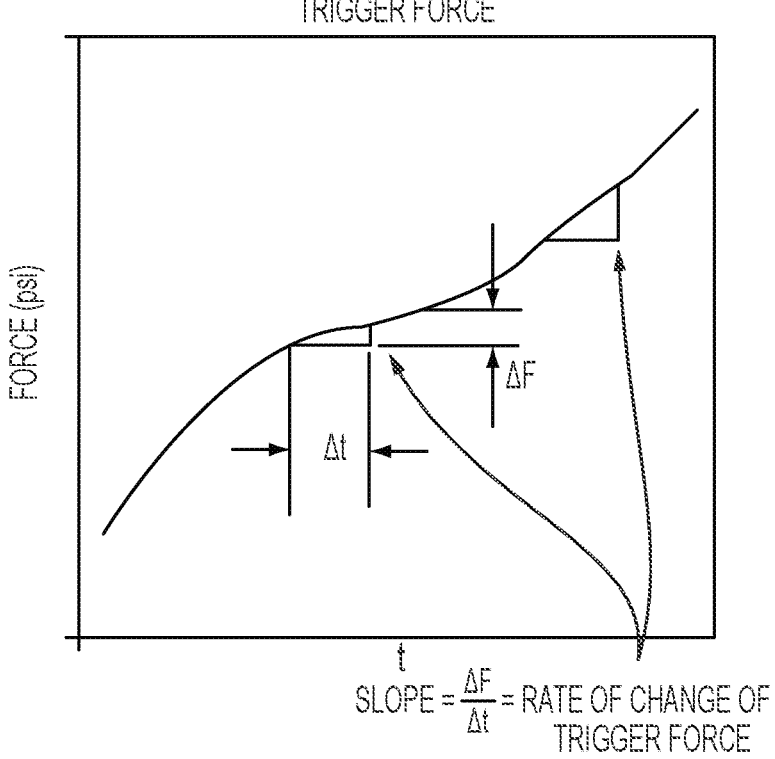

FIG. 78E is an illustrative graph of trigger force over time. The vertical (y) axis is trigger force and the horizontal (x) axis is time. In certain examples, trigger force is progressive, to provide the clinician tactile feedback. Thus, at time zero, trigger 8020 (FIG. 76) pressure may be at its lowest and trigger pressure may increase until completion of an operation (e.g., clamping, cutting, or stapling). The rate of change trigger force can be measured by a pressure sensor or strain gauge positioned on the trigger 8302 of the handle 8019 of the instrument 8010 (FIG. 76) to measure the force required to drive the knife 8305 (FIG. 77) through the tissue grasped between the anvil 8306 and the staple cartridge 8304. The trigger 8032 force can be measured over time as represented graphically in FIG. 78E. The rate of change of strain trigger force "F" over time "t" is the Slope of the curve shown in FIG. 78E, where Slope=ΔF/Δt.

Figure 79:
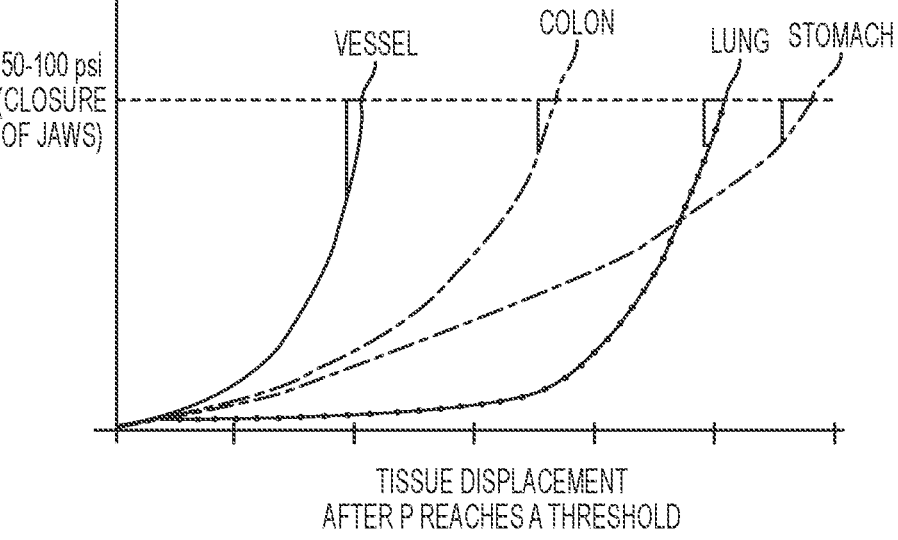
FIG. 79 is a graph plotting tissue displacement as a function of tissue compression for normal tissues.

For example, stomach and lung tissue can be differentiated even though these tissue can have similar thicknesses, and can have similar compressive properties if the lung tissue is calcified. Stomach and lung tissues can be distinguished by analyzing jaw gap distance, tissue compression, force applied, tissue contact area, compression rate of change, and jaw gap rate of change. For example, FIG. 79 shows a graph of tissue pressure "P" versus tissue displacement for various tissues. The vertical (y) axis is tissue pressure and the horizontal (x) axis is tissue displacement. When tissue pressure reaches a predetermined threshold, such as 50-100 pounds per square inch (psi), the amount of tissue displacement as well as the rate of tissue displacement before reaching the threshold can be used to differentiate tissues. For instance, blood vessel tissue reaches the predetermined pressure threshold with less tissue displacement and with a faster rate of change than colon, lung, or stomach tissue. In addition, the rate of change (tissue pressure over displacement) for blood vessel tissue is nearly asymptotic at a threshold of 50-100 psi, whereas the rate of change for colon, lung, and stomach is not asymptotic at a threshold of 50-100 psi. As will be appreciated, any pressure threshold can be used such as, for example, between 1 and 1000 psi, more preferably between 10 and 500 psi, and more preferably still between 50 and 100 psi. In addition, multiple thresholds or progressive thresholds can be used to provide further resolution of tissue types that have similar viscoelastic properties.

Figure 80:
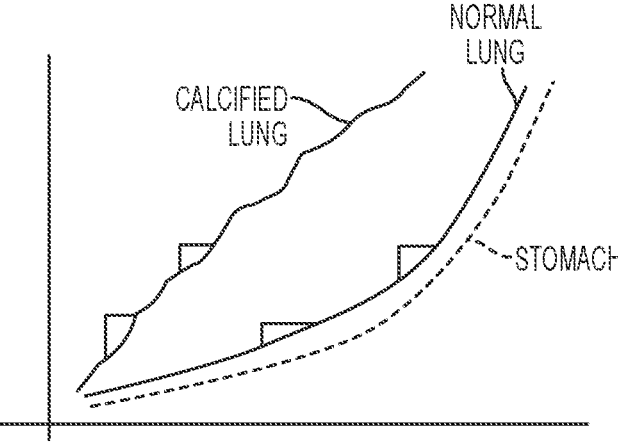
FIG. 80 is a graph plotting tissue displacement as a function of tissue compression to distinguish normal and diseased tissues.

Compression rate of change also can enable the microcontroller to determine if the tissue is "normal" or if some abnormality exists, such as calcification. For example, referring to FIG. 80, compression of calcified lung tissue follows a different curve than compression of normal lung tissue. Tissue displacement and rate of change of tissue displacement therefore can be used to diagnose and/or differentiate calcified lung tissue from normal lung tissue.

In addition, certain sensed measurements may benefit from additional sensory input. For example, in the case of jaw gap, knowing how much of the jaw is covered with tissue can make the gap measurement more useful and accurate. If a small portion of the jaw is covered in tissue, tissue compression may appear to be less than if the entire jaw is covered in tissue. Thus, the amount of jaw coverage can be taken into account by the microcontroller when analyzing tissue compression and other sensed parameters.

In certain circumstances, elapsed time also can be an important parameter. Measuring how much time has passed, together with sensed parameters, and derivative parameters (e.g., rate of change) provides further useful information. For example, if jaw gap rate of change remains constant after a set period of time (e.g., 5 seconds), then the parameter may have reached its asymptotic value.

Rate of change information also is useful in determining when a steady state has been achieved, thus signaling a next step in a process. For example, during clamping, when tissue compression reaches a steady state—e.g., no significant rate of change occurs after a set period of time—the microcontroller can send a signal to the display alerting the clinician to start the next step in the operation, such as staple firing. Alternatively, the microcontroller can be programmed to automatically start the next stage of operation (e.g., staple firing) once a steady state is reached.

Similarly, impedance rate of change can be combined with strain in the anvil to relate force and compression. The rate of change would allow the device to determine the tissue type rather than merely measure the compression value. For example, stomach and lung sometimes have similar thicknesses, and even similar compressive properties if the lung is calcified.

The combination of one or more sensed parameters with derived parameters provides more reliable and accurate assessment of tissue types and tissue health, and allows for better device monitoring, control, and clinician feedback.

Figure 84:
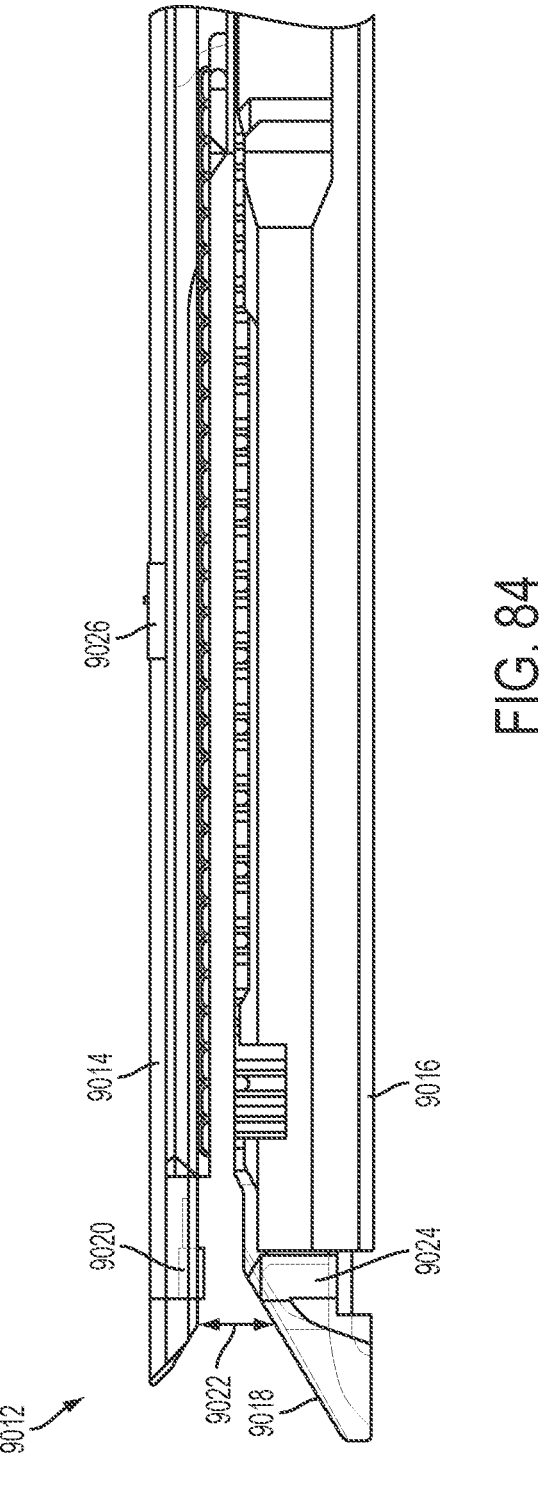
FIG. 84 illustrates a cross-sectional view of an end effector of the surgical instrument of FIG. 81 in accordance with one aspect.

Turning briefly to FIG. 84, the end effector 9012 is one aspect of the end effector 8300 (FIG. 76) that may be adapted to operate with surgical instrument 8010 (FIG. 76) to measure the various derived parameters such as gap distance versus time, tissue compression versus time, and anvil strain versus time. Accordingly, the end effector 9012 shown in FIG. 84 may include one or more sensors configured to measure one or more parameters or characteristics associated with the end effector 9012 and/or a tissue section captured by the end effector 9012. In the example illustrated in FIG. 84, the end effector 9012 comprises a first sensor 9020 and a second sensor 9026. In various examples, the first sensor 9020 and/or the second sensor 9026 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 9012.

In certain instances, the first sensor 9020 and/or the second sensor 9026 may comprise, for example, a magnetic field sensor embedded in the first jaw member 9014 and configured to detect a magnetic field generated by a magnet 9024 embedded in the second jaw member 9016 and/or the staple cartridge 9018. The strength of the detected magnetic field may correspond to, for example, the thickness and/or fullness of a bite of tissue located between the jaw members 9014, 9016. In certain instances, the first sensor 9020 and/or the second sensor 9026 may comprise a strain gauge, such as, for example, a micro-strain gauge, configured to measure the magnitude of the strain in the anvil 9014 during a clamped condition. The strain gauge provides an electrical signal whose amplitude varies with the magnitude of the strain.

In some aspects, one or more sensors of the end effector 9012 such as, for example, the first sensor 9020 and/or the second sensor 9026 may comprise a pressure sensor configured to detect a pressure generated by the presence of compressed tissue between the jaw members 9014, 9016. In some examples, one or more sensors of the end effector 9012 such as, for example, the first sensor 9020 and/or the second sensor 9026 are configured to detect the impedance of a tissue section located between the jaw members 9014, 9016. The detected impedance may be indicative of the thickness and/or fullness of tissue located between the jaw members 9014, 9016.

In one aspect, one or more of the sensors of the end effector 9012 such as, for example, the first sensor 9012 is configured to measure the gap 9022 between the anvil 9014 and the second jaw member 9016. In certain instances, the gap 9022 can be representative of the thickness and/or compressibility of a tissue section clamped between the jaw members 9014, 9016. In at least one example, the gap 9022 can be equal, or substantially equal, to the thickness of the tissue section clamped between the jaw members 9014, 9016. In one example, one or more of the sensors of the end effector 9012 such as, for example, the first sensor 9020 is configured to measure one or more forces exerted on the anvil 9014 by the second jaw member 9016 and/or tissue clamped between the anvil 9014 and the second jaw member 9016. The forces exerted on the anvil 9014 can be representative of the tissue compression experienced by the tissue section captured between the jaw members 9014, 9016. In one embodiment, the gap 9022 between the anvil 9014 and the second jaw member 9016 can be measured by positioning a magnetic field sensor on the anvil 9014 and positioning a magnet on the second jaw member 9016 such that the gap

9022 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the second jaw member 9016 and the magnet is placed on the anvil 9014.

One or more of the sensors such as, for example, the first sensor 9020 and/or the second sensor 9026 may be measured in real-time during a clamping operation. Real-time measurement allows time based information to be analyzed, for example, by a processor, and used to select one or more algorithms and/or look-up tables for the purpose of assessing, in real-time, a manual input of an operator of the surgical instrument 9010. Furthermore, real-time feedback can be provided to the operator to assist the operator in calibrating the manual input to yield a desired output.

In various aspects, the present disclosure provides an instrument 10 (as described in connection with FIGS. 1-29) configured to provide rate and control feedback to the surgeon. In one example, the instrument 10 (FIGS. 1-4) comprises an energy device to provide rate/impedance feedback. In another example, the instrument 10 provides time dependency such as time between steps and/or rate of firing. In another example, the instrument 10 is configured with a display that the surgeon can monitor for error resolution. In one implementation, the display may be a flexible roll up display is contained within handle (no external display) in the event of failure user unrolls display to determine steps to release.

The present disclosure provides a novel feedback system for surgical instruments to enable the surgeon to balance the motor controlled speed of knife actuation with the thickness and stiffness of the tissue grasped between the jaw members of the end effector such as the anvil and the staple cartridge. The present technique for adjusting the knife actuation speed based on the thickness of the tissue and tissue flow can improve the consistency of staple formation to form a stapled seal.

Accordingly, the present disclosure provides the surgeon a feedback mechanism on the shaft or the handle of the endosurgical device. The feedback comprises a combination of the speed of the advancement of the knife, the tissue compression (impedance), the tissue gap (d), and force to advance (motor current draw). This combination can be displayed on an indicator comprising multiple zones, such as 5-9 zones, for example, with the mid zone indicating the most ideal speed for the force and tissue compression being handled. The more compression the slower the speed to keep the indicator balanced in the center. This would provide a surgeon a repeatable relative measure to judge thickness and tissue flow and the surgeon could then decide how far out of balance the endosurgical device can be operated within certain conditions in order to achieve overall good results. The present feedback mechanism also would provide the surgeon a good evaluation when the tissue and/or firing conditions are out of the ordinary to enable the surgeon to proceed cautiously with the operation during that particular firing. The feedback mechanism also can enable the surgeon to learn the best technique for firing the endosurgical device with limited to no in servicing.

Figure 81:
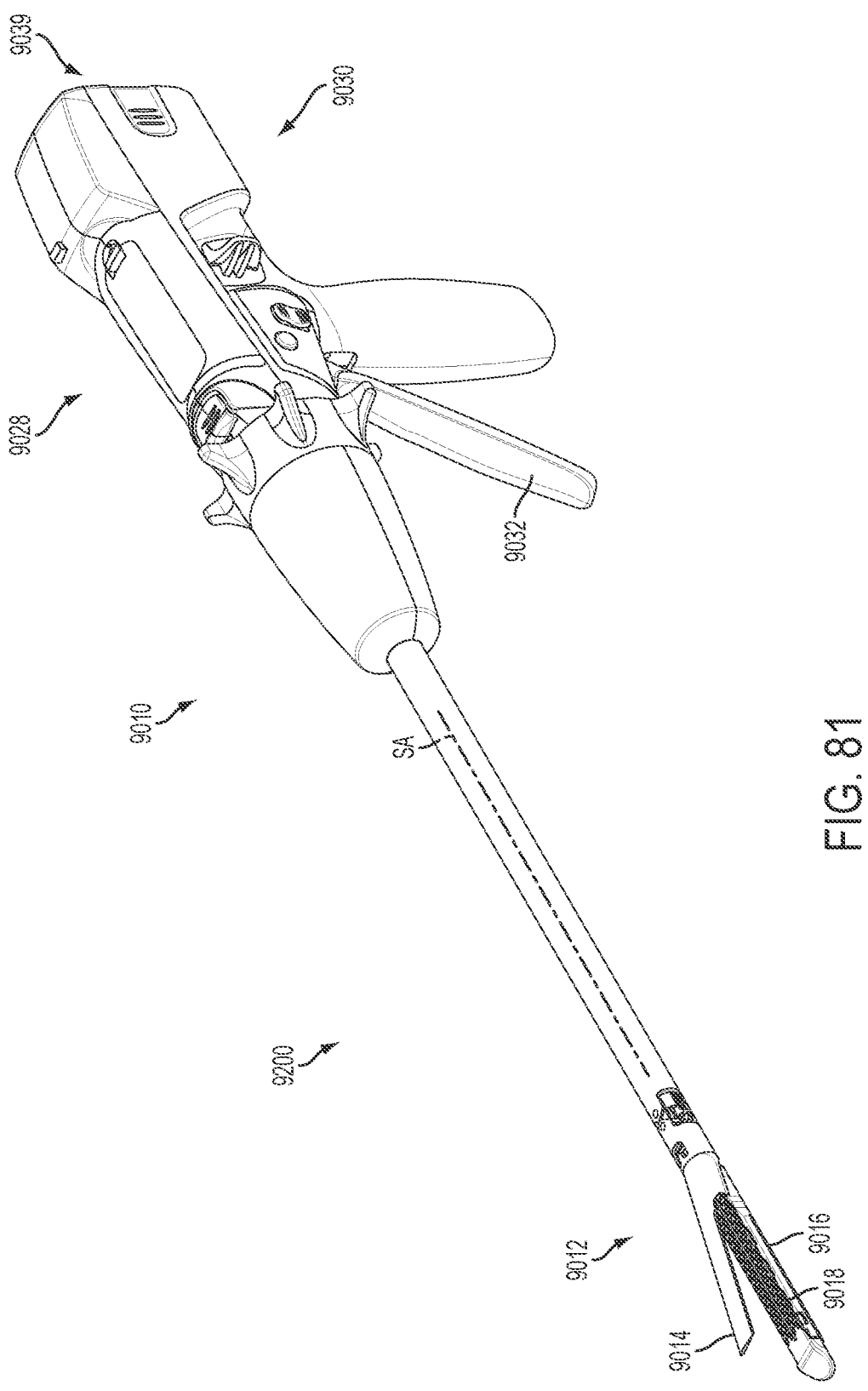
FIG. 81 illustrates a perspective view of a surgical instrument in accordance with one aspect.

Turning to the figures, FIG. 81 illustrates a surgical instrument 9010. The surgical instrument 9010 is similar in many respects to other surgical instruments described in the present disclosure. For example, the surgical instrument 9010 is similarly constructed and equipped as the motor-driven surgical cutting and fastening instrument 10 described in connection with FIGS. 1-29. Therefore, for conciseness and clarity the details of operation and construction will not be repeated here. Accordingly, the surgical instrument 9010, like other surgical instruments described in the present disclosure, comprises an end effector 9012. In the example illustrated in FIGS. 81-82, the end effector 9012 comprises a first jaw member, or anvil, 9014 pivotally coupled to a second jaw member 9016 to capture tissue between the first jaw member 9014 and the second jaw member 9016. The second jaw member 9016 is configured to receive a staple cartridge 9018 therein. The staple cartridge 9018 comprises a plurality of staples 9042. The plurality of staples 9402 is deployable from the staple cartridge 9018 during a surgical operation.

In alternative aspects, the end effector 9012 can be configured to seal tissue captured between the first jaw member 9014 and the second jaw member 9016. For example, the first jaw member 9014 and the second jaw member 9016 may each include an electrically conductive member. The electrically conductive members may cooperate to transmit energy through tissue captured therebetween to treat and/or seal the tissue. A power source such as, for example, a battery can be configured to provide the energy.

In certain instances, as illustrated in FIG. 81, the surgical instrument 9010 can be a motor-driven surgical cutting and fastening instrument that may or may not be reused. In the illustrated example, the instrument 9010 includes a housing 9028 that comprises a handle 9030 that is configured to be grasped, manipulated and actuated by the clinician. In the example illustrated in FIG. 81, the housing 9028 is operably coupled to a shaft assembly 9032 that has a surgical end effector 9012 configured to perform one or more surgical tasks or procedures.

The housing 9028 depicted in FIG. 81 is shown in connection with a shaft assembly 9032 that includes an end effector 9012 that comprises a surgical cutting and fastening device that is configured to operably support a surgical staple cartridge 9018 therein. The housing 9028 may be configured for use in connection with shaft assemblies that include end effectors that are adapted to support different sizes and types of staple cartridges, have different shaft lengths, sizes, and types, etc. In addition, the housing 9028 also may be effectively employed with a variety of other shaft assemblies including those assemblies that are configured to apply other motions and forms of energy such as, for example, radio frequency (RF) energy, ultrasonic energy and/or motion to end effector arrangements adapted for use in connection with various surgical applications and procedures.

Figure 82:
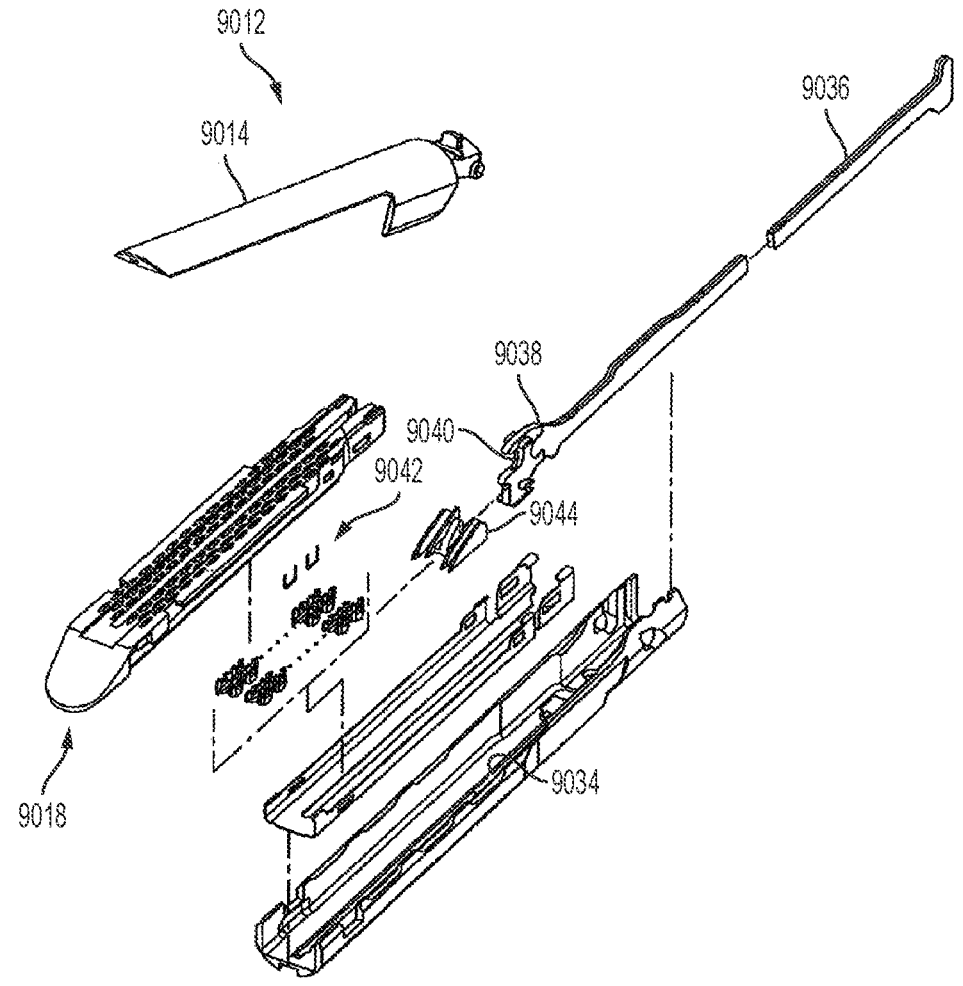
FIG. 82 illustrates an exploded view of the end effector of the surgical instrument of FIG. 81 in accordance with one aspect.

Referring to FIG. 82, a non-limiting form of the end effector 9012 is illustrated. As described above, the end effector 9012 may include the anvil 9014 and the staple cartridge 9018. In this non-limiting example, the anvil 9014 is coupled to an elongate channel 9034. In addition, FIG. 82 shows a firing bar 9036, configured to longitudinally translate into the end effector 9012. A distally projecting end of the firing bar 9036 can be attached to an E-beam 9038 that can, among other things, assist in spacing the anvil 9014 from a staple cartridge 9018 positioned in the elongate channel 9034 when the anvil 9014 is in a closed position. The E-beam 9038 can also include a sharpened cutting member 9040 which can be used to sever tissue as the E-beam 9038 is advanced distally by the firing bar 9036. In operation, the E-beam 9038 can also actuate, or fire, the staple cartridge 9018. The staple cartridge 9018 can include a plurality of staples 9042. A wedge sled 9044 is driven distally by the E-beam 9038 to force out the staples 9042 into deforming contact with the anvil 9012 while a cutting member 9040 of the E-beam 9038 severs clamped tissue.

Figure 83:
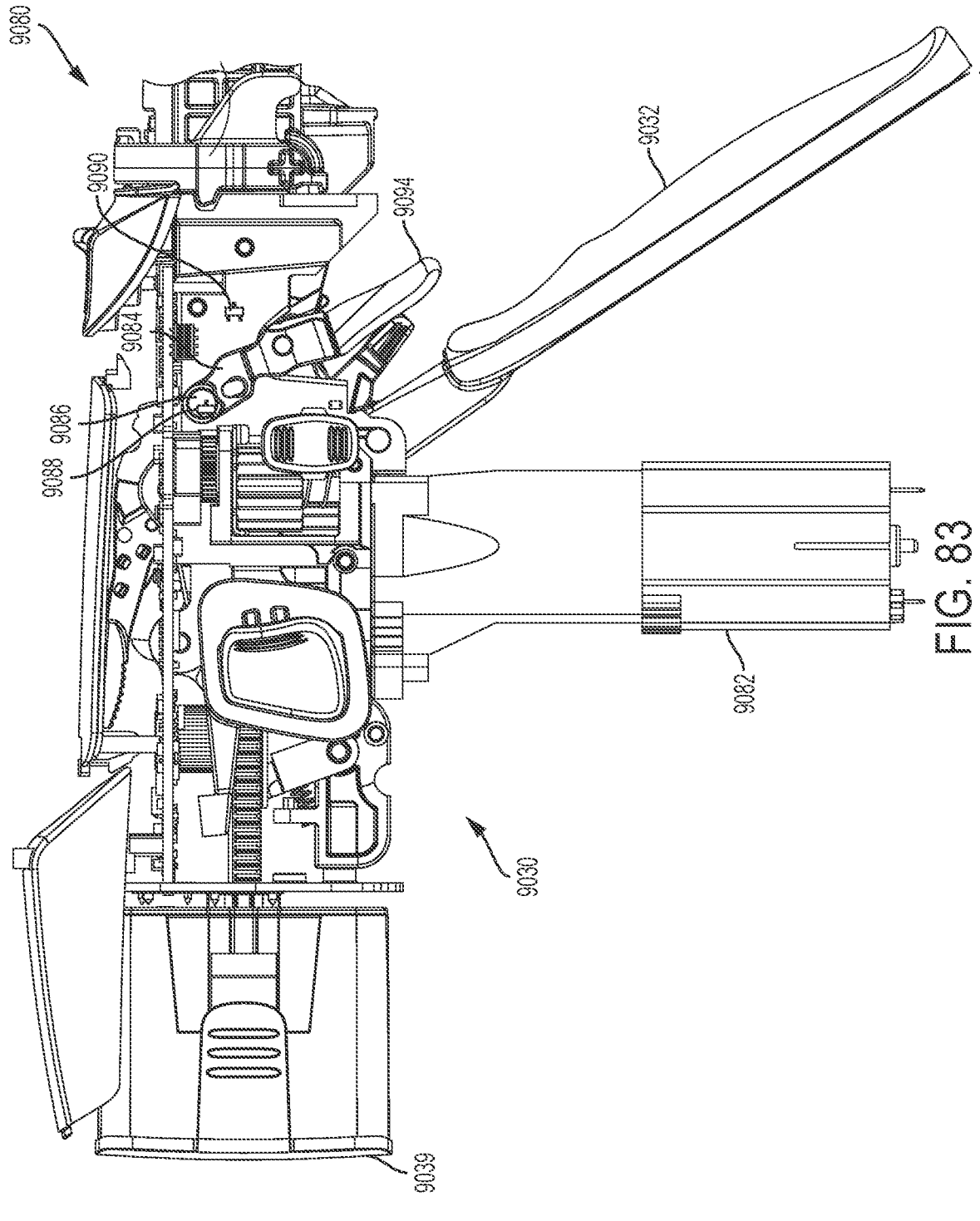
FIG. 83 illustrates a partial side view of a handle of the surgical instrument of FIG. 81 in accordance with one aspect.

In one aspect, as illustrated in FIGS. 81-83, a motor can be operably coupled to the firing bar 9036. The motor can be powered by a power source such as, for example, a battery 9039. The battery 9039 may supply power to the motor 9082 to motivate the firing bar 9036 to advance the E-beam 9038 to fire the staples 9042 into tissue captured between the anvil 9014 and the staple cartridge 9018 and/or advance the cutting member 9040 to sever the captured tissue. Actuation of the motor 9082 can be controlled by a firing trigger 9094 that is pivotally supported on the handle 9030. The firing trigger 9094 can be depressed by an operator of the surgical instrument 9010 to activate the motor 9082.

In one instance, the firing trigger 9094 can be depressed or actuated between a plurality of positions each yielding a different output value. For example, actuating the firing trigger 9094 to a first position may yield a first output value, and actuating the firing trigger 9094 to a second position after the first position may yield a second output value greater than the first output value. In certain instances, the greater the firing trigger 9094 is depressed or actuated, the greater the output value. In certain instances, the output is a characteristic of motion of the firing bar 9036 and/or the cutting member 9040. In one instance, the output can be the speed of the cutting member 9040 during advancement of the cutting member 9040 in a firing stroke. In such instance, actuating the firing trigger 9094 to a first position may cause the cutting member 9040 to travel at a first speed, and actuating the firing trigger 9094 to a second position may cause the cutting member 9040 to travel at a second speed different from the first speed. In certain instances, the greater the firing trigger 9094 is depressed or actuated, the greater the speed of travel of the cutting member 9040.

Figure 87:
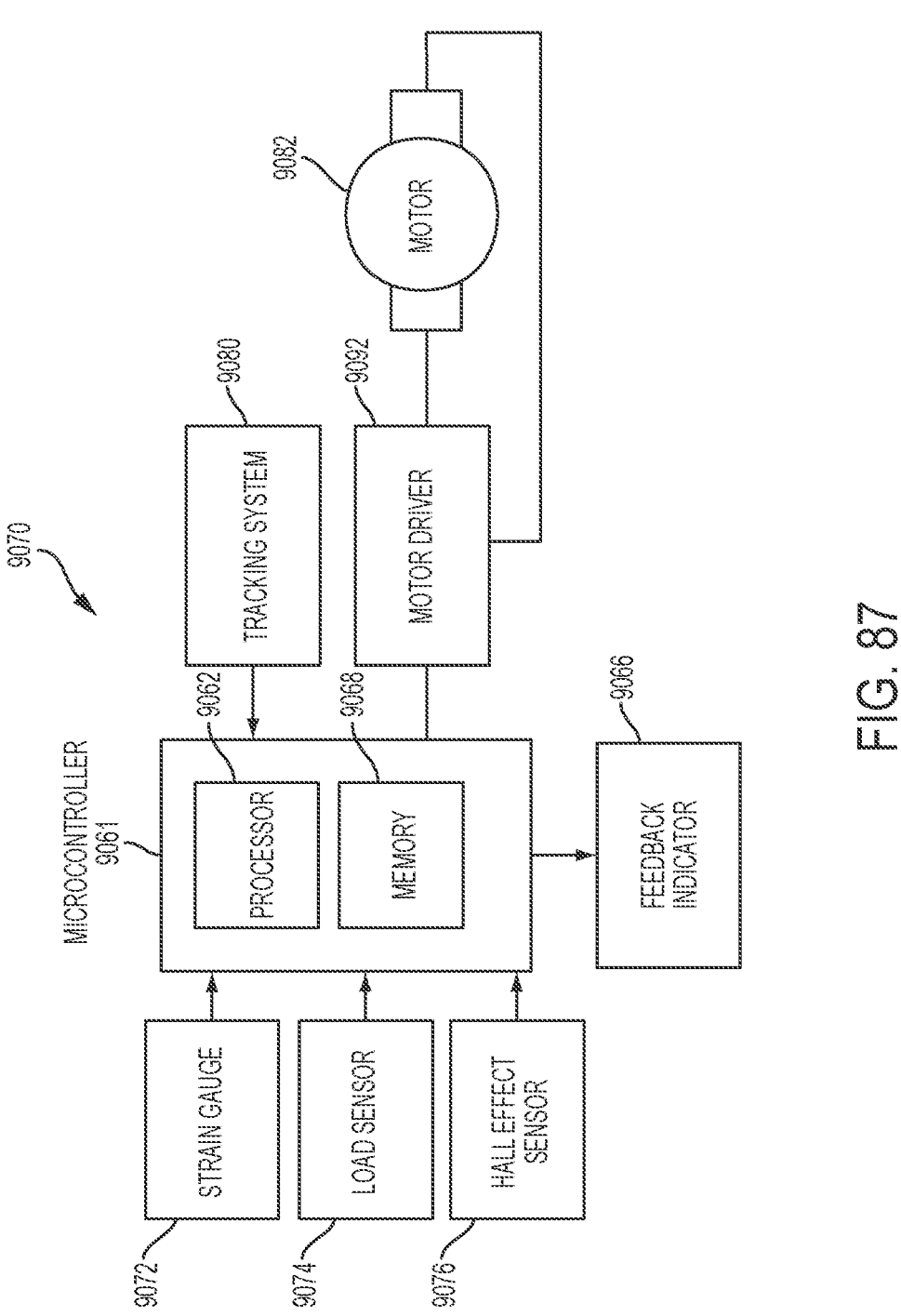
FIG. 87 illustrates a logic diagram of a feedback system in accordance with one aspect.

In the aspect illustrated in FIG. 83, a tracking system 9080 is configured to determine the position of the firing trigger 9094. The tracking system 9080 can include a magnetic element, such as permanent magnet 9086, for example, which is mounted to an arm 9084 extending from the firing trigger 9094. The tracking system 9080 can comprise one or more sensors, such as a first magnetic field sensor 9088 and a second magnetic field sensor 9090, for example, which can be configured to track the position of the magnet 9086. The sensors 9088 and 9090 can track the movement of the magnet 9086 and can be in signal communication with a microcontroller such as, for example, the microcontroller 9061 (FIG. 87). With data from the first sensor 9088 and/or the second sensor 9090, the microcontroller 9061 can determine the position of the magnet 9086 along a predefined path and, based on that position, the microcontroller 9061 can determine an output of the motor 9082. In certain instances, a motor driver 9092 can be in communication with the microcontroller 9061, and can be configured to drive the motor 9082 in accordance with an operator's manual input as detected by the tracking system 9080.

In certain instances, the magnetic field sensors can be configured to detect movement of the firing trigger 9094 through a firing stroke instead of, or in addition to, detecting discrete positions along the firing stroke. The strength of the magnetic field generated by the permanent magnet, as detected by the magnetic field sensors, changes as the permanent magnet 9086 is moved with the firing trigger 9094 through the firing stroke. The change in the strength of the magnetic field can be indicative of a characteristic of motion of the firing trigger 9094, which can detected by a microcontroller as a manual input.

The end effector 9012 may include one or more sensors configured to measure one or more parameters or characteristics associated with the end effector 9012 and/or a tissue section captured by the end effector 9012. In the example illustrated in FIG. 84, the end effector 9012 comprises a first sensor 9020 and a second sensor 9026. In various examples, the first sensor 9020 and/or the second sensor 9026 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 9012.

In certain instances, the first sensor 9020 and/or the second sensor 9026 may comprise, for example, a magnetic field sensor embedded in the first jaw member 9014 and configured to detect a magnetic field generated by a magnet 9024 embedded in the second jaw member 9016 and/or the staple cartridge 9018. The strength of the detected magnetic field may correspond to, for example, the thickness and/or fullness of a bite of tissue located between the jaw members 9014, 9016. In certain instances, the first sensor 9020 and/or the second sensor 9026 may comprise a strain gauge, such as, for example, a micro-strain gauge, configured to measure the magnitude of the strain in the anvil 9014 during a clamped condition. The strain gauge provides an electrical signal whose amplitude varies with the magnitude of the strain.

In some aspects, one or more sensors of the end effector 9012 such as, for example, the first sensor 9020 and/or the second sensor 9026 may comprise a pressure sensor configured to detect a pressure generated by the presence of compressed tissue between the jaw members 9014, 9016. In some examples, one or more sensors of the end effector 9012 such as, for example, the first sensor 9020 and/or the second sensor 9026 are configured to detect the impedance of a tissue section located between the jaw members 9014, 9016. The detected impedance may be indicative of the thickness and/or fullness of tissue located between the jaw members 9014, 9016.

In one aspect, one or more of the sensors of the end effector 9012 such as, for example, the first sensor 9012 is configured to measure the gap 9022 between the anvil 9014 and the second jaw member 9016. In certain instances, the gap 9022 can be representative of the thickness and/or compressibility of a tissue section clamped between the jaw members 9014, 9016. In at least one example, the gap 9022 can be equal, or substantially equal, to the thickness of the tissue section clamped between the jaw members 9014, 9016. In one example, one or more of the sensors of the end effector 9012 such as, for example, the first sensor 9020 is configured to measure one or more forces exerted on the anvil 9014 by the second jaw member 9016 and/or tissue clamped between the anvil 9014 and the second jaw member 9016. The forces exerted on the anvil 9014 can be representative of the tissue compression experienced by the tissue section captured between the jaw members 9014, 9016. In one embodiment, the gap 9022 between the anvil 9014 and the second jaw member 9016 can be measured by positioning a magnetic field sensor on the anvil 9014 and positioning a magnet on the second jaw member 9016 such that the gap 9022 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the second jaw member 9016 and the magnet is placed on the anvil 9014.

One or more of the sensors such as, for example, the first sensor 9020 and/or the second sensor 9026 may be measured in real-time during a clamping operation. Real-time measurement allows time based information to be analyzed, for example, by a processor, and used to select one or more algorithms and/or look-up tables for the purpose of assessing, in real-time, a manual input of an operator of the surgical instrument 9010. Furthermore, real-time feedback can be provided to the operator to assist the operator in calibrating the manual input to yield a desired output.

Figure 85:
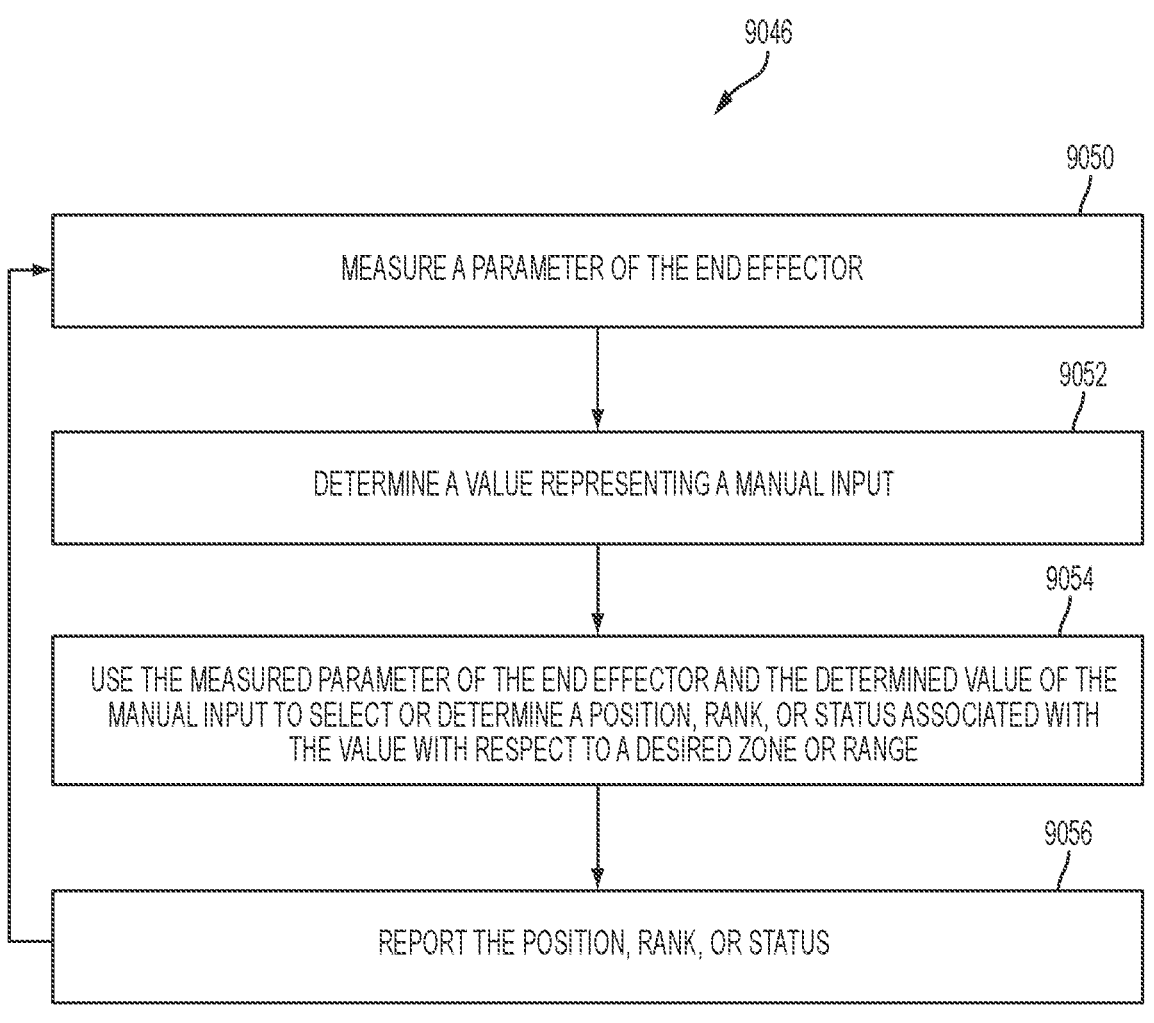
FIG. 85 illustrates a logic diagram of a process in accordance with one aspect.

FIG. 85 is a logic diagram illustrating one aspect of a process 9046 for assessing, in real-time, a manual input of an operator of the surgical instrument 9010 and providing real-time feedback to the operator as to the adequacy of the manual input. In the example illustrated in FIG. 85, the process starts at step or block 9050 where one or more parameters of the end effector 9012 are measured. Next at step 9052, a manual input of an operator of the surgical instrument 9010 is assessed. In one example, a value representative of the manual input is determined. Next at step 9054, the determined value is evaluated or assessed for a position, rank, and/or status with respect to a desired zone or range. The measurement of the parameters of the end effector 9012 and the determined value can be employed to select or determine the position, rank, and/or status associated with the determined value. In a following step 9056 of the process 9046, the position, rank, and/or status associated with the determined value is reported to the operator of the surgical instrument 9010. The real-time feedback allows the operator to adjust the manual input until a position, rank, and/or status within the desired zone or range is achieved. For example, the operator may change the manual input by increasing or decreasing the manual input while monitoring the real-time feedback until the position, rank, and/or status associated with a determined value that corresponds to a present manual input is within the desired zone or range.

Figure 86:
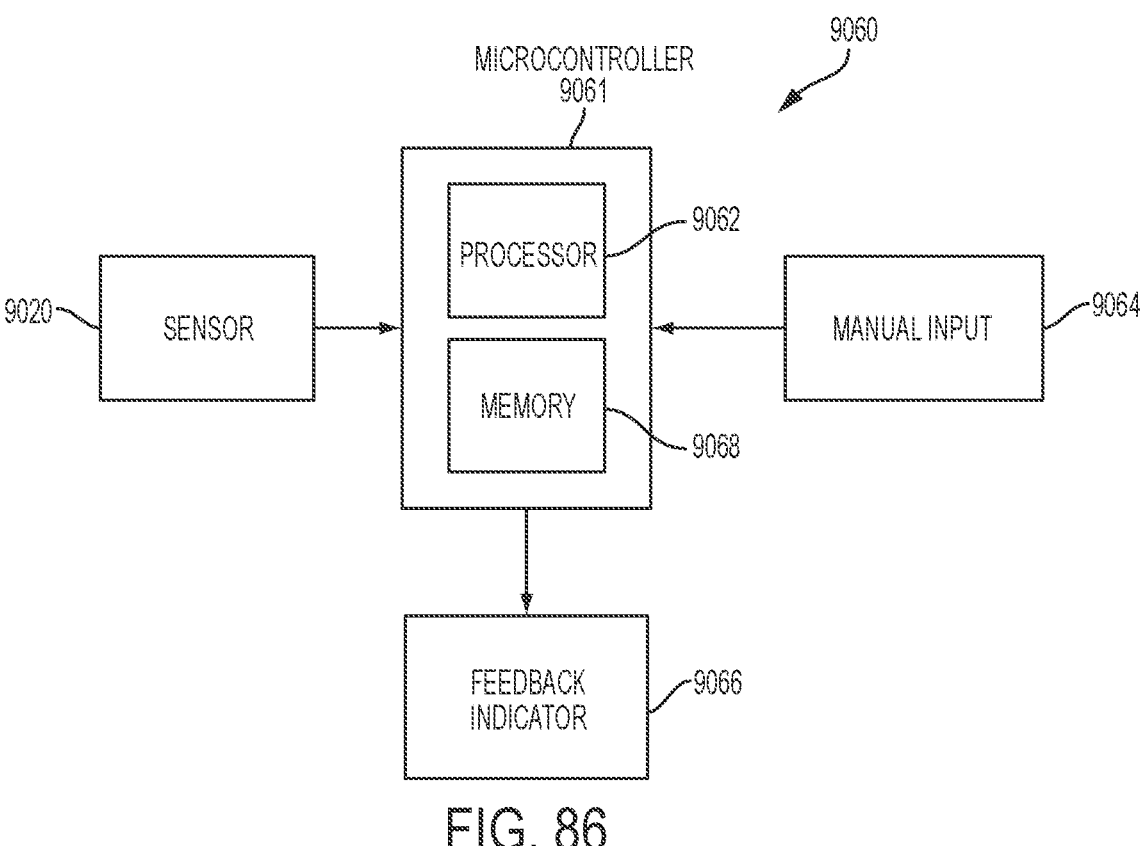
FIG. 86 illustrates a logic diagram of a feedback system in accordance with one aspect.

FIG. 86 is a logic diagram illustrating one aspect of a real-time feedback system 9060 for assessing, in real-time, a manual input 9064 of an operator of the surgical instrument 9010 and providing to the operator real-time feedback as to the adequacy of the manual input 9064. With reference to FIGS. 81-86, in the example illustrated in FIG. 86, the real-time feedback system 9060 is comprised of a circuit. The circuit includes a microcontroller 9061 comprising a processor 9062. A sensor such as, for example, the sensor 9020 is employed by the processor 9062 to measure a parameter of the end effector 9012. In addition, the processor 9062 can be configured to determine or receive a value representative of a manual input 9064 of an operator of the surgical instrument 9010. The manual input 9064 can be continuously assessed by the processor 9062 for as long as the manual input 9064 is being provided by the operator. The processor 9062 can be configured to monitor a value representative of the manual input 9064. Furthermore, the processor 9062 is configured to assign, select, or determine a position, rank, and/or status for the determined value with respect to a desired zone or range. The measurement of the parameter of the end effector 9012 and the determined value can be employed by the processor 9062 to select or determine the position, rank, and/or status associated with the determined value, as described in greater detail below. A change in the manual input 9064 yields a change in the determined value which, in turn, yields a change in the position, rank, and/or status assigned to the determined value with respect to the desired zone or range.

As illustrated in FIG. 86, the real-time feedback system 9060 may further include a feedback indicator 9066 which can be adjusted between a plurality of positions, ranks, and/or statuses inside and outside a desired zone or range. In one example, the processor 9062 may select a first position (P1), rank, and/or status that characterizes the manual input 9064 based on a measurement (M1) of a parameter of the end effector 9012 and a first determined value (V1) representing a first manual input (I1). In certain instances, the first position (P1), rank, and/or status may fall outside the desired zone or range. In such instances, the operator may change the manual input 9064 from the first manual input (I1) to a second manual input (I2) by increasing or decreasing the manual input 9064, for example. In response, the processor 9062 may adjust the feedback indicator 9066 from the first position (P1), rank, and/or status to a second position (P2), rank, and/or status, which characterizes the change to the manual input 9064. The processor 9062 may select the second position (P2), rank, and/or status based on the measurement (M1) of the parameter of the end effector 9012 and a second determined value (V2) representing a second manual input (I2). In certain instances, the second position (P2), rank, and/or status may fall inside the desired zone or range. In such instances, the operator may maintain the second manual input (I2) for a remainder of a treatment cycle or procedure, for example.

In the aspect illustrated in FIG. 86, the microcontroller 9061 includes a storage medium such as, for example, a memory unit 9068. The memory unit 9068 may be configured to store correlations between measurements of one or more parameters of the end effector 9012, values representing manual inputs, and corresponding positions, ranks, and/or statuses characterizing the manual input 9064 with respect to a desired zone or range. In one example, the memory unit 9068 may store the correlation between the measurement (M1), the first determined value (V1), and the first manual input (I1), and the correlation between the measurement (M1), the second determined value (V2), and the second manual input (I2). In one example, the memory unit 9068 may store an algorism, an equation, or a look-up table for determining correlations between measurements of one or more parameters of the end effector 9012, values representing manual inputs, and corresponding positions, ranks, or statuses with respect to a desired zone or range. The processor 9062 may employ such algorism, equation, and/or look-up table to characterize a manual input 9064 provided by an operator of the surgical instrument 9010 and provide feedback to the operator as to the adequacy of the manual input 9064.

FIG. 87 is a logic diagram illustrating one aspect of a real-time feedback system 9070. The system 9070 is similar in many respects to the system 9060. For example, like the system 9060, the system 9070 is configured for assessing, in real-time, a manual input of an operator of the surgical instrument 9010 and providing to the operator real-time feedback as to the adequacy of the manual input. Furthermore, like the system 9060, the system 9070 is comprised of a circuit that may include the microcontroller 9061.

In the aspect illustrated in FIG. 87, a strain gauge 9072, such as, for example, a micro-strain gauge, is configured to measure one or more parameters of the end effector 9012, such as, for example, the amplitude of the strain exerted on the anvil 9014 during a clamping operation, which can be indicative of the tissue compression. The measured strain is converted to a digital signal and provided to the processor 9062. A load sensor 9074 can measure the force to advance the cutting member 9040 to cut tissue captured between the anvil 9014 and the staple cartridge 9018. Alternatively, a current sensor (not shown) can be employed to measure the current drawn by the motor 9082. The force required to advance the firing bar 9036 can correspond to the current drawn by the motor 9082, for example. The measured force is converted to a digital signal and provided to the processor 9062. A magnetic field sensor 9076 can be employed to measure the thickness of the captured tissue, as described above. The measurement of the magnetic field sensor 9076 is also converted to a digital signal and provided to the processor 9062.

In the aspect illustrated in FIG. 87, the system 9070 further includes the tracking system 9080 which can be configured to determine the position of the firing trigger 9094 (FIG. 83). As described above, the firing trigger 9094 can be depressed or actuated by moving the firing trigger 9094 between a plurality of positions, each corresponding to one of a plurality of values of a characteristic of motion of the firing bar 9036 and/or the cutting member 9040 during a firing stroke. As describe above, a characteristic of motion can be a speed of advancement of the firing bar 9036 and/or the cutting member 9040 during the firing stroke. In certain instances, a motor driver 9092 can be in communication with the microcontroller 9061, and can be configured to drive the motor 9082 in accordance with an operator's manual input as detected by the tracking system 9080.

Further to the above, the system 9070 may include a feedback indicator 9066. In one aspect, the feedback indicator 9066 can be disposed in the handle 9030. Alternatively, the feedback indicator can be disposed in the shaft assembly 9032, for example. In any event, the microcontroller 9061 may employ the feedback indicator 9066 to provide feedback to an operator of the surgical instrument 9010 with regard to the adequacy of a manual input such as, for example, a selected position of the firing trigger 9094. To do so, the microcontroller 9061 may assess the selected position of the firing trigger 9094 and/or the corresponding value of the speed of the firing bar 9036 and/or the cutting member 9040. The measurements of the tissue compression, the tissue thickness, and/or the force required to advance the firing bar 9036, as respectively measured by the sensors 9072, 9074, and 9076, can be used by the microcontroller 9061 to characterize the selected position of the firing trigger 9094 and/or the corresponding value of the speed of the firing bar 9036 and/or the cutting member 9040. In one instance, the memory 9068 may store an algorism, an equation, and/or a look-up table which can be employed by the microcontroller 9061 in the assessment. In one example, the measurements of the sensors 9072, 9074, and/or 9076 can be used to select or determine a position, rank, and/or a status that characterizes the selected position of the firing trigger 9094 and/or the corresponding value of the speed of the firing bar 9036 and/or the cutting member 9040. The determined position, rank, and/or status can be communicated to the operator via the feedback indicator 9066.

The reader will appreciate that an optimal speed of the firing bar 9036 and/or the cutting member 9040 during a firing stroke can depend on several parameters of the end effector 9012 such as, for example, the thickness of the tissue captured by the end effector 9012, the tissue compression, and/or the force required to advance the firing bar 9036 and, in turn, the cutting member 9040. As such, measurements of these parameters can be leveraged by the microcontroller 9061 in assessing whether a current speed of advancement of the cutting member 9040 through the captured tissue is within an optimal zone or range.

Figure 88:
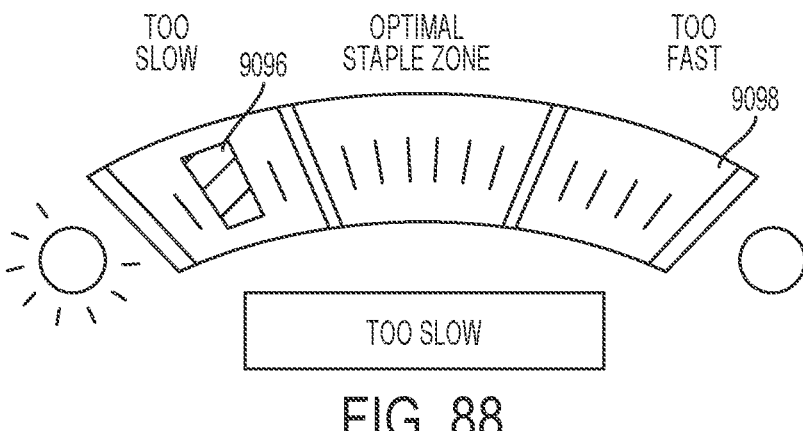
FIG. 88 illustrates a feedback indicator of a feedback system in accordance with one aspect.
Figure 89:
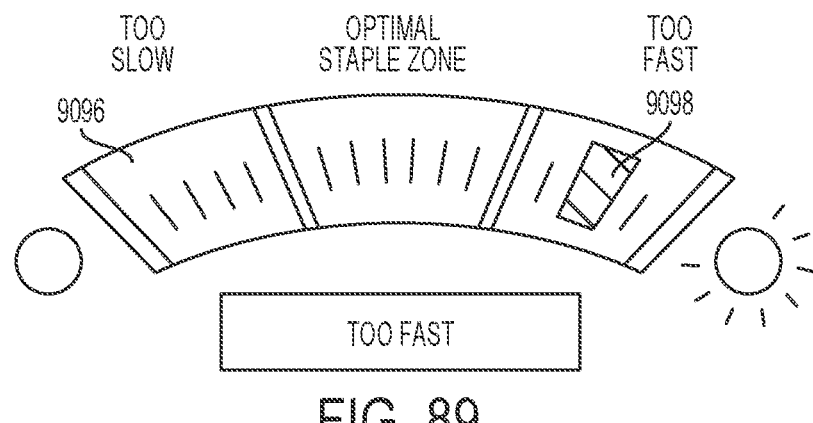
FIG. 89 illustrates a feedback indicator of a feedback system in accordance with one aspect.
Figure 90:
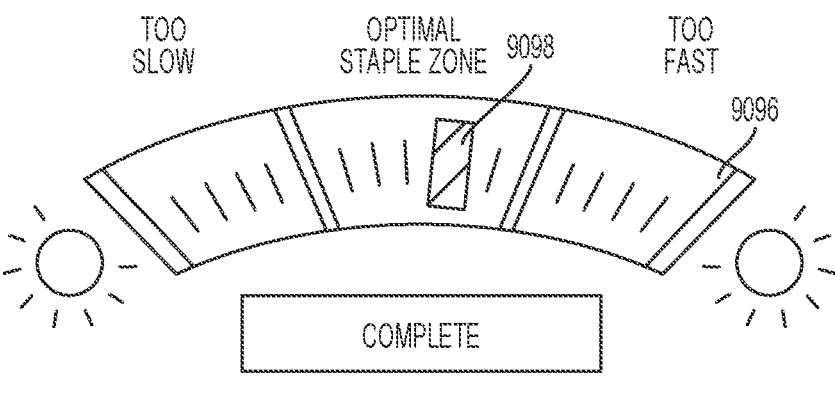
FIG. 90 illustrates a feedback indicator of a feedback system in accordance with one aspect.

In one aspect, as illustrated in FIGS. 88-90, the feedback indicator 9066 includes a dial 9096 and a pointer 9098 movable between a plurality positions relative to the dial 9096. The dial 9096 is divided to define an optimal zone, a so-called "TOO FAST" zone, and a so-called "TOO SLOW" zone. The pointer 9098 can be set to one of a plurality of positions within the three zones. In one example, as illustrated in FIG. 88, the pointer is set to a position in the "TOO SLOW" zone to alert the operator that a selected speed of advancement of the cutting member 9040 through the tissue captured by the end effector 9012 is below an optimal or a desired zone. As described above, such a characterization of the selected speed can be performed by the microcontroller 9061 based on one or more measurements of one or more parameters of the end effector 9012. In another example, perhaps after the operator increases the speed of the cutting member 9040 in response to the previous alert, the pointer is moved to a new position in the "TOO FAST" zone, as illustrated in FIG. 89, to alert the operator that a newly selected speed of the cutting member 9040 exceeds the optimal zone. The operator may continue to adjust the speed of the cutting member 9040 by adjusting the position of the firing trigger 9094 until the pointer lands in the optimal zone, as illustrated in FIG. 90. At such point, the operator may maintain the current position of the firing trigger 9094 for the remainder of the firing stroke.

Figure 91:
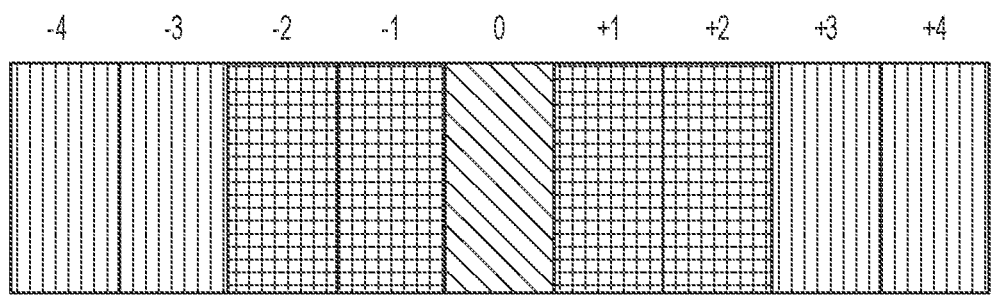
FIG. 91 illustrates a feedback indicator of a feedback system in accordance with one aspect.
Figure 92:
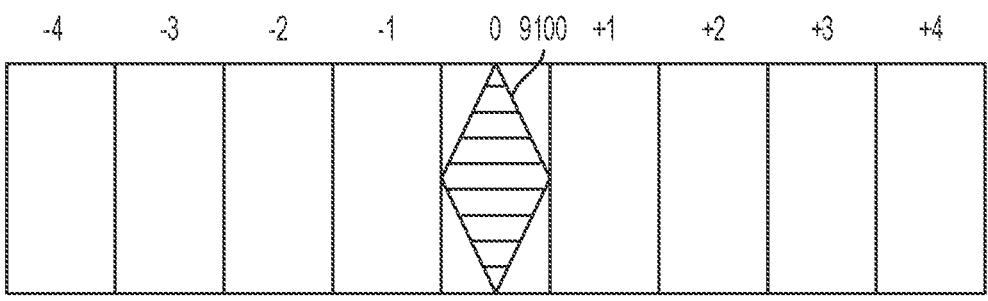
FIG. 92 illustrates a feedback indicator of a feedback system in accordance with one aspect.
Figure 93:
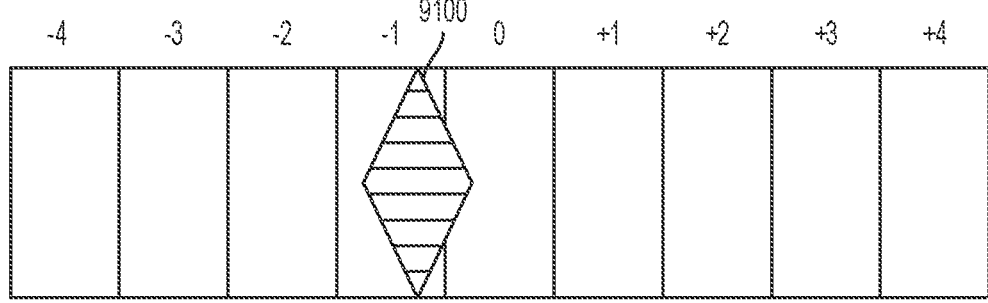
FIG. 93 illustrates a feedback indicator of a feedback system in accordance with one aspect.
Figure 94:
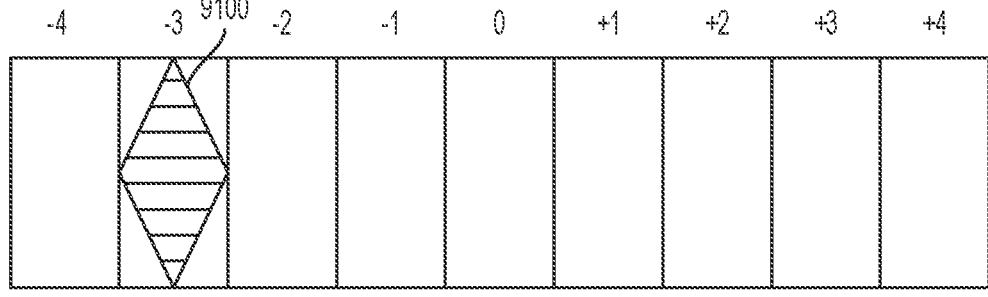
FIG. 94 illustrates a feedback indicator of a feedback system in accordance with one aspect.
Figure 95:
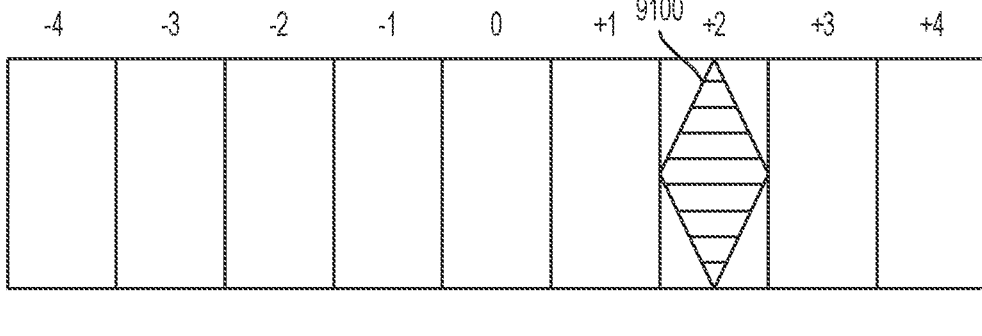
FIG. 95 illustrates a feedback indicator of a feedback system in accordance with one aspect.

In certain instances, the dial 9096 and the pointer 9098 can be replaced with a digital indicator. In one example, the digital indicator includes a screen that illustrates the above-identified three zones. A digital pointer can be transitioned between a plurality of positions on the screen to provide feedback to the operator in accordance with the present disclosure. In certain instances, as illustrated in FIGS. 91-93, the feedback indicator 9066 includes a plurality of zones with a middle zone indicating an optimal or ideal speed of the cutting member 9040. In the example illustrated in FIG. 91, nine zones are illustrated. However, in alternative examples, the feedback indicator 9066 may include five or seven zones, for example. As illustrated in FIG. 91, the plurality of zones can be color coded. For example, the middle zone can be in green. The first two zones to the right and the first two zones to the left of the middle zone can be in yellow. The remaining zones can be in red. In certain instances, as illustrated in FIG. 91, the nine zones can be numbered with the numbers −4, −3, −2, 0, +1, +2, +3, and +4, respectively from left to right. In at least one example, the plurality of zones can be numbered and color coded.

Figure 96:
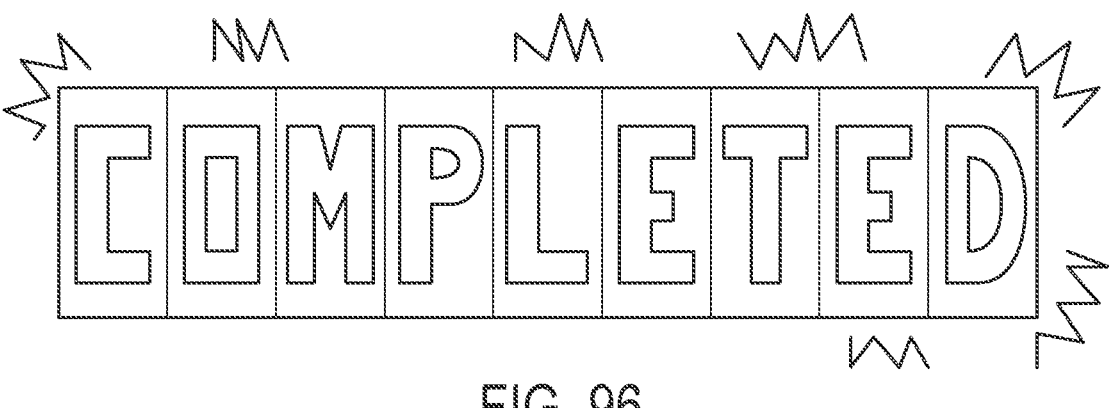
FIG. 96 illustrates a feedback indicator of a feedback system in accordance with one aspect.

In any event, as illustrated in FIGS. 92-95, a pointer 9100 is movable between a plurality of positions to point to one of the nine zones. An operator of the surgical instrument 9010 may squeeze the firing trigger 9094 while monitoring the position of the pointer 9100. Depending on the position taken by the pointer 9100, the operator may reduce or increase the pressure on the trigger 9094 until the pointer 9100 rests in the middle or optimal zone. At such point, the operator may maintain the current pressure on the firing trigger 9094 for the remainder of the firing stroke. In certain instances, as illustrated in FIG. 96, the feedback indicator 9066 may alert the operator that the firing stroke is completed.

In certain instances, as described above, the jaw members 9014, 9016 include electrically conductive layers configured to deliver energy to tissue captured between the jaw members 9014, 9016. An energy trigger or actuator can be moved or depressed between a plurality of positions or settings, in a similar manner to the firing trigger 9094, to deliver the energy to the tissue. The level or intensity of the energy delivered to the tissue may depend on the selected position. For example, depressing the energy trigger to a first position may yield a first energy level, and depressing the energy trigger to a second position, different from the first position, may yield a second energy level different from the first energy level. A tracking system, like the tracking system 9080, can track the position of the energy trigger and report such manual input to the microcontroller 9061. Alternatively, the resulting energy level can be monitored and reported to the microcontroller 9061. A current sensor or a voltage sensor, for example, can be employed to monitor the resulting energy level.

In any event, the microcontroller 9061 may be configured to characterize the selected position of the energy trigger and/or the resulting energy level in view of one or more measured parameters of the end effector 9012 and/or one or more characteristics of the captured tissue such as tissue thickness, tissue compression, and/or tissue impedance. One or more sensors can be employed to obtain measurements of one or parameters of the end effector and/or one or more characteristics of the captured tissue, which can be reported in real-time to the microcontroller 9061. In response, the microcontroller 9061 may characterize the selected position of the energy trigger and/or the resulting energy level by selecting or determining a position, rank, and/or status of the selected position of the energy trigger and/or the resulting energy level with respect to a desired zone or range. As described above, the memory unit 9068 can include an algorism, equation, and/or look-up table for determining the position, rank, and/or status of the selected position of the energy trigger and/or the resulting energy level. Furthermore, the position, rank, and/or status can be reported to the operator of the energy trigger in real-time via a feedback indicator, similar to the feedback indicator 9066, for example.

One of the advantages of the feedback methods and systems of the present disclosure is that they reduce the number of variables that an operator need to consider while providing a manual input such as, for example, actuating the firing trigger 9094. As such, the operator is relieved from having to manually consider each of the measured parameters of the end effector 9012 to estimate the adequacy of a manual input and/or an output value resulting from the manual input such as the speed of the cutting member 9040. Instead, a current manual input and/or an output value of the manual input can be automatically characterized by the microcontroller 9061 in view of all the measured parameters of the end effector 9012 to provide the operator with one consolidated real-time feedback through the feedback indicator 9066. The operator may then focus on such feedback and adjust the manual input to achieve an optimal result.

Further to the above, the feedback methods and systems of the present disclosure would give the operator a repeatable relative measure to judge the adequacy of a manual input. In addition, the operator could decide for themselves how far beyond an optimal zone, with respect to such relative measure, they are willing to reach comfortably to achieve a good outcome. Furthermore, the feedback methods and systems of the present disclosure would also give the operator a warning if the firing was out of the ordinary so that additional caution may be exercised. Furthermore, by focusing on the one consolidated real-time feedback, an operator can learn quicker the best way to fire a surgical instrument.

The present disclosure also provides novel techniques for modular reload to identify itself and define a program of operation of a motor controller to actuate the module.

One technique includes defining a table of programs and configuring a module to communicate to the handle which software programs (or other machine executable instructions) to select and execute. By way of contrast, other techniques are contemplated that do not include no operating programs in the handle portion of the endosurgical device and instead store the program in the module itself and uploads the program at the time of attachment for the handle to execute. In another technique, no programs would be executed in the handle. The handle would contain the motor controller, the actuation buttons, and even the power controller, but not the operating programs. The module would contain all the upper level logic and a sub-processor to execute the program such that each module includes a main processor and the program specific to that reload. When the shaft is attached to the handle, the processor becomes energized and it identifies the handle to which it is attached. Once identified the handle is slaved to the modular reload with the module giving and processing all commands. When a button is depressed, for example, the module responds and determines the next action and then communicates to the slaved motor controller how far and how fast to move and when to stop. With the inclusion of the master processor in the module there also should be a relatively high bandwidth communication bus between the module and the handle to enable the necessary communication traffic. This can be accomplished by holding the rotary shaft component of the modular attachment within a station frame attachment component such that the stationary part houses the processor and control program. Therefore, the communication bus does not have to also serve as a slip ring contact set.

As described herein, a surgical system can include modular components, which can be attached and/or combined together to form a surgical instrument. Such modular components can be configured to communicate and interact to affect surgical functions. Referring again to the surgical instrument 10 (FIGS. 1-4), the surgical instrument 10 includes a first modular component 14 (FIG. 1), e.g., a handle assembly 14, and a second modular component 200 (FIG. 1), e.g., an attachment assembly that includes an elongate shaft 260 (FIG. 1) and an end effector 300 (FIG. 1), which are described herein. The handle assembly 14 and the attachment assembly 200 can be assembled together to form the modular surgical instrument 10 or at least a portion thereof. Optionally, a different modular component may be coupled to the handle assembly 14, such as an attachment having different dimensions and/or features than those of the attachment assembly 200 (FIG. 1), for example. For example, alternative attachments can be interchangeable with the attachment assembly 200. In various instances, the surgical instrument 10 can include additional modular components, such as a modular battery 90 (FIG. 4), for example.

The modular surgical instrument 10 (FIGS. 1-4) can include a control system that is designed and configured to control various elements and/or functions of the surgical instrument 10. For example, the handle assembly 14 (FIG. 1) and the attachment assembly 200 (FIG. 1) can each comprise a circuit board 100 (FIG. 4), 610 (FIG. 7), respectively, having at least one control system. The control systems of the modular components 14, 200 can communicate and/or cooperate. In certain instances, a table of control modules can be accessible to the controller in the handle assembly 14 of the surgical system 10. The controller in the attachment assembly 200 can instruct the handle assembly 14 to select and implement at least one of the control module(s) from the table. In such instances, the controller in the handle assembly 14 can access and run the control module(s). In other instances, the controller in the attachment assembly 200 can include at least one control module. The appropriate control module(s) can be uploaded to the controller in the handle assembly 14, which can run the control module(s). In such instances, the controller in the handle assembly 14 can also access and run the control module(s). Additionally or alternatively, various control module(s) in the handle assembly 14 and/or the attachment assembly 200 can be updated. For example, the controller in the handle assembly 14 can be configured to download updated and/or modified control module(s) from the controller in the attachment assembly 200. U.S. patent application Ser. No. 14/226,133, entitled MODULAR SURGICAL INSTRUMENT SYSTEM, filed Mar. 26, 2014, now U.S. Patent Application Publication No. 2015/0272557, which describes various surgical systems and control systems thereof, is hereby incorporated by reference herein in its entirety.

In still other instances, a processor of the surgical instrument 10 (FIGS. 1-4) can comprise a master processor, and another processor of the surgical instrument 10 can comprise a slave processor. An operating system and/or a plurality of control modules can be accessible to the master processor. The operating system and/or the control modules can affect at least one surgical function with and/or by an element or subsystem of the surgical instrument 10, for example. A control module can comprise software, firmware, a program, a module, and/or a routine, for example, and/or can include multiple software, firmware, programs, control modules, and/or routines, for example. The control modules can affect a surgical function based on a pre-programmed routine, operator input, and/or system feedback, for example. In various instances, the master processor can be configured to direct information and/or commands to the slave processor. Moreover, the slave processor can be configured to receive information and/or commands from the master processor. The slave processor can act in response to the commands from the master processor. In various instances, the slave processor may not include a control module(s) and/or operating system, and the actions of the slave processor can be attributed to command(s) from the master processor and the control module(s) accessible to the master processor. As described herein, the control system in the attachment assembly 200 (FIG. 1) of the surgical instrument system 10 can include a master processor, and the control system in the handle assembly 14 (FIG. 1) of the surgical instrument system 10 can include at least one slave processor, for example.

Referring again to the surgical instrument 10 (FIGS. 1-4), the handle assembly 14 can be compatible with different attachments, which can be configured to affect different surgical functions. The various attachments can be interchangeable, and the different surgical functions can correspond to different tissue types and/or different surgical procedures, for example. Because different attachments can be configured to affect different surgical functions, control modules specific to the particular attachments can be stored on the respective attachments. For example, the attachment assembly 200 (FIG. 1) can store the specific control module(s) for operating the attachment assembly 200. Additionally, the attachment assembly 200 can include the upper level logic and sub-processor to run the control module(s). In such instances, the processor in the attachment assembly 200 can comprise a master control system and/or master processor that is configured to command a slave processor in the handle assembly 14 to implement the control module(s) stored on the attachment assembly 200.

Because each attachment includes the specific control module(s) for its operation and because the processor in the attachment comprises the master processor, the modular surgical instrument 10 is configured to run the most appropriate and up-to-date control module(s) for the particular attachment. Additionally, as updated and/or revised attachments and/or control module(s) therefor and designed and implemented, the updated and/or revised attachments are designed to properly work with handle assemblies that have less recent updates and/or revisions. In other words, updated and/or revised attachments can be retrofit to operate properly with existing and/or out-of-date handle assemblies.

As described herein, the handle assembly 14 (FIG. 1) includes a firing drive system 80 that includes a motor 82 (FIG. 4). The handle assembly 14 also includes a battery 90 (FIG. 90), a handle circuit board 100 (FIG. 4), and an electrical connector 1400 (FIG. 4). A motor controller, such as the motor controller 2043 (FIGS. 21A and 21B), for example, which is described herein, can be configured to control the operation of the motor 82. For example, the motor controller 2043 can initiate rotation of the motor 82 and/or can control the direction and/or speed of motor rotation.

As described herein, the attachment assembly 200 (FIG. 1) can include a shaft circuit board 610 and an electrical connector 1410 (FIG. 7). The electrical connector 1410 (FIG. 3) on the attachment assembly 200 can be configured to engage the electrical connector 1400 (FIG. 4) on the handle assembly 14 (FIG. 1) to provide a conduit and/or conductive pathway for transferring power and/or information between the handle assembly 14 and the attachment assembly 200. The electrical connectors 1400, 1410 can be mounted to stationary components of the surgical instrument 10 (FIGS. 1-4). Referring to FIG. 3, for example, the electrical connection 1410 in the attachment assembly 200 is mounted to the shaft chassis 244, which remains stationary relative to the intermediate firing shaft 222. Because the electrical connections 1400, 1410 are stationary relative to each other, the connections 1400, 1410 can provide a high bandwidth communication bus to enable traffic between the connections 1400, 1410.

In various instances, when the attachment assembly 200 (FIG. 1) is attached to the handle assembly 14 (FIG. 1), the electrical connectors 1400 (FIG. 3), 1410 (FIG. 3) can be engaged and the battery 90 (FIG. 4) in the handle assembly 14 can power the handle assembly 14 and the attachment assembly 200. For example, the battery 90 can provide power to the shaft circuit board 610 (FIG. 7) when the attachment assembly 200 is coupled to the handle assembly 14. In various instances, the battery 90 can automatically power the shaft circuit board 610 and/or components thereof when the attachment assembly 200 is connected to the handle assembly 14.

Figure 97:
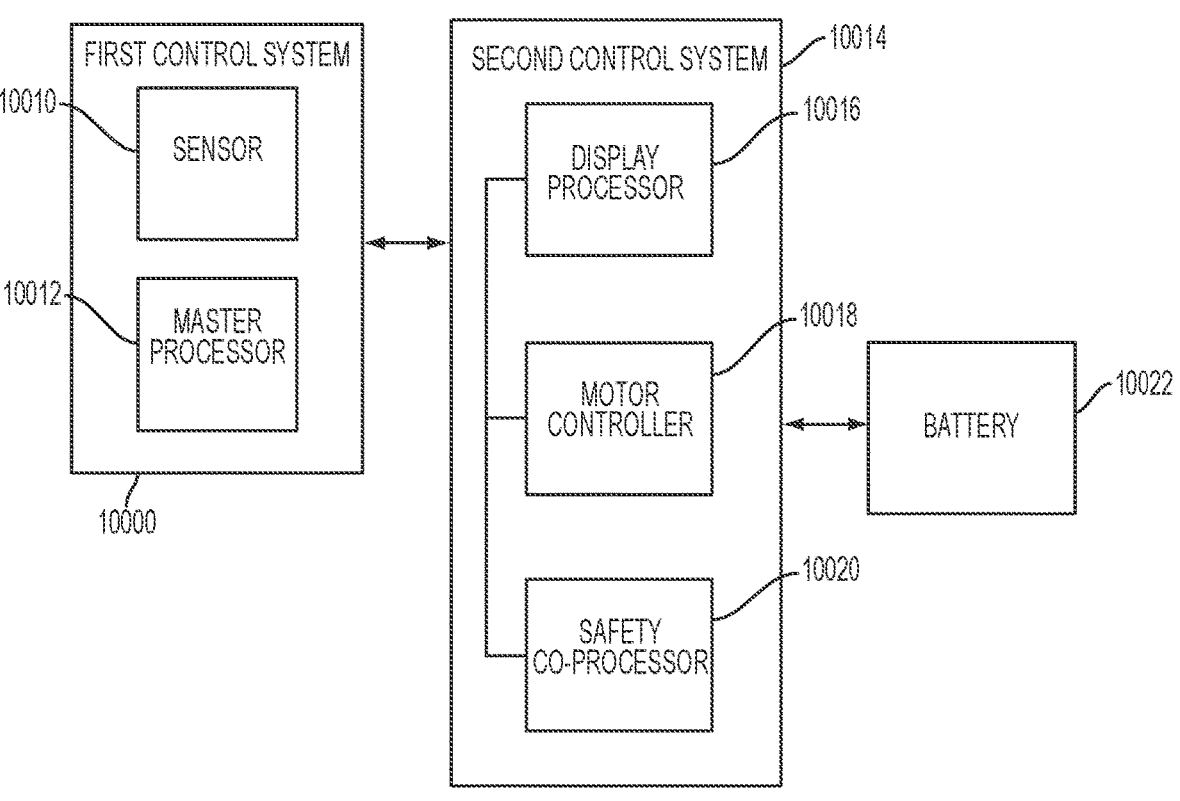
FIG. 97 is a schematic depicting control systems of the modular surgical instrument system of FIG. 1, according to various aspects of the present disclosure.

Referring now to FIG. 97, a schematic depicting the various control systems for a modular surgical instrument system, such as the surgical instrument 10 (FIGS. 1-4), for example, is depicted. A first control system 10000 can be positioned in a modular attachment, such as the attachment assembly 200 (FIG. 1), and a second control system 10014 can be positioned in a modular handle, such as the handle assembly 14 (FIG. 1). The attachment control system 10000 includes a master processor 10012, which is configured to issue commands to a slave processor. For example, the handle control system 10014 includes a slave processor 10018, which can be slaved to the master processor 10012 in the modular attachment 200. In various instances, the slave processor 10018 can correspond to a motor controller, such as the motor controller 2043 (FIGS. 21A and 21B), for example. In such instances, the motor controller 2043 in the handle assembly 14 of the surgical instrument 10 can be slaved to the master processor 10012 in the modular attachment 200. For example, the master processor 10012 can issue commands to the motor controller 2043, which can affect actuation of the motor 82 (FIG. 4), for example, and can control the direction and/or speed of motor rotation.

Referring still to FIG. 97, the control system 10000 in the modular attachment 200 can also include at least one sensor 10010, which can be in communication with the master processor 10012 in the modular attachment 200 (FIG. 1). Various exemplary sensors for detecting conditions within the shaft 260, within the end effector 300 (FIGS. 1 and 2), and/or at the surgical site are described herein. In certain instances, the master processor 10012 can select a control module and/or program to run based on feedback from the sensors 10010. For example, the thickness, density, and/or temperature of tissue detected by one of the sensors 10010 can be communicated to the master processor 10012 and the operating module(s) and/or program selected by the master processor 10012 can account for the detected condition(s) within the end effector 300.

The handle control system 10014 depicted in FIG. 97 also includes a display processor 10016, which can be similar to the display segment 2002*d* of segmented circuit 2000 (FIGS. 21A and 21B), for example. In certain instances, the display processor 10016 can be configured to control the information provided to and presented by a display. In various examples, the display can be integrally formed on the handle assembly 14 (FIG. 1) of the surgical instrument system 10 (FIG. 1). In still other instances, the display can be separate and/or remote from the handle assembly 14 and the attachment assembly 200 (FIG. 1). In at least one instance, the display processor 10016 is a slave to the master processor 10012 in the attachment assembly 200. For example, the master processor 10012 can send commands to the display processor 10016 and the display processor 10016 can implement the commands.

Referring still to FIG. 97, the control system 10014 in the handle assembly 14 (FIG. 1) can include a safety coprocessor 10020, which can be similar to the safety processor 2004 (FIGS. 21A and 21B), for example. In various instances, the safety coprocessor 10020 can be in signal communication with the master processor 10012 in the modular attachment 200 (FIG. 1). The master processor 10012 can issue commands to the safety coprocessor 10020, which can be specific to the modular attachment and/or the surgical functions performed by the particular modular attachment. For example, the master processor 10012 can initiate the safety operations of the safety coprocessor 10020. In various instances, after the safety operations of the safety coprocessor 10020 have been initiated, the safety coprocessor 10020 can run independently and can notify the master processor 10012 if a triggering event occurs.

The control system 10014 in the handle assembly 14 (FIG. 1) can be coupled to a battery 10022, which can be similar to the battery 90 (FIG. 4) positioned in the handle assembly 14 and the battery 2008 (FIGS. 21A and 21B) in the power segment 2002*h* (FIGS. 21A and 21B) of the segmented circuit 2000, which are described herein. The battery 10022 can power the control system 10014 in the handle assembly 14. Moreover, when the attachment assembly 200 is connected to the handle assembly 14, the battery 10022 can power the master control system 10000 in the attachment assembly 200 (FIG. 1). For example, the battery 10022 can power the master processor 10012 in the attachment assembly 200. In various instances, when the attachment assembly 200 is attached to the handle assembly 14, the battery 10022 can automatically power the master processor 10012. For example, current can flow to the master processor 10012 via the electrical connector 1400 (FIGS. 3 and 4) in the handle assembly 14 and the electrical connector 1410 (FIG. 7) in the attachment assembly 200.

In various instances, the master processor 10012 can include a plurality of control modules, which are specific to the surgical functions and/or components of the attachment assembly 200 (FIG. 1). The control modules can be accessible to and/or integral with the master processor 10012. In various circumstances, the master processor 10012 can include multiple tiers and/or levels of command and the control modules can be organized into multiple tiers. For example, the master processor 10012 can include a first tier of control modules, a second tier of control modules, and/or a third tier of control modules. Control modules of the first tier can be configured to issue commands to the control modules of the second tier, for example, and the control modules of the second tier can be configured to issue commands to the control modules of the third tier. In various instances, the master processor 10012 can include less than three tiers and/or more than three tiers, for example.

The control module(s) in the first tier can comprise high-level software, or a clinical algorithm. Such a clinical algorithm can control the high-level functions of the surgical instrument 10 (FIGS. 1-4), for example. In certain instances, the control module(s) in the second tier can comprise intermediate software, or framework module(s), which can control the intermediate-level functions of the surgical instrument 10, for example. In certain instances, the clinical algorithm of the first tier can issue abstract commands to the framework module(s) of the second tier to control the surgical instrument 10. Furthermore, the control modules in the third tier can comprise firmware modules, for example, which can be specific to a particular hardware component, or components, of the surgical instrument 10. For example, the firmware modules can correspond to a particular cutting element, firing bar, trigger, sensor, and/or motor of the surgical instrument 10, and/or can correspond to a particular subsystem of the surgical instrument 10, for example. In various instances, a framework module can issue commands to a firmware module to implement a surgical function with the corresponding hardware component. Accordingly, the various control modules of the surgical system 10 can communicate and/or cooperate during a surgical procedure.

The master processor 10012 can include and/or access the control modules of various tiers, which can affect different surgical functions. In certain instances, the motor controller 10018 may not include any control modules, and control modules may not be accessible to the motor controller 10018. For example, the motor controller 10018 may not include an operating system, framework module, and/or firmware module. In such instances, the motor controller 10018 can be slaved to the master processor 10012, and the motor controller 10018 can be configured to implement the commands issued by the master processor 10012.

As described herein, the master control system 1000 in the attachment assembly 200 can communicate with the control system 10014 in the handle assembly 14 (FIG. 1) to affect a surgical function. In use, referring primarily now to FIG. 98, modular components of a surgical instrument, such as the handle assembly 14 and the attachment assembly 200 (FIG. 1), can be attached 11000. Thereafter, at least one function can be initiated by a master processor, such as the master processor 10012 (FIG. 97), for example, which can include the control module(s) and/or operating program(s) specific to the attachment assembly 200 (FIG. 1) and the surgical function(s) to be performed by the attachment assembly 200.

Figure 98:
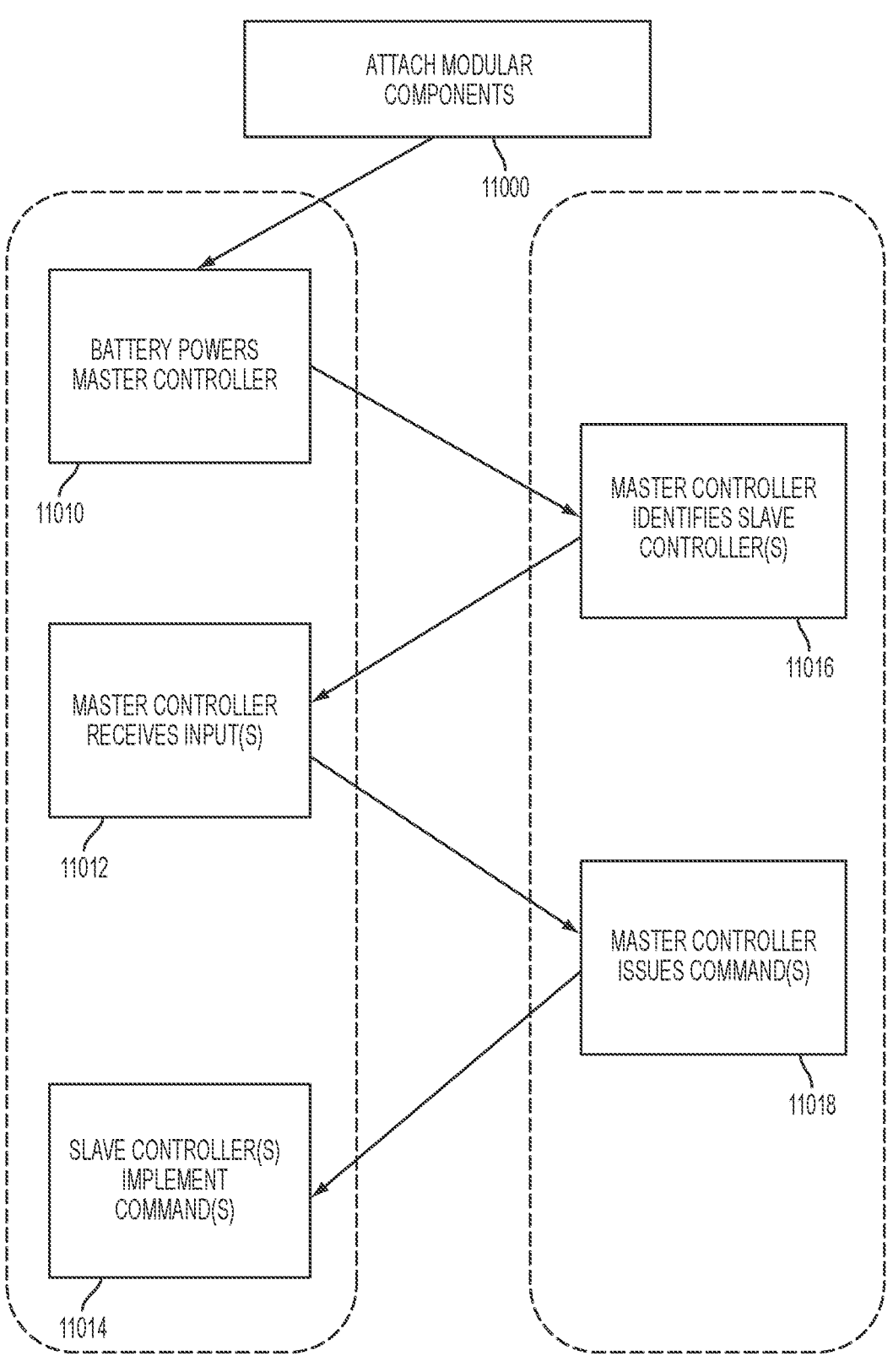
FIG. 98 is a logic diagram of a method for implementing a surgical function with the modular surgical instrument system of FIG. 1, according to various aspects of the present disclosure.

With reference primarily to both FIGS. 97 and 98, a battery, such as the battery 10022 can power 11010 the master processor 10012. As described herein, when the attachment assembly 200 (FIG. 1) is properly coupled to the handle assembly 14 (FIG. 1), the battery 10022 in the handle assembly 14 can power the master processor 10012. The powered master processor 10012 can identify 11016 at least one slave processor, such as the slave processors 10016 and 10018, for example. After the master processor 10012 identifies 11016 at least one of the slave processor(s) 10016, 10018, the master processor 10012 can issue commands to the slave processor(s) 10016, 10018. The commands can be based on a pre-programmed routine found in a control module accessible to the master processor 10012.

In various instances, the master processor 10012 can request information from other systems and/or controllers in the surgical instrument 10 (FIGS. 1-4). For example, the master processor 10012 can request information from a slaved processor. In certain instances, the master processor 10012 can request information from an input system, such as an actuation button and/or trigger on the handle assembly 14 (FIG. 1). Additionally or alternatively, the master processor 10012 can request information from a sensor and/or feedback system. For example, the master processor 10012 can communicate with at least one sensor 10010 to obtain information on at least one condition in the surgical instrument 10 and/or surgical site. The master processor 10012 can receive 11012 information and/or inputs.

The master processor 10012 can issue at least one command to at least one slave processor 10016, 10018 at step 11018. In certain instances, the command(s) can be based on the control module(s) accessible to the master processor 10012 and/or the feedback and/or input received at step 11012. For example, the master processor 10012 can command the slaved motor controller 10018 to operate the motor 82 (FIG. 4) in the handle assembly 14 at a particular power level, in a particular direction, and/or for a particular duration. The control sequence of the motor 82 can be determined and provided by a control module in the attachment assembly 200 (FIG. 1). As a result, the control sequence can correspond to the particular attachment assembly 200 and the surgical function to be performed by that attachment assembly 200.

At step 11014, the slaved processors 10016 and/or 10018 can implement the command(s) from the master processor 10012. In various instances, the master processor 10012 can request information from various slaved systems during and/or throughout implementation of the control sequence. In certain instances, based on the updated information, the master processor 10012 can issue a new and/revised command and/or commands. Additionally or alternatively, the master processor 10012 can issue additional commands to the slaved processor(s) throughout the operation of the surgical instrument 10 (FIGS. 1-4).

The present disclosure provides additional techniques to overcome challenges with conventional modular endosurgical devices. Two of these techniques, in the context of modular endocutters, include wire contacts to transmit power and receive signals from an end effector shaft configured to rotate, and the ability to upgrade the modular attachment with new tech and sensors while allowing the handle to readily accept the new tech.

The ability for the sensors in the end-effector to have the signal processing capability built into the sensor itself helps improve both of these issues. In one aspect, the sensor can be configured to supply the handle with processed information rather than supplying the handle with raw data to minimize the impact of newer sensors and the number of wires necessary to run them. In one aspect, a series of smart sensors can be placed in parallel along a single power line with the shaft of the device as the return path and using current draw "signal" the handle to stop, or start, or end etc. In accordance with this technique, the handle does not need to know what the sensor actually is or how to interpret the processed information being fed back to the controller. Likewise, the current draw can be monitored using a standard Morse Code like encoding technique on the power line to enable the handle to know what the issue is and which sensor identified the issue without any pairing or other couple communication requirement.

Figure 99:
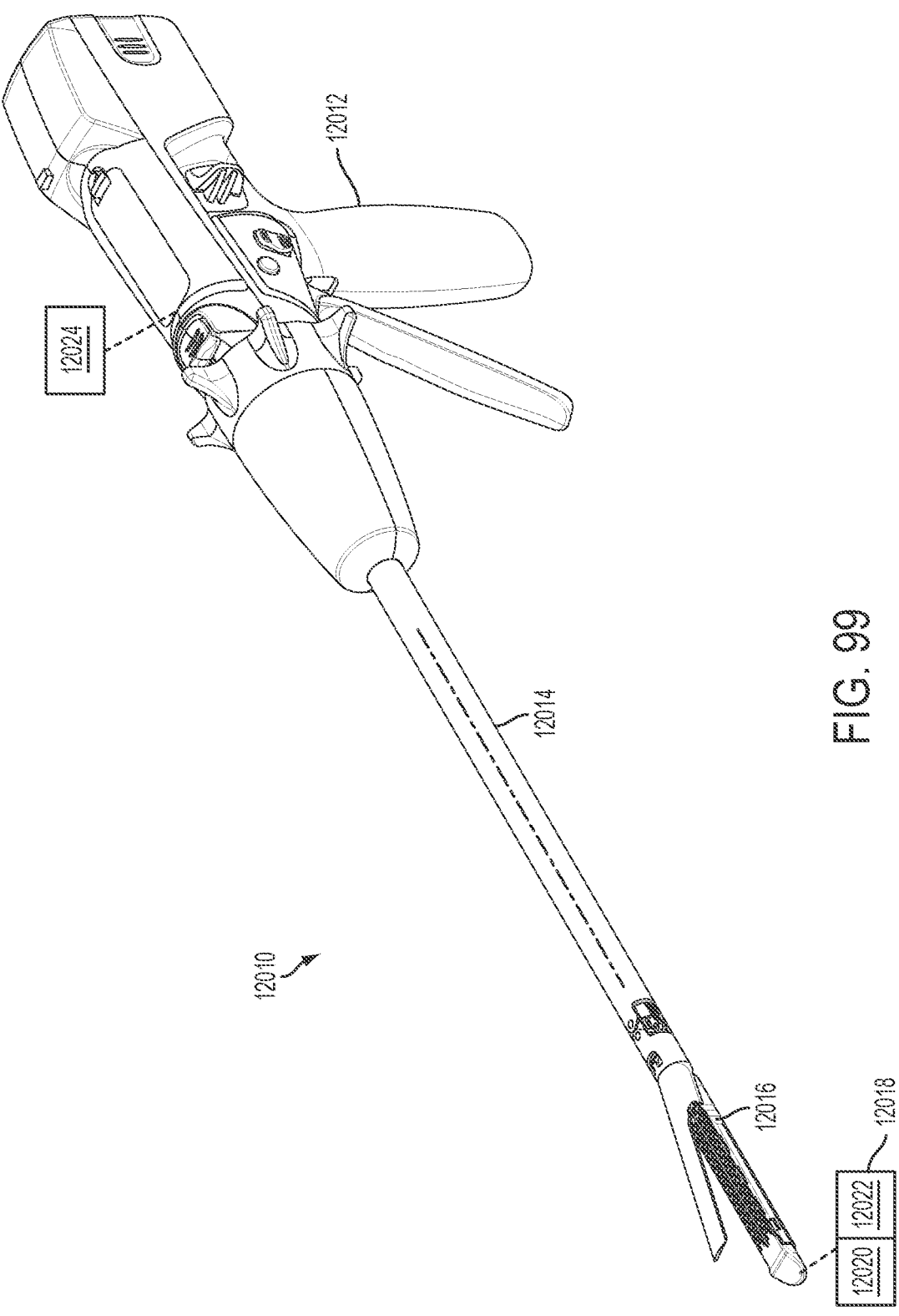
FIG. 99 depicts an example medical device that can include one or more aspects of the present disclosure.

Medical devices may be modular devices that include several separate components. For example, an endocutter such as endocutter 12010 as shown in FIG. 99 may include several large and small separate components. The endocutter 12010 is similarly constructed and equipped as the motor-driven surgical cutting and fastening instrument 10 described in connection with FIGS. 1-29. Accordingly, for conciseness and clarity the details of operation and construction will not be repeated here. Endocutter 12010 may include a handle component 12012, a shaft component 12014, and an end-effector component 12016. Each of the handle, the shaft, and the end-effector may include smaller but separate components such as sensors, transducers, motors, switches, controllers, processors etc., which may be programmable and interoperable with one another. In this way, endocutter 12010 may be a modular medical device.

In general, modular devices may have several challenges to overcome. For example, modular endocutter 12010 may require multiple wire contacts configured to transmit power and receive signals. A power source, such as a battery 90 (FIG. 4), may transfer power to one or more sensors, transducers, motors, switches, controllers, processors, or other modular components of the endocutter through various wires and wire contacts. One or more of these modular components may receive signals from one another in order to perform various calculations, processes, or actions to operate the endocutter. For example, a sensor in end-effector 12016 may be powered from a battery in handle 12012 through a wire in shaft 12014 and may send back signals or data to a microprocessor or microcontroller in handle 12012 through a different wire in shaft 12014. The shaft 12014 may be only a half inch in diameter and may have the ability to rotate, which may lead to challenges when swapping or upgrading modular components such as sensors.

In some systems, a sensor in the end-effector may send data to the handle. The data may require signal processing or other processing by one or more components in the handle in order to be used to operate the endocutter. Adding a new sensor or upgrading an existing sensor may require new wires to enable communication with the one or more components (e.g., a microprocessor) in the handle. Having to add new wires or wire contacts may negatively impact the ability to use new sensors or upgrade existing sensors and may be undesirable. The ability to upgrade the modular components (e.g., sensors) in, for example, the end-effector 12016, with new technology such as more advanced sensors, while allowing components in the handle 12012 (e.g., a microcontroller 12024) to readily accept output from the new sensors without adding new wires or new wire contacts may be desirable.

In one aspect of the present disclosure, one or more sensors in the end-effector (e.g., end-effector 12016) may have local or built-in signal processing capability. These sensors may be referred to as smart sensors. Rather than supplying the handle or one or more components therein with data that may require further processing, smart sensors with local signal processing may supply the handle with already processed data or information that can be used to operate the endocutter while minimizing or eliminating further processing.

For example, the end-effector 12016 may include a sensor 12020 and signal processing component 12022. The signal processing component 12022 may correspond to the sensor 12020 (i.e., may be configured to process data from sensor 12020). In one example, the signal processing component 12022 may be specially designed or configured to process signals or data received from the sensor 12020. Further, the signal processing component 12022 may generate processed information based on the signals or data received from sensor 12020. In this way, the signal processing component 12022 may process data received from the sensor 12020 of a surgical instrument (i.e., the endocutter 12010) locally to the sensor and into information usable by the surgical instrument.

The handle 12012 (or a component therein) may be configured to receive the processed information from the signal processing component 12022. For example, the signal processing component 12022 may transmit the processed information to handle 12012 via shaft 12014 (through, e.g., one or more wires). In this way, the processed information may be transmitted from the signal processing component 12022 to a controller 12024 (e.g., a microcontroller) of the surgical instrument (e.g., the endocutter 12010). Further, the surgical instrument (e.g., the endocutter 12010) may be controlled based on the processed information from the signal processing component 12022. For example, the end-effector 12016 may be stopped or started or a process of the endocutter 12010 may be ended based on the processed information. In one example, the controller 12024 may stop or start the end-effector based on the processed information.

The signal processing component 12022 and the sensor 12020 may be part of a single module 12018. The single module 12018 may be positioned in the end-effector 12016 and may be a modular component easily swapped into or out of the end-effector 12016. The sensor 12020 may be, for example, a magnetic field sensor, a magnetic sensor, an inductive sensor, a capacitive sensor, or another type of sensor used in medical devices or endocutters. The signal processing component 12022 may be the microcontroller 2006 (FIGS. 21A, 21B) or microcontroller 3017 (FIGS. 28A, 28B).

Figure 100:
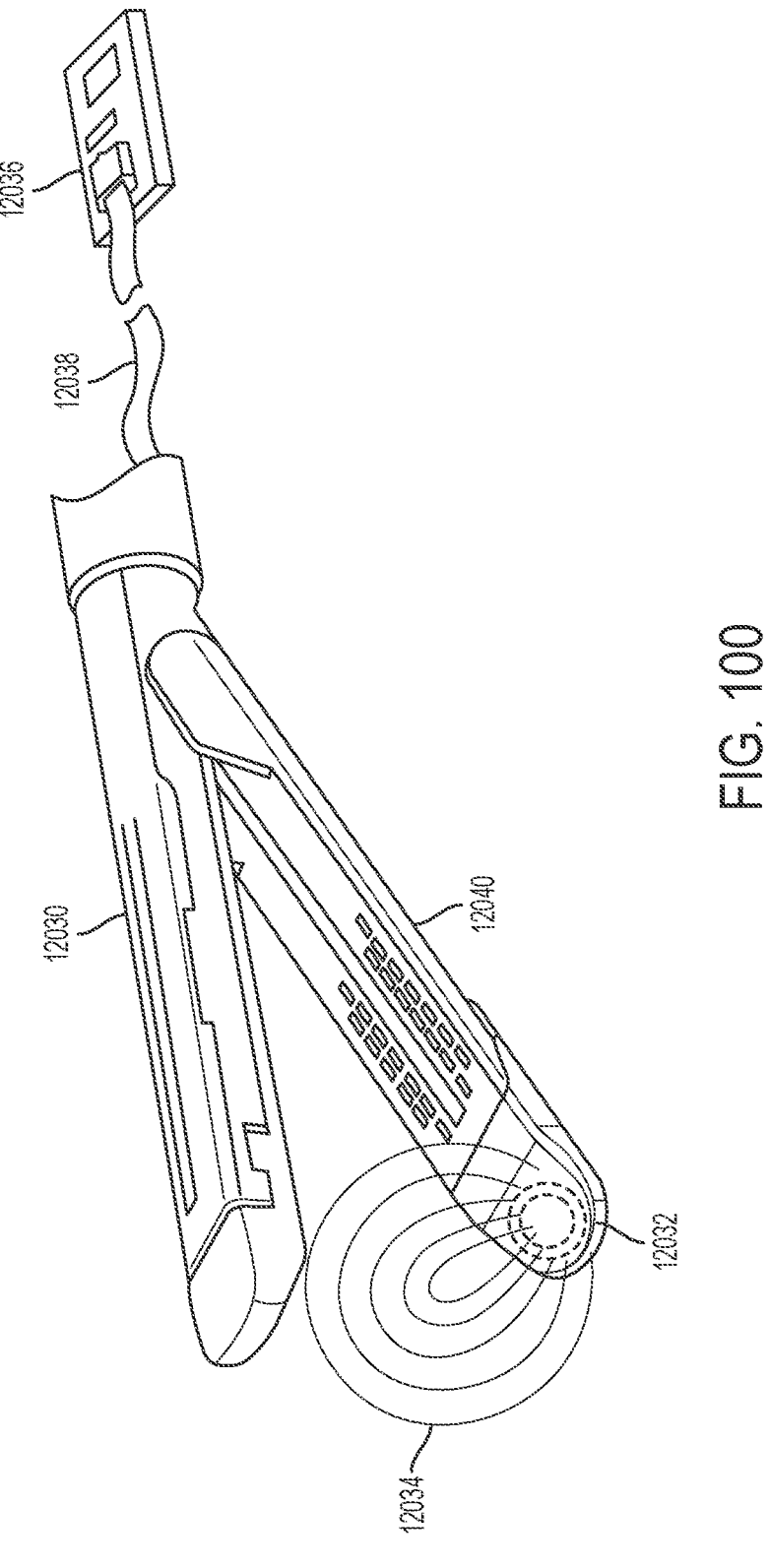
FIG. 100 depicts an example end-effector of a medical device that can include one or more aspects of the present disclosure.

In one aspect, the signal processing component may be a sensor circuit 12036 as shown in FIG. 100. The sensor circuit 12036 may be any suitable circuit configured to read signals from a sensor component such as an inductive coil 12032. The sensor circuit 12036 may be in communication with or be communicatively coupled to a sensor component in the end-effector 12030. For example, the sensor circuit 12036 may be communicatively coupled to an inductive coil 12032 via a wire or cable 12038. The inductive coil 12032 may produce a magnetic field 12034 and may be located at a distal end of an anvil 12040 of the end-effector 12030. The sensor circuit 12036 may receive data or signals from the sensor component (e.g., inductive coil 12032) and may process the data or signals to generate processed information which may be used to operate the end-effector 12030.

Figure 101:
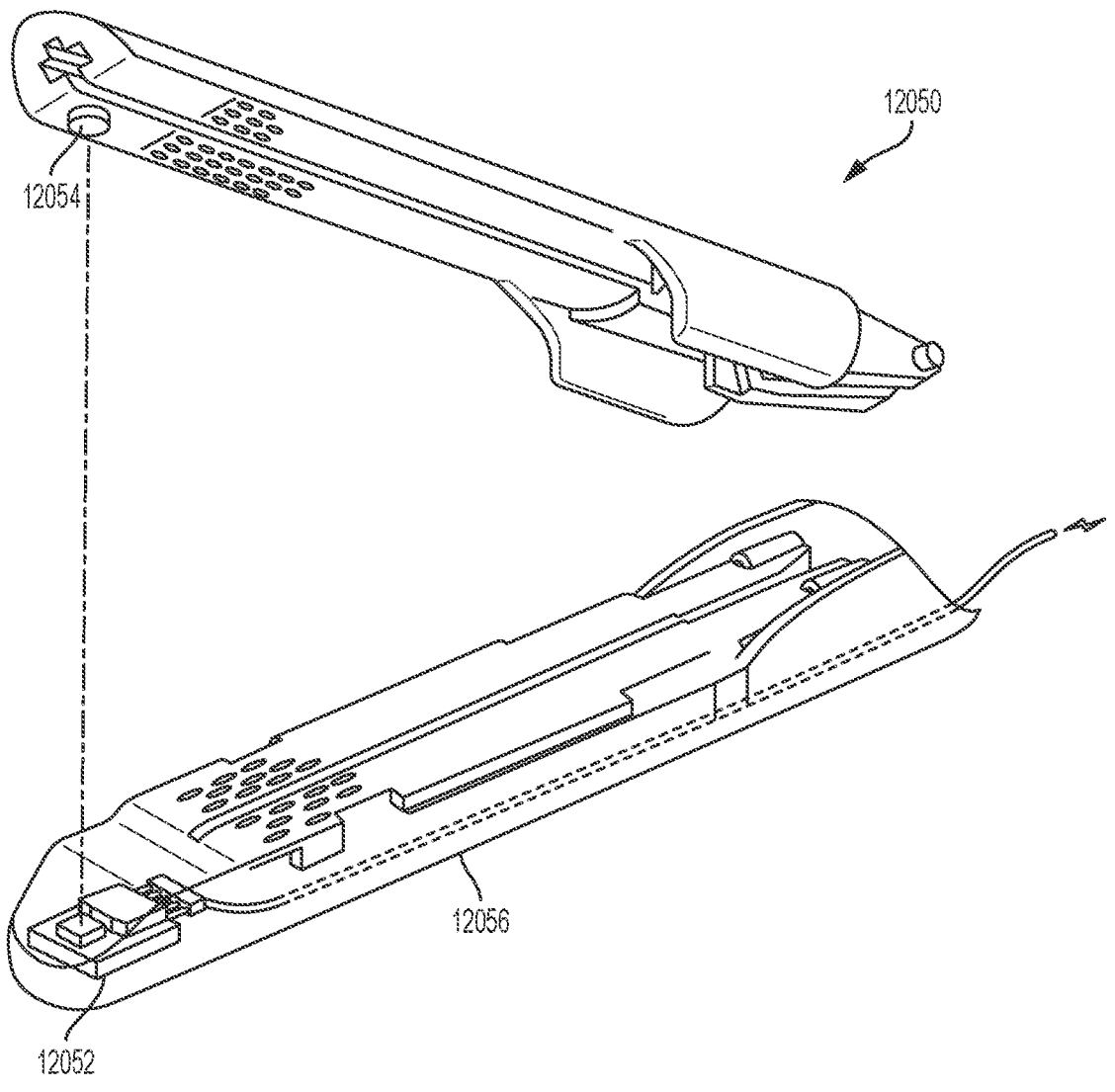
FIG. 101 also depicts an example end-effector of a medical device that can include one or more aspects of the present disclosure.
Figure 102:
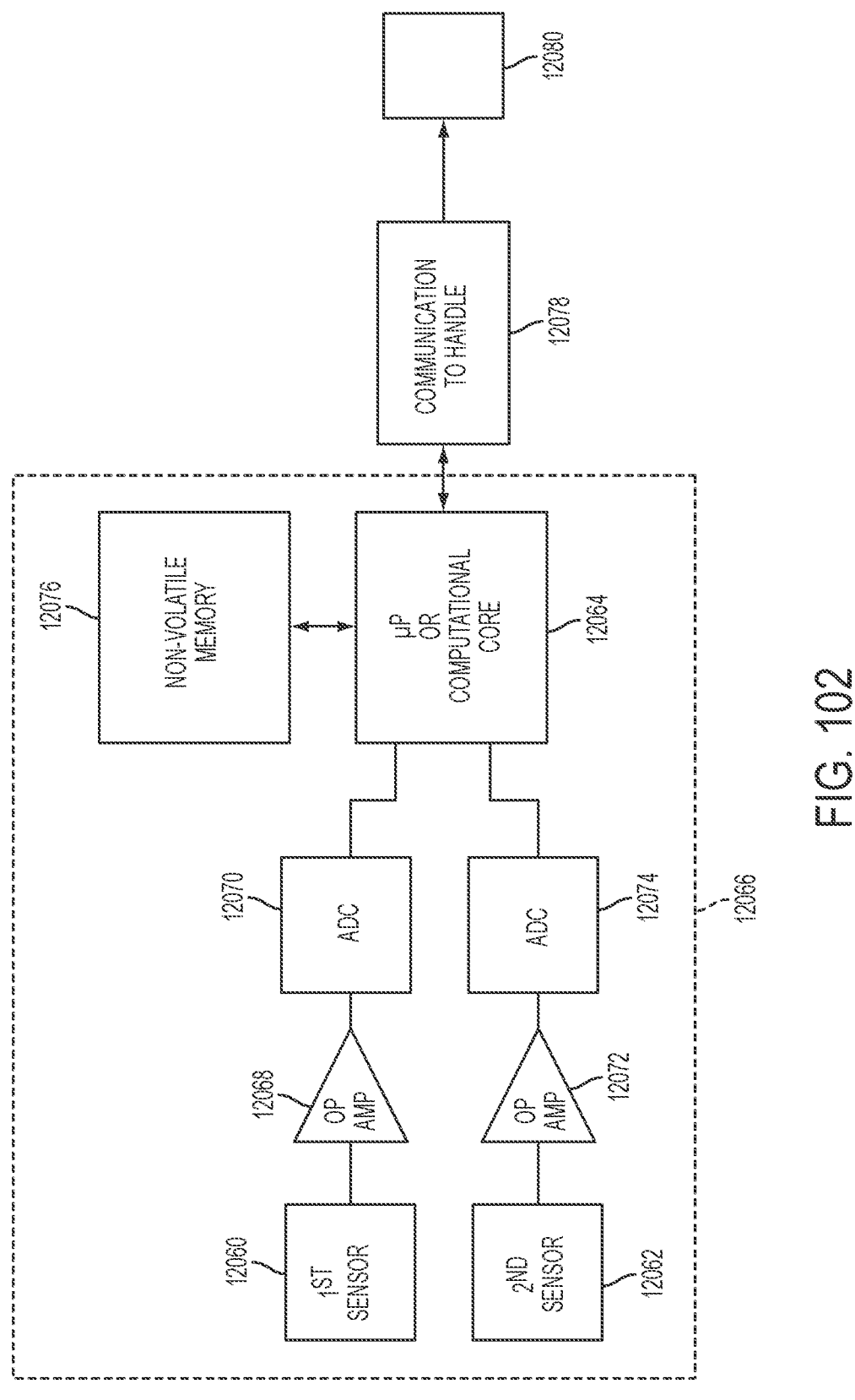
FIG. 102 is a diagram of a smart sensor component in accordance with an aspect the present disclosure.

While the sensor circuit 12036 is shown outside of the end-effector 12030 and the anvil 12040 in FIG. 100 for ease of disclosure, the sensor circuit 12036 may be local to the sensor component (e.g., inductive coil 12032) or may be part of a single module including the sensor component and the sensor circuit, such as single module 12018 of FIG. 99. For example, as shown in FIG. 101, a sensor circuit 12052 also may be positioned at a distal end of an anvil 12056 of an end-effector 12050. The sensor circuit 12052 may be local to, and in communication with, a sensing component such as magnet 12054.

Referring back to FIG. 99, the handle 12012 may include a controller 12024 which may be configured to control or otherwise operate the endocutter 12010. In one example, the controller 12012 may be a microcontroller and may be configured to receive the processed information from the signal processing component 12022 or the single module 12018. For example the shaft 12014 may be configured to communicatively couple the signal processing component 12022 of the end-effector 12016 and the handle 12012. The microcontroller 12024 in the handle 12012 may be in wired communication with the signal processing component 12022 via shaft 12014. In one example, the signal processing component 12022 may be in wireless communication with the microcontroller 12024 or with another component in handle 12012. While the controller 12024 may be configured to receive the processed information from the signal processing component 12022 or the single module 12018, this is not intended to be a limitation of the present disclosure as various other components (e.g., a microprocessor, display, interface, switch, etc.) in handle 12012 may be configured to receive the processed information from the signal processing component 12022 or the single module 12018.

In one aspect, a plurality of smart sensors may be positioned on a power line of an end-effector and may be communicatively coupled to a handle of an endocutter. The smart sensors may be positioned in series or parallel with respect to the power line. Referring now to FIG. 14, smart sensors 12060 and 12062 may be in communication with a signal processing component or a microprocessor 12064 which may be local to the smart sensors. Both the smart sensors 12060 and 12062 and the microprocessor 12064 may be located at the end-effector (represented by dashed-box 12066). For example, smart sensor 12060 may output signals or data to an operational amplifier 12068 and an ADC converter 12070, which may condition the signals or data for input into microprocessor 12064. Similarly, smart sensor 12062 may output signals or data to an operational amplifier 12072 and an ADC converter 12074, which may condition the signals or data for input into microprocessor 12064.

Smart sensors 12060 and/or 12062 may be different types of sensors or the same type of sensor, which may be, for example, magnetic field sensors, magnetic sensors, inductive sensors, capacitive sensors, or other types of sensors used in medical devices or endocutters. Component 12064, previously referred to as a microprocessor, also may be a computational core, FPGA (field programmable gate array), logic unit (e.g., logic processor or logic controller), signal processing unit, or other type of processor. The microprocessor 12064 may be in communication with a memory, such as non-volatile memory 12076, which may store calculation data, equipment information such as a type of cartridge inserted in the end-effector 12066, tabular data, or other reference data that may enable the microprocessor 12064 to process signals or data received from one or more of the smart sensors 12060 or 12062 for use in operating the end-effector 12066 or an endocutter.

Further, a shaft 12078 may include a return path through which at least one of the plurality of smart sensors (e.g., smart sensors 12060 or 12062) and the handle 12080 are communicatively coupled. The shaft may include one or more wires which may transfer information from the microprocessor 12064 to the handle 12080 for operation of the end-effector 12066 or endocutter. In one example, the information from the microprocessor 12064 may be communicated to the handle 12080 (by way of shaft 12078 or directly without use of shaft 12078) over one or more of: a wired-line, a single-wired line, a multi-wired line, a wireless communication protocol such as Bluetooth, an optical line, or an acoustic line.

In one aspect, at least one of a plurality of smart sensors positioned at an end-effector may include a signal processing component. For example, the signal processing component may be built into the smart sensor or may be locally coupled to the smart sensor as shown in single module 12018 of FIG. 99. The signal processing component may be configured to process data received from a sensor component (e.g., sensor component 12020) of at least one of the plurality of smart sensors. A controller 12024 (e.g., a microcontroller) at the handle may be communicatively coupled to at least one of the plurality of smart sensors.

In one aspect, a smart sensor may be configured for local signal processing in a medical device. The smart sensor may include at least one sensor component (e.g., sensor component 12020) and at least one processing component (e.g., processing component 12022). The processing component may be configured to receive data from the at least one sensor component and to process the data into information for use by the medical device. The medical device may be, for example, an endocutter, however this is not intended to be a limitation of the present disclosure. It should be understood that the techniques and features discussed herein for smart sensors with local signal processing may be used in any medical device where processing of sensor signals or data is used for operation of the medical device.

Further, a controller (e.g., controller 12024, microcontroller) in the medical device may be configured to receive the information (i.e., processed signals or data) from the at least one processing component (e.g., processing component 12022). As discussed above, the medical device may be a surgical instrument such as an endocutter and the smart sensor may be configured for local signal processing in the surgical instrument. Local signal processing may refer to, for example, processing signals or data from a sensor component at a processing component coupled to the sensor, where the resulting processed information may be used by a separate component. For example, the controller 12024 may be positioned in the handle 12012 of the surgical instrument (i.e., the endocutter 12010) and the smart sensor may be configured to be positioned in a separate component (i.e., the end-effector 12016) of the surgical instrument (i.e., the endocutter 12010), separate from the handle 12012. Thus, the controller 12024 may be positioned at the handle 12012 of the surgical instrument and the signal processing component 12022 and the sensor 12020 may be located in a component separate from the handle 12012 (e.g., end-effector 12016).

In this way, the handle or controller 12024 need not have information about the smart sensor, knowledge of what the smart sensor is doing, or capability to interpret data feed back from the smart sensor. This is because the processing component 12022 may transform or condition the data from the smart sensor and generate information from the data directly usable by the handle or controller 12024. The information generated by the processing component may be used directly, without the data from the smart sensor needing to be processed in another part of the medical device (e.g., near the handle 12012 or controller 12024). Thus, the surgical instrument may be controlled based on the (processed) information from the signal processing component local to the sensor.

In one aspect, a current draw on a power line communicatively coupled to the signal processing component 12022 (i.e., local to the sensor 12020) may be monitored. The current draw may be monitored by a microprocessor or other monitoring device at the shaft 12014 or the handle 12012, or at another microprocessor or other monitoring device separate from the signal processing component 12022. For example, the monitoring may be a standard Morse Code type monitoring of the current draw on the power line. An issue with the surgical instrument based on the current draw and a particular sensor may be determined by the separate microprocessor at, e.g., the handle 12012. In this way, the monitoring may allow the handle (or a processor or controller therein) to be informed of various issues related to signals or data received by one or more sensor and which particular sensor identified the issue, without a further communication requirement (e.g., pairing, or other coupled communication).

Figure 103:
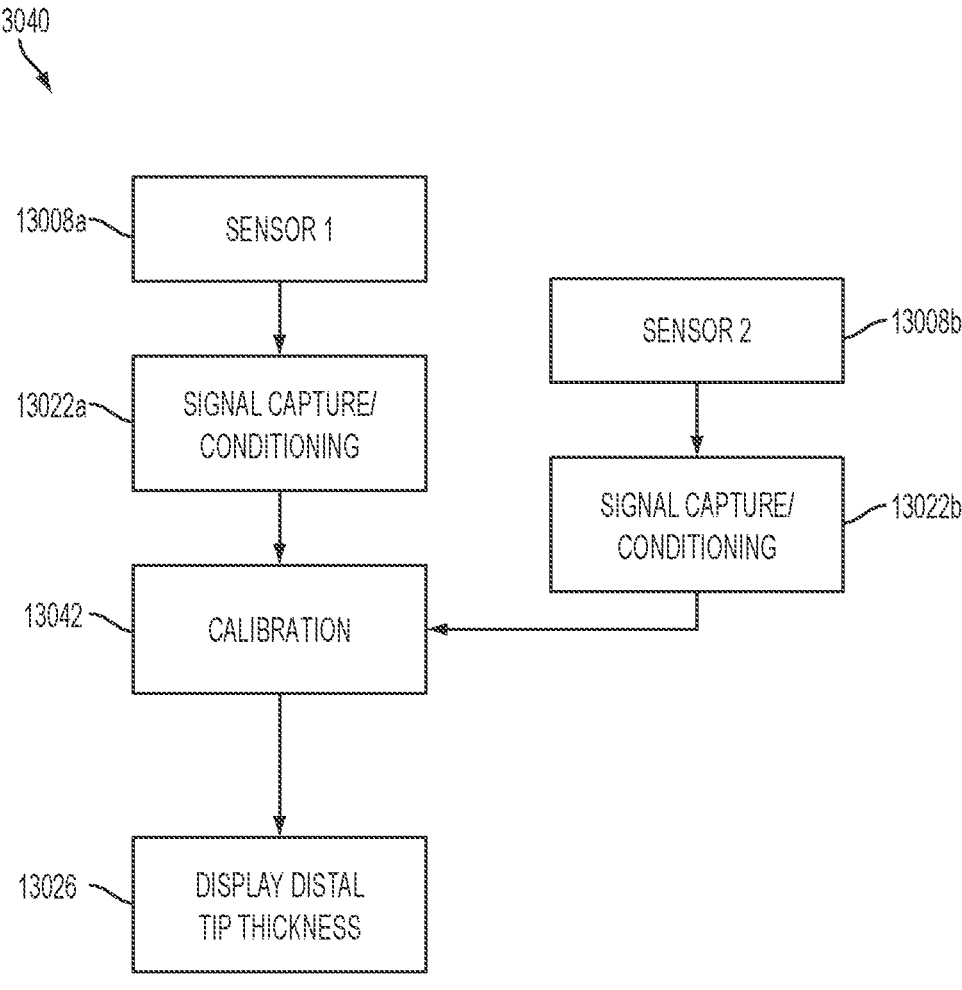
FIG. 103 is a logic diagram illustrating one aspect of a process for calibrating a first sensor in response to an input from a second sensor.

Turning now to FIG. 103, which is a logic diagram illustrating one aspect of a process 13040 for calibrating a first sensor 13008a in response to an input from a second sensor 13008b. The first sensor 13008a is configured to capture 13022a a signal indicative of one or more parameters of the end effector 13000. The first signal 13022a may be conditioned based on one or more predetermined parameters, such as, for example, a smoothing function, a look-up table, and/or any other suitable conditioning parameters. A second signal is captured 13022b by the second sensor 13008b. The second signal 13022b may be conditioned based on one or more predetermined conditioning parameters. The first signal 13022a and the second signal 13022b are provided to a processor, such as, for example, the primary processor 2006 (FIGS. 21A-21B). The primary processor 2006 calibrates 13042 the first signal 13022a in response to the second signal 13022b. The first signal 13022a is calibrated 13042 to reflect the fullness of the bite of tissue in the end effector 13000. The calibrated signal is displayed 13026 to an operator by, for example, a display 12026 embedded in the surgical instrument 10 (FIGS. 1-6).

Figure 104:
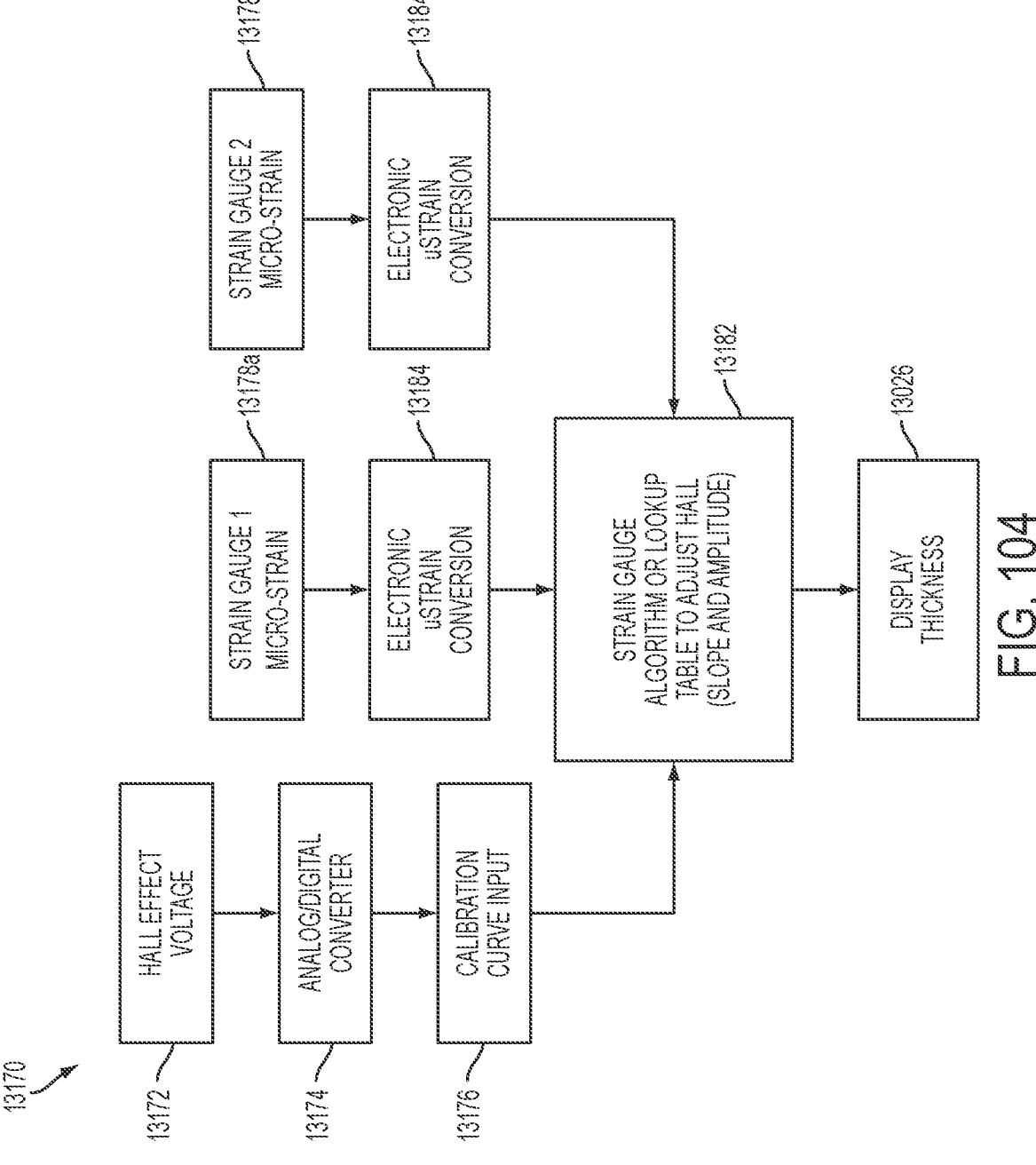
FIG. 104 is a logic diagram illustrating one aspect of a process for adjusting a measurement of a first sensor in response to a plurality of secondary sensors.

FIG. 104 is a logic diagram illustrating one aspect of a process 13170 for adjusting a measurement of a first sensor 13158 in response to a plurality of secondary sensors 13160a, 13160. In one example, a Hall effect voltage is obtained 13172, for example, by a magnetic field sensor. The Hall effect voltage is converted 13174 by an analog to digital convertor. The converted Hall effect voltage signal is calibrated 13176. The calibrated curve represents the thickness of a tissue section located between the anvil 13152 and the staple cartridge 13156. A plurality of secondary measurements are obtained 13178a, 13178b by a plurality of secondary sensors, such as, for example, a plurality of strain gauges. The input of the strain gauges is converted 13180a, 13180b into one or more digital signals, for example, by a plurality of electronic μStrain conversion circuits. The calibrated Hall effect voltage and the plurality of secondary measurements are provided to a processor, such as, for example, the primary processor 2006 (FIGS. 21A-21B). The primary processor utilizes the secondary measurements to adjust 13182 the Hall effect voltage, for example, by applying an algorithm and/or utilizing one or more look-up tables. The adjusted Hall effect voltage represents the true thickness and fullness of the bite of tissue clamped by the anvil 13152 and the staple cartridge 13156. The adjusted thickness is displayed 13026 to an operator by, for example, a display 12026 embedded in the surgical instrument 10 (FIGS. 1-6).

Figure 105:
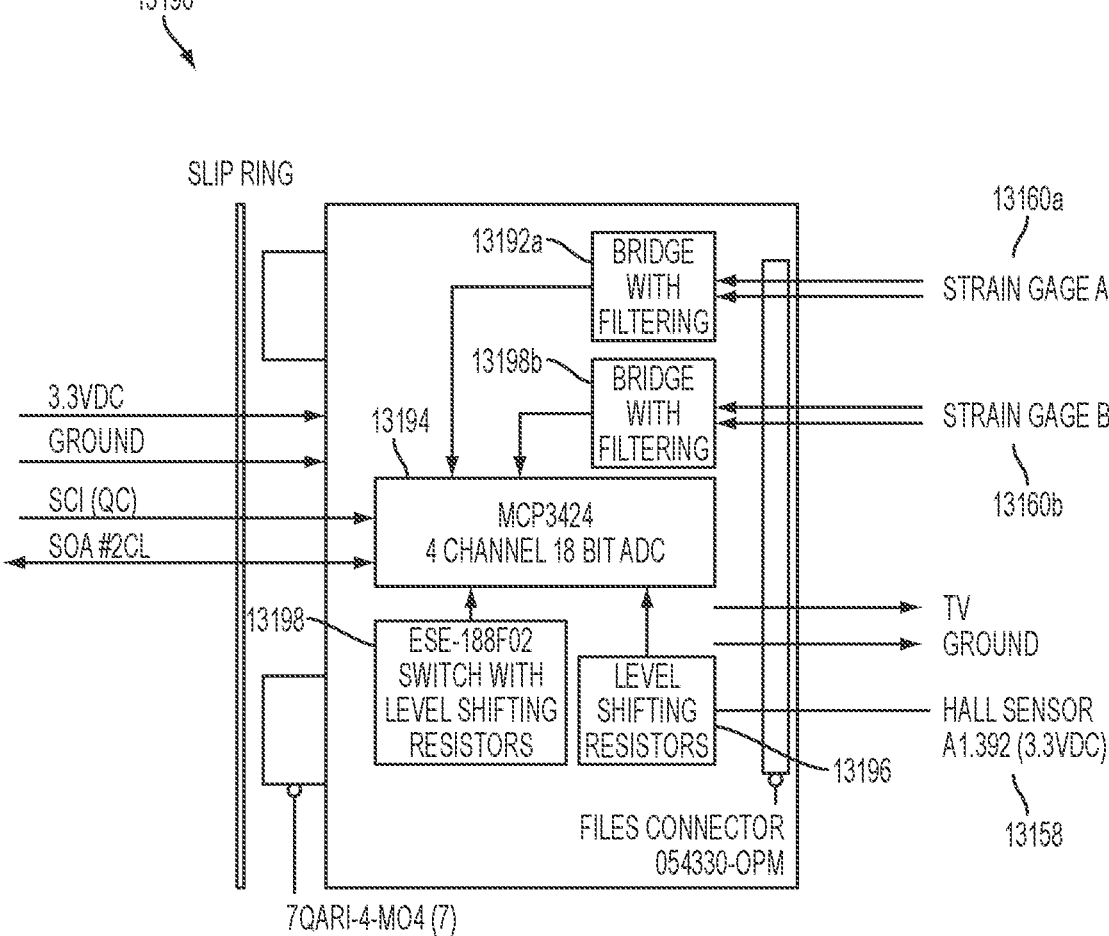
FIG. 105 illustrates one aspect of a circuit configured to convert signals from a first sensor and a plurality of secondary sensors into digital signals receivable by a processor.

FIG. 105 illustrates one aspect of a circuit 13190 configured to convert signals from the first sensor 13158 and the plurality of secondary sensors 13160a, 13160b into digital signals receivable by a processor, such as, for example, the primary processor 2006 (FIGS. 21A-21B). The circuit 13190 comprises an analog-to-digital convertor 13194. In some examples, the analog-to-digital convertor 13194 comprises a 4-channel, 18-bit analog to digital convertor. Those skilled in the art will recognize that the analog-to-digital convertor 13194 may comprise any suitable number of channels and/or bits to convert one or more inputs from analog to digital signals. The circuit 13190 comprises one or more level shifting resistors 13196 configured to receive an input from the first sensor 13158, such as, for example, a magnetic field sensor. The level shifting resistors 13196 adjust the input from the first sensor, shifting the value to a higher or lower voltage depending on the input. The level shifting resistors 13196 provide the level-shifted input from the first sensor 13158 to the analog-to-digital convertor.

In some aspects, a plurality of secondary sensors 13160a, 13160b are coupled to a plurality of bridges 13192a, 13192b within the circuit 13190. The plurality of bridges 13192a, 13192b may provide filtering of the input from the plurality of secondary sensors 13160a, 13160b. After filtering the input signals, the plurality of bridges 13192a, 13192b provide the inputs from the plurality of secondary sensors 13160a, 13160b to the analog-to-digital convertor 13194. In some examples, a switch 13198 coupled to one or more level shifting resistors may be coupled to the analog-to-digital convertor 13194. The switch 13198 is configured to calibrate one or more of the input signals, such as, for example, an input from a magnetic field sensor. The switch 13198 may be engaged to provide one or more level shifting signals to adjust the input of one or more of the sensors, such as, for example, to calibrate the input of a magnetic field sensor. In some examples, the adjustment is not necessary, and the switch 13198 is left in the open position to decouple the level shifting resistors. The switch 13198 is coupled to the analog-to-digital convertor 13194. The analog-to-digital convertor 13194 provides an output to one or more processors, such as, for example, the primary processor 2006 (FIGS. 21A-21B). The primary processor 2006 calculates one or more parameters of the end effector 13150 based on the input from the analog-to-digital convertor 13194. For example, in one example, the primary processor 2006 calculates a thickness of tissue located between the anvil 13152 and the staple cartridge 13156 based on input from one or more sensors 13158, 13160a, 13160b.

Figure 106:
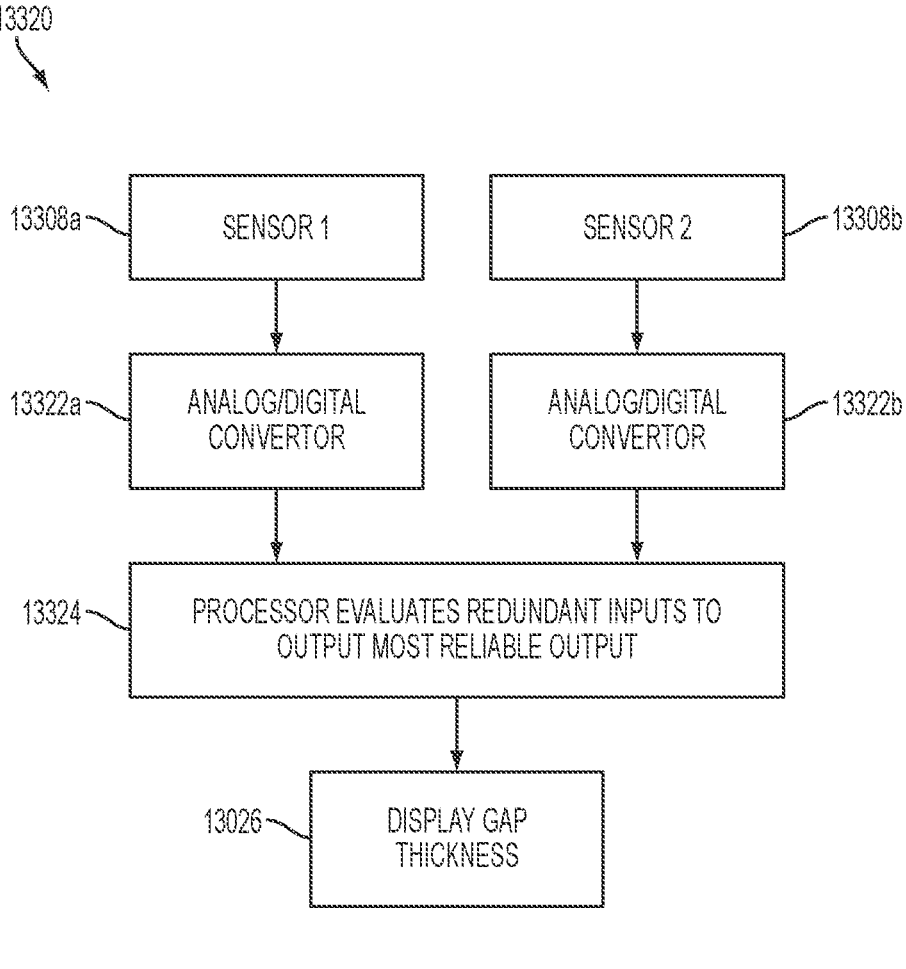
FIG. 106 is a logic diagram illustrating one aspect of a process for selecting the most reliable output from a plurality of redundant sensors.

FIG. 106 is a logic diagram illustrating one aspect of a process 13320 for selecting the most reliable output from a plurality of redundant sensors, such as, for example, the plurality of sensors 13308a, 13308b. In one example, a first signal is generated by a first sensor 13308a. The first signal is converted 13322a by an analog-to-digital convertor. One or more additional signals are generated by one or more redundant sensors 13308b. The one or more additional signals are converted 13322b by an analog-to-digital convertor. The converted signals are provided to a processor, such as, for example, the primary processor 2006 (FIGS. 21A-21B). The primary processor 2006 evaluates 13324 the redundant inputs to determine the most reliable output. The most reliable output may be selected based on one or more parameters, such as, for example, algorithms, look-up tables, input from additional sensors, and/or instrument conditions. After selecting the most reliable output, the processor may adjust the output based on one or more additional sensors to reflect, for example, the true thickness and bite of a tissue section located between the anvil 13302 and the staple cartridge 13306. The adjusted most reliable output is displayed 13026 to an operator by, for example, a display 2026 embedded in the surgical instrument 10 (FIGS. 1-6).

Figure 107:
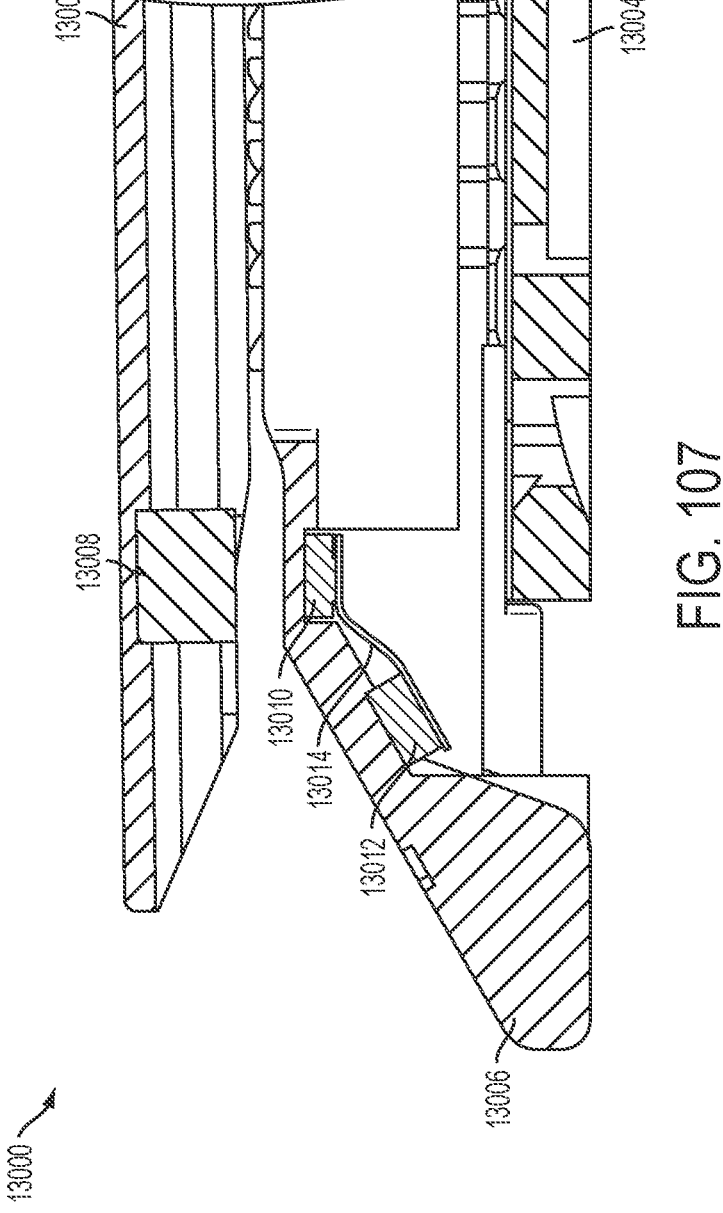
FIG. 107 illustrates a sideways cross-sectional view of one aspect of an end effector comprising a magnet and a magnetic field sensor in communication with processor.

FIG. 107 illustrates one aspect of an end effector 13000 comprising a magnet 13008 and a magnetic field sensor 13010 in communication with a processor 13012. The end effector 13000 is similar to the end effector 300 (FIG. 1) described above in connection with surgical instrument 10 (FIGS. 1-6). The end effector 13000 comprises a first jaw member, or anvil 13002, pivotally coupled to a second jaw member, or elongated channel 13004. The elongated channel 13004 is configured to operably support a staple cartridge 13006 therein. The staple cartridge 13006 is similar to the staple cartridge 304 (FIG. 1) described above in connection with surgical instrument 10 (FIGS. 1-6). The anvil 13008 comprises a magnet 13008. The staple cartridge comprises a magnetic field sensor 13010 and a processor 13012. The magnetic field sensor 13010 is operable to communicate with the processor 13012 through a conductive coupling 13014. The magnetic field sensor 13010 is positioned within the staple cartridge 13006 to operatively couple with the magnet 13008 when the anvil 13002 is in a closed position. The magnetic field sensor 13010 can be configured to detect changes in the magnetic field surrounding the magnetic field sensor 13010 caused by the movement of or location of magnet 13008.

Figures 108, 109, 110:
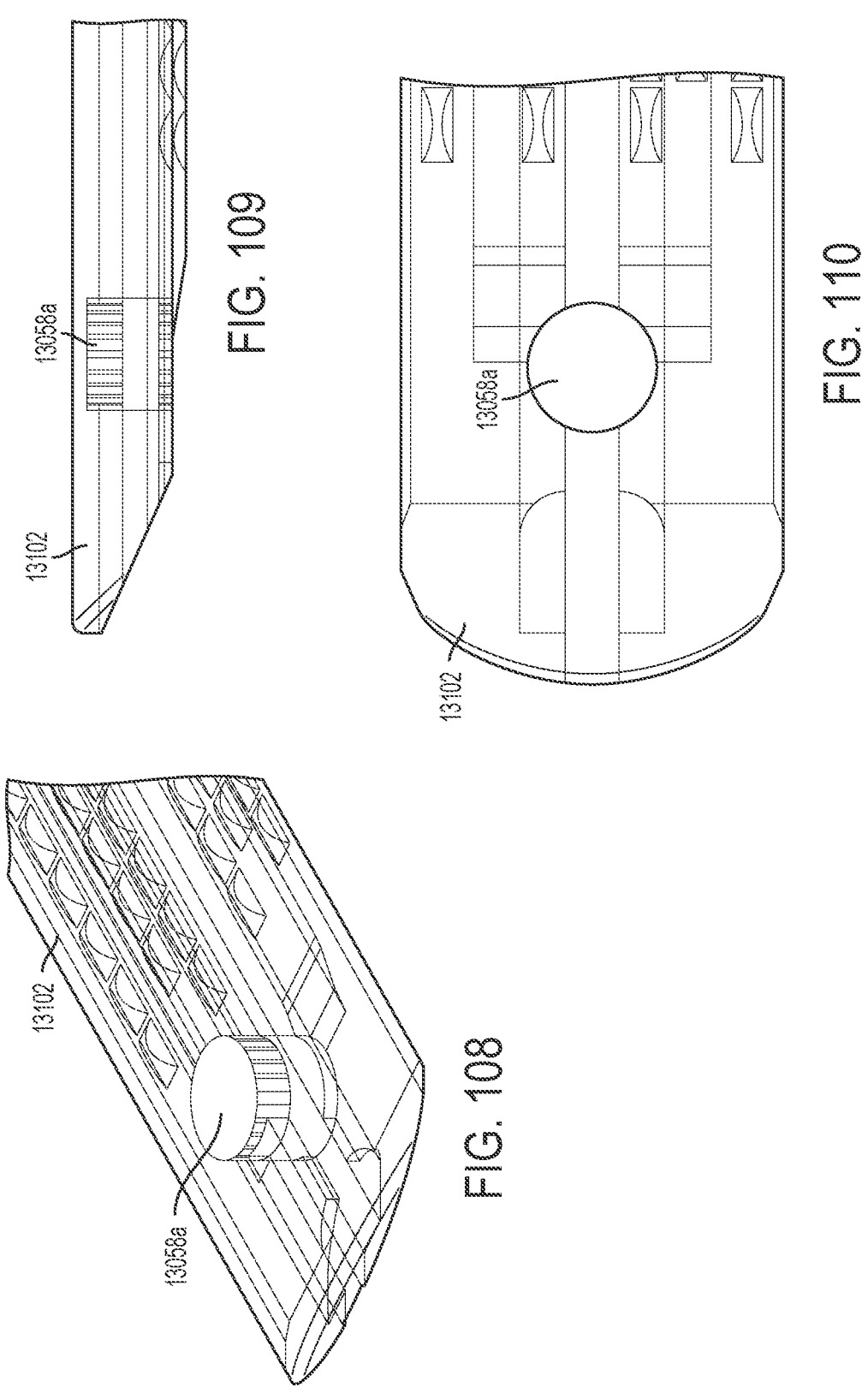
FIGS. 108-110 illustrate one aspect of an end effector that comprises a magnet where

FIGS. 108-110 illustrate one aspect of an end effector that comprises a magnet where FIG. 108 illustrates a perspective cutaway view of the anvil 13102 and the magnet 13058a, in an optional location. FIG. 109 illustrates a side cutaway view of the anvil 13102 and the magnet 13058a, in an optional location. FIG. 110 illustrates a top cutaway view of the anvil 13102 and the magnet 13058a, in an optional location.

Figure 111:
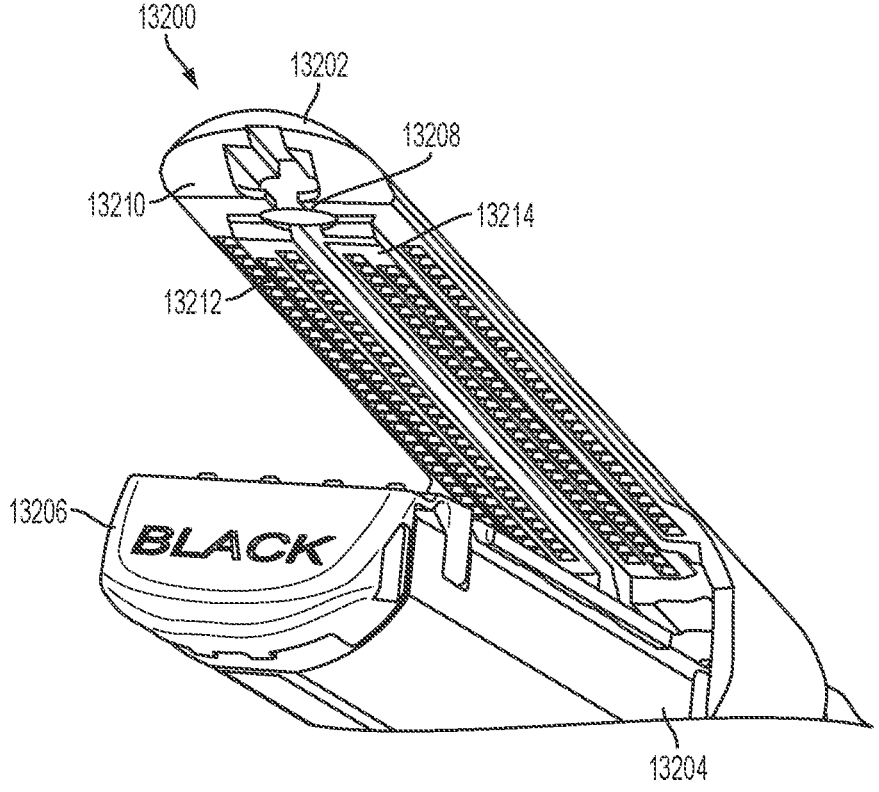
FIG. 111 illustrates one aspect of an end effector that is operable to use conductive surfaces at the distal contact point to create an electrical connection.

FIG. 111 illustrates one aspect of an end effector 13200 that is operable to use conductive surfaces at the distal contact point to create an electrical connection. The end effector 13200 is similar to the end effector 300 (FIG. 1) described above in connection with surgical instrument 10 (FIGS. 1-6). The end effector 13200 comprises an anvil 13202, an elongated channel 13204, and a staple cartridge 13206. The anvil 13202 further comprises a magnet 13208 and an inside surface 13210, which further comprises a number of staple-forming indents 13212. In some examples, the inside surface 13210 of the anvil 13202 further comprises a first conductive surface 13214 surrounding the staple-forming indents 13212. The first conductive surface 13214 can come into contact with second conductive surfaces 13222 on the staple cartridge 13206. The cartridge body comprises a number of staple cavities designed to hold staples (not pictured). In some examples the staple cavities further comprise staple cavity extensions that protrude above the surface of the cartridge body. The staple cavity extensions can be coated with the second conductive surfaces. Because the staple cavity extensions protrude above the surface of the cartridge body, the second conductive surfaces will come into contact with the first conductive surfaces 13214 when the anvil 13202 is in a closed position. In this manner the anvil 13202 can form an electrical contact with the staple cartridge 13206.

Figure 112:
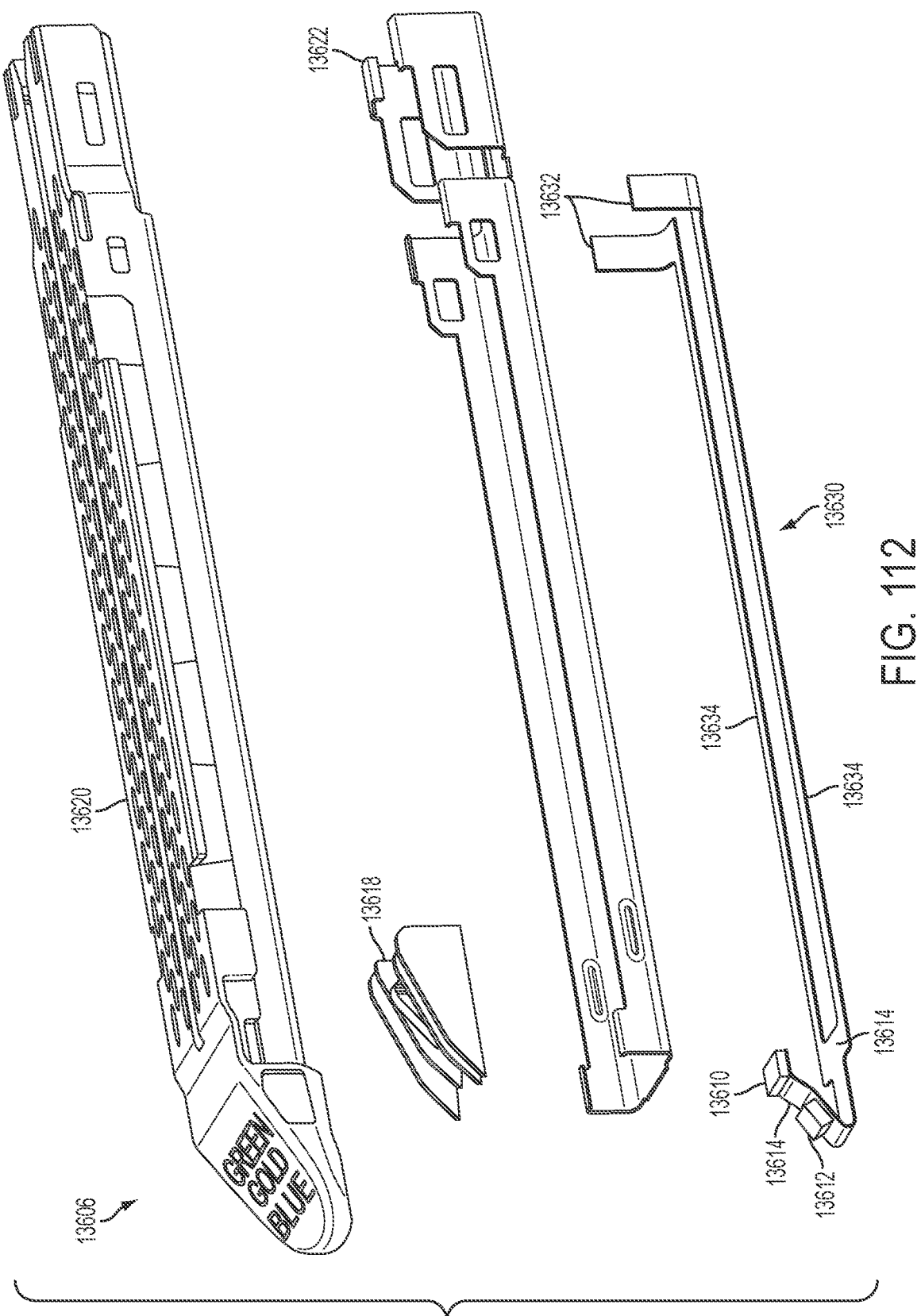
FIG. 112 illustrates one aspect of an exploded view of a staple cartridge that comprises a flex cable connected to a magnetic field sensor and processor.

FIG. 112 illustrates one aspect of a staple cartridge 13606 that comprises a flex cable 13630 connected to a magnetic field sensor 13610 and processor 13612. The staple cartridge 13606 is similar to the staple cartridge 13606 is similar to the staple cartridge 306 (FIG. 1) described above in connection with surgical instrument 10 (FIGS. 1-6). FIG. 112 is an exploded view of the staple cartridge 13606. The staple cartridge comprises 13606 a cartridge body 13620, a wedge sled 13618, a cartridge tray 13622, and a flex cable 13630. The flex cable 13630 further comprises electrical contacts 13632 at the proximal end of the staple cartridge 13606, placed to make an electrical connection when the staple cartridge 13606 is operatively coupled with an end effector, such as end effector 13800 described below. The electrical contacts 13632 are integrated with cable traces 13634, which extend along some of the length of the staple cartridge 13606. The cable traces 13634 connect 13636 near the distal end of the staple cartridge 13606 and this connection 13636 joins with a conductive coupling 13614. A magnetic field sensor 13610 and a processor 13612 are operatively coupled to the conductive coupling 13614 such that the magnetic field sensor 13610 and the processor 13612 are able to communicate.

Figures 113, 114, 115, 116:
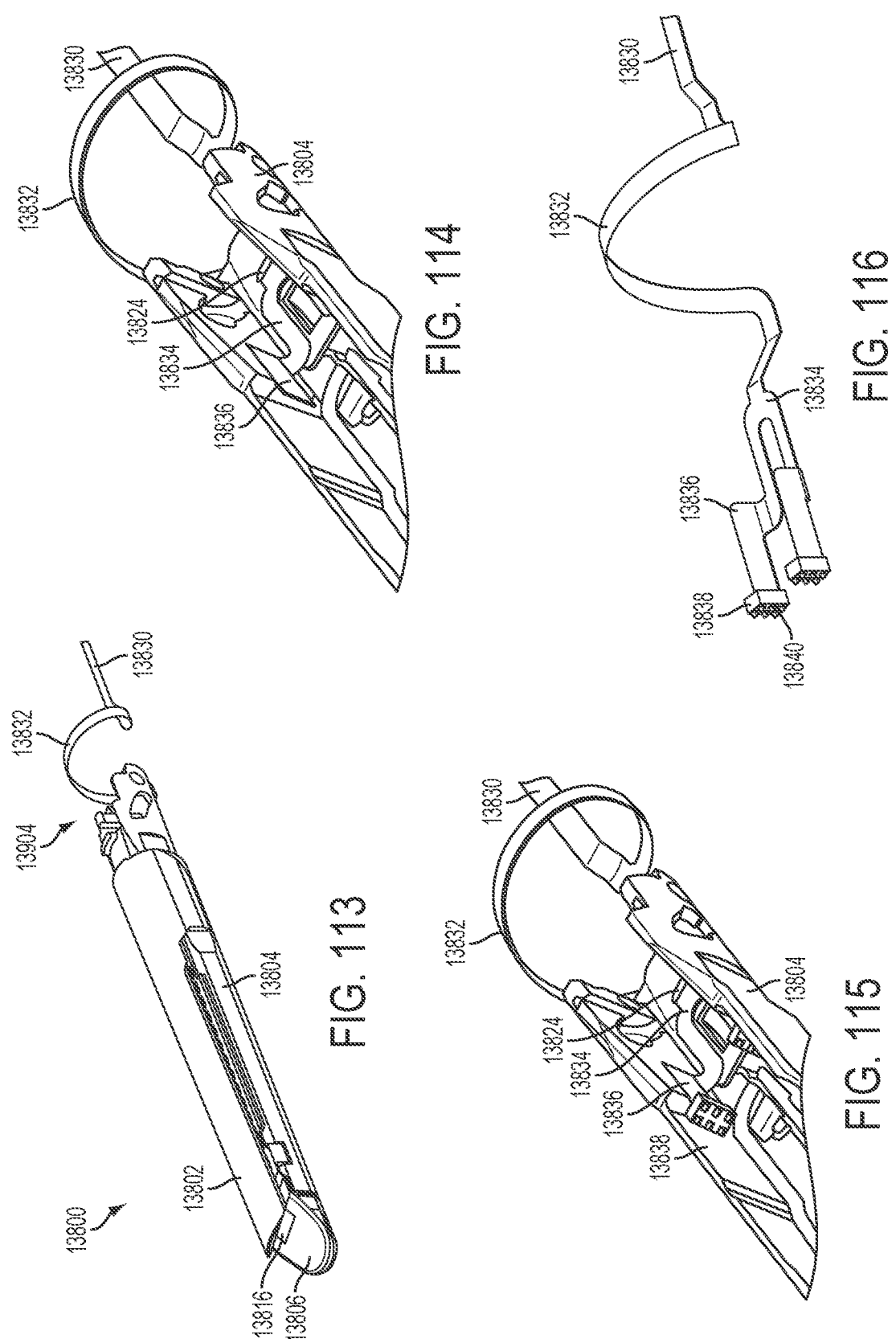
FIG. 113 illustrates the end effector shown in FIG. 112 with a flex cable and without the shaft assembly.
FIGS. 114 and 115 illustrate an elongated channel portion of an end effector without the anvil or the staple cartridge, to illustrate how the flex cable shown in FIG. 113 can be seated within the elongated channel.
FIG. 116 illustrates a flex cable, shown in FIGS. 113-115, alone.

FIG. 113 illustrates one aspect of an end effector 13800 with a flex cable 13830 operable to provide power to a staple cartridge 13806 that comprises a distal sensor plug 13816. The end effector 13800 is similar to the end effector 300 (FIG. 1) described above in connection with surgical instrument 10 (FIGS. 1-6). The end effector 13800 comprises a first jaw member or anvil 13802, a second jaw member or elongated channel 13804, and a staple cartridge 13806 operatively coupled to the elongated channel 13804. The end effector 13800 is operatively coupled to a shaft assembly. The shaft assembly is similar to shaft assembly 200 (FIG. 1) described above in connection with surgical instrument 10 (FIGS. 1-6). The shaft assembly further comprises a closure tube that encloses the exterior of the shaft assembly. In some examples the shaft assembly further comprises an articulation joint 13904, which includes a double pivot closure sleeve assembly. The double pivot closure sleeve assembly includes an end effector closure sleeve assembly that is operable to couple with the end effector 13800.

FIGS. 114 and 115 illustrate the elongated channel 13804 portion of the end effector 13800 without the anvil 13802 or the staple cartridge, to illustrate how the flex cable 13830 can be seated within the elongated channel 13804. In some examples, the elongated channel 13804 further comprises a third aperture 13824 for receiving the flex cable 13830. Within the body of the elongated channel 13804 the flex cable splits 13834 to form extensions 13836 on either side of the elongated channel 13804. FIG. 115 further illustrates that connectors 13838 can be operatively coupled to the flex cable extensions 13836.

FIG. 116 illustrates the flex cable 13830 alone. As illustrated, the flex cable 13830 comprises a single coil 13832 operative to wrap around the articulation joint 13904 (FIG. 113), and a split 13834 that attaches to extensions 13836. The extensions can be coupled to connectors 13838 that have on their distal facing surfaces prongs 13840 for coupling to the staple cartridge 13806, as described below.

Figure 117:
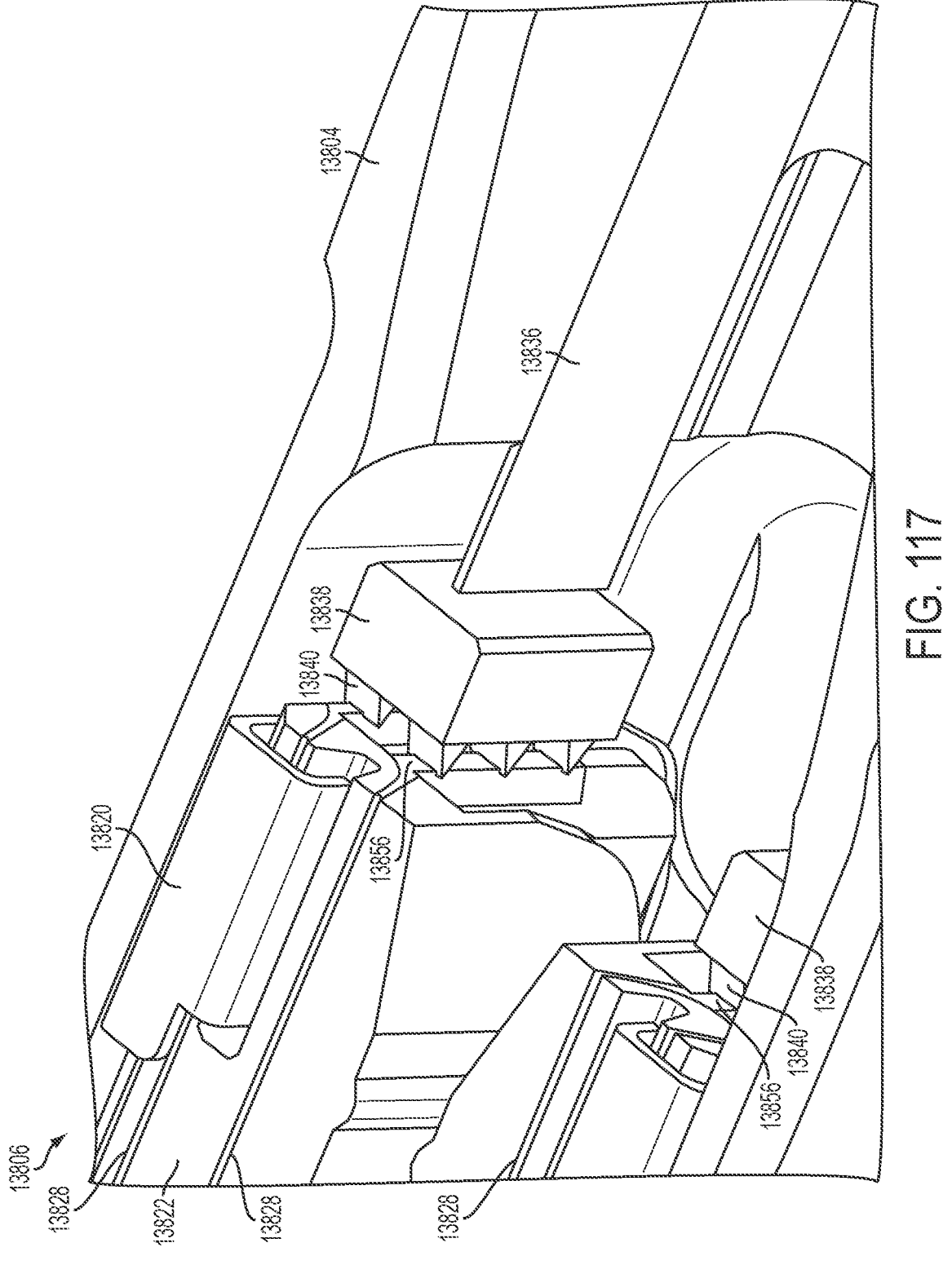
FIG. 117 illustrates a close up view of the elongated channel shown in FIGS. 114 and 115 with a staple cartridge coupled thereto.

FIG. 117 illustrates a close up view of the elongated channel 13804 shown in FIGS. 114 and 115 with a staple cartridge 13804 coupled thereto. The staple cartridge 13804 comprises a cartridge body 13822 and a cartridge tray

13820. In some examples the staple cartridge 13806 further comprises electrical traces 13828 that are coupled to proximal contacts 13856 at the proximal end of the staple cartridge 13806. The proximal contacts 13856 can be positioned to form a conductive connection with the prongs 13840 of the connectors 13838 that are coupled to the flex cable extensions 13836. Thus, when the staple cartridge 13806 is operatively coupled with the elongated channel 13804, the flex cable 13830, through the connectors 13838 and the connector prongs 13840, can provide power to the staple cartridge 13806.

Figure 118:
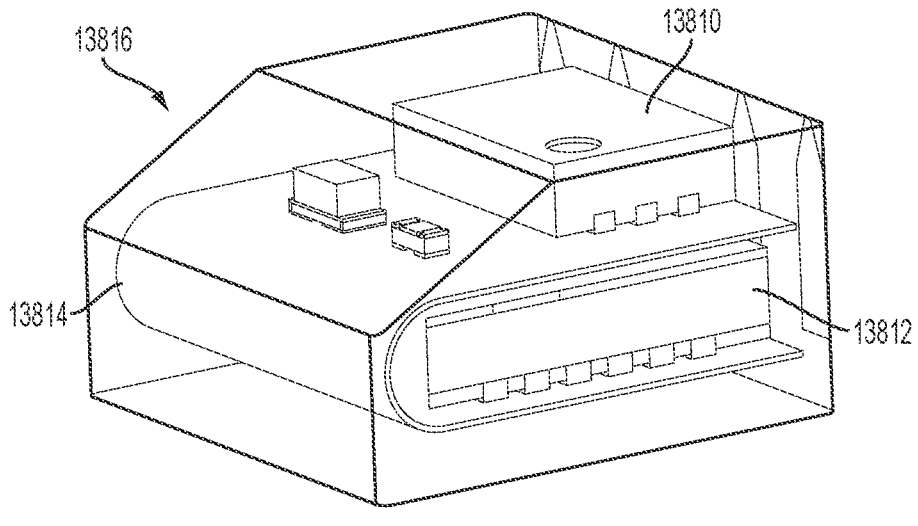
FIGS. 118 and 119 illustrate one aspect of a distal sensor plug where
Figure 119:
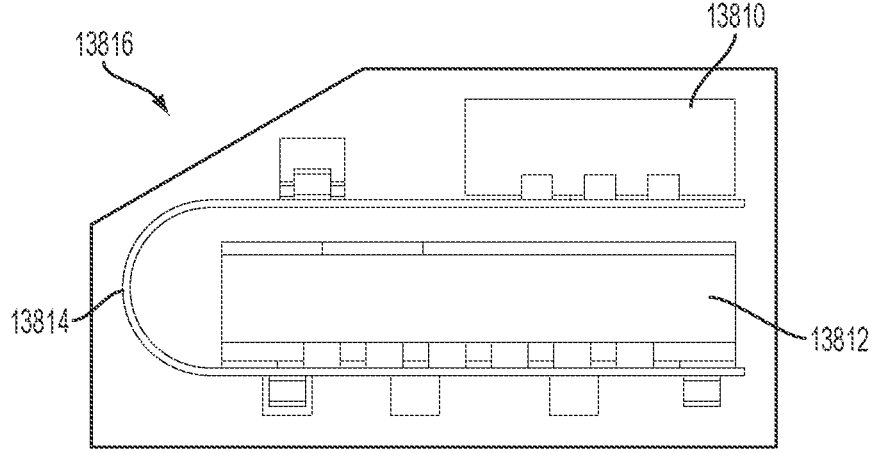

FIGS. 118 and 119 illustrate one aspect of a distal sensor plug 13816. FIG. 118 illustrates a cutaway view of the distal sensor plug 13816. As illustrated, the distal sensor plug 13816 comprises a magnetic field sensor 13810 and a processor 13812. The distal sensor plug 13816 further comprises a flex board 13814. As further illustrated in FIG. 119, the magnetic field sensor 13810 and the processor 13812 are operatively coupled to the flex board 13814 such that they are capable of communicating.

Figure 120:
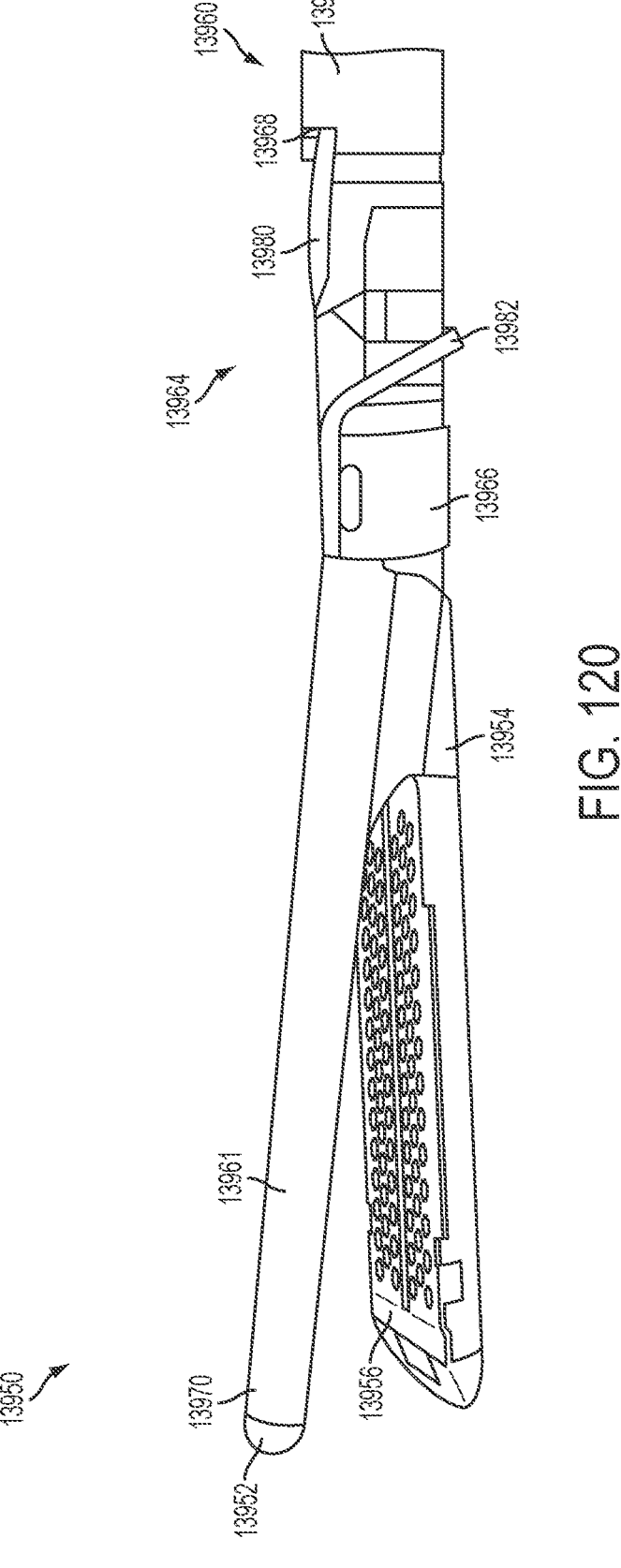

FIG. 120 illustrates one aspect of an end effector 13950 with a flex cable 13980 operable to provide power to sensors and electronics in the distal tip 13952 of the anvil 13961 portion. The end effector 13950 comprises a first jaw member or anvil 13961, a second jaw member or elongated channel 13954, and a staple cartridge 13956 operatively coupled to the elongated channel. The end effector 13950 is operatively coupled to a shaft assembly 13960. The shaft assembly 13960 further comprises a closure tube 13962 that encloses the shaft assembly 13960. In some examples the shaft assembly 13960 further comprises an articulation joint 13964, which includes a double pivot closure sleeve assembly 13966.

In various aspects, the end effector 13950 further comprises a flex cable 13980 that is configured to not interfere with the function of the articulation joint 13964. In some examples, the closure tube 13962 comprises a first aperture 13968 through which the flex cable 13980 can extend. In some examples, flex cable 13980 further comprises a loop or coil 13982 that wraps around the articulation joint 13964 such that the flex cable 13980 does not interfere with the operation of the articulation joint 13964, as further described below. In some examples, the flex cable 13980 extends along the length of the anvil 13961 to a second aperture 13970 in the distal tip of the anvil 13961.

FIGS. 121-123 illustrate the operation of the articulation joint 13964 and flex cable 13980 of the end effector 13950. FIG. 121 illustrates a top view of the end effector 13952 with the end effector 13950 pivoted −45 degrees with respect to the shaft assembly 13960. As illustrated, the coil 13982 of the flex cable 13980 flexes with the articulation joint 13964 such that the flex cable 13980 does not interfere with the operation of the articulation joint 13964. FIG. 122 illustrates a top view of the end effector 13950. As illustrated, the coil 13982 wraps around the articulation joint 13964 once. FIG. 123 illustrates a top view of the end effector 13950 with the end effector 13950 pivoted +45 degrees with respect to the shaft assembly 13960. As illustrated, the coil 13982 of the flex cable 13980 flexes with the articulation joint 13964 such that the flex cable 13980 does not interfere with the operation of the articulation joint 13964.

FIG. 124 illustrates cross-sectional view of the distal tip of one aspect of an anvil 13961 with sensors and electronics 13972. The anvil 13961 comprises a flex cable 13980, as described with respect to FIGS. 121-123. As illustrated in FIG. 124, the anvil 13961 further comprises a second aperture 13970 through which the flex cable 13980 can pass such that the flex cable 13980 can enter a housing 13974 in the within the anvil 13961. Within the housing 13974 the flex cable 13980 can operably couple to sensors and electronics 13972 located within the housing 13974 and thereby provide power to the sensors and electronics 13972.

FIG. 125 illustrates a cutaway view of the distal tip of the anvil 13961. FIG. 125 illustrates one aspect of the housing 13974 that can contain sensors and electronics 13972 as illustrated by FIG. 124.

A surgical instrument can be powered by a battery. In at least one embodiment, the handle of the surgical instrument comprises a battery cavity and the battery can be inserted into and removed from the battery cavity. In certain embodiments, the surgical instrument can comprise a shaft assembly which includes a battery cavity and a battery removably positioned in the battery cavity. When the battery is seated in the battery cavity, the battery can supply power to the handle. The battery and/or the handle, for example, can comprise a releasable lock which releasably holds the battery in the battery cavity. In various instances, the releasable lock comprises a latch which can be depressed by the user of the surgical instrument to unlock the battery and permit the battery to be removed from the battery cavity. In various instances, the battery can be removed from the handle and replaced with another battery. U.S. Patent Application Publication No. 2012/0071711, entitled SURGICAL INSTRUMENTS AND BATTERIES FOR SURGICAL INSTRUMENTS, which was filed on Sep. 17, 2010, now U.S. Pat. Nos. 9,289,212, and 8,632,525, entitled POWER CONTROL ARRANGEMENTS FOR SURGICAL INSTRUMENTS AND BATTERIES, which was filed on Sep. 17, 2010 are incorporated by reference herein in their respective entireties.

Referring now to FIGS. 126-128, a surgical instrument 14000 comprises a handle 14010 including a housing 14011 and a battery cavity 14012 defined in the housing 14011. The surgical instrument 14000 further comprises an end effector configured to deploy staples from a staple cartridge; however, the surgical instrument 14000 can comprise any suitable end effector. The handle 14010 further comprises a firing member 14050 which is movable proximally and distally to articulate the end effector of the surgical instrument 14000 about an articulation joint. The firing member 14050 is also movable distally to fire staples from the staple cartridge and retractable proximally after the staples have been fired. FIGS. 126-128 depict the firing member 14050 in an unfired position. The firing member 14050 is movable proximally and distally by an electric motor and/or a hand crank, for example, and is translatable within a proximally-extending chamber 14016. The chamber 14016 comprises a proximal end 14013 which encloses the firing member 14050 and extends proximally into the battery cavity 14012. The chamber 14016 is sized and configured to provide a clearance gap 14055 for the firing member 14050 which, in at least one instance, permits the firing member 14050 to be retracted proximally from its unfired position in order to articulate the end effector. In other instances, as discussed in greater detail further below, the chamber 14016 comprises an open proximal end.

The surgical instrument 14000 further comprises a battery 14020 which is positionable in the battery cavity 14012 to supply power to the handle 14010. The battery 14020 comprises a battery housing 14021 having an outer surface 14022. The battery cavity 14012 and the outer surface 14022 of the battery 14020 are configured such that the battery 14020 is closely received in the battery cavity 14012. In at least one instance, the battery cavity 14012 and the outer surface 14022 are configured such that the battery 14020 can be inserted into the battery cavity 14012 in only one orientation, or in a limited number of orientations. The battery 14020 comprises a clearance aperture 14026 defined therein configured to receive the chamber 14016 when the battery 14020 is positioned in the battery cavity 14012. The handle 14010 further comprises one or more electrical contacts 14014 (FIG. 131) which are engaged by corresponding electrical contacts 14024 (FIG. 131) defined on the battery 14020 when the battery 14020 is fully seated in the battery cavity 14012. Moreover, a proximal end 14025 of the battery 14020 is flush, or at least substantially flush, with the handle housing 14011 when the battery 14020 is fully seated in the battery cavity 14012. When the battery 14020 is not fully seated in the battery cavity 14012, the battery contacts 14024 may not be engaged with the handle contacts 14014 and, in such a position, the battery 14020 cannot supply power to the handle 14010.

In various embodiments, the battery 14020 is the only power source available to the handle 14010. In other embodiments, more than one power source is available to the handle 14010. In at least one such embodiment, the battery 14020 is the primary power source for the handle 14010. Regardless of the embodiment utilized, the battery 14020 can provide a large portion of, if not all of, the power needed by the handle 14010. In the event that the battery 14020 were to be disconnected from the handle 14010 and/or removed from the battery cavity 14012 during a surgical procedure, the handle 14010 would become unpowered and/or underpowered. In some instances, removing the battery 14020 from the battery cavity 14012 may be preferred or required to replace a depleted battery 14020 with a fully-charged battery 14020, for instance. In other instances, removing the battery 14020 from the battery cavity 14012 during a critical point of the surgical procedure may not be preferred, such as when the firing member 14050 is being advanced distally to fire the staples from the staple cartridge, for example. In at least one such instance, a sudden loss of power may render a control circuit 14015 and/or display screen 14040 of the handle 14010 inoperable, for example. In light of the above, the handle 14010 includes a battery lock, or means which can prevent the battery 14020 from becoming electrically de-coupled from the handle 14010 and/or removed from the battery cavity 14012 at certain points during the operation of the handle 14010. There are other reasons for locking the battery 14020 in the handle 14010. For instance, the battery 14020 can be locked to the handle 14010 so that the handle 14010 and/or battery 14020 can be disposed of safely.

Referring again to FIGS. 126-128, the handle 14010 comprises one or more deployable locks 14017. Each lock 14017 is movable between an undeployed, or unlocked, position (FIG. 127) and a deployed, or locked, position (FIGS. 126 and 128). Each lock 14017 comprises a cantilever beam extending from a sidewall of the chamber 14016; however, any suitable configuration could be utilized. Each lock 14017 comprises a proximal end mounted to a sidewall of the chamber 14016 and a distal end which is movable relative to the proximal end. The proximal end of each lock 14017 can be pivotably attached to a sidewall of the chamber 14016. The locks 14017, and/or the sidewalls of the chamber 14016, can be comprised of a resilient material and can be configured to deflect when a biasing force is applied thereto. Each lock 14017 comprises a cam surface 14018 defined on the distal end thereof.

The handle 14010 further includes a lock actuator 14030 configured to move the locks 14017 between their undeployed position (FIG. 127) to their deployed position (FIG. 128). The lock actuator 14030 comprises a solenoid; however, the lock actuator 14030 could comprise any suitable actuator, such as an electric motor, for example. The lock actuator 14030 comprises a wire coil 14034 mounted in the handle housing 14011 and, in addition, an armature 14032 movable relative to the wire coil 14034. The armature 14032 comprises an elongate aperture 14031 defined therein which is sized and configured to permit the firing member 14050 to slide therein. In various instances, a clearance gap can be present between the firing member 14050 and the armature 14032.

The armature 14032 is comprised of a ferrous material, for example, and the wire coil 14034 is comprised of a conductive wire, such as copper wire, for example. When electrical current flows through the wire coil 14034 in a first direction, the field generated by the flowing current pushes the armature 14032 from a first, or distal, position (FIG. 127) to a second, or proximal, position (FIG. 128). The armature 14032 comprises a proximal end 14038 configured to engage the cam surfaces 14018 of the locks 14017 when the armature 14032 is moved proximally and deflect the locks 14017 outwardly, as illustrated in FIG. 128. When electrical current flows through the wire coil 14034 in a second, or opposite, direction, the field generated by the flowing current pushes the armature 14032 from its second, or proximal, position (FIG. 128) to its first, or distal, position (FIG. 127). When the armature 14032 is moved distally, the proximal end 14038 of the armature 14032 is disengaged from the cam surfaces 14018 of the locks 14017 and the locks 14017 can then resiliently deflect inwardly back to their undeployed positions. The locks 14017 can comprise any suitable configuration and, in at least one instance, the locks 14017 are integrally-molded with the chamber 14016 and can be attached to the chamber 14016 in a living-hinge arrangement, for example. In other instances, the locks 14017 can comprise separate components which are mounted to the chamber 14016, for example.

Further to the above, each lock 14017 comprises a lock shoulder 14019 which is displaced outwardly when the locks 14017 are displaced outwardly, as described above. When the locks 14017 are moved into their deployed positions, as illustrated in FIG. 128, the lock shoulders 14019 of the locks 14017 are moved behind lock shoulders 14029 defined in the battery housing 14021. When the lock shoulders 14019 are positioned behind the lock shoulders 14029 of the battery 14020 by the lock actuator 14030, the battery 14020 cannot be disengaged from the handle 14010. As a result, the battery contacts 14024 remain engaged with the handle contacts 14014 and the power supplied to the handle 14010 by the battery 14020 may not be interrupted. In the event that the user of the surgical instrument 14000 pulls on the battery 14020 when the battery lock 14030 has been actuated, the lock shoulders 14029 of the battery 14020 can abut the lock shoulders 14019 of the lock arms 14017. Moreover, the armature 14032 can buttress and support the lock arms 14017 in their deployed positions such that battery contacts 14024 do not break contact with the handle contacts 14014. It is envisioned that some relative movement between the battery 14020 and the handle 14010 may occur even though the battery lock 14030 has been actuated; however, such movement is insufficient to electrically decouple the battery 14020 from the handle 14010.

The armature 14032 comprises a stop 14033 defined on the distal end thereof which is configured to limit the proximal travel of the armature 14032. In at least one embodiment, the stop 14033 is configured to contact the wire coil 14034, as illustrated in FIG. 128. In various instances, the wire coil 14034 can remain energized to hold the armature 14032 in its proximal, or locked, position (FIG. 128). In certain instances, the armature 14032 can be held in place by friction forces between the armature 14032 and the walls of the chamber 14026, for example, even though the wire coil 14034 is not being energized. Similar to the above, the handle 14010 can include a distal stop configured to limit the distal movement of the armature 14032. As mentioned above, the wire coil 14034 of the lock actuator 14030 can be energized to actively move the armature 14032 proximally and distally; however, the lock actuator 14030 can include a biasing member, such as a spring, for example, which can be configured to bias the armature 14032 in either the proximal direction or the distal direction. For instance, in at least one embodiment, the wire coil 14034 is energized to move the armature 14032 proximally and a return spring is configured to move the armature 14032 distally after the wire coil 14034 is no longer energized. Alternatively, in at least one embodiment, the wire coil 14034 is energized to move the armature 14032 distally and a return spring is configured to move the armature 14032 proximally after the wire coil 14034 is no longer energized.

As discussed above, the lock actuator 14030 can be selectively actuated to deploy the locks 14017 and de-actuated to retract the locks 14017. The lock actuator 14030 is in signal communication with the control circuit 14015 which can control the actuation of the lock actuator 14030. The control circuit 14015 can include a microprocessor which can determine when to activate and de-activate the lock actuator 14030. The microprocessor can be configured to evaluate one or more operating parameters of the surgical instrument 14000 to determine whether to activate or de-activate the lock actuator 14030. For instance, the microprocessor can be configured to evaluate the voltage and/or current of the battery 14020 to determine whether the battery 14020 is sufficiently charged to operate the handle 14010 and, if the battery 14020 has a sufficient charge, activate the lock actuator 14030 to deploy the locks 14017, or, if the battery 14020 does not have a sufficient charge, de-activate the lock actuator 14030 to permit the battery 14020 to be removed from the handle 14010.

Alternatively, the control circuit 14015 can utilize the lock actuator 14030 to prevent the battery 14020 from being removed from the handle 14010 in the event that the control circuit 14015 determines that the handle 14010 has exceeded its useful life. The control circuit 14015 can determine that the handle 14010 has exceeded its useful life if the firing system of the handle 14010 has been operated a certain number of times and/or if the handle 14010 has been sterilized a certain number of times, for example. In certain instances, the lock actuator 14030 can prevent the battery 14020 from being moved relative to the handle 14010. In at least one such instance, the control circuit 14015 of the handle 14010 can utilize the display screen 14040 to indicate to the user that the battery 14020 has been locked in position and that the handle 14010 should be either disposed of or serviced. In certain instances, the battery 14020 can include indicia thereon and the lock actuator 14030 can be configured to permit the battery 14020 to be translated a limited distance to expose the indicia when a clinician pulls on the battery 14020. The indicia can be on the side of the battery housing 14021 and can visible above the handle housing 14011 after the battery 14020 has been displaced. The indicia can have a contrasting color to other portions of the battery housing 14021, for example, and/or written instructions to the user of the surgical instrument 14000 such as the word "dispose" and/or "service", for example. In certain instances, the battery housing 14021 can include detention features which can engage the handle housing 14011 and hold the battery 14020 in its displaced position.

In certain embodiments, further to the above, a battery housing can comprise a two-part housing—a first portion which includes the battery cells 14023 and the electrical contacts 14024 and a second portion which is separable from the first portion, for example. In ordinary use, the first portion and the second portion of the battery housing are connected together and are unmovable relative to one another. The first portion can include a gripping portion, such as the proximal end 14025, for example, which allows the user of the surgical instrument 14000 to grab the battery housing and remove both portions of the battery housing simultaneously. If the control circuit 14015 has determined that the handle 14010 has reached its end of life, the control circuit 14015 can actuate a lock actuator which engages and holds the second portion of the battery housing. When the user of the surgical instrument 14000 attempts to remove the battery 14020 from the battery cavity 14012 of the handle 14010 after the lock actuator has been actuated, the first portion of the battery housing can separate from the second portion thereby leaving the second portion behind in the battery cavity 14012. As a result of the second portion being locked within and unremovable from the battery cavity 14012, a new battery 14020 is not positionable in the battery cavity 14012. In various instances, the first portion and/or the second portion of such a battery housing can include indicia thereon explaining to the user of the surgical instrument 14000 that the handle 14010 is no longer usable. Such indicia may only be visible after the first housing portion has separated from the second housing portion. In certain instances, the first housing portion and the second housing portion can be connected by a ribbon which is exposed, or unfurled, when the first housing portion detaches from the second housing portion. The ribbon can include instructions thereon for handling, disposing, and/or refurbishing the handle 14010. When the handle 14010 is refurbished, the lock actuator can be reset and the second housing portion can be removed from the battery cavity 14012.

Further to the above, the handle and/or the battery can comprise an exposable portion which can be exposed by the control system when the control system determines that the handle and/or the battery is no longer suitable for use. The exposable portion can be displaced and/or otherwise exposed by an actuator operated by the control system. The exposable portion can include indicia, such as words and/or a contrasting color, for example, which only become visible when the control system has deactivated the handle and/or the battery in at least one way.

In various embodiments, the handle 14010 can include an override button in communication with the microprocessor which, when actuated, can instruct the microprocessor to deactivate the lock actuator and permit the battery to be removed. Other embodiments may not include such an override button.

In various instances, a surgical instrument may become unsuitable for use in a surgical procedure. A handle of a surgical instrument can become unsuitable for use when the handle has exceeded its intended number of uses, for example. A handle of a surgical instrument may also become unsuitable for use when it experiences excessive force loading and/or electrical faults, for example. Moreover, a handle of a surgical instrument may become unsuitable for use when another component of the surgical instrument is incorrectly attached to the handle and/or an incorrect component is attached to the handle. When the control system of the handle determines that the handle may be unsuitable for use, the control system may employ a battery lockout which can prevent a battery from being operably coupled to the handle, as described in greater detail further below.

A handle 14110 is depicted in FIGS. 129 and 130. The handle 14110 is similar to the handle 14010 in many respects. The handle 14110 comprises a handle housing 14111 which includes a battery cavity 14012 configured to receive a battery 14020, as described above. The handle housing 14111 further comprises a chamber 14116 configured to receive the firing member 14050 which, similar to the chamber 14016, extends into the battery cavity 14012. The handle 14110 further comprises one or more deployable lockout arms 14117. Each lockout 14117 is movable between an undeployed position (FIG. 129) and a deployed position (FIG. 130). Each lockout 14117 comprises a cantilever beam extending from a sidewall of the chamber 14116; however, any suitable configuration could be utilized. Each lockout 14117 comprises a distal end mounted to a sidewall of the chamber 14116 and a proximal end which is movable relative to the distal end. The distal end of each lockout 14117 can be pivotably attached to a sidewall of the chamber 14116. The lockouts 14117, and/or the sidewalls of the chamber 14116, can be comprised of a resilient material and can be configured to deflect when a biasing force is applied thereto. Each lockout 14117 comprises a cam surface 14118 defined on the proximal end thereof.

The handle 14110 further includes a lock actuator 14030 configured to move the lockouts 14117 from their undeployed position (FIG. 129) to their deployed position (FIG. 130). The lock actuator 14030 comprises a solenoid; however, the lock actuator 14030 could comprise any suitable actuator, such as a motor, for example. The lock actuator 14030 comprises a wire coil 14034 mounted in the handle housing 14111 and, in addition, an armature 14032 movable relative to the wire coil 14034. The armature 14032 comprises an elongate aperture 14031 defined therein which is sized and configured to permit the firing member 14050 to slide therein. In various instances, a clearance gap can be present between the firing member 14050 and the armature 14032.

The armature 14032 is comprised of a ferrous material, for example, and the wire coil 14034 is comprised of a conductive wire, such as copper wire, for example. When electrical current flows through the wire coil 14034 in a first direction, the field generated by the flowing current pushes the armature 14032 from a first, or distal, position (FIG. 129) to a second, or proximal, position (FIG. 130). The armature 14032 comprises a proximal end 14038 configured to engage the cam surfaces 14118 of the lockouts 14117 when the armature 14032 is moved proximally and deflect the lockouts 14117 outwardly, as illustrated in FIG. 130. When electrical current flows through the wire coil 14034 in a second, or opposite, direction, the field generated by the flowing current pushes the armature 14032 from its second, or proximal, position (FIG. 130) to its first, or distal, position (FIG. 129). When the armature 14032 is moved distally, the proximal end 14038 of the armature 14032 is disengaged from the cam surfaces 14118 of the lockouts 14117 and the lockouts 14117 can then resiliently deflect inwardly back to their undeployed positions.

Further to the above, each lockout 14117 comprises a lock shoulder 14119 which is displaced outwardly when the lockouts 14117 are displaced outwardly, as described above. When the lockouts 14117 are moved into their deployed positions, as illustrated in FIG. 130, the lock shoulders

14119 of the lockouts 14117 are moved in front of lock shoulders 14028 defined in the battery housing 14021. When the lock shoulders 14119 are positioned in front of the lock shoulders 14028 of the battery 14020 by the lock actuator 14030, the battery 14020 cannot be fully seated in the handle 14110. As a result, the battery contacts 14024 cannot engage the handle contacts 14014 and the battery 14020 cannot supply power to the handle 14110. In the event that the user of the handle 14100 pushes on the battery 14020 when the battery lockout 14130 has been actuated, the armature 14032 can buttress and support the lockouts 14117 in their deployed positions.

A handle 14210 is depicted in FIG. 131. The handle 14210 is similar to the handle 14010 and/or the handle 14110 in many respects. The handle 14210 comprises a handle housing 14211 including a battery cavity 14012 configured to receive a battery 14020. The handle housing 14211 further comprises a chamber 14216 configured to receive the firing member 14050 which, similar to the chamber 14016 and the chamber 14116, extends into the battery cavity 14012. The chamber 14216 of the handle 14210, however, comprises an open proximal end 14213. As illustrated in FIG. 131, the open proximal end 14213 is sized and configured to permit the firing member 14050 to extend therethrough. When the control system of the handle 14210 has determined that the handle 14210 is not suitable for use, further to the above, the control system can operate the electric motor which advances and retracts the firing member 14050 to position the firing member 14050 in a lockout position, i.e., a position in which the firing member 14050 prevents the electrical contacts 14024 of the battery 14020 from engaging the electrical contacts 14014 of the handle 14210. As illustrated in FIG. 131, the firing member 14050 can be retracted to a position in which the proximal end 14025 of the battery 14020, for example, contacts the firing member 14050 before the battery 14020 is sufficiently seated enough in the battery cavity 14012 to supply power to the handle 14210.

In at least one alternative embodiment, a handle of a surgical instrument system can include a battery cavity and at least one first electrical contact and at least one second electrical contact positioned in the battery cavity which are in communication with the control system of the handle. When the battery is fully seated in the battery cavity, the battery is electrically coupled with the first electrical contact and can fully power the handle. Similar to the above, the handle can include a battery lockout system which can be activated to prevent the battery from being fully seated in the battery cavity. Moreover, the battery lockout system can prevent the battery from being electrically coupled with the first electrical contact when the battery lockout system is activated. In contrast to the battery lockout systems described above, however, the battery lockout system of the current embodiment can permit the battery to be electrically coupled with the second electrical contact even though the battery lockout has been activated. In such instances, the control system of the handle can utilize the power supplied to the second electrical contact by the battery to operate the handle in a limited function mode.

In a limited function mode, further to the above, the control system may only be able to perform diagnostic functions to assess the condition of the handle and/or communicate the condition of the handle to the user. In at least one limited function mode, the control system may not be able to operate the electric motor to advance the firing member 14050 distally but it may be able to operate the electric motor to retract the firing member 14050 proximally, for example. The control system may also operate the display and/or permit the control buttons which interface with the display to be operated when the handle is being operated in a limited function mode, for example.

In at least one embodiment, further to the above, the first handle contact can be positioned deeper in the battery cavity than the second handle contact. In at least one such instance, the battery can include a battery contact which can engage the first handle contact or the second handle contact, depending on the depth in which the battery is inserted into the battery cavity. In at least one instance, the battery can comprise a first battery contact configured to engage the first handle contact when the battery is inserted to a first depth and a second battery contact configured to engage the second handle contact when the battery is inserted to a second depth which is different than the first depth.

In certain embodiments, further to the above, the firing member 14050 can be pushed proximally into the battery cavity 14012 to displace the battery 14020 proximally and electrically decouple the battery 14020 from the handle 14210. In such instances, the firing member 14050 can displace the battery 14020 proximally such that the battery contacts 14024 are no longer engaged with the handle contacts 14014. The control system of the handle can decouple the battery 14020 from the handle when the control system has determined that the handle is no longer suitable for use. In certain other embodiments, further to the above, the firing member 14050 can push a battery from a first position in which the battery is electrically coupled to a first electrical contact to a second position in which the battery is electrically decoupled from the first electrical contact and electrically coupled to a second electrical contact. Similar to the above, the control system of the handle may only use the power supplied to the second electrical contact to perform a limited number of functions. In such instances, the control system can switch itself between a fully-functional operating mode and a limited-function operating mode. In various instances, the handle housing can include a catch feature which can prevent the battery from being electrically decoupled from the second electrical contact and/or pushed entirely out of the battery cavity in the handle housing.

As discussed herein, the firing member 14050 can enter into a battery cavity to prevent a battery from being fully installed into a handle and/or contact a battery to at least partially displace the battery out of the battery cavity. In various other instances, the firing member 14050 itself may not block a battery cavity and/or push a battery proximally; rather, the proximal movement of the firing member 14050 out of its ordinary range of motion can trip a spring-loaded mechanism which can block a battery cavity and/or push a battery proximally, for example. In at least one instance, the spring-loaded mechanism can include at least one pre-stretched and/or at least one pre-compressed spring member that is released when tripped by the firing member 14050, for example. Such a spring-loaded mechanism can also deploy an indicator, for example, when it is tripped which can indicate to the user that the handle has entered into a different operating mode. In certain embodiments, the control system of a handle may actuate a spring-loaded mechanism directly without using the firing member 14050 to trip the spring-loaded mechanism. While a spring could be utilized to store energy and deliver that energy to a cocked actuator to perform the functions discussed herein, any suitable device capable of storing and releasing energy could be utilized. In various instances, the device can be pre-energized or pre-loaded when the handle is supplied to the user.

In addition to or in lieu of the above, the control system of a handle can move the firing member 14050, either proximally or distally, to an inoperative position to render the handle unusable if the control system detects a defect in the handle and/or otherwise determines that the handle should not be used. In at least one instance, the firing member 14050 can be moved, either proximally or distally, to a position in which the electric motor becomes mechanically decoupled from the firing member 16050 and the electric motor can no longer move the firing member 14050 proximally or distally, for example. In another instance, the firing member 14050 can be moved, either proximally or distally, to a position in which the firing member 14050 impedes the operability of another system of the handle, such as a closing system used to close an end effector of the surgical instrument. In certain instances, the firing member 14050 can be moved, either proximally or distally, to a position in which a modular shaft assembly cannot be operably coupled to the handle and/or the firing member 14050. In some instances, the firing member 14050 can be moved, either proximally or distally, to a position in which a modular shaft assembly cannot be operably de-coupled from the handle and/or the firing member 14050. In view of the above, the firing member 14050 of a handle can be moved out of a typical operating range of positions to render the handle inoperable in at least one capacity.

Further to the above, the firing member 14050 is movable within a firing operating range to fire staples from a staple cartridge and/or an articulation operating range to articulate the end effector of the surgical instrument. In certain embodiments, the firing member 14050 is movable within a clamping operating range to close an end effector and/or clamp tissue within the end effector. The firing operating range, the articulation operating range, and/or the clamping operating range can comprise the typical operating range of positions discussed above. As also discussed above, the firing member 14050 can be moved out of this typical operating range to change the operating state of the handle in some manner. In at least one embodiment, the firing member 14050 can be moved proximally out of its typical operating range to cycle or index a use counter after every time that the handle has been used. The use counter can be cycled mechanically and/or electronically. The use counter can be in communication with the processor of the handle which can utilize data from the use counter to determine whether the handle is still suitable for use. The control system of the handle, including the handle microprocessor, the use counter, and/or one or more sensors configured to monitor the electric motor which drives the firing member 14050, for example, can be part of a diagnostic system which determines whether the handle is suitable for use.

The exemplary embodiments illustrated in FIGS. 126-131 depict two lock arms or two lockout arms, as the case may be; however, one lock arm, or lockout arm, could be used. Moreover, more than two lock arms, or lockout arms, could be used. The lock arms, or lockout arms, of the exemplary embodiments are deployed simultaneously; however, other embodiments are envisioned in which they are deployed sequentially. Furthermore, the embodiment of FIGS. 126-128, which comprises a battery lock system, could be combined with the embodiment of FIGS. 129 and 130 and/or the embodiment of FIG. 131, which comprise battery lockout systems. In various embodiments, a single system can perform the battery lock and battery lockout functions described herein.

As discussed above, a surgical instrument can include a handle, a shaft assembly, and an end effector. The handle can include an electric motor having a rotatable output shaft which is operably coupled to a drive shaft in the shaft assembly. The output shaft can rotate the drive shaft or, alternatively, the rotary motion of the output shaft can be converted to translational motion before being transmitted to the drive shaft. In either event, a property of the output shaft can be measured while it is driving the drive shaft. Various embodiments can include one or more sensors, for example, positioned relative to the output shaft which can measure the motion of the drive shaft, for example. Such sensors are positioned off-board with respect to the shaft. Such embodiments can be useful; however, the off-board positioning of the sensors can limit the properties of the drive shaft which can be detected and/or the manner in which the properties of the drive shaft are detected. Various embodiments are discussed below which comprise one or more sensors which are positioned on the output shaft which can detect a property of the drive shaft. Such sensors are positioned on-board with respect to the shaft. Also discussed below are embodiments which can include a control circuit mounted to the shaft and/or means for transmitting power to the control circuit.

Referring now to FIGS. 132 and 133, a surgical instrument system 15000 comprises an electric motor 15010 including a rotatable shaft 15020. The electric motor 15010 can comprise any suitable electric motor, such as a direct current (DC) electric motor, for example. The electric motor 15010 is mounted in a handle of a surgical instrument; however, the electric motor 15010 can be mounted in any suitable portion of a surgical instrument, such as the shaft assembly extending from the handle, for example. In certain other embodiments, the electric motor 15010 can be part of a robotically-controlled assembly. In any event, the motor shaft 15020 is rotatably supported by any suitable number of bearings such that the shaft 15020 is rotatable by the electric motor 15010 about a longitudinal axis 15021.

Referring primarily to FIG. 132, the surgical instrument system 15000 further comprises a drive system 15030 operably coupled with the motor shaft 15020. The drive system 15030 is positioned in the handle of the surgical instrument; however, the drive system 15030 may be positioned in any suitable portion of the surgical instrument, such as the shaft assembly extending from the handle, for example. In certain other embodiments, the drive system 15030 can be part of a robotically-controlled assembly. In any event, the drive system 15030 comprises a transmission 15031 and an output shaft 15032. The transmission 15031 is configured to transmit rotary motion between the motor shaft 15020 to the output shaft 15032. The transmission 15031 comprises a plurality of intermeshed gears, for example. In various instances, the gears of the transmission 15031 are configured such that the rotational velocity of the output shaft 15032 is different than the rotational velocity of the motor shaft 15020. In at least one such instance, the rotational velocity of the output shaft 15032 is less than the rotational velocity of the motor shaft 15020. In various alternative embodiments, the gears of the transmission 15031 are configured such that the rotational velocity of the output shaft 15032 is the same as the rotational velocity of the motor shaft 15020.

Referring again to FIGS. 132 and 133, the surgical instrument system 15000 further comprises a sensor 15050 mounted to the output shaft 15020. The sensor 15050 comprises a strain gauge; however, any suitable sensor could be utilized. For instance, the sensor 15050 could comprise an accelerometer, for example. The strain gauge 15050 is mounted to the outside surface 15023 of the output shaft 15020. The strain gauge 15050 comprises a substrate, or backing, 15052 comprised of an insulative material which is flexible and conformable to the outside surface 15023 of the shaft 15020. The backing 15052 is attachable to the outside surface 15023 of the shaft 15020 by any suitable adhesive, such as cyanoacrylate, for example. The strain gauge 15050 further comprises a metallic wire 15053 mounted to the substrate 15052. When the shaft 15020 experiences a load and is elastically and/or plastically deformed by the load, the metallic wire 15053 is also deformed by the load and, as a result, the electrical resistance of the metallic wire 15053 changes. This change in resistance, usually measured using a Wheatstone bridge, is related to the strain, or deformation, being experienced by the shaft 15020 by a ratio known as a gauge factor.

When an electrical conductor, such as the metallic wire 15053, for example, is stretched within the limits of its elasticity such that it does not break or permanently deform, the electrical conductor will become narrower and longer which increases its electrical resistance from end-to-end. Conversely, when the electrical conductor is compressed such that it does not buckle, it will broaden and shorten which decreases its electrical resistance from end-to-end. The electrical conductor of a resistive strain gauge often comprises a long, thin conductive strip arranged in a continuous zig-zag pattern of parallel lines. These parallel lines of the conductive strip are usually spaced close together such that a large length of the conductive strip is positioned over a small area. Owing to the large length of the conductive strip, a small amount of stress in the direction of the orientation of the parallel lines results in a multiplicatively larger strain measurement over the effective length of the conductor—and hence a multiplicatively larger change in resistance—than would be observed with a single straight-line conductive wire. From the measured electrical resistance of the strain gauge 15050, the amount of stress being applied to the motor shaft 15020 may be inferred.

The surgical instrument system 15000 further comprises a control system 15040 which is positioned on the motor shaft 15020. The control system 15040 includes a circuit board 15046 mounted to the motor shaft 15020. The circuit board 15046 can be comprised of a printed circuit board and/or a flexible laminate, for example, and can be attached to the outside surface 15023 of the shaft 15020 utilizing one or more adhesives, for example. The control system 15040 can include a control circuit on the circuit board 15046. The control circuit comprises, among other things, a microprocessor 15047 and at least one memory chip 15048 in signal communication with the microprocessor 15047. The strain gauge 15050 is also in signal communication with the microprocessor 15047 which is configured to detect the resistance change in the metallic wire 15053 of the strain gauge 15050, as discussed above. When the shaft 15020 is rotated to operate the end effector articulation system, the tissue-clamping system, and/or the staple-firing system of a surgical instrument, for example, the shaft 15020 will experience forces and/or torques T that create strain within the shaft 15020 which is detected by the strain gauge 15050 and the microprocessor 15047, as discussed in greater detail further below. The microprocessor 15047 can include the Wheatstone bridge discussed above.

The strain gauge 15050, further to the above, can comprise any suitable strain gauge. For instance, the strain gauge 15050 can comprise a semiconductor strain gauge, a piezoresistor, a nano-particle based strain gauge, a fiber optic strain gauge, and/or a capacitive strain gauge, for example. Certain strain gauges are configured to measure strain along one axis while other strain gauges are configured to measure strain along more than one axis, such as two axes or three axes, for example. More than one strain gauge can be used to assess the strain of the shaft 15020. For example, a first strain gauge can be used to assess the strain of the shaft 15020 along a first axis and a second strain gauge can be used to assess the strain of the shaft 15020 along a second axis. In at least one such instance, a first strain gauge can be positioned and arranged to measure the strain along the longitudinal axis 5021 of the shaft 15020 and a second strain gauge can be positioned and arranged to measure the strain around the circumference of the shaft 15020. The strain measured along the circumferential axis of the shaft 15020 is orthogonal to the strain measured along the longitudinal axis; however, other embodiments are envisioned in which the first axis and the second axis are transverse, but not orthogonal to one another. In various instances, one or more strain gauges can be utilized to evaluate the total, or overall, strain being experienced by the shaft 15020 at a particular location on the shaft 15020. In certain instances, a plurality of strain gauges can be utilized to evaluate the strain of the shaft 15020 at a plurality of locations on the shaft 15020.

The strain gauge 15050 can be utilized to evaluate the strain, and the stress, being experienced by the shaft 15020. When the shaft 15020 is being utilized to drive an articulation system, a large increase in strain can indicate that the end effector of the surgical instrument may not be articulating properly. Similarly, a large increase in strain can indicate that the firing member of the surgical instrument may have become stuck when the shaft 15020 is being utilized to drive a firing system. The microprocessor 15047, and/or any other microprocessor of the surgical instrument, can be programmed to interpret the strain data and utilize the strain data to interpret whether the operation of the surgical instrument should be modified. For example, a strain reading supplied by the strain gauge 15050 to the microprocessor 15047 when the shaft 15020 is being utilized to articulate an end effector may exceed a maximum articulation strain threshold and, in such instances, the microprocessor 15047, for example, can be programmed to interrupt the operation of the motor 15010 driving the shaft 15020 when the strain reading exceeds the maximum articulation strain threshold. The same strain reading, if provided when the shaft 15020 is being utilized to fire staples from the end effector, may or may not exceed a maximum firing strain threshold. If the strain reading does not exceed the maximum firing strain threshold, then the microprocessor 15047 may not interrupt the operation of the electric motor 15010. If the strain reading exceeds the maximum firing strain threshold, then the microprocessor 15047 may interrupt the operation of the motor 15010. In certain instances, the maximum firing strain threshold is different than the maximum articulation strain threshold while, in other instances, they may be the same.

In some instances, further to the above, interrupting the motor 15010 may mean that the microprocessor 15047, and/or any other microprocessor of the surgical instrument, immediately pauses the motor 15010 until receiving an input from the user of the surgical instrument. Such an input can be a command to reverse the operation of the motor 15010 or a command to override the interruption of the motor 15010 and restart the motor 15010 to complete the articulation or firing process, as the case may be. In certain instances, interrupting the motor 15010 may mean slowing the motor 15010 down which can give the microprocessor 15047, for example, a longer period of time to evaluate the loading conditions being experienced by the shaft 15020. If the increase in strain represents a transient, or temporary, increase and the measured strain drops back below the relevant threshold, the microprocessor 15047 may not interrupt the motor 15010. If the microprocessor 15047 has slowed the motor 15010 in response to an elevated strain reading, the microprocessor 15047 may restore the original speed of the motor 15010 after the strain drops back below the relevant threshold. In other instances, the microprocessor 15047 may continue to operate the motor 15010 at the slower speed even though the strain has dropped back below the relevant threshold. If, however, the elevated strain reading above the relevant threshold persists, the microprocessor 15047 can operate the motor 15010 at the slower speed and/or pause the motor 15010 after a predetermined period of time has elapsed. In the event that the measured strain continues to increase over the threshold, the microprocessor 15047 can be programmed to stop the motor 15010.

As discussed above, the microprocessor 15047 is positioned on the shaft 15020. In order for the microprocessor 15047 to control the motor 15010 driving the shaft 15020, the microprocessor 15047 needs to be able to communicate with the motor 15010. In at least one instance, a slip ring system can be utilized to transmit one or more signals from the microprocessor 15047 to the motor 15010. The slip ring system can also be utilized to transmit and/or one or more signals from the motor 15010, and/or sensors monitoring the motor 15010, to the microprocessor 15047. In certain instances, a transmitter 15060 can be utilized to transmit data between the microprocessor 15047 and the motor 15010. The transmitter 15060 is mounted to the shaft 15020 and rotates with the shaft 15020. The transmitter 15060 is in signal communication with the microprocessor 15047 and, in at least one instance, can comprise a wireless frequency emitter configured to generate a wireless signal utilizing data provided by the microprocessor 15047. The frequency emitter can be in communication with the microprocessor 15047 via one or more power wires and/or one or more signal wires which are mounted to the shaft 15020. Alternatively, as described in greater detail further below, the transmitter 15060 can comprise an impendence field generator.

When the transmitter 15060 comprises a wireless frequency emitter, the surgical instrument can comprise a wireless frequency receiver 15070 configured to receive the signal emitted by the frequency emitter. The frequency receiver 15070 is positioned in the handle of the surgical instrument; however, the frequency receiver 15070 can be positioned in any suitable location in the surgical instrument. In various instances, the frequency receiver 15070 is in signal communication with the motor 15010 such that the data transmitted within the wireless signal and received by the frequency receiver 15070 can directly control the motor 15010. In other instances, the frequency receiver 15070 is in signal communication with a second microprocessor 15080 in the surgical instrument. The second microprocessor 15080 is positioned in the handle of the surgical instrument; however, the second microprocessor 15080 can be positioned in any suitable location in the surgical instrument. The second microprocessor 15080 can utilize the data transmitted from the microprocessor 15047, and/or any other data from one or more suitable inputs, to control the motor 15010. The second microprocessor 15080 is in signal communication with the motor 15010 via one or more signal and/or power wires 15082, for example. The second microprocessor 15080 can also be programmed to control the motor 15010 in the manner described above. In various instances, the microprocessors 15047 and 15080 can co-operate to control the motor 15010.

The control system 15040, the sensor 15050, and the transmitter 15060 comprise an on-board detection system configured to detect and evaluate one or more conditions of the shaft 15020. In the embodiment described above, the condition of the shaft 15020 is the operating load being experienced by the shaft 15020 and the sensor 15050 comprises a strain gauge configured to detect the operating load; however, any suitable condition of the shaft 15020 can be detected by one or more on-board sensors positioned on the shaft 15020. Moreover, the microprocessor 15047 can be configured to arrange the data provided to the microprocessor 15047 from a plurality of sensors into two or more signals and the wireless frequency emitter can be configured to emit those signals to the frequency receiver 15070. Such signals can then be provided to the microprocessor 15080 which can control the motor 15010 in response to the signals that it has received. One or more signal multiplexers and demultiplexers could be utilized.

While a wireless frequency emitter can be useful to communicate data between a rotating plane, i.e., the shaft 15020, and a fixed plane, i.e., the handle of the surgical instrument, for example, the transmitter 15060 can be configured to communicate data in any suitable manner. In at least one embodiment, as mentioned above, the transmitter 15060 can comprise an impedance field generator. In at least one instance, the impedance field generator can comprise an impedance coil mounted to the outside surface 15023 of the shaft 15020. The impedance field generator can be configured to generate a field which can be sensed by a field sensor 15070 positioned in the handle, for example. Similar to the above, the impedance field generator moves within a rotating plane and the field sensor is positioned within a fixed plane.

Further to the above, the magnitude of the field generated by the impedance field generator corresponds to the magnitude of the strain detected by the strain gauge 15050. For instance, higher emitted field intensities can be associated with larger strains while lower emitted field intensities can be associated with smaller strains. In at least one instance, the magnitude of the field emitted by the impedance field generator can be directly proportional to the magnitude of the strain detected by the strain gauge 15050. In such an embodiment, the field sensor can measure the intensity of the field created by the impedance field generator and communicate such information to the microprocessor 15080, for example. The microprocessor 15080 can comprise a calibration table which relates the data received from the field sensor to the load being experienced by the motor shaft 15020. The microprocessor 15080 can also be configured to adjust the speed of the electric motor 15010 in response to the data received from the strain gauge 15050 and the impedance field generator. For instance, the microprocessor 15080 can slow the electric motor 15010 when the measured strain is high. The microprocessor 15080 can also utilize any other suitable data to adjust the performance characteristics of the electric motor 15010. Such data could include the current draw of the motor 15010, the impedance of the tissue being stapled, the tissue gap between the anvil and the staple cartridge, and/or the strain that the anvil is experiencing, for example.

The impedance field generator described above transmits data between a moving shaft 15020 and the handle without the use of electrical contacts. As a result, it can be said that the impedance field generator communicates data from the shaft 15020 to the handle 'wirelessly'; however, it can also be stated that the impedance field generator is being used to affect a measurement that is being made adjacent to the moving shaft 15020 which is then turned into a data stream and interpreted.

As the reader will appreciate, the control system 15040, the sensor 15050, and the transmitter 15060 may require electrical power to operate. In at least one instance, one or more batteries can be mounted to shaft 15020 which can supply power to the control system 15040, the sensor 15050, and/or the transmitter 15060, for example. In addition to or in lieu of a battery, power can be supplied to the control system 15040, the sensor 15050, and/or the transmitter 15060, for example, via a slip ring system, such as the one described above, for example. In addition to or in lieu of the above, power can be transmitted wirelessly to the control system 15040, the sensor 15050, and/or the transmitter 15060, for example. In at least one such instance, the surgical instrument can include a magnet 15041 configured to generate a magnetic field 15042 which induces a current in a wire coil 15043 wound around the shaft 15020 when the shaft 15020 is rotated by the electric motor 15010. The wire coil 15043 is in electrical communication with the control system 15040 such that the current induced within the wire coil 15043 can supply power to the microprocessor 15047, the strain gauge sensor 15050, and/or the transmitter 15060, for example. In at least one such instance, the wire coil 15043 comprises a first end 15044 and a second end 15045 mounted to contacts on the board 15046.

The magnet 15041 comprises a permanent magnet; however, the magnet 15041 can comprise any suitable magnet, such as an electromagnet, for example. When the magnet 15041 comprises a permanent magnet, the magnet 15041 can continuously generate the magnetic field 15042. The permanent magnet 15041 is securely positioned in the surgical instrument such that the orientation and/or magnitude of the magnetic field 15042 does not change. The wire coil 15043 comprises a copper, or coper alloy, wire wrapped around the outside surface 15023 of the shaft 15020; however, the wire coil 15043 can be comprised of any suitable conductive material, such as aluminum, for example. The wire coil 15043 can be wrapped around the shaft 15020 any suitable number of times. Moreover, the wire coil 15043 can be positioned on the shaft 15020 at a location in which the intensity of the magnetic field 15042 is high, or at its highest. In at least one instance, the wire coil 15043 can be wrapped around the shaft 15020 such that the wire coil 15043 is aligned, or at least substantially aligned, with a polar axis of the magnetic field 15042. Generally, the current that is generated within the wire coil 15043 is directly proportional to the number of times that the wire coil 15043 is wound around the shaft 15020. Moreover, the current that is generated within the wire coil 15043 is directly proportional to the speed in which the shaft 15020 is rotated.

As discussed above, the magnet 15041 can comprise an electromagnet. The electromagnet 15041 can be powered by a battery of the surgical instrument, for example, to generate the magnetic field 15042. The electromagnet 15041 can be selectively activated, or energized, to selectively generate the magnetic field 15042. For instance, the electromagnet 15041 can be energized only when the shaft 15020 is being rotated by the motor 15010. In such instances, the electromagnet 15041 will not be energized when the shaft 15020 is not rotating. Such instances may be useful when prolonged pauses in the operation of the shaft 15020 are anticipated or are in the process of occurring. In at least one instance, the electromagnet 15041 may be energized prior to shaft 15020 being rotated by the motor 15010. In certain instances, the electromagnet 15041 may be de-energized after the shaft

15020 has stopped rotating. Such approaches can assure that the motion of the shaft 15020 can be fully utilized to induce current within the wire coil 15043. In various instances, the electromagnet 15041 may be energized whether or not the shaft 15020 is rotating. Such instances may be useful when only short pauses in the operation of the shaft 15020 are anticipated or are in the process of occurring.

When the shaft 15020 is not rotating, further to the above, the magnetic field 15042 does not induce a current within the wire coil 15043 and, as a result, the control system 15040, the sensor 15050, and the transmitter 15060 are not being powered by the magnetic field 15042. In at least one such instance, the microprocessor 15047 can enter into a sleep mode. When the motor 15010 begins to rotate the shaft 15020, the wire coil 15043 is rotated within the magnetic field 15042 and a current is generated within the wire coil 15043. The wire coil 15043 can be in electrical communication with an input gate in the microprocessor 15047 and can apply a voltage potential to the input gate which can, one, power the microprocessor 15047 and, two, cause the microprocessor 15047 to awaken from its sleep mode. In such an embodiment, as a result, the control system 15040 can be in a sleep mode when the shaft 15020 is not rotating and an active, or fully-powered, operating mode when the shaft 15020 is rotating.

In various instances, the control system 15040 can include and/or can have access to a power source when the shaft 15020 is not rotating. In such instances, the microprocessor 15047 can enter a low-power mode. In at least one instance, the control system 15040 can include one or more capacitive elements, such as supercapacitors, for example, that can be configured to store electrical power when the shaft 15020 is being rotated and current from the wire coil 15043 is being supplied to the control system 15040. When the shaft 15020 is no longer rotating and current from the wire coil 15043 is no longer being supplied to the control circuit 15040, the capacitive elements can supply electrical power to the microprocessor 15047, and/or any other portion of the control system 15040, and prevent the microprocessor 15047, and/or control system 15040, from entering into a completely unpowered state, at least for a period of time. Such capacitive elements could also release power to the microprocessor 15047, and/or any other portion of the control system 15040, the strain gauge 15050, and/or the transmitter 15060 when the shaft 15020 is rotating at a slow speed, i.e., a speed which is insufficient to generate the power necessary to operate such components in their fully-powered operating mode. In addition to or in lieu of the above, a battery mounted to the shaft 15020 can supply power to the microprocessor 15047, and/or any other portion of the control system 15040, the strain gauge 15050, and/or the wireless transmitter 15060 when the shaft 15020 is not rotating. Such a battery could also provide power to the microprocessor 15047, and/or any other portion of the control system 15040, the strain gauge 15050, and/or the transmitter 15060 when the shaft 15020 is rotating slowly and/or when such components are otherwise underpowered, for example.

Further to the above, the shaft 15020 may be stopped for a multitude of reasons. For instance, the user of the surgical instrument may choose to pause or stop the advancement of a firing member to assess whether the firing stroke of the firing member could or should be completed and, in such circumstances, the shaft 15020, which advances the firing member, may be paused or stopped. As discussed above, a current is not induced in the wire coil 15043 when the shaft 15020 is not rotating; however, it may be desirable to power the control system 15040, the sensor 15050, and/or the transmitter 15060 in order to collect, evaluate, and/or transmit data from the sensor 15050 while the shaft 15020 is not being rotated. A secondary power source described above is capable of facilitating such an operating state of the surgical instrument. In at least one alternative embodiment, a current can be induced in the wire coil 15043 even though the shaft 15020 is not rotating. For instance, a plurality of electromagnets 15041 can be positioned around the wire coil 15043 which can be selectively energized to create a rotating magnetic field 15042. In such an embodiment, the magnetic field 15042 can be rotated relative to the wire coil 15043 to induce a current in the wire coil 15043 and power the control system 15040, the sensor 15050, and/or the transmitter 15060 even though the shaft 15020 has been stopped.

In use, further to the above, a power source, such as a battery, for example, can be utilized to power the electric motor 15010 and rotate the shaft 15020. As described above, the rotation of the wire coil 15043 within a magnetic field 15042 generates a current within the wire coil 15043 which supplies power to the control circuit 15040, the sensor 15050, and/or the transmitter 15060 positioned on the shaft 15020. In such instances, this on-board shaft system recaptures a portion of the energy expended to rotate the shaft 15020 and utilizes that energy to sense, evaluate, and/or monitor the performance of the shaft 15020.

Various examples disclosed herein have been discussed in connection with the motor shaft 15020; however, such examples could be applied to any rotatable shaft and/or rotatable system, such as the shaft 15032, for example. Moreover, the examples disclosed herein could be applied to the rotatable shaft and/or rotatable system of any suitable surgical instrument. For instance, the examples disclosed herein could be applied to a robotic system, such as the DAVINCI robotic surgical system manufactured by Intuitive Surgical, Inc., for example. The entire disclosure of U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein. The examples disclosed herein could also be applied to non-surgical applications, such as the crankshaft and/or camshaft of a motor, for example.

A portion of a surgical stapling instrument 16000 is illustrated in FIGS. 134-139. The stapling instrument 16000 is usable with a manually-operated system and/or a robotically-controlled system, for example. The stapling instrument 16000 comprises a shaft 16010 and an end effector 16020 extending from the shaft 16010. The end effector 16020 comprises a cartridge channel 16030 and a staple cartridge 16050 positioned in the cartridge channel 16030. Referring primarily to FIGS. 137 and 138, the staple cartridge 16050 comprises a cartridge body 16051 and a retainer 16057 attached to the cartridge body 16051. The cartridge body 16051 is comprised of a plastic material, for example, and the retainer 16057 is comprised of metal, for example; however, the cartridge body 16051 and the retainer 16057 can be comprised of any suitable material. The cartridge body 16051 comprises a deck 16052 configured to support tissue, a longitudinal slot 16056, and a plurality of staple cavities 16053 defined in the deck 16052. Referring primarily to FIGS. 135 and 136, staples 16055 are removably positioned in the staple cavities 16053 and are supported by staple drivers 16054 which are also movably positioned in the staple cavities 16053. The retainer 16057 extends around the bottom of the cartridge body 16051 to keep the staple drivers 16054 and/or the staples 16055 from falling out of the bottom of the staple cavities 16053. The staple drivers 16054 and the staples 16055 are movable between an unfired position (FIG. 135) and a fired position by a sled 16060. The sled 16060 is movable between a proximal, unfired position (FIG. 135) toward a distal, fired position to eject the staples 16055 from the staple cartridge 16050, as illustrated in FIG. 136. The sled 16060 comprises one or more ramped surfaces 16064 which are configured to slide under the staple drivers 16054. The end effector 16020 further comprises an anvil 16040 configured to deform the staples 16055 when the staples 16055 are ejected from the staple cartridge 16050. In various instances, the anvil 16040 can comprise forming pockets 16045 defined therein which are configured to deform the staples 16055.

The shaft 16010 comprises a frame 16012 and an outer sleeve 16014 which is movable relative to the frame 16012. The cartridge channel 16030 is mounted to and extends from the shaft frame 16012. The outer sleeve 16014 is operably engaged with the anvil 16040 and is configured to move the anvil 16040 between an open position (FIG. 134) and a closed position (FIG. 135). In use, the anvil 16040 is movable toward a staple cartridge 16050 positioned in the cartridge channel 16030 to clamp tissue against the deck 16052 of the staple cartridge 16050. In various alternative embodiments, the cartridge channel 16030 and the staple cartridge 16050 are movable relative to the anvil 16040 to clamp tissue therebetween. In either event, the shaft 16010 further comprises a firing member 16070 configured to push the sled 16060 distally. The firing member 16070 comprises a knife edge 16076 which is movable within the longitudinal slot 16056 and is configured to incise the tissue positioned intermediate the anvil 16040 and the staple cartridge 16050 as the firing member 16070 is advanced distally to eject the staples 16055 from the staple cartridge 16050. The firing member 16070 further comprises a first cam 16071 configured to engage the cartridge channel 16030 and a second cam 16079 configured to engage the anvil 16040 and hold the anvil 16040 in position relative to the staple cartridge 16050. The first cam 16071 is configured to slide under the cartridge channel 16030 and the second cam 16079 is configured to slide within an elongate slot 16049 defined in the anvil 16040.

Further to the above, the staple cartridge 16050 is a replaceable staple cartridge. When a staple cartridge 16050 has been at least partially used, it can be removed from the cartridge channel 16030 and replaced with another staple cartridge 16050, or any other suitable staple cartridge. Each new staple cartridge 16050 comprises a cartridge body 16051, staple drivers 16054, staples 16055, and a sled 16060. The firing member 16070 is part of the shaft 16010. When a staple cartridge 16050 is removed from the cartridge channel 16030, the firing member 16070 remains with the shaft 16010. That said, the shaft 16010 itself may be replaceable as well; however, such a replacement shaft 16010 could still be used in the manner described herein. In at least one such instance, the surgical instrument system 16000 could comprise a handle, a shaft 16010 replaceably attached to the handle, and a staple cartridge 16050 replaceably positioned in the cartridge channel 16030 extending from the shaft 16010, for example. FIG. 137 depicts a staple cartridge 16050 positioned over an opening 16031 defined in the cartridge channel 16030 and FIG. 138 depicts the staple cartridge 16050 fully seated in the cartridge channel 16030; however, it should be appreciated that several components of the end effector 16020, such as the anvil 16040, for example, and the firing member 16070 have been removed from FIGS. 137 and 138 to demonstrate the general premise of a staple cartridge 16050 being inserted into the cartridge channel 16030. It should be appreciated, however, that a staple cartridge 16050 is often inserted into the cartridge channel 16030 through the distal end 16038 of the channel 16030. In such instances, the proximal end 16059 of the staple cartridge 16050 is aligned with the distal end 16038 of the cartridge channel 16030 and the staple cartridge 16050 is then moved proximally to align the proximal end 16059 of the staple cartridge 16050 with the proximal end 16039 of the cartridge channel 16030 and, correspondingly, align the distal end 16058 of the staple cartridge 16050 with the distal end 16038 of the cartridge channel 16030. The cartridge channel 16030 comprises a datum 16033 configured to stop the proximal insertion of the staple cartridge 16050. More particularly, the cartridge body 16051 comprises a datum shoulder 16034 defined thereon configured to abut the datum 16033 when the staple cartridge 16050 has been inserted to the proper depth; however, it is possible for the staple cartridge 16050 to be inserted into the cartridge channel 16030 in a number of ways which can prevent the datum shoulder 16034 from contacting the datum 16033.

Regardless of the manner used to position a staple cartridge 16050 in the cartridge channel 16030, it is desired to position the sled 16060 of the staple cartridge 16050 directly in front of the firing member 16070 when the staple cartridge 16050 is positioned in the cartridge channel 16030. When the sled 16060 is positioned directly in front of the firing member 16070, the sled 16060 can keep the firing member 16070 from falling into a lockout when the firing member 16070 is advanced distally. More specifically, referring to FIG. 135, the sled 16060 includes a support shoulder 16067 which is configured to support a support tab 16077 extending distally from the firing member 16070 and hold a lock shoulder 16078 of the firing member 16070 above a lockout window 16037 (FIG. 137) defined in the cartridge channel 16030. If the sled 16060 has been advanced distally prior to the staple cartridge 16050 being fully seated in the cartridge channel 16030, as illustrated in FIG. 136, the support tab 16077 of the firing member 16070 will not be supported, or supportable, by the support shoulder 16067 of the sled 16060 and, as a result, the lock shoulder 16078 of the firing member 16070 will enter the lockout window 16037 when the firing member 16070 is advanced distally. In fact, the shaft 16010 includes a biasing spring 16018 resiliently engaged with a top surface 16072 of the firing member 16070 which biases the firing member 16070 toward the lockout window 16037. The entire disclosures of U.S. Pat. No. 7,143,923, entitled SURGICAL STAPLING INSTRU-MENT HAVING A FIRING LOCKOUT FOR AN UNCLOSED ANVIL, which issued on Dec. 5, 2006; U.S. Pat. No. 7,044,352, SURGICAL STAPLING INSTRU-MENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOS-ING AND FIRING SYSTEMS, which issued on Feb. 21, 2006; U.S. Pat. No. 6,988,649, SURGICAL STAPLING INSTRUMENT HAVING A SPENT CARTRIDGE LOCK-OUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein. The above being said, it may be difficult for the clinician inserting the staple cartridge 16050 into the cartridge channel 16030 to determine whether the sled 16060 has been accidentally, or prematurely, pushed forward prior to inserting, and/or during the insertion of, the staple cartridge 16050 into the cartridge channel 16030. As described in detail further below, the surgical instrument system 16000 comprises means for assessing whether the sled 16060 has been prematurely advanced when the staple cartridge 16050 is positioned in the cartridge channel 16030.

When moving a staple cartridge 16050 proximally to insert the staple cartridge 16050 in the cartridge channel 16030, as described above, the sled 16060 can be acciden-tally or unintentionally bumped and pushed distally from its unfired position (FIG. 135) to a partially-fired position (FIG. 136). More particularly, referring now to FIG. 139, the sled 16060 in the staple cartridge 16050 can contact the firing member 16070 in the shaft 16010 in the event that the staple cartridge 16050 is m is-inserted into the cartridge channel 16030, i.e., inserted too far proximally into the cartridge channel 16030, which can move the sled 16060 distally a distance X. Even though the clinician may subsequently place the staple cartridge 16050 in its proper position in the cartridge channel 16030, the sled 16060 will have already been pushed out of its proper position in the staple cartridge 16050 and, as a result, the firing member 16070 will enter the lockout when the firing member 16070 is advanced distally. Accordingly, the surgical instrument system 16000 will be unable to fire the staple cartridge 16050. Turning now to FIG. 140, the surgical instrument system 16000 comprises a mis-insertion sensor 16090 configured to detect when a staple cartridge 16050 has been over-inserted, or moved too far proximally within the end effector 16020, at some point during the process of inserting the staple car-tridge 16050 into the cartridge channel 16030.

Further to the above, the mis-insertion sensor 16090 is in signal communication with a control system of the surgical instrument system 16000. The control system can include a microprocessor and the mis-insertion sensor 16090 can be in signal communication with the microprocessor via at least one signal wire 16092 and/or a wireless signal transmitter and receiver system, for example. The m is-insertion sensor 16090 can comprise any suitable sensor. In at least one instance, the m is-insertion sensor 16090 can comprise a contact switch which is in an open condition when a staple cartridge 16050 is not in contact with the sensor 16090 and a closed condition when a staple cartridge 16050 is in contact with the sensor 16090. The mis-insertion sensor 16090 is positioned in the cartridge channel 16030 such that, if the staple cartridge 16050 is inserted properly in the cartridge channel 16030, the staple cartridge 16050 will not contact the m is-insertion sensor 16090. In various instances, the control system of the surgical instrument system 16000 can include an indicator which can indicate to the user of the surgical instrument system 16000 that the m is-insertion sensor 16090 and the microprocessor have not detected a mis-insertion of a staple cartridge 16050.

In the event that the staple cartridge 16050 is over-inserted into the cartridge channel 16030 and the staple cartridge 16050 contacts the m is-insertion sensor 16090, further to the above, the microprocessor can detect the closure of the sensor 16090 and take an appropriate action. Such an appropriate action may include warning the user of the surgical instrument system 16000 that the staple car-tridge 16050 has been over-inserted and that the sled 16060 of the staple cartridge 16050 may have been moved distally pre-maturely. In at least one instance, the surgical instrument system 16000 can include an indicator which, when illumi-nated, can indicate to the user that the condition of the staple cartridge 16050 positioned in the cartridge channel 16030 is unreliable and that it should be removed and replaced with another staple cartridge 16050. In addition to or in lieu of the above, the surgical instrument system 16000 can include a display screen, for example, which could communicate this information to the user of the surgical instrument system 16000. In addition to or in lieu of the above, the microprocessor can deactivate the closure system of the surgical instrument system 16000 to prevent the anvil 16040 from being moved into a closed position when the microprocessor has determined that a staple cartridge 16050 has been over-inserted into the cartridge channel 16030 and/or that the condition of the staple cartridge 16050 positioned in the cartridge channel 16030 is unreliable. By preventing the anvil 16040 from closing, in the embodiments where the surgical instrument system 16000 comprises an endoscopic surgical stapler, for example, the end effector 16020 of the surgical instrument system 16000 cannot be inserted through a trocar into a patient and, thus, the surgical instrument system 16000 can require the user to replace the staple cartridge 16050 before the surgical instrument 16000 can be used.

When the mis-insertion sensor 16090 comprises a contact switch, further to the above, the sensor 16090 can be positioned in any suitable location in the cartridge channel 16030 in which a staple cartridge 16050 would make contact with the sensor 16090 if the staple cartridge 16050 is mis-inserted. As illustrated in FIG. 140, the m is-insertion sensor 16090 can be positioned on either side of a longitudinal slot 16036 extending through the cartridge channel 16030, for example. As discussed above, however, the m is-insertion sensor 16090 can comprise any suitable type of sensor and, as a result, the sensor 16090 can be positioned in any suitable position in the end effector 16020 and/or shaft 16010, depending on the type of sensor that is being used. For instance, the mis-insertion sensor 16090 can comprise a Hall Effect sensor, for example, which can emit a magnetic field and detect changes to that magnetic field when the staple cartridge 16050 is inserted into the cartridge channel 16030. In various instances, a large disturbance to the magnetic field can indicate that the staple cartridge 16050 is close to the sensor 16090. If the disturbance to the magnetic field exceeds a threshold level, then the microprocessor can determine that the staple cartridge 16050 was positioned too close to the sensor 16090 during the insertion of the staple cartridge 16050 into the cartridge channel 16030 and, as a result, the staple cartridge 16050 has been over-inserted into the cartridge channel 16030 at some point. In at least one instance, the cartridge body 16051, the retainer 16057, and/or the sled 16060 can include one or more magnetic elements which can be configured to disturb the magnetic field of the sensor 16090, for example.

In addition to or in lieu of the above, referring now to FIGS. 141 and 142, the surgical instrument system 16000 can comprise a sensor 16080 configured to directly detect whether the sled 16060 is in its correct, or unfired, position when the staple cartridge 16050 is positioned in the cartridge channel 16030. The sensor 16080 is positioned in a recess 16032 defined in the cartridge channel 16030; however, the sensor 16080 can be positioned in any suitable location. The sensor 16080 is aligned with the proximal end of the sled 16060 when the sled 16060 is in its unfired position, as illustrated in FIG. 141. In such instances, the sled 16060 is positioned over the sensor 16080 and is in contact with the sensor 16080. The sensor 16080 comprises a contact switch which is in a closed condition when the sled 16060 is engaged with the sensor 16080, for example. In various instances, the sensor 16080 can comprise a continuity sensor, for example. When the sled 16060 is advanced distally, the sled 16060 is no longer aligned with or in contact with the sensor 16080. In such instances, the contact switch of the sensor 16080 is in an open condition. The sensor 16080 is in signal communication with the microprocessor of the control system of the surgical instrument system 16000 via at least one signal wire 16082 and/or a wireless signal transmitter and receiver system, for example. When a staple cartridge 16050 is inserted into the channel, the sensor 16080 and the microprocessor can evaluate whether the sled 16060 is in its unfired position and, if it is not, take an appropriate action, such as the appropriate actions discussed above, for example.

Referring now to FIG. 143, the sensor 16080 comprises a first contact 16084 and a second contact 16085. The second contact 16085 comprises a free end positioned over the first contact 16084 which is movable between an open position in which a gap 16086 is present between the second contact 16085 and the first contact 16084 and a closed position in which the second contact 16085 is deflected into contact with the first contact 16084. The first contact 16084 and the second contact 16085 are comprised of an electrically conductive material, such as copper, for example, and, when the second contact 16085 is in contact with the first contact 16084, the sensor 16080 closes a circuit which permits current to flow therethrough. The sensor 16080 further comprises a flexible housing 16083 which surrounds the ends of the first contact 16084 and the second contact 16085. The housing 16083 comprises a sealed deformable membrane; however, any suitable configuration could be used. The housing 16083 is comprised of an electrically insulative material, such as plastic, for example. When the sled 16060 contacts the sensor 16080, as discussed above, the sled 16060 can push the housing 16083 downwardly and deflect the second contact 16085 toward the first contact 16084 to close the sensor 16080. If the sled 16060 has been advanced distally prior to the staple cartridge 16050 being fully seated in the cartridge channel 16030, the sled 16060 will not deflect the housing 16083 and the second contact 16085 downwardly. As a result of the above, the sensor 16080 can not only detect whether a staple cartridge 16050 is present in the cartridge channel 16030, but it can also detect whether the staple cartridge 16050 has been at least partially fired.

In addition to or in lieu of the above, the sensor 16080 can comprise any suitable sensor, such as a Hall Effect sensor, for example, which is configured to emit a magnetic field and detect changes to the magnetic field. The sled 16060 can include a magnetic element mounted thereto, such as on the bottom of the sled 16060, for example, and, when the staple cartridge 16050 is positioned in the cartridge channel 16030, the magnetic element can disrupt the magnetic field emitted by the sensor 16080. The sensor 16080 and the microprocessor of the surgical instrument control system can be configured to evaluate the magnitude in which the magnetic field has been disrupted and correlate the disruption of the magnetic field with the position of the sled 16060. Such an arrangement may be able to determine whether the sled 16060 is in an acceptable range of positions. For instance, the microprocessor may assess whether the disturbance of the magnetic field has exceeded a threshold and, if it has, the microprocessor can indicate to the user that the staple cartridge 16050 is suitable for use and, if the threshold has not been exceeded, the microprocessor can take a suitable action, as described above.

In addition to or in lieu of assessing whether a staple cartridge has been inserted to its proper depth in the cartridge channel 16030, the sensor 16080 can be configured to assess whether a staple cartridge 16050 has been fully seated in the cartridge channel 16030. For instance, referring again to FIG. 143, the sled 16060 may deflect the second contact 16085 enough to contact the first contact 16084 only when the staple cartridge 16050 is fully seated in the staple channel 16030. When the sensor 16080 comprises a Hall Effect sensor, for example, the threshold disturbance that the sled 16060 must create to indicate that the staple cartridge 16050 is suitable for use may not only require that the staple cartridge 16050 be inserted to its proper depth in the cartridge channel 16030 and that the sled 16060 be in its unfired position but it may also require that the staple cartridge 16050 be in its fully seated condition. Referring now to FIG. 144, an alternative sensor 16080' is depicted which comprises a pressure sensitive switch. The sensor 16080' comprises a variable resistive element 16086' positioned intermediate the first contact 16084 and the second contact 16085. In at least one instance, the variable resistive element 16086' can comprise a semi-conductive spacer, for example. The resistance of the variable resistive element 16086' is a function of the pressure, or force, being applied to it. For instance, if a low pressure is applied to the variable resistive element 16086' then the variable resistive element 16086' will have a low resistance and, correspondingly, if a high pressure is applied to the resistive element 16086' then the resistive element 16086' will have a high resistance. The microprocessor can be configured to correlate the resistance of the resistive element 16086' with the pressure being applied to the sensor 16080' and, ultimately, correlate the pressure being applied to the sensor 16080' with the height in which the staple cartridge 16050 is seated in the cartridge channel 16030. Once the resistance of the resistive element 16086' has exceeded a threshold resistance, the microprocessor can determine that the staple cartridge 16050 is ready to be fired. If, however, the resistance of the resistive element 16086' is below the threshold resistance, the microprocessor can determine that the staple cartridge 16050 has not been fully seated in the cartridge channel 16030 and take an appropriate action.

The present disclosure will now be described in connection with various examples and various combinations of such examples as described hereinbelow.

1. One example provides an electronic system for a surgical instrument, the electronic system comprising: an electric motor coupled to the end effector; a motor controller coupled to the motor; a parameter threshold detection module configured to monitor multiple parameter thresholds; a sensing module configured to sense tissue compression; a processor coupled to the parameter threshold detection module and the motor controller; and a memory coupled to the processor, the memory storing executable instructions that when executed by the processor cause the processor to monitor multiple levels of action thresholds and monitor speed of the motor and increment a drive unit of the motor, sense tissue compression, and provide rate and control feedback to the user of the surgical instrument.

2. Another example provides the electronic system of example 1, wherein the processor provides automatic compensation for motor load when thresholds detected by the parameter threshold detection module are within acceptable limits.

3. Another example provides the electronic system of example 1 or 2, wherein the parameter threshold detection module is configured to detect battery current and speed of the motor such that when the battery current increases or the speed of the motor decreases the motor controller increase a pulse width or frequency modulation to maintain the speed of the motor constant.

4. Another example provides the electronic system of any one of examples 1-3, wherein the parameter threshold detection module is configured to detect minimum and maximum threshold limits to control operation of the surgical instrument.

5. Another example provides the electronic system of example 4, wherein the parameter threshold detection module is configured to detect end effector closing force, end effector opening force, and speed of the motor.

6. Another example provides the electronic system of example 5, wherein when the end effector closing force decreases while a knife is translating through a knife channel in the end effector, the processor is configured to control the speed of the motor.

7. Another example provides the electronic system of example 5 or 6, wherein when the end effector closing force decreases while a knife is translating through a knife channel, the processor is configured to activate an alarm.

8. Another example provides the electronic system of any one of examples 4-7, wherein the processor is configured to activate the motor only after a minimum parameter threshold is detected.

9. Another example provides the electronic system of any one of examples 1-8, wherein the parameter threshold detection module is configured to detect an ultimate threshold associated with current draw, end effector pressure applied to tissue, firing load, or torque, wherein when the ultimate threshold is exceeded, the processor is configured to shut down the motor or cause the motor to retract the knife.

10. Another example provides the electronic system of example 9, wherein the parameter threshold detection module is configured to detect a secondary threshold which is less than the ultimate threshold, wherein control parameters are changed by the processor to accommodate the change in operation.

11. Another example provides the electronic system of example 9 or 10, wherein the parameter threshold detection module is configured to detect a marginal threshold in the form of either a step function or ramp function based on a proportional response to another input to the parameter threshold detection module.

12. Yet another example provides an electronic system for a surgical instrument, the electronic system comprising: an electric motor coupled to the end effector; a motor controller coupled to the motor; a sensing module configured to sense tissue compression; a processor coupled to the parameter threshold detection module and the motor controller; and a memory coupled to the processor, the memory storing executable instructions that when executed by the processor cause the processor to monitor the sensing module, wherein the sensing module is configured to sense multiple tissue parameters.

13. Another example provides the electronic system of example 12, wherein the sensing module is configured to sense tissue compression.

14. Another example provides the electronic system of example 12 or 13, wherein the sensing module is configured to sense tissue impedance.

15. Another example provides the electronic system of example 14, wherein the sensing module is coupled to electrodes to measure tissue impedance via sub-therapeutic RF energy.

16. Another example provides the electronic system of example 15, wherein the sensing module is configured to read overlaid multiple frequency signals to measure impedance in different locations simultaneously.

17. Another example provides the electronic system of example 15 or 16, wherein the sensing module comprises a multiplexor to measure impedance at variable RF frequencies sequentially.

18. Another example provides the electronic system of any one of examples 12-17, wherein the sensing module is configured to sense tissue pressure.

19. Another example provides the electronic system of any one of examples 12-18, wherein the sensing module is configured to sense tissue contact.

20. Another example provides the electronic system of any one of examples 12-19, wherein the sensing module is configured to sense viscoelasticity rate of change.

21. Yet another example provides an electronic system for a surgical instrument, the electronic system comprising: an electric motor coupled to the end effector; a motor controller coupled to the motor; a sensing module configured to sense tissue compression; a feedback module configured to provide rate and control feedback to a user of the surgical instrument; a processor coupled to the parameter threshold detection module and the motor controller; and a memory coupled to the processor, the memory storing executable instructions that when executed by the processor cause the processor to monitor the sensing module, wherein the sensing module is configured to sense multiple tissue parameters and provide feedback over the feedback module to a user of the instrument.

In accordance with various examples, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various aspects, the operating logic may be configured to perform the initial processing, and transmit the data to the computer hosting the application to determine and generate instructions. For these examples, the operating logic may be further configured to receive information from and provide feedback to a hosting computer. In alternate examples, the operating logic may be configured to assume a larger role in receiving information and determining the feedback. In either case, whether determined on its own or responsive to instructions from a hosting computer, the operating logic may be further configured to control and provide feedback to the user.

In various aspects, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other examples, the operating logic may be implemented in hardware such as a gate array.

In various aspects, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various examples, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various aspects, the processor may be packaged together with the operating logic. In various examples, the processor may be packaged together with the operating logic to form a SiP. In various examples, the processor may be integrated on the same die with the operating logic. In various examples, the processor may be packaged together with the operating logic to form a System on Chip (SoC).

Various aspects may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some examples also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some aspects may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other examples, the functional components such as software, engines, and/or modules may be implemented by hardware elements that may include processors, microprocessors, circuits, circuit elements (e.g., transistors, resistors, capacitors, inductors, and so forth), integrated circuits, ASICs, PLDs, DSPs, FPGAs, logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether one example is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application APIs, and so forth. The firmware may be stored in a memory of the controller and/or the controller which may comprise a nonvolatile memory (NVM), such as in bit-masked ROM or flash memory. In various implementations, storing the firmware in ROM may preserve flash memory. The NVM may comprise other types of memory including, for example, programmable ROM (PROM), erasable programmable ROM (EPROM), EEPROM, or battery backed RAM such as dynamic RAM (DRAM), Double-Data-Rate DRAM (DDRAM), and/or synchronous DRAM (SDRAM).

In some cases, various aspects may be implemented as an article of manufacture. The article of manufacture may include a computer readable storage medium arranged to store logic, instructions and/or data for performing various operations of one or more examples. In various examples, for example, the article of manufacture may comprise a magnetic disk, optical disk, flash memory or firmware containing computer program instructions suitable for execution by a general purpose processor or application specific processor. The examples, however, are not limited in this context.

The functions of the various functional elements, logical blocks, modules, and circuits elements described in connection with the examples disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some examples also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the aspects described herein illustrate example implementations, and that the functional elements, logical blocks, modules, and circuits elements may be implemented in various other ways which are consistent with the described examples. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual examples described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one example" or "an example" means that a particular feature, structure, or characteristic described in connection with the example is comprised in at least one example. The appearances of the phrase "in one example" or "in one aspect" in the specification are not necessarily all referring to the same example.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some aspects may be described using the expression "coupled" and "connected" along with their derivatives. These terms are not intended as synonyms for each other. For example, some aspects may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, API, exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure applies to conventional endoscopic and open surgical instrumentation as well as application in robotic-assisted surgery.

Aspects of the devices disclosed herein can be designed to be disposed of after a single use, or they can be designed to be used multiple times. Examples may, in either or both cases, be reconditioned for reuse after at least one use. Reconditioning may include any combination of the steps of disassembly of the device, followed by cleaning or replacement of particular pieces, and subsequent reassembly. In particular, examples of the device may be disassembled, and any number of the particular pieces or parts of the device may be selectively replaced or removed in any combination. Upon cleaning and/or replacement of particular parts, examples of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically matable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing disclosure has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various examples and with various modifications as are suited to the particular use contemplated. It is intended that the claims submitted herewith define the overall scope.

What is claimed is:

1. A surgical system, comprising:
a motor;
a motor control circuit configured to control the motor;
a processing circuit coupled to the motor control circuit; and
a memory coupled to the processing circuit, wherein the memory stores:
a predetermined threshold associated with a parameter associated with the surgical system, the parameter comprising a value which varies based on operation of the surgical system; and
wherein the processing circuit is configured to:
monitor, by the processing circuit, the value of the parameter during use of the surgical system in a surgical procedure;
compare, by the processing circuit, the monitored value of the parameter to the predetermined threshold associated with the parameter to determine when the monitored value exceeds the predetermined threshold;
interrupt, by the motor control circuit, an operation of the motor when the monitored value of the parameter exceeds the predetermined threshold;
receive, by the processing circuit, an override input, to override the interruption of the operation of the motor;
resume, by the motor control circuit, the operation of the motor based on the override input;
permit, by the motor control circuit subsequent to the resumption of the operation of the motor, the operation of the motor regardless of the monitored value of the parameter continuing to exceed the predetermined threshold; and
monitor, by the processing circuit, the value of the parameter beyond the predetermined threshold.

2. The surgical system of claim 1, wherein the processing circuit is configured to adjust a speed of the motor based on the override input.

3. The surgical system of claim 1, wherein the parameter comprises a current draw of the motor of the surgical system.

4. The surgical system of claim 1, wherein the parameter comprises a velocity parameter.

5. The surgical system of claim 1, wherein the parameter comprises a firing force parameter.

6. The surgical system of claim 1, wherein the processing circuit is configured to adjust the operation of the motor based on the monitoring of the value of the parameter beyond the predetermined threshold.

7. The surgical system of claim 6, wherein the processing circuit is configured to adjust the operation of the motor based on the monitored value of the parameter exceeding the predetermined threshold for a predetermined period of time.

8. A surgical system, comprising:
a motor; and
a control circuit, configured to:
monitor a value of a parameter associated with the surgical system during use of the surgical system in a surgical procedure, the value varying based thereon;
compare the monitored value of the parameter to a predetermined threshold associated with the parameter to determine when the monitored value deviates from the predetermined threshold;
interrupt an operation of the motor of the surgical system when the monitored value of the parameter and deviates from the predetermined threshold;
receive an override input to override the interruption of the operation of the motor;
resume the operation of the motor based on the override input;
permit, subsequent to the resumption of the operation of the motor, the operation of the motor regardless of the monitored value of the parameter continuing to deviate from the predetermined threshold; and
monitor the value of the parameter beyond the predetermined threshold.

9. The surgical system of claim 8, wherein the control circuit is further configured to adjust a speed of the motor based on the override input.

10. The surgical system of claim 8, wherein the parameter comprises a current draw of the motor of the surgical system.

11. The surgical system of claim 8, wherein the parameter comprises a velocity parameter.

12. The surgical system of claim 8, wherein the parameter comprises a firing force parameter.

13. The surgical system of claim 8, wherein the control circuit is further configured to adjust the operation of the motor based on the monitoring of the value of the parameter beyond the predetermined threshold.

14. The surgical system of claim 13, wherein the control circuit is further configured to adjust the operation of the motor based on the monitored value of the parameter deviating from the predetermined threshold for a predetermined period of time.

* * * * *